United States Patent
Chen et al.

(10) Patent No.: US 9,115,195 B2
(45) Date of Patent: Aug. 25, 2015

(54) THERAPEUTIC DLL4 BINDING PROTEINS

(75) Inventors: Ming-Jiu Chen, Shrewsbury, MA (US); Chung-Ming Hsieh, Newton, MA (US); Jijie Gu, Shrewsbury, MA (US); Susan E. Morgan-Lappe, Chicago, IL (US); Yingchun Li, Buffalo Grove, IL (US)

(73) Assignee: ABBVIE INC., North Chicago, IL (US)

( * ) Notice: Subject to any disclaimer, the term of this patent is extended or adjusted under 35 U.S.C. 154(b) by 1211 days.

(21) Appl. No.: 13/037,932

(22) Filed: Mar. 1, 2011

(65) Prior Publication Data
US 2011/0217237 A1 Sep. 8, 2011

Related U.S. Application Data

(60) Provisional application No. 61/309,494, filed on Mar. 2, 2010.

(51) Int. Cl.
*C07K 16/00* (2006.01)
*C07K 16/28* (2006.01)

(52) U.S. Cl.
CPC ........... *C07K 16/28* (2013.01); *C07K 2317/24* (2013.01)

(58) Field of Classification Search
None
See application file for complete search history.

(56) References Cited

U.S. PATENT DOCUMENTS

| | | |
|---|---|---|
| 4,526,938 A | 7/1985 | Churchill et al. |
| 4,554,101 A | 11/1985 | Hopp |
| 4,816,397 A | 3/1989 | Boss et al. |
| 4,816,567 A | 3/1989 | Cabilly et al. |
| 4,880,078 A | 11/1989 | Inoue et al. |
| 4,880,780 A | 11/1989 | Trainor et al. |
| 4,946,778 A | 8/1990 | Ladner et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,294,404 A | 3/1994 | Grandone et al. |
| 5,403,484 A | 4/1995 | Ladner et al. |
| 5,427,908 A | 6/1995 | Dower et al. |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,627,052 A | 5/1997 | Schrader |
| 5,641,870 A | 6/1997 | Rinderknecht et al. |
| 5,648,260 A | 7/1997 | Winter et al. |
| 5,658,727 A | 8/1997 | Barbas et al. |
| 5,679,377 A | 10/1997 | Bernstein et al. |
| 5,693,762 A | 12/1997 | Queen et al. |
| 5,698,426 A | 12/1997 | Huse |
| 5,714,352 A | 2/1998 | Jakobovits |
| 5,723,323 A | 3/1998 | Kauffman et al. |
| 5,733,743 A | 3/1998 | Johnson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,780,225 A | 7/1998 | Wigler et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,855,913 A | 1/1999 | Hanes et al. |
| 5,874,064 A | 2/1999 | Edwards et al. |
| 5,912,015 A | 6/1999 | Bernstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jokobovits et al. |

(Continued)

FOREIGN PATENT DOCUMENTS

| | | |
|---|---|---|
| CN | 101210049 A | 7/2008 |
| EP | 0 592 106 A1 | 4/1994 |

(Continued)

OTHER PUBLICATIONS

Rudikoff et al (Proc Natl Acad Sci USA 1982 vol. 79 p. 1979).*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. (2002) 320, 415-428.*
Lamminmaki et al. (JBC 2001, 276:36687-36694).*
Chen et al. J. Mol. Bio. (1999) 293, 865-881.*
Wu et al. J. Mol. Biol. (1999) 294, 151-162.*
Padlan et al. (PNAS 1989, 86:5938-5942).*
"Infliximab," in The Merck Index, 14th Ed., John Wiley & Sons, 2006; p. 863.
Hoey et al., "DLL4 blockade inhibits tumor growth and reduces tumor-initiating cell frequency," *Cell Stem Cell*, 5: 168-177 (2009).
Sainson, "Anti-Dll4 Therapy: Can We Block Tumour Growth by Increasing Angiogenesis?" *Trends Mol. Med.*, 13(9) 389-395 (2007).
International Search Report and Written Opinion for Application No. PCT/US11/26489, mailed on Aug. 22, 2011, 15 pages.

(Continued)

*Primary Examiner* — Laura B Goddard
*Assistant Examiner* — Meera Natarajan
(74) *Attorney, Agent, or Firm* — Finnegan, Henderson, Farabow, Garrett & Dunner, LLP

(57) ABSTRACT

DLL4 binding proteins are described herein, including antibodies, CDR-grafted antibodies, humanized antibodies, and DLL4 binding fragments thereof, proteins that bind DLL4 with high affinity, and DLL4 binding proteins that neutralize DLL4 and/or VEGF activity. The DLL4 binding proteins are useful for treating or preventing cancers and tumors and especially for treating or preventing tumor angiogenesis.

91 Claims, No Drawings

(56) References Cited

U.S. PATENT DOCUMENTS

| | | |
|---|---|---|
| 6,019,968 A | 2/2000 | Platz et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,660,843 B1 | 12/2003 | Feige et al. |
| 6,699,658 B1 | 3/2004 | Wittrup et al. |
| 6,914,128 B1 | 7/2005 | Salfeld et al. |
| 7,262,028 B2 | 8/2007 | Van Berkel et al. |
| 7,419,821 B2 | 9/2008 | Davis et al. |
| 7,429,486 B2 | 9/2008 | Van Berkel et al. |
| 7,612,181 B2 | 11/2009 | Wu et al. |
| 7,682,833 B2 | 3/2010 | Miller et al. |
| 8,586,714 B2 | 11/2013 | Ghayur et al. |
| 8,623,358 B2 | 1/2014 | Benatuil et al. |
| 8,624,002 B2 | 1/2014 | Gu et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,822,645 B2 | 9/2014 | Ghayur et al. |
| 2002/0137134 A1 | 9/2002 | Gerngross |
| 2002/0142390 A1 | 10/2002 | Allen et al. |
| 2003/0176672 A1 | 9/2003 | Salceda et al. |
| 2003/0186374 A1 | 10/2003 | Hufton et al. |
| 2004/0018577 A1 | 1/2004 | Emerson Campbell et al. |
| 2004/0018590 A1 | 1/2004 | Gerngross et al. |
| 2004/0029129 A1 | 2/2004 | Wang et al. |
| 2004/0031072 A1 | 2/2004 | La Rosa et al. |
| 2004/0141964 A1 | 7/2004 | Abdel-Meguid et al. |
| 2005/0042664 A1 | 2/2005 | Wu et al. |
| 2005/0154192 A1 | 7/2005 | Shirakawa et al. |
| 2005/0187167 A1 | 8/2005 | Bachmann et al. |
| 2006/0078901 A1 | 4/2006 | Buchrieser et al. |
| 2006/0134121 A1 | 6/2006 | Thurston et al. |
| 2006/0160164 A1 | 7/2006 | Miller et al. |
| 2007/0148749 A1 | 6/2007 | Yasuda et al. |
| 2007/0248584 A1 | 10/2007 | Kent |
| 2008/0175847 A1 | 7/2008 | Yan et al. |
| 2008/0187532 A1 | 8/2008 | Gurney et al. |
| 2008/0233140 A1 | 9/2008 | Banchereau et al. |
| 2009/0035308 A1 | 2/2009 | Gill et al. |
| 2009/0041783 A1 | 2/2009 | Takayama et al. |
| 2009/0130114 A1 | 5/2009 | Qian et al. |
| 2009/0175880 A1 | 7/2009 | Keler et al. |
| 2009/0175881 A1 | 7/2009 | Presta et al. |
| 2009/0239259 A1 | 9/2009 | Hsieh |
| 2009/0246199 A1 | 10/2009 | Noguera-Troise et al. |
| 2009/0304693 A1 | 12/2009 | Ghayur et al. |
| 2009/0311253 A1 | 12/2009 | Ghayur et al. |
| 2010/0021953 A1 | 1/2010 | Belfield et al. |
| 2010/0076178 A1 | 3/2010 | Ghayur et al. |
| 2010/0099103 A1 | 4/2010 | Hsieh et al. |
| 2010/0233079 A1 | 9/2010 | Jakob et al. |
| 2010/0260668 A1 | 10/2010 | Ghayur et al. |
| 2011/0008766 A1 | 1/2011 | Ghayur et al. |
| 2011/0044980 A1 | 2/2011 | Ghayur et al. |
| 2011/0117079 A1 | 5/2011 | Benatuil et al. |
| 2011/0189176 A1 | 8/2011 | Skokos |
| 2011/0217237 A1 | 9/2011 | Chen et al. |
| 2011/0263827 A1 | 10/2011 | Ghayur et al. |
| 2011/0318349 A1 | 12/2011 | Ghayur et al. |
| 2012/0014957 A1 | 1/2012 | Ghayur et al. |
| 2012/0087858 A1 | 4/2012 | Ghayur et al. |
| 2012/0258108 A1 | 10/2012 | Ghayur et al. |
| 2012/0263722 A1 | 10/2012 | Ghayur et al. |
| 2013/0171059 A1 | 7/2013 | Ghayur et al. |
| 2013/0195871 A1 | 8/2013 | Ghayur et al. |
| 2013/0236458 A1 | 9/2013 | Hsieh et al. |
| 2014/0093521 A1 | 4/2014 | Benatuil et al. |
| 2014/0134171 A1 | 5/2014 | Ghayur et al. |
| 2014/0134172 A1 | 5/2014 | Gu et al. |
| 2014/0186377 A1 | 7/2014 | Gu et al. |
| 2014/0219912 A1 | 8/2014 | Ghayur et al. |
| 2014/0234208 A1 | 8/2014 | Ghayur et al. |
| 2014/0271458 A1 | 9/2014 | Ghayur et al. |
| 2014/0308286 A1 | 10/2014 | Ghayur et al. |
| 2014/0348835 A1 | 11/2014 | Gu et al. |
| 2014/0356281 A1 | 12/2014 | Ghayur et al. |

FOREIGN PATENT DOCUMENTS

| | | |
|---|---|---|
| EP | 239400 B1 | 8/1994 |
| EP | 592106 B1 | 11/2004 |
| EP | 519596 B1 | 2/2005 |
| GB | 2 449 354 A | 11/2008 |
| WO | WO9002809 A1 | 3/1990 |
| WO | WO9005144 A1 | 5/1990 |
| WO | WO9014424 A1 | 11/1990 |
| WO | WO9014430 A1 | 11/1990 |
| WO | WO9014443 A1 | 11/1990 |
| WO | WO9105548 A1 | 5/1991 |
| WO | WO9109967 A1 | 7/1991 |
| WO | WO9110737 A1 | 7/1991 |
| WO | WO9110741 A1 | 7/1991 |
| WO | WO9117271 A1 | 11/1991 |
| WO | WO9201047 A1 | 1/1992 |
| WO | WO9202551 A1 | 2/1992 |
| WO | WO9203461 A1 | 3/1992 |
| WO | WO9209690 A2 | 6/1992 |
| WO | WO9211272 A1 | 7/1992 |
| WO | WO9215679 A1 | 9/1992 |
| WO | WO9218619 A1 | 10/1992 |
| WO | WO9219244 A2 | 11/1992 |
| WO | WO9220791 A1 | 11/1992 |
| WO | WO9222324 A1 | 12/1992 |
| WO | WO9301288 A1 | 1/1993 |
| WO | WO9306213 A1 | 4/1993 |
| WO | WO9311236 A1 | 6/1993 |
| WO | WO9402602 A1 | 2/1994 |
| WO | WO9418219 A1 | 8/1994 |
| WO | WO9515982 A2 | 6/1995 |
| WO | WO9520401 A1 | 8/1995 |
| WO | WO9620698 A2 | 7/1996 |
| WO | WO9633735 A1 | 10/1996 |
| WO | WO9634096 A1 | 10/1996 |
| WO | WO9636358 A1 | 11/1996 |
| WO | WO9720032 A1 | 6/1997 |
| WO | WO9729131 A1 | 8/1997 |
| WO | WO9732572 A2 | 9/1997 |
| WO | WO9744013 A1 | 11/1997 |
| WO | WO9816654 A1 | 4/1998 |
| WO | WO9824893 A2 | 6/1998 |
| WO | WO9831346 A1 | 7/1998 |
| WO | WO9831700 A1 | 7/1998 |
| WO | WO9850433 A2 | 11/1998 |
| WO | WO9906834 A2 | 2/1999 |
| WO | WO9915154 A1 | 4/1999 |
| WO | WO9920253 A1 | 4/1999 |
| WO | WO9925044 A1 | 5/1999 |
| WO | WO9945031 A2 | 9/1999 |
| WO | WO9953049 A1 | 10/1999 |
| WO | WO9966903 A2 | 12/1999 |
| WO | WO0009560 A2 | 2/2000 |
| WO | WO 00/24782 A2 | 5/2000 |
| WO | WO0037504 A2 | 6/2000 |
| WO | WO0056772 A1 | 9/2000 |
| WO | WO 01/77342 A1 | 10/2001 |
| WO | WO0183525 A2 | 11/2001 |
| WO | WO0202773 A2 | 1/2002 |
| WO | WO02072636 A2 | 9/2002 |
| WO | WO2006070290 A2 | 7/2006 |
| WO | WO2007024715 A9 | 3/2007 |
| WO | WO 2007/070671 A2 | 6/2007 |
| WO | WO 2007/143689 A2 | 12/2007 |
| WO | WO 2008/019144 A2 | 2/2008 |
| WO | WO 2008/042236 A2 | 4/2008 |
| WO | WO 2008/060705 A2 | 5/2008 |
| WO | WO 2008/076379 A2 | 6/2008 |
| WO | WO 2008/091222 A1 | 7/2008 |
| WO | WO 2008/139202 A1 | 11/2008 |
| WO | WO2009026660 A1 | 3/2009 |

(56) References Cited

FOREIGN PATENT DOCUMENTS

| WO | WO 2009/124931 A2 | 10/2009 |
|---|---|---|
| WO | WO 2009/134776 A2 | 11/2009 |
| WO | WO 2010/032060 A1 | 3/2010 |

OTHER PUBLICATIONS

Presta, et al. "Engineering of Therapeutic Antibodies to Minimize Immunogenicity and Optimize Function", Advanced Drug Delivery Reviews, Elsevier, vol. 58, No. 5-6, Aug. 7, 2006, pp. 640-656.

European Application No. 11751147.7 Extended European Search Report dated Nov. 7, 2013, 13 pages.

Ames R.S., et al., "Conversion of Murine Fabs Isolated from a Combinatorial Phage Display Library to Full Length Immunoglobulins," Journal of Immunological Methods, 1995, vol. 184, pp. 177-186.

Anthony R.M., et al., "Recapitulation of IVIG Anti-Inflammatory Activity with a Recombinant IgG Fc," Science, 2008, vol. 320 (5874), pp. 373-376.

Ausubel, et al., Current Protocols in Molecular Biology, 1993, Table of Contents.

Azzazy H.M., et al., "Phage Display Technology: Clinical Applications and Recent Innovations," Clinical Biochemistry, 2002, vol. 35 (6), pp. 425-445.

Babcook J.S., et al., "A Novel Strategy for Generating Monoclonal Antibodies from Single, Isolated Lymphocytes Producing Antibodies of Defined Specificities," Proceedings of the National Academy of Sciences, 1996, vol. 93, pp. 7843-7848.

Barbas C.F. III, et al., "In Vitro Evolution of a Neutralizing Human Antibody to Human Immunodeficiency Virus Type 1 to Enhance Affinity and Broaden Strain Cross-Reactivity," Proceedings of the National Academy of Sciences of the United States of America, 1994, vol. 91 (9), pp. 3809-3813.

Barbas C.F. III, et al., "Assembly of Combinatorial Antibody Libraries on Phage Surfaces: The Gene III Site," The Proceedings of the National Academy of Sciences of the United States of America, 1991, vol. 88, pp. 7978-7982.

Better M., et al., "*Escherichia coli* Secretion of an Active Chimeric Antibody Fragment," Science, 1988, vol. 240, pp. 1041-1043.

Biewenga J., et al., "IgA1 Half Molecules in Human Multiple Myeloma and the in Vitro Production of Similar Fragments from Intact IgA1 Molecules," Clinical and Experimental Immunology, 1983, vol. 51 (2), pp. 395-400.

Bird R.E., et al., "Single-Chain Antigen Binding Proteins," Science, 1988, vol. 242 (4877), pp. 423-426.

Brinkmann U., et al., "Phage Display of Disulfide-stabilized Fv Fragments," Journal of Immunological Methods , 1995, vol. 182, pp. 41-50.

Buchwald H., et al., "Long-term, Continuous Intravenous Heparin Administration by an Implantable Infusion Pump in Ambulatory Patients with Recurrent Venous Thrombosis," Surgery, 1980, vol. 88, pp. 507-516.

Burton D.R., et al., "Human Antibodies from Combinatorial Libraries," Advances in Immunology, 1994, vol. 57, pp. 191-280.

Carter P., et al., "Humanization of an Anti-p185$^{HER2}$ Antibody for Human Cancer Therapy ," Proceedings of the National Academy of Sciences of the United States of America, 1992, vol. 89, pp. 4285-4289.

Chothia C., et al., "Canonical Structures for the Hypervariable Regions of Immunoglobulins," Journal of Molecular Biology, 1987, vol. 196 (4), pp. 901-917.

Chothia C., et al., "Conformations of Immunoglobulin Hypervariable Regions," Nature, 1989, vol. 342 (6252), pp. 877-883.

Chothia C., et al., "Structural Repertoire of the Human $V_H$ Segments," Journal of Molecular Biology, 1992, vol. 227 (3), pp. 799-817.

Clackson T., et al., "Making Antibody Fragments Using Phage Display Libraries," Nature, 1991, vol. 352 (6336), pp. 624-628.

Cleek R.L., et al., "Biodegradable Polymeric Carriers for a bFGF Antibody for Cardiovascular Application," Proc. Intl. Symp. Control. Rel. Bioact. Mater., 1997, vol. 24, pp. 853-854.

Dall'Acqua W., et al., "Contribution of Domain Interface Residues to the Stability of Antibody CH3 Domain Homodimers," Biochemistry, 1998, vol. 37 (26), pp. 9266-9273.

Duarte A., et al., "Dosage-Sensitive Requirement for Mouse Dll4 in Artery Development," Genes & Development, 2004, vol. 18 (20), pp. 2474-2478.

During M. J., et al., "Controlled Release of Dopamine from a Polymeric Brain Implant: In Vivo Characterization," Annals of Neurology, 1989, vol. 25 (4), pp. 351-356.

Durocher Y., et al., "High-Level and High-Throughput Recombinant Protein Production by Transient Transfection of Suspension-Growing Human 293-EBNA1 Cells," Nucleic Acids Research, 2002, vol. 30 (2), pp. e9.

Foote J., et al., "Antibody Framework Residues Affecting the Conformation of the Hypervariable Loops," Journal of Molecular Biology, 1992, vol. 224 (2), pp. 487-499.

Fuchs P., et al., "Targeting Recombinant Antibodies to the Surface of *Escherichia coli*: Fusion to a Peptidoglycan Associated Lipoprotein," BioTechnology, 1991, vol. 9 (12), pp. 1369-1372.

Gale N.W., et al., "Haploinsufficiency of Delta-Like 4 Ligand Results in Embryonic Lethality Due to Major Defects in Arterial and Vascular Development," Proceedings of the National Academy of Sciences, 2004, vol. 101 (45), pp. 15949-15954.

Garrard L.J., et al., "F,, Assembly and Enrichment in a Monovalent Phage Display System," BioTechnology, 1991, vol. 9 (12), pp. 1373-1377.

Gavilondo J.V., et al., "Antibody Engineering at the Millennium," Biotechniques, 2000, vol. 29 (1), pp. 128-132.

Giege R., et al., "An introduction to the crystallogenesis of biological macromolecules,": Crystallization of Nucleic Acids and Proteins, 2nd Edition, Ducruix A., et al., eds., Oxford University Press, 1999, 18 pages.

Gillies S.D., et al., "High-Level Expression of Chimeric Antibodies Using Adapted cDNA Variable Region Cassettes," Journal of Immunological Methods , 1989, vol. 125 (1-2), pp. 191-202.

Goldspiel B.R., et al., "Human Gene therapy," Clinical Pharmacy, 1993, vol. 12 (7), pp. 488-505.

Goodson, "Medical Applications of Controlled Release," Langer and Wise, Eds., 1984, 2, 115-138.

Gram H., et al., "In Vitro Selection and Affinity Maturation of Antibodies from a Naïve Combinatorial Immunoglobulin Library," Proceedings of the National Academy of Sciences, 1992, vol. 89 (8), pp. 3576-3580.

Green L. L., et al., "Regulation of B Cell Development by Variable Gene Complexity in Mice Reconstituted with Human Immunoglobulin Yeast Artificial Chromosomes," Journal of Experimental Medicine, 1998, vol. 188 (3), pp. 483-495.

Green L.L., et al., "Antigen-Specific Human Monoclonal Antibodies from Mice Engineered with Human Ig Heavy and Light Chain YACs," Nature Genetics, 1994, vol. 7 (1), pp. 13-21.

Griffiths A.D., et al., "Human Anti-Self Antibodies with High Specificity from Phage Display Libraries," European Molecular Biology Organization, 1993, vol. 12 (2), pp. 725-734.

Hammerling G.J., et al., "Monoclonal Antibodies and T-Cell Hybridomas" 1981, pp. 563-587.

Harlow E., et al., Antibodies: A Laboratory Manual, Cold Spring Harbor Laboratory Press, 1988, pp. 555-561, 578-582 and 591-592.

Harlow E., et al., "Antibodies: A Laboratory Manual", Table of Contents, 1999, Cold Spring Harbor Press.

Harrington L.S., et al., "Regulation of Multiple Angiogenic Pathways by Dll4 and Notch in Human Umbilical Vein Endothelial Cells," Microvascular Research, 2008, vol. 75 (2), pp. 144-154.

Hawkins R.E., et al., "Selection of Phage Antibodies by Binding Affinity Mimicking Affinity Maturation," Journal of Molecular Biology, 1992, vol. 226 (3), pp. 889-896.

Hay B.N., et al., "Bacteriophage Cloning and *Escherichia coli* Expression of a Human IgM Fab," Human Antibodies and Hybridomas, 1992, vol. 3 (2), pp. 81-85.

Holliger P., et al., "Diabodies: Small Bivalent and Bispecific Antibody Fragments," Proceedings of the National Academy of Sciences of the USA, 1993, vol. 90 (14), pp. 6444-6448.

(56) References Cited

OTHER PUBLICATIONS

Hoogenboom H.R., et al., "Designing and Optimizing Library Selection Strategies for Generating High-Affinity Antibodies," Trends in Biotechnology, 1997, vol. 15 (2), pp. 62-70.
Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.
Hoogenboom H.R., et al., "Natural and Designer Binding Sites Made by Phage Display Technology," Immunology Today, 2000, vol. 21 (8), pp. 371-378.
Howard M.A., et al., "Intracerebral Drug Delivery in Rats with Lesion-Induced Memory Deficits," Journal of Neurosurgery, 1989, vol. 71 (1), pp. 105-112.
Huber R., et al., "Crystallographic Structure Studies of an IgG Molecule and an Fc Fragment," Nature, 1976, vol. 264 (5585), pp. 415-420.
Huse W.D., et al., "Generation of a Large Combinatorial Library of the Immunoglobulin Repertoire in Phage Lambda," Science, 1989, vol. 246 (4935), pp. 1275-1281.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the USA, 1988, vol. 85 (16), pp. 5879-5883.
Huston J.S., et al., "Protein Engineering of Single-Chain Fv Analogs and Fusion Proteins," Methods in Enzymology, 1991, vol. 203, pp. 46-88.
Jackson J.R., et al., "In Vitro Antibody Maturation Improvement of a High Affinity, Neutralizing Antibody Against IL-1β," The Journal of Immunology, 1995, vol. 154 (7), pp. 3310-3319.
Johnsson B., et al., "Comparison of Methods for Immobilization to Carboxymethyl Dextran Sensor Surfaces by Analysis of the Specific Activity of Monoclonal Antibodies," Journal of Molecular Recognition, 1995, vol. 8 (1-2), pp. 125-131.
Johnsson B., et al., "Immobilization of Proteins to a Carboxymethyldextran-Modified Gold Surface for Biospecific Interaction Analysis in Surface Plasmon Resonance Sensors," Analytical Biochemistry, 1991, vol. 198 (2), pp. 268-277.
Joliot A., et al., "Antennapedia Homeobox Peptide Regulates Neural Morphogenesis," Proceedings of the National Academy of Sciences, 1991, vol. 88 (5), pp. 1864-1868.
Jones P.T., et al., "Replacing the Complementarity-Determining Regions in a Human Antibody with those from a Mouse," Nature, 1986, vol. 321 (6069), pp. 522-525.
Jonsson U., et al., "Introducing a Biosensor Based Technology for Real-Time Biospecific Interaction Analysis," Annales de Biologie Clinique, 1993, vol. 51 (1), pp. 19-26.
Jonsson U., et al., "Real-Time Biospecific Interaction Analysis Using Surface Plasmon Resonance and a Sensor Chip Technology," Biotechniques, 1991, vol. 11 (5), pp. 620-627.
Kabat E.A., et al., "Attempts to Locate Complementarity-Determining Residues in the Variable Positions of Light and Heavy Chains," Annals New York Academy of Sciences, 1971, vol. 190, pp. 382-393.
Kabat, E.A., et al., "Sequence of Proteins of Immunological Interest, Fifth Edition, U.S. Department of Health and Human Services, NIH Publication No. 91/3242," 1991, Table of Contents (pp. iii-xi).
Kabat E.A., et al., Sequences of Proteins of Immunological Interest, 1987, Table of Contents.
Kabat, "Sequences of Proteins of Immunological Interest," 1983, Table of Contents.
Kaufman R.J., et al., "Amplification and Expression of Sequences Cotransfected with a Modular Dihydrofolate Reductase Complementary DNA Gene," Journal of Molecular Biology, 1982, vol. 159 (4), pp. 601-621.
Kellermann S.A., et al., "Antibody Discovery: The Use of Transgenic Mice to Generate Human Monoclonal Antibodies for Therapeutics," Current Opinion in Biotechnology, 2002, vol. 13 (6), pp. 593-597.
Kettleborough C.A., et al., "Isolation of Tumor Cell-specific Single-chain Fv from Immunized Mice using Phage-antibody Libraries and the Re-construction of Whole Antibodies from these Antibody Fragments," European Journal of Immunology, 1994, vol. 24 (4), pp. 952-958.
Kim J.K., et al., "Identifying Amino Acid Residues that Influence Plasma Clearance of Murine IgG1 Fragments by Site-Directed Mutagenesis," European Journal of Immunology, 1994, vol. 24 (3), pp. 542-548.
Kipriyanov S.M., et al., "Recombinant Single-Chain Fv Fragments Carrying C-Terminal Cysteine Residues: Production of Bivalent and Biotinylated Miniantibodies," Molecular Immunology, 1994, vol. 31 (14), pp. 1047-1058.
Kipriyanov S.M., et al., "Single-Chain Antibody Streptavidin Fusions: Tetrameric Bifunctional scFv-Complexes with Biotin Binding Activity and Enhanced Affinity to Antigen," Human Antibodies and Hybridomas, 1995, vol. 6 (3), pp. 93-101.
Kohler G., et al., "Continuous Cultures of Fused Cells Secreting Antibody of Predefined Specificity," Nature, 1975, vol. 256 (5517), pp. 495-497.
Kontermann R., et al., eds., Antibody Engineering, Springer-Verlag Berlin Heidelberg, 2001, Table of Contents.
Krebs L.T., et al., "Haploinsufficient Lethality and Formation of Arteriovenous Malformations in Notch Pathway Mutants," Genes & Development, 2004, vol. 18 (20), pp. 2469-2473.
Krebs L.T., et al., "Notch Signaling is Essential for Vascular Morphogenesis in Mice," Genes & Development, 2000, vol. 14 (11), pp. 1343-1352.
Kriegler M., Gene Transfer and Expression: A Laboratory Manual, Stockton Press, 1990, Table of Contents.
Kyte J., et al., "A Simple Method for Displaying the Hydropathic Character of a Protein," Journal of Molecular Biology, 1982, vol. 157 (1), pp. 105-132.
Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.
Langer R., et al., "Chemical and Physical Structure of Polymers as Carriers for Controlled Release of Bioactive Agents: A Review," Journal of Macromolecular Science—Reviews in Macromolecular Chemistry & Physics, 1983, vol. C23 (1), pp. 61-126.
Langer R., "New Methods of Drug Delivery," Science, 1990, vol. 249 (4976), pp. 1527-1533.
Levy R.D., et al., "Inhibition of Calcification of Bioprosthetic Heart Valves by Local Controlled-Release Diphosphonate," Science, 1985, vol. 228 (4696), pp. 190-192.
Little M., et al., "Of Mice and Men: Hybridoma and Recombinant Antibodies," Immunology Today, 2000, vol. 21 (8), pp. 364-370.
Liu Z.J., et al., "Regulation of *Notch1* and *Dll4* by Vascular Endothelial Growth Factor in Arterial Endothelial Cells: Implications for Modulating Arteriogenesis and Angiogenesis," Molecular and Cellular Biology, 2003, vol. 23 (1), pp. 14-25.
Lobov I.B., et al., "Delta-Like Ligand 4 (Dll4) is Induced by VEGF as a Negative Regulator of Angiogenic Sprouting," Proceedings of the National Academy of Sciences, 2007, vol. 104 (9), pp. 3219-3224.
MacCallum R.M., et al., "Antibody-Antigen Interactions: Contact Analysis and Binding Site Topography," The Journal of Molecular Biology, 1996, vol. 262, pp. 732-745.
Mailhos C., et al., "Delta4, an Endothelial Specific Notch Ligand Expressed at Sites of Physiological and Tumor Angiogenesis," Differentiation, 2001, vol. 69 (2-3), pp. 135-144.
Marchalonis J.J., et al., "Evolutionary Factors in the Emergence of the Combinatorial Germline Antibody Repertoire," Advances in Experimental Medicine and Biology, 2001, vol. 484, pp. 13-30.
Marks J.D., et al., "By-Passing Immunization: Building High Affinity Human Antibodies by Chain Shuffling," Bio Technology, 1992, vol. 10 (7), pp. 779-783.
Martin A.C., "Protein Sequence and Structure Analysis of Antibody Variable Domains" in: Antibody Engineering, Kontermann R., ed., Springer Verlag, 2001, pp. 432-433.
McCafferty J., et al., "Phage Antibodies: Filamentous Phage Displaying Antibody Variable Domains," Nature, 1990, vol. 348, pp. 552-554.

(56) References Cited

OTHER PUBLICATIONS

Mendez M.J., et al., "Functional Transplant of Megabase Human Immunoglobulin Loci Recapitulates Human Antibody Response in Mice," Nature Genetics, 1997, vol. 15 (2), pp. 146-156.
Milstein C., et al, "Hybrid Hybridomas and their use in Immunohistochemistry," Nature, 1983, vol. 305 (5934), pp. 537-540.
Mizushima S., et al., "pEF-BOS, a Powerful Mammalian Expression Vector," Nucelic Acids Research, 1990, vol. 18 (17), pp. 5322.
Morgan R.A., et al., "Human Gene Therapy," Annual Review of Biochemistry, 1993, vol. 62, 191-217.
Morrison S.L., et al., "Chimeric Human Antibody Molecules: Mouse Antigen-Binding Domains with Human Constant Region Domains," Proceedings of National Academy of Sciences, 1984, vol. 81 (21), pp. 6851-6855.
Morrison S.L., "Transfectomas Provide Novel Chimeric Antibodies," Science, 1985, vol. 229 (4719), pp. 1202-1207.
Mulligan R.C., "The Basic Science of Gene Therapy," Science (New York, N.Y.), 1993, vol. 260 (5110), pp. 926-932.
Mullinax R.L., et al., "Expression of a Heterodimeric Fab Antibody Protein in One Cloning Step," Bio Techniques,, 1992, vol. 12 (6), pp. 864-869.
Nakatsu M.N., et al., "Angiogenic Sprouting and Capillary Lumen Formation Modeled by Human Umbilical Vein Endothelial Cells (HUVEC) in Fibrin Gels: The Role of Fibroblasts and Angiopoietin-1," Microvascular Research, 2003, vol. 66 (2), pp. 102-112.
Neuberger M.S., et al., "Recombinant Antibodies Possessing Novel Effector Functions," Nature, 1984, vol. 312 (5995), pp. 604-608.
Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.
Noguera-Troise I., et al., "Blockade of Dll4 Inhibits Tumour Growth by Promoting Non-Productive Angiogenesis," Nature, 2006, vol. 444 (7122), pp. 1032-1037.
Oi V.T., et al., "Chimeric Antibodies," BioTechniques, 1986, vol. 4 (3), pp. 214-221.
Padlan E.A., "A Possible Procedure for Reducing the Immunogenicity of Antibody Variable Domains While Preserving Their Ligand-Binding Properties," Molecular Immunology, 1991, vol. 28 (4-5), pp. 489-498.
Padlan E.A., et al., "Identification of Specificity-Determining Residues in Antibodies," The FASEB Journal: Official Publication of the Federation of American Societies for Experimental Biology, 1995, vol. 9 (1), pp. 133-139.
Patel N.S., et al., "Up-Regulation of Delta-Like 4 Ligand in Human Tumor Vasculature and the Role of Basal Expression in Endothelial Cell Function," Cancer Research, 2005, vol. 65 (19), pp. 8690-8697.
Patel N.S., et al., "Up-Regulation of Endothelial Delta-Like 4 Expression Correlates with Vessel Maturation in Bladder Cancer," Clinical Cancer Research, 2006, vol. 12 (16), pp. 4836-4844.
Persic L., et al., "An Integrated Vector System for the Eukaryotic Expression of Antibodies or their Fragments After Selection from Phage Display Libraries," Gene, 1997, vol. 187 (1), pp. 9-18.
Poljak R.J., "Production and Structure of Diabodies," Structure, 1994, vol. 2 (12), pp. 1121-1123.
Presta L.G., et al., "Humanization of an Antibody Directed Against IgE," Journal of Immunology, 1993, vol. 151 (5), pp. 2623-2632.
Remington, "The Science and Practice of Pharmacy," Table of Contents, 1995.
Remmele R.L., et al., "Differential Scanning Calorimetry a Practical Tool for Elucidating Stability of liquid Biopharmaceuticals," Biopharm, 2000, vol. 13, pp. 36-46.
Remmele R.L., et al., "Interleukin-1 Receptor (IL-1R) Liquid Formulation Development using Differential Scanning Calorimetry," Pharmaceutical Research, 1998, vol. 15 (2), pp. 200-208.
Ridgway J., et al., "Inhibition of Dll4 Signalling Inhibits Tumour Growth by Deregulating Angiogenesis," Nature, 2006, vol. 444 (7122), pp. 1083-1087.
Riechmann L., et al., "Reshaping Human Antibodies for Therapy," Nature, 1988, vol. 332 (6162), pp. 323-327.
Roberts R.W., et al., "RNA-Peptide Fusions for the in Vitro Selection of Peptides and Proteins," PNAS USA, 1997, vol. 94(23), pp. 12297-12302.
Robinson, "Gene Therapy—Proceeding from Laboratory to Clinic," TIBTECH, 1993, 11 (5), 155-215.
Robinson J.R., Sustained and Controlled Release Drug Delivery Systems, Marcel Dekker, Inc., 1978, Table of Contents.
Roguska M.A., et al., "Humanization of Murine Monoclonal Antibodies through Variable Domain Resurfacing," Proceedings of the National Academy of Sciences, 1994, vol. 91 (3), pp. 969-973.
Sambrook J., et al., "Molecular Cloning—A Laboratory Manual," 1989, Cold Spring Harbor Laboratory Press, Table of Contents.
Saudek C.D., et al., "A Preliminary Trial of the Programmable Implantable Medication System for Insulin Delivery," The New England Journal of Medicine, 1989, vol. 321 (9), pp. 574-579.
Sawai H., et al., "Direct Production of the Fab Fragment Derived from the Sperm Immobilizing Antibody using Polymerase Chain Reaction and cDNA Expression Vectors," American Journal of Reproductive Immunology, 1995, vol. 34 (1), pp. 26-34.
Scehnet J.S., et al., "Inhibition of Dll4-Mediated Signaling Induces Proliferation of Immature Vessels and Results in Poor Tissue Perfusion," Blood, 2007, vol. 109 (11), pp. 4753-4760.
Schier R., et al., "Identification of Functional and Structural Amino-Acid Residues by Parsimonious Mutagenesis," Gene, 1996, vol. 169 (2), 147-155.
Sefton M.V., et al., "Implantable Pumps," Critical Reviews in Biomedical Engineering, 1987, vol. 14 (3), pp. 201-240.
Seligmann M., et al., "Immunochemical Study of a Human Myeloma IgG1 Half Molecule," Annales D Immunologie, 1978, vol. 129 C (6), pp. 855-870.
Shapiro G.S., et al., "DNA Target Motifs of Somatic Mutagenesis in Antibody Genes," Critical Reviews in Immunology, 2002, vol. 22 (3), pp. 183-200.
Shu L., et al., "Secretion of a Single-Gene-Encoded Immunoglobulin from Myeloma Cells," Proceedings of the National Academy of Sciences USA, 1993, vol. 90 (17), pp. 7995-7999.
Shutter J.R., et al., "Dll4, a Novel Notch Ligand Expressed in Arterial Endothelium," Genes & Development, 2000, vol. 14 (11), pp. 1313-1318.
Sims M.J., et al., "A Humanized CD18 Antibody Can Block Function Without Cell Destruction," Journal of Immunology, 1993, vol. 151 (4), pp. 2296-2308.
Skerra A., et al., "Assembly of a Functional Immunoglobulin $F_v$ Fragment in *Escherichia coli*," Science, 1988, vol. 240, pp. 1038-1041.
Song Y.K., et al., "Antibody Mediated Lung Targeting of Long-Circulating Emulsions," PDA Journal of Pharmaceutical Science and Technology, 1995, vol. 50 (6), pp. 372-397.
Staerz U.D., et al., "Hybrid Antibodies Can Target Sites for Attack by T Cells," Nature, 1985, vol. 314 (6012), pp. 628-631.
Studnicka G.M., et al., "Human-Engineered Monoclonal Antibodies Retain full Specific Binding Activity by Preserving Non-CDR Complementarity-Modulating Residues," Protein Engineering, 1994, vol. 7 (6), pp. 805-814.
Suchting S., et al., "The Notch Ligand Delta-Like 4 Negatively Regulates Endothelial Tip Cell Formation and Vessel Branching," Proceedings of the National Academy of Sciences, 2007, vol. 104 (9), pp. 3225-3230.
Takeda S., et al., "Construction of Chimaeric Processed Immunoglobulin Genes Containing Mouse Variable and Human Constant Region Sequences," Nature, 1985, vol. 314 (6010), pp. 452-454.
Taylor L.D., et al., "A Transgenic Mouse that Expresses a Diversity of Human Sequence Heavy and Light Chain Immnoglobulins," Nucleic Acids Research, 1992, vol. 20 (23), 6287-6295.
Thies M.J., et al., "Folding and Association of the Antibody Domain $C_H3$: Prolyl Isomerization Preceeds Dimerization," Journal of Molecular Biology, 1999, vol. 293 (1), pp. 67-79.
Tolstoshev P., "Gene Therapy, Concepts, Current Trials and Future Directions," Annual Review of Pharmacology and Toxicology, 1993, vol. 32, pp. 573-596.

(56) References Cited

OTHER PUBLICATIONS

Urlaub G., et al., "Isolation of Chinese Hamster Cell Mutants Deficient in Dihydrofolate Reductase Activity," Proceedings of the National Academy of Sciences of the USA, 1980, vol. 77 (7), pp. 4216-4220.
Verhoeyen M., et al., "Reshaping Human Antibodies: Grafting an Antilysozyme Activity", Science, 1988, vol. 239, pp. 1534-1536.
Ward E.S., et al., "Binding Activities of a Repertoire of Single Immunoglobulin Variable Domains Secreted from *Escherichia coli*," Nature, 1989, vol. 341 (6242), pp. 544-546.
West A.P., et al., "Crystal Structure and Immunoglobulin G Binding Properties of the Human Major Histocompatibility Complex-Related Fc Receptor," Biochemistry, 2000, vol. 39 (32), pp. 9698-9708.
Winnaker E., "From Genes to Clones", TOC, 1987.
Wu C., et al., "Simultaneous Targeting of Multiple Disease Mediators by a Dual-Variable-Domain Immunoglobulin," Nature Biotechnology, 2007, vol. 25 (11), pp. 1290-1297.
Wu G.Y., et al., "Delivery Systems for Gene Therapy," Biotherapy, 1991, vol. 3 (1), pp. 87-95.
Wu G.Y., et al., "Receptor-Mediated in Vitro Gene Transformation by a Soluble DNA Carrier System," The Journal of Biological Chemistry, 1987, vol. 262 (10), pp. 4429-4432.
Yan M., et al., "Delta-Like 4/Notch Signaling and its Therapeutic Implications," Clinical Cancer Research, 2007, vol. 13 (24), pp. 7243-7246.
Yelton D.E., et al., "Affinity Maturation of the BR96 Anti-Carcinoma Antibody by Codon-Based Mutagenesis," The Journal of Immunology, 1995, vol. 155 (4), pp. 1994-2004.
Zapata G., et al., "Engineering Linear F(ab')$_2$ Fragments for Efficient Production in *Escherichia coli* and Enhanced Antiproliferative Activity," Protein Engineering, 1995, vol. 8 (10), pp. 1057-1062.
Billiard et al., "Dll4-Notch signaling in Flt3-independent dendritic cell development and autoimmunity in mice," *J. Exp. Med.*, 209(5): 1011-1028 (2012).
Burke et al., "Zotarolimus (ABT-578) eluting stents," *Adv. Drug Del. Rev.*, 58: 437-446 (2006).
European Application No. 10752666.7: Communication Pursuant to Article 94(3) EPC, dated Mar. 15, 2013, 5 pages.
Fukuda et al "Notch ligand Delta-like 4 blockade attenuates atherosclerosis and metabolic disorders," *Proc. Natl. Acad. Sci. USA*, 109(27): E1868-1877 (2012).
Furukawa et al., "A Role for the Third Complementarity-determining Region in the Affinity Maturation of an Antibody," *J. Biol. Chem.*, 276:27622-27628 (2001).
Gennaro, A.R. (ed.) *Remington: The Science and Practice of Pharmacy.* 19th Edition, Mack Publishing, 1995; Table of Contents.
Hammerling et al., eds., "Appendix: Production of Antibody-Producing Hybridomas in the Rodent Systems," In *Monoclonal Antibodies and T-Cell Hybridomas. Research Monographs in Immunology*, vol. 3. (J.L. Turk, General Editor) (Elsevier, New York, 1981), pp. 563-681.
Harding et al., "The immunogenicity of humanized and fully human antibodies," *MAbs*, 2(3): 256-265 (2010).
Harlow et al., *Antibodies: A Laboratory Manual.* 2nd Edition, Cold Spring Harbor Laboratory Press, 1988: Table of Contents.
Hildebrand et al., "Surface coatings for biological activation and functionalization of medical devices," *Surface & Coatings Technology*, 200: 6318-6324 (2006).
Holm et al., "Functional mapping and single chain construction of the anti-cytokeratin 8 monoclonal antibody TS1," *Mol. Immunol.*, 44:1075-1084 (2007).
Inoue et al., "Vascular Endothelial Growth Factor (VEGF) Expression in Human Coronary Atherosclerotic Lesions: Possible Pathophysiological Significance of VEGF in Progression of Atherosclerosis" *Circulation*, 98: 2108-2116 (1998).
Partial International Search Report for Application No. PCT/US2010/047006, mailed Nov. 22, 2010, 5 pages.
International Search Report for Application No. PCT/US2010/047006, mailed on Mar. 10, 2011. 23 pages.
Khamaisi et al., "The emerging role of VEGF in diabetic kidney disease," *Neprol. Dial. Transplant.*, 18(8):1427-1430 (2003).
Lund et al., "Human Fc gamma RI and Fc gamma RII interact with distinct but overlapping sites on human IgG," *J. Immunol.*, 147: 2657-2662 (1991).
Marques et al., "Mediation of the Cytokine Network in the Implantation of Orthopedic Devices," Chapter 21, In *Biodegradable Systems in Tissue Engineering and Regenerative Medicine*, (Reis et al., eds.) (CRC Press LLC, Boca Raton, 2005) pp. 377-397.
Martin, A.C.R., "Protein Sequence and Structure Analysis of Antibody Variable Domains," Chapter 31, In *Antibody Engineering.* (Kontermann and Dübel, eds. ), (Springer-Verlag, Berlin, 2001), pp. 432-433.
Miller et al., "Design, Construction, and In Vitro Analyses of Multivalent Antibodies," *J. Immunol.*, 170: 4854-4861 (2003).
Smolen et al. (Eds.), *Controlled Drug Bioavailability: Drug Product Design and Performance.* vol. 1, John Wiley & Sons, 1984; Table of Contents.
Von Mehren et al., "Monoclonal Antibody Therapy for Cancer," *Ann. Rev. Med.*, 54: 343-369 (2003).
Wu and Grainger, "Drug/device combinations for local drug therapies and infection prophylaxis." *Biomaterials*, 27: 2450-2467 (2006).
U.S. Appl. No. 14/301,305, filed Jun. 10, 2014 by Ghayur et al.
U.S. Appl. No. 14/327,306, filed Jul. 9, 2014 by Ghayur et al.
U.S. Appl. No. 14/332,087, filed Jul. 15, 2014 by Ghayur et al.

\* cited by examiner

SEQUENCE LISTING

<160> NUMBER OF SEQ ID NOS: 206

<210> SEQ ID NO 1
<211> LENGTH: 685
<212> TYPE: PRT
<213> ORGANISM: Homo sapiens

<400> SEQUENCE: 1

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

```
Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
```

```
                  545                 550                 555                 560
Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
                580                 585                 590

Glu Leu Glu Val Asp Cys Gly Leu Asp Lys Ser Asn Cys Gly Lys Gln
                595                 600                 605

Gln Asn His Thr Leu Asp Tyr Asn Leu Ala Pro Gly Pro Leu Gly Arg
            610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
                660                 665                 670

Ser Glu Glu Arg Asn Glu Cys Val Ile Ala Thr Glu Val
            675                 680                 685

<210> SEQ ID NO 2
<211> LENGTH: 2058
<212> TYPE: DNA
<213> ORGANISM: Homo sapiens

<400> SEQUENCE: 2
atggcggcag cgtcccggag cgcctctggc tgggcgctac tgctgctggt ggcactttgg     60
cagcagcgcg cggccggctc cggcgtcttc cagctgcagc tgcaggagtt catcaacgag    120
cgcggcgtac tggccagtgg gcggccttgc gagcccggct gccggacttt cttccgcgtc    180
tgccttaagc acttccaggc ggtcgtctcg cccggaccct gcaccttcgg gaccgtctcc    240
acgccggtat tgggcaccaa ctccttcgct gtccgggacg acagtagcgg cggggggcgc    300
aaccctctcc aactgcccct caatttcacc tggccgggta ccttctcgct catcatcgaa    360
gcttggcacg cgccaggaga cgacctgcgg ccagaggcct gccaccagtg cactcatc     420 agcaagatcg ccatccaggg ctccctagct gtgggtcaga actggttatt ggatgagcaa    480
accagcaccc tcacaaggct cgcgctactct taccgggtca tctgcagtga caactactat    540
ggagacaact gctcccgcct gtgcaagaag cgcaatgacc acttcggcca ctatgtgtgc    600
cagccagatg gcaacttgtc ctgcctgccc ggttggactg ggaatattg ccaacagcct    660 atctgtcttt cgggctgtca tgaacagaat ggctactgca gcaagccagc agagtgcctc    720
tgccgcccag gctggcaggg ccggctgtgt aacgaatgca tcccccacaa tggctgtcgc    780
cacggcacct gcagcactcc ctggcaatgt acttgtgatg agggctgggg aggcctgttt    840
tgtgaccaag atctcaacta ctgcacccac cactccccat gcaagaatgg gcaacgtgc     900 tccaacagtg ggcagcgaag ctacacctgc acctgtcgcc caggctacac tggtgtggac    960
tgtgagctgg agctcagcga gtgtgacagc aaccccgtgtc gcaatggagg cagctgtaag   1020
gaccaggagg atggctacca ctgcctgtgt cctccgggct actatggcct gcattgtgaa   1080
cacagcacct tgagctgcgc cgactccccc tgcttcaatg gggctcctg ccgggagcgc    1140 aaccaggggg ccaactatgc ttgtgaatgt cccccaact tcaccggctc caactgcgag    1200
aagaaagtgg acaggtgcac cagcaacccc gtgccaacg ggacagtg cctgaaccga   1260 ggtccaagcc gcatgtgccg ctgccgtcct ggattcacgg gcacctactg tgaactccac    1320
gtcagcgact gtgcccgtaa cccttgcgcc cacggtggca cttgccatga cctggagaat   1380
```

-continued

```
gggctcatgt gcacctgccc tgccggcttc tctggccgac gctgtgaggt gcggacatcc    1440
atcgatgcct gtgcctcgag tccctgcttc aacagggcca cctgctacac cgacctctcc    1500
acagacacct ttgtgtgcaa ctgcccttat ggctttgtgg gcagccgctg cgagttcccc    1560
gtgggcttgc cgcccagctt ccctggggtg gccgtctcgc tgggtgtggg gctggcagtg    1620
ctgctggtac tgctgggcat ggtggcagtg gctgtgcggc agctgcggct cgacggccg     1680 gacgacggca gcaggaagc catgaacaac ttgtcggact tccagaagga caacctgatt     1740
cctgccgccc agcttaaaaa cacaaaccag aagaaggagc tggaagtgga ctgtggcctg    1800
gacaagtcca actgtggcaa acagcaaaac cacacattgg actataatct ggccccaggg    1860
cccctggggc ggggggaccat gccaggaaag tttccccaca gtgacaagag cttaggagag    1920
aaggcgccac tgcggttaca cagtgaaaag ccagagtgtc ggatatcagc gatatgctcc    1980
cccagggact ccatgtacca gtctgtgtgt ttgatatcag aggagaggaa tgaatgtgtc    2040
attgccacgg aggtataa                                                  2058
```

<210> SEQ ID NO 3
<211> LENGTH: 330
<212> TYPE: PRT
<213> ORGANISM: Homo sapiens

<400> SEQUENCE: 3

```
Ala Ser Thr Lys Gly Pro Ser Val Phe Phe Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 106
<212> TYPE: PRT
<213> ORGANISM: Homo sapiens

<400> SEQUENCE: 5

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 6
<211> LENGTH: 105
<212> TYPE: PRT
<213> ORGANISM: Homo sapiens

<400> SEQUENCE: 6

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
```

-continued

```
<400> SEQUENCE: 7

Phe Gly Xaa Gly
1

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid

<400> SEQUENCE: 8

Cys Xaa Xaa Xaa Xaa Xaa Xaa Xaa Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Glu Trp Ile Gly
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 10

Trp Gly Xaa Gly
1

<210> SEQ ID NO 11
<211> LENGTH: 30
<212> TYPE: PRT
<213> ORGANISM: Homo sapiens

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 12
<211> LENGTH: 14
<212> TYPE: PRT
<213> ORGANISM: Homo sapiens

<400> SEQUENCE: 12

Trp Val Arg Gln Ala Pro Gly Lys Gly Leu Glu Trp Val Ala
```

```
<210> SEQ ID NO 13
<211> LENGTH: 32
<212> TYPE: PRT
<213> ORGANISM: Homo sapiens

<400> SEQUENCE: 13

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 14
<211> LENGTH: 11
<212> TYPE: PRT
<213> ORGANISM: Homo sapiens

<400> SEQUENCE: 14

Trp Gly Gln Gly Thr Leu Val Thr Val Ser Ser
1               5                   10

<210> SEQ ID NO 15
<211> LENGTH: 30
<212> TYPE: PRT
<213> ORGANISM: Homo sapiens

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 16
<211> LENGTH: 14
<212> TYPE: PRT
<213> ORGANISM: Homo sapiens

<400> SEQUENCE: 16

Trp Val Arg Gln Ala Pro Gly Lys Gly Leu Glu Trp Val Ser
1               5                   10

<210> SEQ ID NO 17
<211> LENGTH: 32
<212> TYPE: PRT
<213> ORGANISM: Homo sapiens

<400> SEQUENCE: 17

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 18
<211> LENGTH: 11
<212> TYPE: PRT
<213> ORGANISM: Homo sapiens

<400> SEQUENCE: 18

Trp Gly Gln Gly Thr Leu Val Thr Val Ser Ser
1               5                   10

<210> SEQ ID NO 19
```

```
<211> LENGTH: 30
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 20
<211> LENGTH: 14
<212> TYPE: PRT
<213> ORGANISM: Homo sapiens

<400> SEQUENCE: 20

Trp Val Arg Gln Ala Pro Gly Gln Gly Leu Glu Trp Met Gly
1               5                   10

<210> SEQ ID NO 21
<211> LENGTH: 32
<212> TYPE: PRT
<213> ORGANISM: Homo sapiens

<400> SEQUENCE: 21

Arg Val Thr Met Thr Arg Asp Thr Ser Thr Ser Thr Val Tyr Met Glu
1               5                   10                  15
Leu Ser Ser Leu Arg Ser Glu Asp Thr Ala Val Tyr Tyr Cys Ala Arg
            20                  25                  30

<210> SEQ ID NO 22
<211> LENGTH: 11
<212> TYPE: PRT
<213> ORGANISM: Homo sapiens

<400> SEQUENCE: 22

Trp Gly Gln Gly Thr Leu Val Thr Val Ser Ser
1               5                   10

<210> SEQ ID NO 23
<211> LENGTH: 30
<212> TYPE: PRT
<213> ORGANISM: Homo sapiens

<400> SEQUENCE: 23

Gln Val Gln Leu Val Glu Ser Gly Gly Val Val Gln Pro Gly Arg
1               5                   10                  15
Ser Leu Arg Leu Ser Cys Ala Ala Ser Gly Phe Thr Phe Ser
            20                  25                  30

<210> SEQ ID NO 24
<211> LENGTH: 14
<212> TYPE: PRT
<213> ORGANISM: Homo sapiens

<400> SEQUENCE: 24

Trp Val Arg Gln Ala Pro Gly Lys Gly Leu Glu Trp Val Ala
1               5                   10

<210> SEQ ID NO 25
<211> LENGTH: 32
<212> TYPE: PRT
<213> ORGANISM: Homo sapiens
```

-continued

```
<400> SEQUENCE: 25

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
                20                  25                  30

<210> SEQ ID NO 26
<211> LENGTH: 11
<212> TYPE: PRT
<213> ORGANISM: Homo sapiens

<400> SEQUENCE: 26

Trp Gly Gln Gly Thr Met Val Thr Val Ser Ser
1               5                   10

<210> SEQ ID NO 27
<211> LENGTH: 30
<212> TYPE: PRT
<213> ORGANISM: Homo sapiens

<400> SEQUENCE: 27

Glu Val Gln Leu Val Glu Ser Gly Gly Leu Val Gln Pro Gly Gly
1               5                   10                  15
Ser Leu Arg Leu Ser Cys Ala Ala Ser Gly Phe Thr Phe Ser
                20                  25                  30

<210> SEQ ID NO 28
<211> LENGTH: 14
<212> TYPE: PRT
<213> ORGANISM: Homo sapiens

<400> SEQUENCE: 28

Trp Val Arg Gln Ala Pro Gly Lys Gly Leu Glu Trp Val Ser
1               5                   10

<210> SEQ ID NO 29
<211> LENGTH: 32
<212> TYPE: PRT
<213> ORGANISM: Homo sapiens

<400> SEQUENCE: 29

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
                20                  25                  30

<210> SEQ ID NO 30
<211> LENGTH: 11
<212> TYPE: PRT
<213> ORGANISM: Homo sapiens

<400> SEQUENCE: 30

Trp Gly Gln Gly Thr Met Val Thr Val Ser Ser
1               5                   10

<210> SEQ ID NO 31
<211> LENGTH: 30
<212> TYPE: PRT
<213> ORGANISM: Homo sapiens

<400> SEQUENCE: 31

Glu Val Thr Leu Arg Glu Ser Gly Pro Ala Leu Val Lys Pro Thr Gln
1               5                   10                  15
```

Thr Leu Thr Leu Thr Cys Thr Phe Ser Gly Phe Ser Leu Ser
            20                  25                  30

<210> SEQ ID NO 32
<211> LENGTH: 14
<212> TYPE: PRT
<213> ORGANISM: Homo sapiens

<400> SEQUENCE: 32

Trp Ile Arg Gln Pro Pro Gly Lys Ala Leu Glu Trp Leu Ala
1               5                   10

<210> SEQ ID NO 33
<211> LENGTH: 32
<212> TYPE: PRT
<213> ORGANISM: Homo sapiens

<400> SEQUENCE: 33

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 34
<211> LENGTH: 11
<212> TYPE: PRT
<213> ORGANISM: Homo sapiens

<400> SEQUENCE: 34

Trp Gly Gln Gly Thr Thr Val Thr Val Ser Ser
1               5                   10

<210> SEQ ID NO 35
<211> LENGTH: 30
<212> TYPE: PRT
<213> ORGANISM: Homo sapiens

<400> SEQUENCE: 35

Glu Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
            20                  25                  30

<210> SEQ ID NO 36
<211> LENGTH: 14
<212> TYPE: PRT
<213> ORGANISM: Homo sapiens

<400> SEQUENCE: 36

Trp Ile Arg Gln Pro Pro Gly Lys Ala Leu Glu Trp Leu Ala
1               5                   10

<210> SEQ ID NO 37
<211> LENGTH: 32
<212> TYPE: PRT
<213> ORGANISM: Homo sapiens

<400> SEQUENCE: 37

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 38
<211> LENGTH: 11
<212> TYPE: PRT
<213> ORGANISM: Homo sapiens

<400> SEQUENCE: 38

Trp Gly Gln Gly Thr Thr Val Thr Val Ser Ser
1               5                   10

<210> SEQ ID NO 39
<211> LENGTH: 30
<212> TYPE: PRT
<213> ORGANISM: Homo sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 40
<211> LENGTH: 14
<212> TYPE: PRT
<213> ORGANISM: Homo sapiens

<400> SEQUENCE: 40

Trp Val Arg Gln Ala Pro Gly Lys Gly Leu Glu Trp Val Gly
1               5                   10

<210> SEQ ID NO 41
<211> LENGTH: 32
<212> TYPE: PRT
<213> ORGANISM: Homo sapiens

<400> SEQUENCE: 41

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 42
<211> LENGTH: 11
<212> TYPE: PRT
<213> ORGANISM: Homo sapiens

<400> SEQUENCE: 42

Trp Gly Gln Gly Thr Thr Val Thr Val Ser Ser
1               5                   10

<210> SEQ ID NO 43
<211> LENGTH: 30
<212> TYPE: PRT
<213> ORGANISM: Homo sapiens

<400> SEQUENCE: 43

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 44
<211> LENGTH: 14
<212> TYPE: PRT

```
<213> ORGANISM: Homo sapiens

<400> SEQUENCE: 44

Trp Val Arg Gln Ala Pro Gly Lys Gly Leu Glu Trp Val Ser
1               5                   10

<210> SEQ ID NO 45
<211> LENGTH: 32
<212> TYPE: PRT
<213> ORGANISM: Homo sapiens

<400> SEQUENCE: 45

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 46
<211> LENGTH: 11
<212> TYPE: PRT
<213> ORGANISM: Homo sapiens

<400> SEQUENCE: 46

Trp Gly Gln Gly Thr Thr Val Thr Val Ser Ser
1               5                   10

<210> SEQ ID NO 47
<211> LENGTH: 30
<212> TYPE: PRT
<213> ORGANISM: Homo sapiens

<400> SEQUENCE: 47

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
                20                  25                  30

<210> SEQ ID NO 48
<211> LENGTH: 14
<212> TYPE: PRT
<213> ORGANISM: Homo sapiens

<400> SEQUENCE: 48

Trp Val Arg Gln Ala Pro Gly Gln Gly Leu Glu Trp Met Gly
1               5                   10

<210> SEQ ID NO 49
<211> LENGTH: 32
<212> TYPE: PRT
<213> ORGANISM: Homo sapiens

<400> SEQUENCE: 49

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 50
<211> LENGTH: 11
<212> TYPE: PRT
<213> ORGANISM: Homo sapiens

<400> SEQUENCE: 50
```

```
Trp Gly Gln Gly Thr Thr Val Thr Val Ser Ser
1               5                   10

<210> SEQ ID NO 51
<211> LENGTH: 30
<212> TYPE: PRT
<213> ORGANISM: Homo sapiens

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 52
<211> LENGTH: 14
<212> TYPE: PRT
<213> ORGANISM: Homo sapiens

<400> SEQUENCE: 52

Trp Val Arg Gln Ala Pro Gly Gln Gly Leu Glu Trp Met Gly
1               5                   10

<210> SEQ ID NO 53
<211> LENGTH: 32
<212> TYPE: PRT
<213> ORGANISM: Homo sapiens

<400> SEQUENCE: 53

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 54
<211> LENGTH: 11
<212> TYPE: PRT
<213> ORGANISM: Homo sapiens

<400> SEQUENCE: 54

Trp Gly Gln Gly Thr Thr Val Thr Val Ser Ser
1               5                   10

<210> SEQ ID NO 55
<211> LENGTH: 30
<212> TYPE: PRT
<213> ORGANISM: Homo sapiens

<400> SEQUENCE: 55

Glu Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 56
<211> LENGTH: 14
<212> TYPE: PRT
<213> ORGANISM: Homo sapiens

<400> SEQUENCE: 56

Trp Ile Arg Gln Pro Pro Gly Lys Gly Leu Glu Trp Ile Gly
1               5                   10
```

<210> SEQ ID NO 57
<211> LENGTH: 32
<212> TYPE: PRT
<213> ORGANISM: Homo sapiens

<400> SEQUENCE: 57

Arg Val Thr Ile Ser Val Asp Thr Ser Lys Asn Gln Phe Ser Leu Lys
1               5                   10                  15
Leu Ser Ser Val Thr Ala Ala Asp Thr Ala Val Tyr Tyr Cys Ala Arg
            20                  25                  30

<210> SEQ ID NO 58
<211> LENGTH: 11
<212> TYPE: PRT
<213> ORGANISM: Homo sapiens

<400> SEQUENCE: 58

Trp Gly Gln Gly Thr Leu Val Thr Val Ser Ser
1               5                   10

<210> SEQ ID NO 59
<211> LENGTH: 30
<212> TYPE: PRT
<213> ORGANISM: Homo sapiens

<400> SEQUENCE: 59

Glu Val Gln Leu Val Glu Ser Gly Gly Gly Leu Val Gln Pro Gly Gly
1               5                   10                  15
Ser Leu Arg Leu Ser Cys Ala Val Ser Gly Gly Ser Ile Ser
            20                  25                  30

<210> SEQ ID NO 60
<211> LENGTH: 14
<212> TYPE: PRT
<213> ORGANISM: Homo sapiens

<400> SEQUENCE: 60

Trp Ile Arg Gln Ala Pro Gly Lys Gly Leu Glu Trp Ile Gly
1               5                   10

<210> SEQ ID NO 61
<211> LENGTH: 32
<212> TYPE: PRT
<213> ORGANISM: Homo sapiens

<400> SEQUENCE: 61

Arg Val Thr Ile Ser Val Asp Thr Ser Lys Asn Ser Phe Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 62
<211> LENGTH: 11
<212> TYPE: PRT
<213> ORGANISM: Homo sapiens

<400> SEQUENCE: 62

Trp Gly Gln Gly Thr Leu Val Thr Val Ser Ser
1               5                   10

<210> SEQ ID NO 63
<211> LENGTH: 30
<212> TYPE: PRT
<213> ORGANISM: Homo sapiens -continued

<400> SEQUENCE: 63

Glu Val Gln Leu Gln Glu Ser Gly Pro Gly Leu Val Lys Pro Gly Glu
1               5                   10                  15

Thr Leu Ser Leu Thr Cys Thr Val Ser Gly Gly Ser Ile Ser
            20                  25                  30

<210> SEQ ID NO 64
<211> LENGTH: 14
<212> TYPE: PRT
<213> ORGANISM: Homo sapiens

<400> SEQUENCE: 64

Trp Ile Arg Gln Ala Pro Gly Lys Gly Leu Glu Trp Ile Gly
1               5                   10

<210> SEQ ID NO 65
<211> LENGTH: 32
<212> TYPE: PRT
<213> ORGANISM: Homo sapiens

<400> SEQUENCE: 65

Arg Val Thr Ile Ser Val Asp Thr Ser Lys Asn Gln Phe Tyr Leu Lys
1               5                   10                  15

Leu Ser Ser Val Arg Ala Glu Asp Thr Ala Val Tyr Tyr Cys Ala Arg
            20                  25                  30

<210> SEQ ID NO 66
<211> LENGTH: 11
<212> TYPE: PRT
<213> ORGANISM: Homo sapiens

<400> SEQUENCE: 66

Trp Gly Gln Gly Thr Leu Val Thr Val Ser Ser
1               5                   10

<210> SEQ ID NO 67
<211> LENGTH: 30
<212> TYPE: PRT
<213> ORGANISM: Homo sapiens

<400> SEQUENCE: 67

Glu Val Gln Leu Val Gln Ser Gly Thr Glu Val Lys Lys Pro Gly Glu
1               5                   10                  15

Ser Leu Lys Ile Ser Cys Lys Val Ser Gly Gly Ser Ile Ser
            20                  25                  30

<210> SEQ ID NO 68
<211> LENGTH: 14
<212> TYPE: PRT
<213> ORGANISM: Homo sapiens

<400> SEQUENCE: 68

Trp Ile Arg Gln Met Pro Gly Lys Gly Leu Glu Trp Ile Gly
1               5                   10

<210> SEQ ID NO 69
<211> LENGTH: 32
<212> TYPE: PRT
<213> ORGANISM: Homo sapiens

<400> SEQUENCE: 69

Gln Val Thr Ile Ser Val Asp Thr Ser Phe Asn Thr Phe Phe Leu Gln

```
                1               5                   10                  15
Trp Ser Ser Leu Lys Ala Ser Asp Thr Ala Met Tyr Tyr Cys Ala Arg
            20                  25                  30
```

<210> SEQ ID NO 70
<211> LENGTH: 11
<212> TYPE: PRT
<213> ORGANISM: Homo sapiens

<400> SEQUENCE: 70

```
Trp Gly Gln Gly Thr Met Val Thr Val Ser Ser
1               5                   10
```

<210> SEQ ID NO 71
<211> LENGTH: 30
<212> TYPE: PRT
<213> ORGANISM: Homo sapiens

<400> SEQUENCE: 71

```
Glu Val Thr Leu Arg Glu Ser Gly Pro Ala Leu Val Lys Pro Thr Gln
1               5                   10                  15
Thr Leu Thr Leu Thr Cys Thr Val Ser Gly Gly Ser Ile Ser
            20                  25                  30
```

<210> SEQ ID NO 72
<211> LENGTH: 14
<212> TYPE: PRT
<213> ORGANISM: Homo sapiens

<400> SEQUENCE: 72

```
Trp Ile Arg Gln Pro Pro Gly Lys Gly Leu Glu Trp Ile Gly
1               5                   10
```

<210> SEQ ID NO 73
<211> LENGTH: 32
<212> TYPE: PRT
<213> ORGANISM: Homo sapiens

<400> SEQUENCE: 73

```
Arg Val Thr Ile Ser Val Asp Thr Ser Lys Asn Gln Phe Val Leu Thr
1               5                   10                  15
Met Thr Asn Met Asp Pro Val Asp Thr Ala Thr Tyr Tyr Cys Ala Arg
            20                  25                  30
```

<210> SEQ ID NO 74
<211> LENGTH: 11
<212> TYPE: PRT
<213> ORGANISM: Homo sapiens

<400> SEQUENCE: 74

```
Trp Gly Gln Gly Thr Thr Val Thr Val Ser Ser
1               5                   10
```

<210> SEQ ID NO 75
<211> LENGTH: 30
<212> TYPE: PRT
<213> ORGANISM: Homo sapiens

<400> SEQUENCE: 75

```
Glu Val Gln Leu Leu Glu Ser Gly Gly Gly Leu Val Lys Ser Gly Gly
1               5                   10                  15
Ser Leu Arg Leu Ser Cys Ala Ala Ser Gly Phe Thr Phe Arg
            20                  25                  30
```

<210> SEQ ID NO 76
<211> LENGTH: 14
<212> TYPE: PRT
<213> ORGANISM: Homo sapiens

<400> SEQUENCE: 76

Trp Val Arg Gln Ala Pro Gly Lys Gly Leu Glu Trp Val Ala
1               5                   10

<210> SEQ ID NO 77
<211> LENGTH: 32
<212> TYPE: PRT
<213> ORGANISM: Homo sapiens

<400> SEQUENCE: 77

Arg Phe Thr Ile Ser Arg Asp Asn Ser Lys Asn Thr Leu Tyr Leu Gln
1               5                   10                  15

Leu Asn Ser Leu Arg Ala Glu Asp Thr Ala Val Tyr Tyr Cys Ala Lys
            20                  25                  30

<210> SEQ ID NO 78
<211> LENGTH: 11
<212> TYPE: PRT
<213> ORGANISM: Homo sapiens

<400> SEQUENCE: 78

Trp Gly Gln Gly Thr Met Val Thr Val Ser Ser
1               5                   10

<210> SEQ ID NO 79
<211> LENGTH: 30
<212> TYPE: PRT
<213> ORGANISM: Homo sapiens

<400> SEQUENCE: 79

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly
            20                  25                  30

<210> SEQ ID NO 80
<211> LENGTH: 14
<212> TYPE: PRT
<213> ORGANISM: Homo sapiens

<400> SEQUENCE: 80

Trp Val Arg Gln Ala Pro Gly Lys Gly Leu Glu Trp Val Ala
1               5                   10

<210> SEQ ID NO 81
<211> LENGTH: 32
<212> TYPE: PRT
<213> ORGANISM: Homo sapiens

<400> SEQUENCE: 81

Arg Phe Thr Ile Ser Arg Asp Asn Ser Lys Asn Thr Leu Tyr Leu Gln
1               5                   10                  15

Leu Asn Ser Leu Arg Ala Glu Asp Thr Ala Val Tyr Tyr Cys Ala Lys
            20                  25                  30

<210> SEQ ID NO 82
<211> LENGTH: 11

```
<212> TYPE: PRT
<213> ORGANISM: Homo sapiens

<400> SEQUENCE: 82

Trp Gly Gln Gly Thr Met Val Thr Val Ser Ser
1               5                   10

<210> SEQ ID NO 83
<211> LENGTH: 23
<212> TYPE: PRT
<213> ORGANISM: Homo sapiens

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 84
<211> LENGTH: 15
<212> TYPE: PRT
<213> ORGANISM: Homo sapiens

<400> SEQUENCE: 84

Trp Tyr Gln Gln Lys Pro Gly Lys Ala Pro Lys Leu Leu Ile Tyr
1               5                   10                  15

<210> SEQ ID NO 85
<211> LENGTH: 32
<212> TYPE: PRT
<213> ORGANISM: Homo sapiens

<400> SEQUENCE: 85

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 86
<211> LENGTH: 10
<212> TYPE: PRT
<213> ORGANISM: Homo sapiens

<400> SEQUENCE: 86

Phe Gly Gln Gly Thr Lys Leu Glu Ile Lys
1               5                   10

<210> SEQ ID NO 87
<211> LENGTH: 23
<212> TYPE: PRT
<213> ORGANISM: Homo sapiens

<400> SEQUENCE: 87

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 88
<211> LENGTH: 15
<212> TYPE: PRT
<213> ORGANISM: Homo sapiens

<400> SEQUENCE: 88
```

-continued

```
Trp Tyr Gln Gln Lys Pro Gly Gln Ala Pro Arg Leu Leu Ile Tyr
1               5                   10                  15

<210> SEQ ID NO 89
<211> LENGTH: 32
<212> TYPE: PRT
<213> ORGANISM: Homo sapiens

<400> SEQUENCE: 89

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 90
<211> LENGTH: 10
<212> TYPE: PRT
<213> ORGANISM: Homo sapiens

<400> SEQUENCE: 90

Phe Gly Gln Gly Thr Lys Leu Glu Ile Lys
1               5                   10

<210> SEQ ID NO 91
<211> LENGTH: 23
<212> TYPE: PRT
<213> ORGANISM: Homo sapiens

<400> SEQUENCE: 91

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 92
<211> LENGTH: 15
<212> TYPE: PRT
<213> ORGANISM: Homo sapiens

<400> SEQUENCE: 92

Trp Tyr Gln Gln Lys Pro Gly Gln Pro Pro Lys Leu Leu Ile Tyr
1               5                   10                  15

<210> SEQ ID NO 93
<211> LENGTH: 32
<212> TYPE: PRT
<213> ORGANISM: Homo sapiens

<400> SEQUENCE: 93

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 94
<211> LENGTH: 11
<212> TYPE: PRT
<213> ORGANISM: Homo sapiens

<400> SEQUENCE: 94

Phe Gly Gly Gly Thr Lys Val Glu Ile Lys Arg
1               5                   10
```

<210> SEQ ID NO 95
<211> LENGTH: 23
<212> TYPE: PRT
<213> ORGANISM: Homo sapiens

<400> SEQUENCE: 95

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 96
<211> LENGTH: 15
<212> TYPE: PRT
<213> ORGANISM: Homo sapiens

<400> SEQUENCE: 96

Trp Tyr Gln Gln Lys Pro Gly Gln Ala Pro Arg Leu Leu Ile Tyr
1               5                   10                  15

<210> SEQ ID NO 97
<211> LENGTH: 32
<212> TYPE: PRT
<213> ORGANISM: Homo sapiens

<400> SEQUENCE: 97

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 98
<211> LENGTH: 11
<212> TYPE: PRT
<213> ORGANISM: Homo sapiens

<400> SEQUENCE: 98

Phe Gly Gly Gly Thr Lys Val Glu Ile Lys Arg
1               5                   10

<210> SEQ ID NO 99
<211> LENGTH: 23
<212> TYPE: PRT
<213> ORGANISM: Homo sapiens

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 100
<211> LENGTH: 15
<212> TYPE: PRT
<213> ORGANISM: Homo sapiens

<400> SEQUENCE: 100

Trp Tyr Gln Gln Lys Pro Glu Lys Ala Pro Lys Ser Leu Ile Tyr
1               5                   10                  15

<210> SEQ ID NO 101
<211> LENGTH: 32
<212> TYPE: PRT

<213> ORGANISM: Homo sapiens

<400> SEQUENCE: 101

Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30

<210> SEQ ID NO 102
<211> LENGTH: 11
<212> TYPE: PRT
<213> ORGANISM: Homo sapiens

<400> SEQUENCE: 102

Phe Gly Gly Gly Thr Lys Val Glu Ile Lys Arg
1               5                   10

<210> SEQ ID NO 103
<211> LENGTH: 23
<212> TYPE: PRT
<213> ORGANISM: Homo sapiens

<400> SEQUENCE: 103

Asp Ile Gln Met Thr Gln Ser Pro Ser Ser Val Ser Ala Ser Val Gly
1               5                   10                  15
Asp Arg Val Thr Ile Thr Cys
            20

<210> SEQ ID NO 104
<211> LENGTH: 15
<212> TYPE: PRT
<213> ORGANISM: Homo sapiens

<400> SEQUENCE: 104

Trp Tyr Gln Gln Lys Pro Gly Lys Ala Pro Lys Leu Leu Ile Tyr
1               5                   10                  15

<210> SEQ ID NO 105
<211> LENGTH: 32
<212> TYPE: PRT
<213> ORGANISM: Homo sapiens

<400> SEQUENCE: 105

Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30

<210> SEQ ID NO 106
<211> LENGTH: 11
<212> TYPE: PRT
<213> ORGANISM: Homo sapiens

<400> SEQUENCE: 106

Phe Gly Gly Gly Thr Lys Val Glu Ile Lys Arg
1               5                   10

<210> SEQ ID NO 107
<211> LENGTH: 22
<212> TYPE: PRT
<213> ORGANISM: Homo sapiens

<400> SEQUENCE: 107

```
Ser Tyr Glu Leu Thr Gln Pro Pro Ser Val Ser Val Ser Pro Gly Gln
1               5                   10                  15

Thr Ala Ser Ile Thr Cys
            20
```

<210> SEQ ID NO 108
<211> LENGTH: 15
<212> TYPE: PRT
<213> ORGANISM: Homo sapiens

<400> SEQUENCE: 108

```
Trp Tyr Gln Gln Lys Pro Gly Gln Ser Pro Val Leu Val Ile Tyr
1               5                   10                  15
```

<210> SEQ ID NO 109
<211> LENGTH: 32
<212> TYPE: PRT
<213> ORGANISM: Homo sapiens

<400> SEQUENCE: 109

```
Gly Ile Pro Glu Arg Phe Ser Gly Ser Asn Ser Gly Asp Thr Ala Thr
1               5                   10                  15

Leu Thr Ile Ser Gly Thr Gln Pro Met Asp Glu Ala Tyr Tyr Cys
            20                  25                  30
```

<210> SEQ ID NO 110
<211> LENGTH: 10
<212> TYPE: PRT
<213> ORGANISM: Homo sapiens

<400> SEQUENCE: 110

```
Phe Gly Tyr Gly Thr Lys Val Thr Val Leu
1               5                   10
```

<210> SEQ ID NO 111
<211> LENGTH: 22
<212> TYPE: PRT
<213> ORGANISM: Homo sapiens

<400> SEQUENCE: 111

```
Ser Tyr Glu Leu Thr Gln Pro Pro Ser Val Ser Val Ser Pro Gly Gln
1               5                   10                  15

Thr Ala Ser Ile Thr Cys
            20
```

<210> SEQ ID NO 112
<211> LENGTH: 15
<212> TYPE: PRT
<213> ORGANISM: Homo sapiens

<400> SEQUENCE: 112

```
Trp Tyr Gln Gln Lys Pro Gly Gln Ser Pro Val Leu Val Ile Tyr
1               5                   10                  15
```

<210> SEQ ID NO 113
<211> LENGTH: 32
<212> TYPE: PRT
<213> ORGANISM: Homo sapiens

<400> SEQUENCE: 113

```
Gly Ile Pro Glu Arg Phe Ser Gly Ser Asn Ser Gly Asp Thr Ala Thr
1               5                   10                  15

Leu Thr Ile Ser Gly Thr Gln Pro Met Asp Glu Ala Asp Tyr Tyr Cys
```

<210> SEQ ID NO 114
<211> LENGTH: 10
<212> TYPE: PRT
<213> ORGANISM: Homo sapiens

<400> SEQUENCE: 114

Gly Gly Gly Thr Lys Leu Thr Val Leu Gly
1               5                   10

<210> SEQ ID NO 115
<211> LENGTH: 21
<212> TYPE: PRT
<213> ORGANISM: Homo sapiens

<400> SEQUENCE: 115

Tyr Glu Leu Thr Gln Pro Pro Ser Val Ser Val Pro Gly Gln Thr
1               5                   10                  15

Ala Ser Ile Thr Cys
            20

<210> SEQ ID NO 116
<211> LENGTH: 15
<212> TYPE: PRT
<213> ORGANISM: Homo sapiens

<400> SEQUENCE: 116

Trp Tyr Gln Gln Lys Pro Gly Gln Ser Pro Val Leu Val Ile Tyr
1               5                   10                  15

<210> SEQ ID NO 117
<211> LENGTH: 32
<212> TYPE: PRT
<213> ORGANISM: Homo sapiens

<400> SEQUENCE: 117

Gly Ile Pro Glu Arg Phe Ser Gly Ser Asn Ser Gly Asp Thr Ala Thr
1               5                   10                  15

Leu Thr Ile Ser Gly Thr Gln Pro Met Asp Glu Ala Asp Tyr Tyr Cys
            20                  25                  30

<210> SEQ ID NO 118
<211> LENGTH: 10
<212> TYPE: PRT
<213> ORGANISM: Homo sapiens

<400> SEQUENCE: 118

Gly Gly Gly Thr Lys Leu Thr Val Leu Gly
1               5                   10

<210> SEQ ID NO 119
<211> LENGTH: 22
<212> TYPE: PRT
<213> ORGANISM: Homo sapiens

<400> SEQUENCE: 119

Leu Tyr Val Leu Thr Gln Pro Pro Ser Val Ser Val Ser Pro Gly Gln
1               5                   10                  15

Thr Ala Ser Ile Thr Cys
            20

<210> SEQ ID NO 120

```
<211> LENGTH: 15
<212> TYPE: PRT
<213> ORGANISM: Homo sapiens

<400> SEQUENCE: 120

Trp Tyr Gln Gln Lys Pro Gly Gln Ser Pro Val Leu Val Ile Tyr
1               5                   10                  15

<210> SEQ ID NO 121
<211> LENGTH: 32
<212> TYPE: PRT
<213> ORGANISM: Homo sapiens

<400> SEQUENCE: 121

Gly Ile Pro Glu Arg Phe Ser Gly Ser Asn Ser Gly Asp Thr Ala Thr
1               5                   10                  15

Leu Thr Ile Ser Gly Thr Gln Thr Met Asp Glu Ala Asp Tyr Leu Cys
            20                  25                  30

<210> SEQ ID NO 122
<211> LENGTH: 11
<212> TYPE: PRT
<213> ORGANISM: Homo sapiens

<400> SEQUENCE: 122

Phe Gly Gly Gly Thr Lys Val Thr Val Leu Gly
1               5                   10

<210> SEQ ID NO 123
<211> LENGTH: 23
<212> TYPE: PRT
<213> ORGANISM: Homo sapiens

<400> SEQUENCE: 123

Glu Tyr Val Leu Thr Gln Ser Pro Asp Phe Gln Ser Val Thr Pro Lys
1               5                   10                  15

Glu Lys Val Thr Ile Thr Cys
            20

<210> SEQ ID NO 124
<211> LENGTH: 15
<212> TYPE: PRT
<213> ORGANISM: Homo sapiens

<400> SEQUENCE: 124

Trp Tyr Gln Gln Lys Pro Asp Gln Ser Pro Lys Leu Val Ile Tyr
1               5                   10                  15

<210> SEQ ID NO 125
<211> LENGTH: 32
<212> TYPE: PRT
<213> ORGANISM: Homo sapiens

<400> SEQUENCE: 125

Gly Val Pro Ser Arg Phe Ser Gly Ser Asn Ser Gly Asp Asp Ala Thr
1               5                   10                  15

Leu Thr Ile Asn Ser Leu Glu Ala Glu Asp Ala Ala Thr Tyr Tyr Cys
            20                  25                  30

<210> SEQ ID NO 126
<211> LENGTH: 11
<212> TYPE: PRT
<213> ORGANISM: Homo sapiens
```

```
<400> SEQUENCE: 126

Phe Gly Gln Gly Thr Lys Val Glu Ile Lys Arg
1               5                   10

<210> SEQ ID NO 127
<211> LENGTH: 23
<212> TYPE: PRT
<213> ORGANISM: Homo sapiens

<400> SEQUENCE: 127

Glu Tyr Val Leu Thr Gln Ser Pro Ala Thr Leu Ser Val Ser Pro Gly
1               5                   10                  15

Glu Arg Ala Thr Leu Ser Cys
            20

<210> SEQ ID NO 128
<211> LENGTH: 15
<212> TYPE: PRT
<213> ORGANISM: Homo sapiens

<400> SEQUENCE: 128

Trp Tyr Gln Gln Lys Pro Gly Gln Ser Pro Arg Leu Val Ile Tyr
1               5                   10                  15

<210> SEQ ID NO 129
<211> LENGTH: 32
<212> TYPE: PRT
<213> ORGANISM: Homo sapiens

<400> SEQUENCE: 129

Asp Ile Pro Ala Arg Phe Ser Gly Ser Asn Ser Gly Asp Glu Ala Thr
1               5                   10                  15

Leu Thr Ile Ser Ser Leu Gln Ser Glu Asp Phe Ala Val Tyr Tyr Cys
            20                  25                  30

<210> SEQ ID NO 130
<211> LENGTH: 11
<212> TYPE: PRT
<213> ORGANISM: Homo sapiens

<400> SEQUENCE: 130

Phe Gly Gln Gly Thr Arg Leu Glu Ile Lys Arg
1               5                   10

<210> SEQ ID NO 131
<211> LENGTH: 23
<212> TYPE: PRT
<213> ORGANISM: Homo sapiens

<400> SEQUENCE: 131

Asp Tyr Val Leu Thr Gln Ser Pro Asp Ser Leu Ala Val Ser Leu Gly
1               5                   10                  15

Glu Arg Ala Thr Ile Asn Cys
            20

<210> SEQ ID NO 132
<211> LENGTH: 15
<212> TYPE: PRT
<213> ORGANISM: Homo sapiens

<400> SEQUENCE: 132

Trp Tyr Gln Gln Lys Pro Gly Gln Ser Pro Lys Leu Val Ile Tyr
1               5                   10                  15
```

<210> SEQ ID NO 133
<211> LENGTH: 32
<212> TYPE: PRT
<213> ORGANISM: Homo sapiens

<400> SEQUENCE: 133

Gly Ile Pro Asp Arg Phe Ser Gly Ser Asn Ser Gly Asp Asp Ala Thr
1               5                   10                  15

Leu Thr Ile Ser Ser Leu Gln Ala Glu Asp Val Ala Val Tyr Tyr Cys
            20                  25                  30

<210> SEQ ID NO 134
<211> LENGTH: 11
<212> TYPE: PRT
<213> ORGANISM: Homo sapiens

<400> SEQUENCE: 134

Phe Gly Gly Gly Thr Lys Val Glu Ile Lys Arg
1               5                   10

<210> SEQ ID NO 135
<211> LENGTH: 22
<212> TYPE: PRT
<213> ORGANISM: Homo sapiens

<400> SEQUENCE: 135

Leu Pro Val Leu Thr Gln Pro Pro Ser Val Ser Val Ser Pro Gly Gln
1               5                   10                  15

Thr Ala Ser Ile Thr Cys
            20

<210> SEQ ID NO 136
<211> LENGTH: 15
<212> TYPE: PRT
<213> ORGANISM: Homo sapiens

<400> SEQUENCE: 136

Trp Tyr Gln Gln Lys Pro Gly Gln Ser Pro Val Leu Val Ile Tyr
1               5                   10                  15

<210> SEQ ID NO 137
<211> LENGTH: 32
<212> TYPE: PRT
<213> ORGANISM: Homo sapiens

<400> SEQUENCE: 137

Gly Ile Pro Glu Arg Phe Ser Gly Ser Asn Ser Gly Asn Thr Ala Thr
1               5                   10                  15

Leu Thr Ile Ser Gly Thr Gln Thr Met Asp Glu Ala Asp Tyr Leu Cys
            20                  25                  30

<210> SEQ ID NO 138
<211> LENGTH: 10
<212> TYPE: PRT
<213> ORGANISM: Homo sapiens

<400> SEQUENCE: 138

Phe Gly Gly Gly Thr Lys Val Thr Val Leu
1               5                   10

<210> SEQ ID NO 139
<211> LENGTH: 22

```
<212> TYPE: PRT
<213> ORGANISM: Homo sapiens

<400> SEQUENCE: 139

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 140
<211> LENGTH: 15
<212> TYPE: PRT
<213> ORGANISM: Homo sapiens

<400> SEQUENCE: 140

Trp Tyr Gln Gln Lys Pro Gly Gln Ser Pro Val Leu Val Ile Tyr
1               5                   10                  15

<210> SEQ ID NO 141
<211> LENGTH: 32
<212> TYPE: PRT
<213> ORGANISM: Homo sapiens

<400> SEQUENCE: 141

Gly Ile Pro Glu Arg Phe Ser Gly Ser Asn Ser Gly Asn Thr Ala Thr
1               5                   10                  15

Leu Thr Ile Ser Gly Thr Gln Thr Met Asp Glu Ala Asp Tyr Leu Cys
            20                  25                  30

<210> SEQ ID NO 142
<211> LENGTH: 10
<212> TYPE: PRT
<213> ORGANISM: Homo sapiens

<400> SEQUENCE: 142

Phe Gly Gly Gly Thr Lys Leu Thr Val Leu
1               5                   10

<210> SEQ ID NO 143
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Ser, Arg or Gly

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa
            20                  25                  30

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144
```

```
Trp Val Arg Gln Ala Pro Gly Lys Gly Leu Glu Trp Val Ala
1               5                   10
```

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Asn or Ser
<220> FEATURE:
<221> NAME/KEY: MOD_RES
<222> LOCATION: (31)..(31)
<223> OTHER INFORMATION: Ala or Ser

<400> SEQUENCE: 145

```
Arg Phe Thr Ile Ser Arg Asp Asn Ala Lys Xaa Ser Leu Tyr Leu Gln
1               5                   10                  15

Met Asn Ser Leu Arg Ala Glu Asp Thr Ala Val Tyr Tyr Cys Xaa Arg
            20                  25                  30
```

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Trp Gly Gln Gly Thr Leu Val Thr Val Ser Ser
1               5                   10
```

<210> SEQ ID NO 147
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ala or Ser
<220> FEATURE:
<221> NAME/KEY: MOD_RES
<222> LOCATION: (15)..(15)
<223> OTHER INFORMATION: Phe or Tyr

<400> SEQUENCE: 148

```
Trp Tyr Gln Gln Lys Pro Gly Lys Xaa Pro Lys Leu Leu Ile Xaa
```

<210> SEQ ID NO 149
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Phe or Ser

<400> SEQUENCE: 149

Gly Val Pro Ser Arg Phe Ser Gly Ser Gly Ser Gly Thr Asp Xaa Thr
 1               5                  10                  15

Leu Thr Ile Ser Ser Leu Gln Pro Glu Asp Phe Ala Thr Tyr Tyr Cys
             20                  25                  30

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Phe Gly Gln Gly Thr Lys Leu Glu Ile Lys
 1               5                  10

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, His or Tyr
<220> FEATURE:
<221> NAME/KEY: MOD_RES
<222> LOCATION: (5)..(5)
<223> OTHER INFORMATION: Ala or Ser

<400> SEQUENCE: 151

Xaa Phe Pro Met Xaa
 1               5

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Ser
<220> FEATURE:
<221> NAME/KEY: MOD_RES
<222> LOCATION: (4)..(4)
<223> OTHER INFORMATION: Ser or Gly
<220> FEATURE:
<221> NAME/KEY: MOD_RES
<222> LOCATION: (7)..(7)
<223> OTHER INFORMATION: Gly, Ala, Asp, Ser or Glu

```
<220> FEATURE:
<221> NAME/KEY: MOD_RES
<222> LOCATION: (8)..(8)
<223> OTHER INFORMATION: Thr or Trp
<220> FEATURE:
<221> NAME/KEY: MOD_RES
<222> LOCATION: (9)..(9)
<223> OTHER INFORMATION: Thr, Pro or Ala
<220> FEATURE:
<221> NAME/KEY: MOD_RES
<222> LOCATION: (10)..(10)
<223> OTHER INFORMATION: Tyr, Ser, Thr or Asn
<220> FEATURE:
<221> NAME/KEY: MOD_RES
<222> LOCATION: (11)..(11)
<223> OTHER INFORMATION: Tyr or Ile
<220> FEATURE:
<221> NAME/KEY: MOD_RES
<222> LOCATION: (12)..(12)
<223> OTHER INFORMATION: Arg or Gly

<400> SEQUENCE: 152

Xaa Ile Ser Xaa Ser Asp Xaa Xaa Xaa Xaa Xaa Xaa Asp Ser Val Lys
1               5                   10                  15

Gly

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Tyr, Phe or Ser

<400> SEQUENCE: 153

Gly Tyr Tyr Asn Ser Pro Phe Ala Xaa
1               5

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Gln
<220> FEATURE:
<221> NAME/KEY: MOD_RES
<222> LOCATION: (5)..(5)
<223> OTHER INFORMATION: Asp or Glu
<220> FEATURE:
<221> NAME/KEY: MOD_RES
<222> LOCATION: (7)..(7)
<223> OTHER INFORMATION: Tyr or Trp
<220> FEATURE:
<221> NAME/KEY: MOD_RES
<222> LOCATION: (8)..(8)
<223> OTHER INFORMATION: Ser, Ile, Tyr, Asn or Arg

<400> SEQUENCE: 154

Arg Ala Ser Xaa Xaa Ile Xaa Xaa Asn Leu Ala
1               5                   10

<210> SEQ ID NO 155
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn or Ser
<220> FEATURE:
<221> NAME/KEY: MOD_RES
<222> LOCATION: (4)..(4)
<223> OTHER INFORMATION: Asn, Asp, Ser, Ile, Tyr or Val

<400> SEQUENCE: 155

Asp Thr Xaa Xaa Leu Ala Asp
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Asn, Asp or Thr
<220> FEATURE:
<221> NAME/KEY: MOD_RES
<222> LOCATION: (5)..(5)
<223> OTHER INFORMATION: Asn, Tyr or Trp
<220> FEATURE:
<221> NAME/KEY: MOD_RES
<222> LOCATION: (6)..(6)
<223> OTHER INFORMATION: Tyr or Val

<400> SEQUENCE: 156

Gln Gln Tyr Xaa Xaa Xaa Pro Pro Thr
1               5

<210> SEQ ID NO 157
<211> LENGTH: 118
<212> TYPE: PRT
<213> ORGANISM: Rattus sp.

<400> SEQUENCE: 157

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Gly Met Tyr Trp Ile Arg Gln Ala Pro Thr Lys Gly Leu Gln Trp Val
        35                  40                  45

Ala Phe Ile Ser His Gly Gly Gly Ile Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr His Cys
                85                  90                  95

Ala Ala Leu Asn Trp Glu Leu Gly Ile Asp Tyr Trp Gly Gln Gly Val
            100                 105                 110

Met Val Thr Val Ser Ser
        115

<210> SEQ ID NO 158
```

```
<211> LENGTH: 108
<212> TYPE: PRT
<213> ORGANISM: Rattus sp.

<400> SEQUENCE: 158

Asp Ile Gln Met Thr Gln Ser Pro Ala Ser Leu Ser Ala Ser Leu Gly
1               5                   10                  15

Glu Thr Ile Ser Ile Glu Cys Arg Ala Ser Glu Asp Ile Tyr Ser Asn
            20                  25                  30

Leu Ala Trp Tyr Gln Lys Lys Ser Gly Lys Ser Pro Gln Leu Leu Ile
        35                  40                  45

Tyr Ala Ala Asn Arg Leu Gln Asp Gly Val Pro Ser Arg Phe Ser Gly
    50                  55                  60

Ser Gly Ser Gly Thr Gln Tyr Ser Leu Lys Ile Ser Gly Met Gln Pro
65                  70                  75                  80

Glu Asp Glu Gly Asp Tyr Phe Cys Leu Gln Gly Ser Lys Phe Pro Leu
                85                  90                  95

Thr Phe Gly Ser Gly Thr Lys Leu Glu Ile Lys Arg
            100                 105

<210> SEQ ID NO 159
<211> LENGTH: 118
<212> TYPE: PRT
<213> ORGANISM: Rattus sp.

<400> SEQUENCE: 159

Glu Val Gln Leu Val Glu Ser Gly Gly Leu Val Gln Pro Gly Arg
1               5                   10                  15

Ser Met Lys Leu Ser Cys Ala Ala Ser Gly Phe Thr Phe Arg Asn Phe
            20                  25                  30

Pro Met Ala Trp Val Arg Gln Ala Pro Thr Arg Gly Leu Glu Trp Val
        35                  40                  45

Ala Thr Ile Ser Ser Ser Asp Gly Thr Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Val Asn Ser Leu Arg Ser Glu Asp Thr Ala Thr Tyr Tyr Cys
                85                  90                  95

Ser Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 160
<211> LENGTH: 108
<212> TYPE: PRT
<213> ORGANISM: Rattus sp.

<400> SEQUENCE: 160

Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile Tyr Ser Asn
            20                  25                  30

Leu Ala Trp Tyr Gln Gln Lys Pro Gly Asn Ser Pro Gln Leu Leu Ile
        35                  40                  45

Phe Asp Thr Asn Asn Leu Ala Asp Gly Val Pro Ser Arg Phe Ser Gly
    50                  55                  60
```

Ser Gly Ser Gly Thr Gln Ser Leu Lys Ile Asn Ser Leu Gln Ser
65                  70                  75                  80

Glu Asp Val Ala Ser Tyr Phe Cys Gln Gln Tyr Asn Asn Tyr Pro Pro
                85                  90                  95

Thr Phe Gly Gly Gly Thr Lys Leu Glu Leu Lys Arg
            100                 105

<210> SEQ ID NO 161
<211> LENGTH: 122
<212> TYPE: PRT
<213> ORGANISM: Rattus sp.

<400> SEQUENCE: 161

Ala Val Gln Leu Val Glu Ser Gly Gly Gly Leu Val Gln Pro Lys Glu
1               5                   10                  15

Ser Leu Lys Ile Ser Cys Ala Ala Ser Gly Phe Thr Phe Ser Asn Ala
                20                  25                  30

Ala Met Tyr Trp Val Arg Leu Ala Pro Gly Lys Gly Leu Glu Trp Val
            35                  40                  45

Ala Arg Ile Arg Thr Lys Pro Asn Asn Tyr Ala Thr Tyr Tyr Ala Glu
        50                  55                  60

Ser Val Lys Gly Arg Phe Thr Ile Ser Arg Asp Asp Ser Lys Ser Met
65                  70                  75                  80

Val Tyr Val Gln Met Asp Asn Leu Lys Thr Glu Asp Thr Ala Met Tyr
                85                  90                  95

Tyr Cys Thr Ala Ala Pro Trp Arg Asp Ser Tyr Ala His Val Tyr Trp
            100                 105                 110

Gly Gln Gly Val Met Val Thr Val Ser Ser
        115                 120

<210> SEQ ID NO 162
<211> LENGTH: 108
<212> TYPE: PRT
<213> ORGANISM: Rattus sp.

<400> SEQUENCE: 162

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile His Lys Asn
                20                  25                  30

Leu Asp Trp Tyr Gln Gln Lys His Gly Asp Ala Pro Lys Leu Leu Ile
            35                  40                  45

Tyr Tyr Thr Asp His Leu Gln Thr Gly Val Pro Ser Arg Phe Ser Gly
        50                  55                  60

Ser Gly Ser Ala Thr Asp Tyr Thr Leu Thr Ile Ser Ser Leu Gln Pro
65                  70                  75                  80

Glu Asp Val Ala Thr Tyr Tyr Cys Tyr Gln Tyr Asn Gly Gly Pro Phe
                85                  90                  95

Thr Phe Gly Ser Gly Thr Lys Leu Glu Ile Lys Arg
            100                 105

<210> SEQ ID NO 163
<211> LENGTH: 116
<212> TYPE: PRT
<213> ORGANISM: Rattus sp.

<400> SEQUENCE: 163

Glu Val Gln Leu Val Glu Ser Gly Gly Gly Leu Val Gln Pro Gly Arg

```
                1               5                      10                     15
Ser Leu Lys Leu Ser Cys Leu Ala Ser Gly Phe Pro Phe Ser Ser Val
            20                      25                     30

Trp Met Thr Trp Ile Arg Gln Ala Pro Gly Lys Gly Leu Glu Trp Ile
            35                      40                     45

Ala Thr Ile Thr Asn Ser Gly Ala Ser Thr Tyr Tyr Ser Ala Ser Val
            50                      55                     60

Lys Gly Arg Phe Thr Ile Ser Arg Asp Asn Val Lys Ser Thr Leu Tyr
65                                  70                     75                     80

Leu Gln Met Thr Ser Leu Gly Ser Glu Asp Thr Ala Thr Tyr Tyr Cys
            85                      90                     95

Thr Arg Val Gly Thr Ser Phe Asp Tyr Trp Gly Gln Gly Val Met Val
            100                     105                    110

Thr Val Ser Ser
            115
```

<210> SEQ ID NO 164
<211> LENGTH: 109
<212> TYPE: PRT
<213> ORGANISM: Rattus sp.

<400> SEQUENCE: 164

```
Asp Ile Gln Met Thr Gln Ser Pro Ala Ser Leu Ser Ala Ser Leu Gly
1               5                      10                     15

Glu Thr Val Thr Ile Glu Cys Arg Ala Ser Asp Asp Ile Tyr Asn Gly
            20                      25                     30

Leu Ala Trp Phe Gln Gln Lys Pro Gly Lys Ser Pro Gln Leu Leu Ile
            35                      40                     45

Tyr Asp Ala Asn Thr Leu His Thr Gly Val Pro Ser Arg Phe Ser Gly
            50                      55                     60

Ser Gly Ser Gly Thr Gln Phe Ser Leu Lys Ile Asn Ser Leu Gln Ser
65                                  70                     75                     80

Glu Asp Val Ala Ser Tyr Phe Cys Gln Gln Phe Tyr Asp Tyr Pro Pro
            85                      90                     95

Tyr Thr Phe Gly Ala Gly Thr Lys Leu Glu Leu Lys Arg
            100                     105
```

<210> SEQ ID NO 165
<211> LENGTH: 116
<212> TYPE: PRT
<213> ORGANISM: Rattus sp.

<400> SEQUENCE: 165

```
Glu Val Gln Leu Gln Gln Ser Gly Ala Glu Leu Ala Lys Pro Gly Ser
1               5                      10                     15

Ser Val Lys Ile Ser Cys Lys Ala Ser Gly Tyr Thr Phe Thr Asn Tyr
            20                      25                     30

Asp Ile Ser Trp Ile Lys Gln Thr Asn Gly Gln Gly Leu Glu Tyr Leu
            35                      40                     45

Gly Tyr Ile Asn Thr Gly Ser Gly Gly Ile Tyr Ser Asn Glu Lys Phe
            50                      55                     60

Lys Gly Lys Ala Thr Leu Thr Val Asp Lys Ser Ser Asn Thr Ala Phe
65                                  70                     75                     80

Met Gln Leu Ser Ser Leu Thr Pro Glu Asp Thr Ala Val Tyr Tyr Cys
            85                      90                     95

Val Arg Glu Gly Asn Asn Phe Asp His Trp Gly Gln Gly Val Lys Val
```

```
                    100                 105                 110

Thr Val Ser Ser
            115

<210> SEQ ID NO 166
<211> LENGTH: 108
<212> TYPE: PRT
<213> ORGANISM: Rattus sp.

<400> SEQUENCE: 166

Asp Thr Val Met Thr Gln Ser Pro Ala Ser Met Ser Thr Ser Val Gly
1               5                   10                  15

Glu Arg Val Thr Val Asn Cys Lys Ala Ser Gln Ser Val Gly Thr Ile
            20                  25                  30

Val Ala Trp Phe Gln Gln Lys Pro Gly Gln Ser Pro Lys Arg Leu Ile
        35                  40                  45

Tyr Leu Ala Thr Tyr Arg His Thr Gly Val Pro Asp Arg Phe Ile Gly
    50                  55                  60

Ser Gly Phe Gly Arg Asp Phe Thr Leu Thr Ile Ser Asn Val Glu Ala
65                  70                  75                  80

Glu Asp Leu Ala Val Tyr Tyr Cys Leu Gln Tyr Gly Ser Arg Pro Phe
                85                  90                  95

Thr Phe Gly Ala Gly Thr Lys Leu Glu Ile Lys Arg
            100                 105

<210> SEQ ID NO 167
<211> LENGTH: 121
<212> TYPE: PRT
<213> ORGANISM: Rattus sp.

<400> SEQUENCE: 167

Glu Val Gln Leu Gln Gln Ser Gly Pro Glu Leu Ala Lys Pro Gly Ser
1               5                   10                  15

Ser Val Lys Ile Ser Cys Lys Ala Ser Gly Tyr Thr Phe Thr Asn Ser
            20                  25                  30

Tyr Ile Ser Trp Ile Lys Gln Thr Thr Gly Gln Gly Leu Glu Tyr Val
        35                  40                  45

Gly Tyr Ile Asn Thr Gly Ser Gly Ala Asp Tyr Asn Glu Lys Phe
    50                  55                  60

Lys Gly Lys Ala Thr Leu Thr Val Asp Lys Ser Ser Arg Thr Ala Phe
65                  70                  75                  80

Met Gln Leu Ser Ser Leu Thr Pro Gly Asp Ser Ala Val Tyr Tyr Cys
                85                  90                  95

Ala Lys Ser Ile Leu Leu Gly Ser Thr Cys Tyr Phe Asp Tyr Trp Gly
            100                 105                 110

Gln Gly Val Leu Val Thr Val Ser Ser
        115                 120

<210> SEQ ID NO 168
<211> LENGTH: 111
<212> TYPE: PRT
<213> ORGANISM: Rattus sp.

<400> SEQUENCE: 168

Asn Thr Val Leu Thr Gln Ser Pro Ala Leu Ala Val Ser Leu Gly Gln
1               5                   10                  15

Arg Val Thr Ile Ser Cys Lys Ala Ser Arg Ser Val Ser Ser Pro Met
            20                  25                  30
```

Tyr Ser Tyr Ile Tyr Trp Tyr Gln Gln Lys Pro Gly Gln Gln Pro Lys
                35                  40                  45

Leu Leu Ile Tyr Arg Ala Ser Thr Leu Ala Ser Gly Val Pro Ala Arg
        50                  55                  60

Phe Ser Gly Ser Gly Ser Gly Thr Asp Phe Thr Leu Asn Ile Asp Pro
65                  70                  75                  80

Val Glu Ala Asp Asp Ile Ala Thr Tyr Phe Cys Gln Gln Ser Trp Ser
                85                  90                  95

Asp Pro Phe Thr Phe Gly Ser Gly Thr Lys Leu Glu Ile Lys Arg
                100                 105                 110

<210> SEQ ID NO 169
<211> LENGTH: 121
<212> TYPE: PRT
<213> ORGANISM: Rattus sp.

<400> SEQUENCE: 169

Glu Val Gln Leu Gln Gln Ser Gly Pro Glu Leu Ala Lys Pro Gly Ser
1               5                   10                  15

Ser Val Lys Ile Ser Cys Lys Ala Ser Gly Tyr Thr Phe Thr Ser Ser
                20                  25                  30

Tyr Ile Ser Trp Ile Lys Gln Thr Thr Gly Gln Gly Leu Glu Tyr Ile
                35                  40                  45

Gly Tyr Ile Asn Thr Gly Ser Gly Gly Thr Asp Tyr Asn Glu Lys Phe
        50                  55                  60

Lys Asp Lys Ala Thr Leu Thr Val Asp Lys Ser Ser Arg Thr Val Phe
65                  70                  75                  80

Met Gln Leu Ser Ser Leu Thr Pro Gly Asp Ser Ala Val Tyr Tyr Cys
                85                  90                  95

Ala Lys Ser Ile Leu Leu Gly Ser Thr Tyr Tyr Leu Asp Tyr Trp Gly
                100                 105                 110

Gln Gly Val Met Val Thr Val Ser Ser
        115                 120

<210> SEQ ID NO 170
<211> LENGTH: 111
<212> TYPE: PRT
<213> ORGANISM: Rattus sp.

<400> SEQUENCE: 170

Asp Thr Val Leu Thr Gln Ser Pro Ala Leu Ala Val Ser Leu Gly Gln
1               5                   10                  15

Arg Val Thr Ile Ser Cys Lys Ala Ser Arg Ser Leu Ser Ser Pro Met
                20                  25                  30

Tyr Ser Tyr Ile Tyr Trp Tyr Gln Gln Lys Leu Gly Gln Gln Pro Arg
                35                  40                  45

Leu Leu Ile Tyr Arg Ala Ser Thr Leu Ala Ser Gly Val Pro Ala Arg
        50                  55                  60

Phe Ser Gly Ser Gly Ser Gly Thr Asp Phe Thr Leu Asn Ile Asp Pro
65                  70                  75                  80

Val Glu Ala Asp Asp Ile Ala Thr Tyr Phe Cys Gln Gln Ser Trp Ser
                85                  90                  95

Asp Pro Phe Thr Phe Gly Ser Gly Thr Lys Leu Glu Ile Lys Arg
                100                 105                 110

<210> SEQ ID NO 171

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Gly Thr Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 172
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Gly Thr Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 173
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Gly Thr Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 174
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Gly Thr Thr Tyr Tyr Arg Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ser Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 175
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

```
Tyr Asp Thr Asn Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Pro
                 85                  90                  95

Thr Phe Gly Gln Gly Thr Lys Leu Glu Ile Lys Arg
            100                 105

<210> SEQ ID NO 176
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asp Ile Tyr Ser Asn
                 20                  25                  30

Leu Ala Trp Tyr Gln Gln Lys Pro Gly Lys Ser Pro Lys Leu Leu Ile
             35                  40                  45

Phe Asp Thr Asn Asn Leu Ala Asp Gly Val Pro Ser Arg Phe Ser Gly
 50                  55                  60

Ser Gly Ser Gly Thr Asp Ser Thr Leu Thr Ile Ser Ser Leu Gln Pro
 65                  70                  75                  80

Glu Asp Phe Ala Thr Tyr Phe Cys Gln Gln Tyr Asn Asn Tyr Pro Pro
                 85                  90                  95

Thr Phe Gly Gln Gly Thr Lys Leu Glu Ile Lys Arg
            100                 105

<210> SEQ ID NO 177
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asp Ile Tyr Ser Asn
                 20                  25                  30

Leu Ala Trp Tyr Gln Gln Lys Pro Gly Lys Ala Pro Lys Leu Leu Ile
             35                  40                  45

Phe Asp Thr Asn Asn Leu Ala Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Asn Tyr Pro Pro
                 85                  90                  95

Thr Phe Gly Gln Gly Thr Lys Leu Glu Ile Lys Arg
            100                 105

<210> SEQ ID NO 178
<211> LENGTH: 108
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Asp Ile Tyr Ser Asn
            20                  25                  30

Leu Ala Trp Tyr Gln Gln Lys Pro Gly Gln Ser Pro Arg Leu Leu Ile
        35                  40                  45

Phe Asp Thr Asn Asn Leu Ala Asp Gly Val Pro Ala Arg Phe Ser Gly
    50                  55                  60

Ser Gly Ser Gly Thr Glu Ser Thr Leu Thr Ile Ser Ser Leu Gln Ser
65                  70                  75                  80

Glu Asp Phe Ala Val Tyr Phe Cys Gln Gln Tyr Asn Asn Tyr Pro Pro
                85                  90                  95

Thr Phe Gly Gln Gly Thr Lys Leu Glu Ile Lys Arg
            100                 105

<210> SEQ ID NO 179
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Tyr Trp Val Arg Gln Ala Pro Gly Lys Gly Leu Glu Trp Val
        35                  40                  45

Ala Phe Ile Ser His Gly Gly Gly Ile Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Asn Trp Glu Leu Gly Ile Asp Tyr Trp Gly Gln Gly Thr
            100                 105                 110

Met Val Thr Val Ser Ser
        115

<210> SEQ ID NO 180
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
```

```
                    20                  25                  30
Gly Met Tyr Trp Ile Arg Gln Ala Pro Gly Lys Gly Leu Glu Trp Val
                35                  40                  45

Ala Phe Ile Ser His Gly Gly Gly Ile Thr Tyr Tyr Arg Asp Ser Val
            50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr His Cys
                85                  90                  95

Ala Ala Leu Asn Trp Glu Leu Gly Ile Asp Tyr Trp Gly Gln Gly Thr
                100                 105                 110

Met Val Thr Val Ser Ser
        115

<210> SEQ ID NO 181
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met Tyr Trp Val Arg Gln Ala Pro Gly Lys Gly Leu Glu Trp Val
                35                  40                  45

Ala Phe Ile Ser His Gly Gly Gly Ile Thr Tyr Tyr Arg Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Leu Asn Trp Glu Leu Gly Ile Asp Tyr Trp Gly Gln Gly Thr
                100                 105                 110

Met Val Thr Val Ser Ser
        115

<210> SEQ ID NO 182
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met Tyr Trp Ile Arg Gln Ala Pro Gly Lys Gly Leu Glu Trp Val
                35                  40                  45

Ala Phe Ile Ser His Gly Gly Gly Ile Thr Tyr Tyr Arg Asp Ser Val
            50                  55                  60

Lys Gly Arg Phe Thr Ile Ser Arg Asp Asn Ser Lys Ser Thr Leu Tyr
```

```
                 65                  70                  75                  80
Leu Gln Met Asn Ser Leu Arg Ala Glu Asp Thr Ala Val Tyr His Cys
                 85                  90                  95

Ala Ala Leu Asn Trp Glu Leu Gly Ile Asp Tyr Trp Gly Gln Gly Thr
            100                 105                 110

Met Val Thr Val Ser Ser
            115
```

<210> SEQ ID NO 183
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Asn Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Gly Ser Lys Phe Pro Leu
                85                  90                  95

Thr Phe Gly Gln Gly Thr Lys Leu Glu Ile Lys Arg
            100                 105
```

<210> SEQ ID NO 184
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Glu Asp Ile Tyr Ser Asn
            20                  25                  30

Leu Ala Trp Tyr Gln Lys Lys Pro Gly Lys Ser Pro Lys Leu Leu Ile
        35                  40                  45

Tyr Ala Ala Asn Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Leu Gln Gly Ser Lys Phe Pro Leu
                85                  90                  95

Thr Phe Gly Gln Gly Thr Lys Leu Glu Ile Lys Arg
            100                 105
```

<210> SEQ ID NO 185
<211> LENGTH: 108
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Asn Arg Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Gly Ser Lys Phe Pro Leu
                85                  90                  95

Thr Phe Gly Gln Gly Thr Lys Leu Glu Ile Lys Arg
            100                 105

<210> SEQ ID NO 186
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Asp Ile Tyr Ser Asn
            20                  25                  30

Leu Ala Trp Tyr Gln Lys Lys Pro Gly Gln Ser Pro Arg Leu Leu Ile
        35                  40                  45

Tyr Ala Ala Asn Arg Leu Gln Asp Gly Val Pro Ala Arg Phe Ser Gly
    50                  55                  60

Ser Gly Ser Gly Thr Glu Tyr Thr Leu Thr Ile Ser Ser Leu Gln Ser
65                  70                  75                  80

Glu Asp Phe Ala Val Tyr Phe Cys Leu Gln Gly Ser Lys Phe Pro Leu
                85                  90                  95

Thr Phe Gly Gln Gly Thr Lys Leu Glu Ile Lys Arg
            100                 105

<210> SEQ ID NO 187
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Pro Met Ala Trp Val Arg Gln Ala Pro Gly Lys Gly Leu Glu Trp Val
        35                  40                  45
```

```
Ala Thr Ile Ser Ser Asp Gly Thr Thr Tyr Tyr Arg Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 188
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg His Phe
                20                  25                  30

Pro Met Ala Trp Val Arg Gln Ala Pro Gly Lys Gly Leu Glu Trp Val
            35                  40                  45

Ala Thr Ile Ser Ser Asp Ala Trp Pro Ser Tyr Arg Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ser Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 189
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Val Glu Ser Gly Gly Gly Leu Val Gln Pro Gly Gly
 1               5                  10                  15

Ser Leu Arg Leu Ser Cys Ala Ser Gly Phe Thr Phe Gly Asn Phe
                20                  25                  30

Pro Met Ser Trp Val Arg Gln Ala Pro Gly Lys Gly Leu Glu Trp Val
            35                  40                  45

Ala Ser Ile Ser Ser Asp Ser Trp Ala Thr Ile Gly Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ser Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 190
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Gly Trp Pro Thr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 191
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg His Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Asp Trp Pro Asn Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Tyr Tyr Asn Ser Pro Phe Ala Tyr Trp Gly Gln Gly Thr
            100                 105                 110

Leu Val Thr Val Ser Ser
        115

<210> SEQ ID NO 192
```

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Tyr Phe
            20                  25                  30

Pro Met Ser Trp Val Arg Gln Ala Pro Gly Lys Gly Leu Glu Trp Val
        35                  40                  45

Ala Ser Ile Ser Gly Ser Asp Gly Trp Ala Ser Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Ser Trp Gly Gln Gly Thr
            100                 105                 110

Leu Val Thr Val Ser Ser
        115

<210> SEQ ID NO 193
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Tyr Phe
            20                  25                  30

Pro Met Ala Trp Val Arg Gln Ala Pro Gly Lys Gly Leu Glu Trp Val
        35                  40                  45

Ala Thr Ile Ser Gly Ser Asp Glu Trp Pro Asn Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Phe Trp Gly Gln Gly Thr
            100                 105                 110

Leu Val Thr Val Ser Ser
        115

<210> SEQ ID NO 194
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Tyr Phe
            20                  25                  30

Pro Met Ser Trp Val Arg Gln Ala Pro Gly Lys Gly Leu Glu Trp Val
        35                  40                  45

Ala Ser Ile Ser Gly Ser Asp Gly Trp Ala Ser Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 195
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg His Phe
            20                  25                  30

Pro Met Ala Trp Val Arg Gln Ala Pro Gly Lys Gly Leu Glu Trp Val
        35                  40                  45

Ala Thr Ile Ser Ser Ser Asp Ala Trp Pro Ser Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Asn Ser Pro Phe Ala Tyr Trp Gly Gln Gly Thr
            100                 105                 110

Leu Val Thr Val Ser Ser
            115

<210> SEQ ID NO 196
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Asn Phe
            20                  25                  30

Pro Met Ser Trp Val Arg Gln Ala Pro Gly Lys Gly Leu Glu Trp Val
        35                  40                  45

```
Ala Ser Ile Ser Ser Ser Asp Ser Trp Ala Thr Ile Gly Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Tyr Tyr Asn Ser Pro Phe Ala Phe Trp Gly Gln Gly Thr
            100                 105                 110

Leu Val Thr Val Ser Ser
        115

<210> SEQ ID NO 197
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Tyr Ser Asn
            20                  25                  30

Leu Ala Trp Tyr Gln Gln Lys Pro Gly Lys Ala Pro Lys Leu Leu Ile
        35                  40                  45

Tyr Asp Thr Asn Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Pro
                85                  90                  95

Thr Phe Gly Gln Gly Thr Lys Leu Glu Ile Lys
            100                 105

<210> SEQ ID NO 198
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Tyr Ile Asn
            20                  25                  30

Leu Ala Trp Tyr Gln Gln Lys Pro Gly Lys Ser Pro Lys Leu Leu Ile
        35                  40                  45

Phe Asp Thr Asn Asp Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Tyr Val Pro Pro
                85                  90                  95

Thr Phe Gly Gln Gly Thr Lys Leu Glu Ile Lys
            100                 105
```

<210> SEQ ID NO 199
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Tyr Tyr Asn
            20                  25                  30

Leu Ala Trp Tyr Gln Gln Lys Pro Gly Lys Ser Pro Lys Leu Leu Ile
        35                  40                  45

Phe Asp Thr Ser Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Trp Tyr Pro Pro
                85                  90                  95

Thr Phe Gly Gln Gly Thr Lys Leu Glu Ile Lys
            100                 105

<210> SEQ ID NO 200
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Tyr Ile Asn
            20                  25                  30

Leu Ala Trp Tyr Gln Gln Lys Pro Gly Lys Ala Pro Lys Leu Leu Ile
        35                  40                  45

Phe Asp Thr Ser Asp Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Tyr Tyr Pro Pro
                85                  90                  95

Thr Phe Gly Gln Gly Thr Lys Leu Glu Ile Lys
            100                 105

<210> SEQ ID NO 201
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Tyr Tyr Asn

```
            20                  25                  30

Leu Ala Trp Tyr Gln Gln Lys Pro Gly Lys Ala Pro Lys Leu Leu Ile
            35                  40                  45

Phe Asp Thr Asn Ile Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Tyr Val Pro Pro
                85                  90                  95

Thr Phe Gly Gln Gly Thr Lys Leu Glu Ile Lys
            100                 105

<210> SEQ ID NO 202
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Trp Asn Asn
            20                  25                  30

Leu Ala Trp Tyr Gln Gln Lys Pro Gly Lys Ser Pro Lys Leu Leu Ile
            35                  40                  45

Phe Asp Thr Ser Tyr Leu Ala Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Trp Tyr Pro Pro
                85                  90                  95

Thr Phe Gly Gln Gly Thr Lys Leu Glu Ile Lys
            100                 105

<210> SEQ ID NO 203
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Tyr Arg Asn
            20                  25                  30

Leu Ala Trp Tyr Gln Gln Lys Pro Gly Lys Ser Pro Lys Leu Leu Ile
            35                  40                  45

Phe Asp Thr Ser Val Leu Ala Asp Gly Val Pro Ser Arg Phe Ser Gly
        50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Thr Tyr Tyr Pro Pro
                85                  90                  95

Thr Phe Gly Gln Gly Thr Lys Leu Glu Ile Lys
```

```
                      100                 105
```

```
<210> SEQ ID NO 204
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Ser, Arg, Asn, Gly, Lys, Thr or Leu
<220> FEATURE:
<221> NAME/KEY: MOD_RES
<222> LOCATION: (31)..(31)
<223> OTHER INFORMATION: Asn, Tyr, His, Ser or Ala
<220> FEATURE:
<221> NAME/KEY: MOD_RES
<222> LOCATION: (32)..(32)
<223> OTHER INFORMATION: Phe or Tyr
<220> FEATURE:
<221> NAME/KEY: MOD_RES
<222> LOCATION: (35)..(35)
<223> OTHER INFORMATION: Ala, Ser or Thr
<220> FEATURE:
<221> NAME/KEY: MOD_RES
<222> LOCATION: (50)..(50)
<223> OTHER INFORMATION: Thr, Ser or Ala
<220> FEATURE:
<221> NAME/KEY: MOD_RES
<222> LOCATION: (53)..(53)
<223> OTHER INFORMATION: Ser or Gly
<220> FEATURE:
<221> NAME/KEY: MOD_RES
<222> LOCATION: (56)..(56)
<223> OTHER INFORMATION: Gly, Ser, Ala, Glu, Asp, Phe, Gln or Cys
<220> FEATURE:
<221> NAME/KEY: MOD_RES
<222> LOCATION: (57)..(57)
<223> OTHER INFORMATION: Thr, Ser, Phe or Trp
<220> FEATURE:
<221> NAME/KEY: MOD_RES
<222> LOCATION: (58)..(58)
<223> OTHER INFORMATION: Thr, Ala, Asp, Ser or Pro
<220> FEATURE:
<221> NAME/KEY: MOD_RES
<222> LOCATION: (59)..(59)
<223> OTHER INFORMATION: Tyr, Ser, Asn, Thr, Ala or Asp
<220> FEATURE:
<221> NAME/KEY: MOD_RES
<222> LOCATION: (60)..(60)
<223> OTHER INFORMATION: Tyr or Ile
<220> FEATURE:
<221> NAME/KEY: MOD_RES
<222> LOCATION: (61)..(61)
<223> OTHER INFORMATION: Arg or Gly
<220> FEATURE:
<221> NAME/KEY: MOD_RES
<222> LOCATION: (77)..(77)
<223> OTHER INFORMATION: Asn or Ser
<220> FEATURE:
<221> NAME/KEY: MOD_RES
<222> LOCATION: (78)..(78)
<223> OTHER INFORMATION: Ser or Leu
<220> FEATURE:
<221> NAME/KEY: MOD_RES
<222> LOCATION: (89)..(89)
<223> OTHER INFORMATION: Glu or Asp
<220> FEATURE:
<221> NAME/KEY: MOD_RES
<222> LOCATION: (106)..(106)
<223> OTHER INFORMATION: Ala or Asp
<220> FEATURE:
<221> NAME/KEY: MOD_RES
<222> LOCATION: (107)..(107)
<223> OTHER INFORMATION: Tyr, Phe or Ser
```

```
<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Xaa
                20                  25                  30

Pro Met Xaa Trp Val Arg Gln Ala Pro Gly Lys Gly Leu Glu Trp Val
            35                  40                  45

Ala Xaa Ile Ser Xaa Ser Asp Xaa Xaa Xaa Xaa Xaa Asp Ser Val
    50                  55                  60

Lys Gly Arg Phe Thr Ile Ser Arg Asp Asn Ala Lys Xaa Xaa Leu Tyr
65                  70                  75                  80

Leu Gln Met Asn Ser Leu Arg Ala Xaa Asp Thr Ala Val Tyr Tyr Cys
                85                  90                  95

Ala Arg Gly Tyr Tyr Asn Ser Pro Phe Xaa Xaa Trp Gly Gln Gly Thr
            100                 105                 110

Leu Val Thr Val Ser Ser
            115

<210> SEQ ID NO 205
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Ser or Thr
<220> FEATURE:
<221> NAME/KEY: MOD_RES
<222> LOCATION: (27)..(27)
<223> OTHER INFORMATION: Glu or Gln
<220> FEATURE:
<221> NAME/KEY: MOD_RES
<222> LOCATION: (28)..(28)
<223> OTHER INFORMATION: Asp, Glu or Thr
<220> FEATURE:
<221> NAME/KEY: MOD_RES
<222> LOCATION: (30)..(30)
<223> OTHER INFORMATION: Tyr, Trp, Glu, Asp or Asn
<220> FEATURE:
<221> NAME/KEY: MOD_RES
<222> LOCATION: (31)..(31)
<223> OTHER INFORMATION: Ser, Asn, Ile, Thr, Arg, Met or Gly
<220> FEATURE:
<221> NAME/KEY: MOD_RES
<222> LOCATION: (43)..(43)
<223> OTHER INFORMATION: Ala or Ser
<220> FEATURE:
<221> NAME/KEY: MOD_RES
<222> LOCATION: (49)..(49)
<223> OTHER INFORMATION: Tyr or Phe
<220> FEATURE:
<221> NAME/KEY: MOD_RES
<222> LOCATION: (53)..(53)
<223> OTHER INFORMATION: Asn, Ser, Asp, Gln, Thr, Val or Glu
<220> FEATURE:
<221> NAME/KEY: MOD_RES
<222> LOCATION: (71)..(71)
<223> OTHER INFORMATION: Phe or Ser
<220> FEATURE:
<221> NAME/KEY: MOD_RES
<222> LOCATION: (87)..(87)
<223> OTHER INFORMATION: Tyr or Phe
<220> FEATURE:
<221> NAME/KEY: MOD_RES
<222> LOCATION: (91)..(91)
<223> OTHER INFORMATION: Tyr or Ser
<220> FEATURE:
```

```
<221> NAME/KEY: MOD_RES
<222> LOCATION: (92)..(92)
<223> OTHER INFORMATION: Asn, Asp, Thr or Tyr
<220> FEATURE:
<221> NAME/KEY: MOD_RES
<222> LOCATION: (93)..(93)
<223> OTHER INFORMATION: Asn, Trp, Tyr, Ile, Phe or Pro
<220> FEATURE:
<221> NAME/KEY: MOD_RES
<222> LOCATION: (94)..(94)
<223> OTHER INFORMATION: Tyr or Val
<220> FEATURE:
<221> NAME/KEY: MOD_RES
<222> LOCATION: (97)..(97)
<223> OTHER INFORMATION: Thr or Pro

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Xaa Xaa Xaa Ile Xaa Xaa Asn
            20                  25                  30

Leu Ala Trp Tyr Gln Gln Lys Pro Gly Lys Xaa Pro Lys Leu Leu Ile
        35                  40                  45

Xaa Asp Thr Asn Xaa Leu Ala Asp Gly Val Pro Ser Arg Phe Ser Gly
    50                  55                  60

Ser Gly Ser Gly Thr Asp Xaa Thr Leu Thr Ile Ser Ser Leu Gln Pro
65                  70                  75                  80

Glu Asp Phe Ala Thr Tyr Xaa Cys Gln Gln Xaa Xaa Xaa Xaa Pro Pro
                85                  90                  95

Xaa Phe Gly Gln Gly Thr Lys Leu Glu Ile Lys
            100                 105

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 206

His His His His His His
1               5
```

THERAPEUTIC DLL4 BINDING PROTEINS

REFERENCE TO RELATED APPLICATIONS

This application claims priority to U.S. provisional application No. 61/309,494, filed Mar. 2, 2010, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 24, 2011, is named 10920USO.txt and is 111,513 bytes in size.

FIELD OF THE INVENTION

The present invention relates to the development and use of DLL4 binding proteins and uses thereof in the inhibition, prevention, and/or treatment of cancers, tumors, other angiogenesis-dependent diseases, angiogenesis-independent diseases, and macular degeneration and age-related macular degeneration diseases characterized by aberrant DLL4 expression or activity.

BACKGROUND OF THE INVENTION

Cell-to-cell communication is required for many biological processes such as differentiation, proliferation, and homeostasis. One system utilized by a wide range of eukaryotes is the Notch-signaling pathway. This pathway, especially the Notch receptor, is also critical for functional tumor angiogenesis. Thus, inhibition of Notch receptor function, blockage of the Notch receptor, and/or blockage of the Notch-signaling pathway are potential strategies for anti-cancer compositions and therapies. Small molecule inhibitors of the Notch receptor have proven to be toxic because they suppress wild type (normal) tissue expression of Notch receptors throughout the body. Thus, different members of the Notch-signaling pathway should be considered as potential targets for therapeutics.

A vasculature ligand for the Notch receptor is Delta 4 or Delta-like 4 (DLL4). Largely expressed in the vasculature, DLL4 is critical for vascular development (Yan et al., Clin. Cancer Res., 13(24): 7243-7246 (2007); Shutter et al., Genes Dev., 14(11): 1313-1318 (2000); Gale et al., Proc. Natl. Acad. Sci. USA, 101(45): 15949-15954 (2004); Krebs et al., Genes Dev., 14(11): 1343-1352 (2000)). Mice heterozygous for DLL4 are embryonically lethal due to major defects in vascular development (Gale et al., Proc. Natl. Acad. Sci. USA, 101(45): 15949-15954 (2004); Duarte et al., Genes Dev., 18(20): 2474-2478 (2004); Krebs et al., Genes Dev., 18(20): 2469-2473 (2004)). The expression of DLL4 can be induced by VEGF (Liu et al., Mol. Cell. Biol., 23(1): 14-25 (2003); Lobov et al., Proc. Natl. Acad. Sci. USA, 104(9): 3219-3224 (2007)). In sum, DLL4 can negatively regulate VEGF signaling, in part through repressing VEGFR2 and inducing VEGFR1 (Harrington et al., Microvasc. Res., 75(2): 144-154 (2008); Suchting et al., Proc. Natl. Acad. Sci. USA, 104(9): 3225-3230 (2007)). Exquisite coordination between DLL4 and VEGF is essential for functional angiogenesis.

In addition to its physiological role, DLL4 is up-regulated in tumor blood vessels (Gale et al., Proc. Natl. Acad. Sci. USA, 101(45): 15949-15954 (2004); Mailhos et al., Differentiation, 69(2-3): 135-144 (2001); Patel et al., Cancer Res., 65(19): 8690-8697 (2005); Patel et al., Clin. Cancer Res., 12(16): 4836-4844 (2006); Noguera-Troise et al., Nature, 444(7122): 1032-1037 (2006)). Blockade of DLL4 potently inhibited primary tumor growth in multiple models (Noguera-Troise et al., Nature, 444(7122): 1032-1037 (2006); Ridgway et al., Nature, 444(7122): 1083-1087 (2006); Scehnet et al., Blood, 109(11): 4753-4760 (2007)). The inhibition of DLL4 was even effective against tumors that are resistant to anti-VEGF therapy. The combinatorial inhibition of both DLL4 and VEGF provided an enhanced anti-tumor activity. Interestingly, unlike VEGF inhibition that reduces tumor vessel formation, DLL4 blockade leads to an increase in tumor vasculature density wherein the vessels are abnormal, cannot support efficient blood transport, and are effectively nonfunctional. Thus, DLL4 provides a potential target for cancer treatment.

There is a need in the art for therapeutic agents capable of targeting the DLL4-Notch pathway and thereby inhibiting, or even preventing, tumor angiogenesis and growth.

SUMMARY OF THE INVENTION

The invention provides proteins that bind human DLL4. DLL4 binding proteins of the invention include, but are not limited to, rat monoclonal antibodies, chimeric antibodies, CDR-grafted antibodies, humanized antibodies, primate-ized antibodies, affinity matured antibodies, and fragments thereof that are capable of binding human DLL4. Preferably, a binding protein described herein binds human DLL4 with high affinity. More preferably, a binding protein according to the invention is capable of neutralizing human DLL4. The invention also provides methods of making and using DLL4 binding proteins.

One aspect of the invention provides a binding protein capable of binding human DLL4, wherein the binding protein comprises at least one amino acid sequence selected from the group of amino acid sequences consisting of SEQ ID NO:157, SEQ ID NO:158, SEQ ID NO:159, SEQ ID NO:160, SEQ ID NO:161, SEQ ID NO:162, SEQ ID NO:163, and SEQ ID NO:164.

An aspect of this invention pertains to a binding protein comprising an antigen binding domain wherein the binding protein is capable of binding human DLL4, said antigen binding domain comprising at least one or more (i.e., two, three, four, five, or six) CDRs wherein:

CDR-H1 is selected from the group consisting of:
$X_1$-$X_2$-$X_3$-$X_4$-$X_5$ (SEQ ID NO:151), wherein;
$X_1$ is N, H, or Y;
$X_2$ is F;
$X_3$ is P;
$X_4$ is M;
$X_5$ is A or S;
residues 31-35 of SEQ ID NO:157 (CDR-H1 38H12);
residues 31-35 of SEQ ID NO:161 (CDR-H1 37D10);
residues 31-35 of SEQ ID NO:163 (CDR-H1 32C7);
residues 31-35 of SEQ ID NO:165 (CDR-H1 14G1);
residues 31-35 of SEQ ID NO:167 (CDR-H1 14A11);
residues 31-35 of SEQ ID NO:169 (CDR-H1 15D6);
residues 31-35 of SEQ ID NO:171 (CDR-H1 VH.1 1A11);
residues 31-35 of SEQ ID NO:172 (CDR-H1 VH.1a 1A11);
residues 31-35 of SEQ ID NO:173 (CDR-H1 VH.1b 1A11);
residues 31-35 of SEQ ID NO:174 (CDR-H1 VH.2a 1A11);
residues 31-35 of SEQ ID NO:179 (CDR-H1 VH.1 38H12);

residues 31-35 of SEQ ID NO:180 (CDR-H1 VH.1A 38H12);
residues 31-35 of SEQ ID NO:181 (CDR-H1 VH.1b 38H12);
residues 31-35 of SEQ ID NO:182 (CDR-H1 VH.2a 38H12);
residues 31-35 of SEQ ID NO:187 (CDR-H1 h1A11VH.1);
residues 31-35 of SEQ ID NO:188 (CDR-H1 h1A11.A6);
residues 31-35 of SEQ ID NO:189 (CDR-H1 h1A11.A8);
residues 31-35 of SEQ ID NO:190 (CDR-H1 h1A11.C6);
residues 31-35 of SEQ ID NO:191 (CDR-H1 h1A11.A11);
residues 31-35 of SEQ ID NO:192 (CDR-H1 h1A11.B5);
residues 31-35 of SEQ ID NO:193 (CDR-H1 h1A11.E12);
residues 31-35 of SEQ ID NO:194 (CDR-H1 h1A11.G3);
residues 31-35 of SEQ ID NO:195 (CDR-H1 h1A11.F5); and
residues 31-35 of SEQ ID NO:196 (CDR-H1 h1A11.H2);
CDR-H2 is selected from the group consisting of:
$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$ (SEQ ID NO:152), wherein;
$X_1$ is T or S;
$X_2$ is I;
$X_3$ is S;
$X_4$ is S or G;
$X_5$ is S;
$X_6$ is D;
$X_7$ is G, A, D, S, or E;
$X_8$ is T or W;
$X_9$ is T, P, or A;
$X_{10}$ is Y, S, T, or N;
$X_{11}$ is Y or I;
$X_{12}$ is R or G;
$X_{13}$ is D;
$X_{14}$ is S;
$X_{15}$ is V;
$X_{16}$ is K; and
$X_{17}$ is G;
residues 50-66 of SEQ ID NO:157 (CDR-H2 38H12);
residues 50-68 of SEQ ID NO:161 (CDR-H2 37D10);
residues 50-66 of SEQ ID NO:163 (CDR-H2 32C7);
residues 50-66 of SEQ ID NO:165 (CDR-H2 14G1);
residues 50-66 of SEQ ID NO:167 (CDR-H2 14A11);
residues 50-66 of SEQ ID NO:169 (CDR-H2 15D6);
residues 50-66 of SEQ ID NO:171 (CDR-H2 VH.1 1A11);
residues 50-66 of SEQ ID NO:172 (CDR-H2 VH.1a 1A11);
residues 50-66 of SEQ ID NO:173 (CDR-H2 VH.1b 1A11);
residues 50-66 of SEQ ID NO:174 (CDR-H2 VH.2a 1A11);
residues 50-66 of SEQ ID NO:179 (CDR-H2 VH.1 38H12);
residues 50-66 of SEQ ID NO:180 (CDR-H2 VH.1A 38H12);
residues 50-66 of SEQ ID NO:181 (CDR-H2 VH.1b 38H12);
residues 31-35 of SEQ ID NO:182 (CDR-H1 VH.2a 38H12);
residues 50-66 of SEQ ID NO:187 (CDR-H2 h1A11VH.1);
residues 50-66 of SEQ ID NO:188 (CDR-H2 h1A11.A6);
residues 50-66 of SEQ ID NO:189 (CDR-H2 h1A11.A8);
residues 50-66 of SEQ ID NO:190 (CDR-H2 h1A11.C6);
residues 50-66 of SEQ ID NO:191 (CDR-H2 h1A11.A11);
residues 50-66 of SEQ ID NO:192 (CDR-H2 h1A11.B5);
residues 50-66 of SEQ ID NO:193 (CDR-H2 h1A11.E12);
residues 50-66 of SEQ ID NO:194 (CDR-H2 h1A11.G3);
residues 50-66 of SEQ ID NO:195 (CDR-H2 h1A11.F5); and
residues 50-66 of SEQ ID NO:196 (CDR-H2 h1A11.H2);
CDR-H3 is selected from the group consisting of:
$X_1$-$X_2$-$X_3$-$X_4$-$X_5$-$X_6$-$X_7$-$X_8$-$X_9$ (SEQ ID NO:153), wherein;
$X_1$ is G;
$X_2$ is Y;
$X_3$ is Y;
$X_4$ is N;
$X_5$ is S;
$X_6$ is P;
$X_7$ is F;
$X_8$ is A; and
$X_9$ is Y, F, or S;
residues 99-107 of SEQ ID NO:157 (CDR-H3 38H12);
residues 101-111 of SEQ ID NO:161 (CDR-H3 37D10);
residues 99-105 of SEQ ID NO:163 (CDR-H3 32C7);
residues 99-105 of SEQ ID NO:165 (CDR-H3 14G1);
residues 99-110 of SEQ ID NO:167 (CDR-H3 14A11);
residues 99-110 of SEQ ID NO:169 (CDR-H3 15D6);
residues 99-107 of SEQ ID NO:171 (CDR-H3 VH.1 1A11);
residues 99-107 of SEQ ID NO:172 (CDR-H3 VH.1a 1A11);
residues 99-107 of SEQ ID NO:173 (CDR-H3 VH.1b 1A11);
residues 99-107 of SEQ ID NO:174 (CDR-H3 VH.2a 1A11);
residues 99-107 of SEQ ID NO:179 (CDR-H3 VH.1 38H12);
residues 99-107 of SEQ ID NO:180 (CDR-H3 VH.1A 38H12);
residues 99-107 of SEQ ID NO:181 (CDR-H2 VH.1b 38H12);
residues 99-107 of SEQ ID NO:182 (CDR-H1 VH.2a 38H12);
residues 99-107 of SEQ ID NO:187 (CDR-H3 h1A11VH.1);
residues 99-107 of SEQ ID NO:188 (CDR-H3 h1A11.A6);
residues 99-107 of SEQ ID NO:189 (CDR-H3 h1A11.A8);
residues 99-107 of SEQ ID NO:190 (CDR-H3 h1A11.C6);
residues 99-107 of SEQ ID NO:191 (CDR-H3 h1A11.A11);

residues 99-107 of SEQ ID NO:192 (CDR-H3 h1A11.B5);
residues 99-107 of SEQ ID NO:193 (CDR-H3 h1A11.E12);
residues 99-107 of SEQ ID NO:194 (CDR-H3 h1A11.G3);
residues 99-107 of SEQ ID NO:195 (CDR-H3 h1A11.F5); and
residues 99-107 of SEQ ID NO:196 (CDR-H3 h1A11.H2);

CDR-L1 is selected from the group consisting of:
$X_1$-$X_2$-$X_3$-$X_4$-$X_5$-$X_6$-$X_7$-$X_8$-$X_9$-$X_{10}$-$X_{11}$ (SEQ ID NO:154), wherein;
 $X_1$ is R;
 $X_2$ is A;
 $X_3$ is S;
 $X_4$ is E or Q;
 $X_5$ is D or E;
 $X_6$ is I;
 $X_7$ is Y or W;
 $X_8$ is S, I, Y, N, or R;
 $X_9$ is N;
 $X_{10}$ is L; and
 $X_{11}$ is A;
residues 24-34 of SEQ ID NO:158 (CDR-L1 38H12);
residues 24-34 of SEQ ID NO:162 (CDR-L1 37D10);
residues 24-34 of SEQ ID NO:164 (CDR-L1 32C7);
residues 24-34 of SEQ ID NO:166 (CDR-L1 14G1);
residues 23-37 of SEQ ID NO:168 (CDR-L1 14A11);
residues 23-37 of SEQ ID NO:170 (CDR-L1 15D6);
residues 24-34 of SEQ ID NO:175 (CDR-L1 VL.1 1A11);
residues 24-34 of SEQ ID NO:176 (CDR-L1 VL.1a 1A11);
residues 24-34 of SEQ ID NO:177 (CDR-L1 VL.1b 1A11);
residues 24-34 of SEQ ID NO:178 (CDR-L1 VL.2a 1A11);
residues 24-34 of SEQ ID NO:183 (CDR-L1 VL.1 38H12);
residues 24-34 of SEQ ID NO:184 (CDR-L1 VL.1a 38H12);
residues 24-34 of SEQ ID NO:185 (CDR-L1 VL.1b 38H12);
residues 24-34 of SEQ ID NO:186 (CDR-L1 VL.2a 38H12);
residues 24-34 of SEQ ID NO:197 (CDR-L1 h1A11VL.1);
residues 24-34 of SEQ ID NO:198 (CDR-L1 h1A11.A2);
residues 24-34 of SEQ ID NO:199 (CDR-L1 h1A11.A12);
residues 24-34 of SEQ ID NO:200 (CDR-L1 h1A11.A7);
residues 24-34 of SEQ ID NO:201 (CDR-L1 h1A11.B4);
residues 24-34 of SEQ ID NO:202 (CDR-L1 h1A11.B5); and
residues 24-34 of SEQ ID NO:203 (CDR-L1 h1A11.E12);

CDR-L2 is selected from group consisting of:
$X_1$-$X_2$-$X_3$-$X_4$-$X_5$-$X_6$-$X_7$ (SEQ ID NO:155), wherein;
 $X_1$ is D;
 $X_2$ is T;
 $X_3$ is N or S;
 $X_4$ is N, D, S, I, Y, or V;
 $X_5$ is L;
 $X_6$ is A; and
 $X_7$ is D;
residues 50-56 of SEQ ID NO:158 (CDR-L2 38H12);
residues 50-56 of SEQ ID NO:162 (CDR-L2 37D10);
residues 50-56 of SEQ ID NO:164 (CDR-L2 32C7);
residues 50-56 of SEQ ID NO:166 (CDR-L2 14G1);
residues 53-59 of SEQ ID NO:168 (CDR-L2 14A11);
residues 53-59 of SEQ ID NO:170 (CDR-L2 15D6);
residues 50-56 of SEQ ID NO:175 (CDR-L2 VL.1 1A11);
residues 50-56 of SEQ ID NO:176 (CDR-L2 VL.1a 1A11);
residues 50-56 of SEQ ID NO:177 (CDR-L2 VL.1b 1A11);
residues 50-56 of SEQ ID NO:178 (CDR-L2 VL.2a 1A11);
residues 50-56 of SEQ ID NO:183 (CDR-L2 VL.1 38H12);
residues 50-56 of SEQ ID NO:184 (CDR-L2 VL.1a 38H12);
residues 50-56 of SEQ ID NO:185 (CDR-L2 VL.1b 38H12);
residues 50-56 of SEQ ID NO:186 (CDR-L2 VL.2a 38H12);
residues 50-56 of SEQ ID NO:197 (CDR-L2 h1A11VL.1);
residues 50-56 of SEQ ID NO:198 (CDR-L2 h1A11.A2);
residues 50-56 of SEQ ID NO:199 (CDR-L2 h1A11.A12);
residues 50-56 of SEQ ID NO:200 (CDR-L2 h1A11.A7);
residues 50-56 of SEQ ID NO:201 (CDR-L2 h1A11.B4);
residues 50-56 of SEQ ID NO:202 (CDR-L2 h1A11.B5); and
residues 50-56 of SEQ ID NO:203 (CDR-L2 h1A11.E12); and CDR-L3 is selected from the group consisting of:
$X_1$-$X_2$-$X_3$-$X_4$-$X_5$-$X_6$-$X_7$-$X_8$-$X_9$ (SEQ ID NO:156), wherein;
 $X_1$ is Q;
 $X_2$ is Q;
 $X_3$ is Y;
 $X_4$ is N, D, or T;
 $X_5$ is N, Y, or W;
 $X_6$ is Y or V;
 $X_7$ is P;
 $X_8$ is P; and
 $X_9$ is T.
residues 89-97 of SEQ ID NO:158 (CDR-L3 38H12);
residues 89-97 of SEQ ID NO:162 (CDR-L3 37D10);
residues 89-97 of SEQ ID NO:164 (CDR-L3 32C7);
residues 89-98 of SEQ ID NO:166 (CDR-L3 14G1);
residues 92-100 of SEQ ID NO:168 (CDR-L3 14A11);
residues 92-100 of SEQ ID NO:170 (CDR-L3 15D6);
residues 89-97 of SEQ ID NO:175 (CDR-L3 VL.1 1A11);
residues 89-97 of SEQ ID NO:176 (CDR-L3 VL.1a 1A11);
residues 89-97 of SEQ ID NO:177 (CDR-L3 VL.1b 1A11);
residues 89-97 of SEQ ID NO:178 (CDR-L3 VL.2a 1A11);
residues 89-97 of SEQ ID NO:183 (CDR-L3 VL.1 38H12);

residues 89-97 of SEQ ID NO:184 (CDR-L3 VL.1a 38H12);
residues 89-97 of SEQ ID NO:185 (CDR-L3 VL.1b 38H12);
residues 89-97 of SEQ ID NO:186 (CDR-L3 VL.2a 38H12);
residues 89-97 of SEQ ID NO:197 (CDR-L3 h1A11VL.1);
residues 89-97 of SEQ ID NO:198 (CDR-L3 h1A11.A2);
residues 89-97 of SEQ ID NO:199 (CDR-L3 h1A11.A12);
residues 89-97 of SEQ ID NO:200 (CDR-L3 h1A11.A7);
residues 89-97 of SEQ ID NO:201 (CDR-L3 h1A11.B4);
residues 89-97 of SEQ ID NO:202 (CDR-L3 h1A11.B5);
residues 89-97 of SEQ ID NO:203 (CDR-L3 h1A11.E12).

Preferably, a DLL4 binding protein of the invention comprises at least one CDR comprising an amino acid sequence selected from the group consisting of: residues 31-35 of SEQ ID NO:157 (CDR-H1 38H12); residues 50-66 of SEQ ID NO:157 (CDR-H2 38H12); residues 99-107 of SEQ ID NO:157 (CDR-H3 38H12); residues 24-34 of SEQ ID NO:158 (CDR-L1 38H12); residues 50-56 of SEQ ID NO:158 (CDR-L2 38H12); residues 89-97 of SEQ ID NO:158 (CDR-L3 38H12); residues 31-35 of SEQ ID NO:159 (CDR-H1 1A11); residues 50-66 of SEQ ID NO:159 (CDR-H2 1A11); residues 99-107 of SEQ ID NO:159 (CDR-H3 1A11); residues 24-34 of SEQ ID NO:160 (CDR-L1 1A11); residues 50-56 of SEQ ID NO:160 (CDR-L2 1A11); residues 89-97 of SEQ ID NO:160 (CDR-L3 1A11); residues 31-35 of SEQ ID NO:161 (CDR-H1 37D10); residues 50-68 of SEQ ID NO:161 (CDR-H2 37D10); residues 101-111 of SEQ ID NO:161 (CDR-H3 37D10);

residues 24-34 of SEQ ID NO:162 (CDR-L1 37D10); residues 50-56 of SEQ ID NO:162 (CDR-L2 37D10); residues 89-97 of SEQ ID NO:162 (CDR-L3 37D10); residues 31-35 of SEQ ID NO:163 (CDR-H1 32C7); residues 50-66 of SEQ ID NO:163 (CDR-H2 32C7); residues 99-105 of SEQ ID NO:163 (CDR-H3 32C7); residues 24-34 of SEQ ID NO:164 (CDR-L1 32C7); residues 50-56 of SEQ ID NO:164 (CDR-L2 32C7); residues 89-98 of SEQ ID NO:164 (CDR-L3 32C7); residues 31-35 of SEQ ID NO:165 (CDR-H1 14G1); residues 50-66 of SEQ ID NO:165 (CDR-H2 14G1); residues 99-105 of SEQ ID NO:165 (CDR-H3 14G1); residues 24-34 of SEQ ID NO:166 (CDR-L1 14G1); residues 50-56 of SEQ ID NO:166 (CDR-L2 14G1); residues 89-98 of SEQ ID NO:166 (CDR-L3 14G1); residues 31-35 of SEQ ID NO:167 (CDR-H1 14A11); residues 50-66 of SEQ ID NO:167 (CDR-H2 14A11); residues 99-110 of SEQ ID NO:167 (CDR-H3 14A11); residues 23-37 of SEQ ID NO:168 (CDR-L1 14A11); residues 53-59 of SEQ ID NO:168 (CDR-L2 14A11); residues 92-100 of SEQ ID NO:168 (CDR-L3 14A11); residues 31-35 of SEQ ID NO:169 (CDR-H1 15D6); residues 50-66 of SEQ ID NO:169 (CDR-H2 15D6); residues 99-110 of SEQ ID NO:169 (CDR-H3 15D6); residues 23-37 of SEQ ID NO:170 (CDR-L1 15D6); residues 53-59 of SEQ ID NO:170 (CDR-L2 15D6); residues 92-100 of SEQ ID NO:170 (CDR-L3 15D6); residues 31-35 of SEQ ID NO:171 (CDR-H1 VH.1 1A11); residues 50-66 of SEQ ID NO:171 (CDR-H2 VH.1 1A11); residues 99-107 of SEQ ID NO:171 (CDR-H3 VH.1 1A11); residues 31-35 of SEQ ID NO:172 (CDR-H1 VH.1a 1A11); residues 50-66 of SEQ ID NO:172 (CDR-H2 VH.1a 1A11); residues 99-107 of SEQ ID NO:172 (CDR-H3 VH.1a 1A11); residues 31-35 of SEQ ID NO:173 (CDR-H1 VH.1b 1A11); residues 50-66 of SEQ ID NO:173 (CDR-H2 VH.1b 1A11); residues 99-107 of SEQ ID NO:173 (CDR-H3 VH.1b 1A11); residues 31-35 of SEQ ID NO:174 (CDR-H1 VH.2a 1A11); residues 50-66 of SEQ ID NO:174 (CDR-H2 VH.2a 1A11); residues 99-107 of SEQ ID NO:174 (CDR-H3 VH.2a 1A11); residues 24-34 of SEQ ID NO:175 (CDR-L1 VL.1 1A11); residues 50-56 of SEQ ID NO:175 (CDR-L2 VL.1 1A11); residues 89-97 of SEQ ID NO:175 (CDR-L3 VL.1 1A11); residues 24-34 of SEQ ID NO:176 (CDR-L1 VL.1a 1A11); residues 50-56 of SEQ ID NO:176 (CDR-L2 VL.1a 1A11); residues 89-97 of SEQ ID NO:176 (CDR-L3 VL.1a 1A11); residues 24-34 of SEQ ID NO:177 (CDR-L1 VL.1b 1A11); residues 50-56 of SEQ ID NO:177 (CDR-L2 VL.1b 1A11); residues 89-97 of SEQ ID NO:177 (CDR-L3 VL.1b 1A11); residues 24-34 of SEQ ID NO:178 (CDR-L1 VL.2a 1A11); residues 50-56 of SEQ ID NO:178 (CDR-L2 VL.2a 1A11); residues 89-97 of SEQ ID NO:178 (CDR-L3 VL.2a 1A11); residues 31-35 of SEQ ID NO:179 (CDR-H1 VH.1 38H12); residues 50-66 of SEQ ID NO:179 (CDR-H2 VH.1 38H12); residues 99-107 of SEQ ID NO:179 (CDR-H3 VH.1 38H12); residues 31-35 of SEQ ID NO:180 (CDR-H1 VH.1A 38H12); residues 50-66 of SEQ ID NO:180 (CDR-H2 VH.1A 38H12); residues 99-107 of SEQ ID NO:180 (CDR-H3 VH.1A 38H12); residues 31-35 of SEQ ID NO:181 (CDR-H1 VH.1b 38H12); residues 50-66 of SEQ ID NO:181 (CDR-H2 VH.1b 38H12); residues 99-107 of SEQ ID NO:181 (CDR-H3 VH.1b 38H12); residues 31-35 of SEQ ID NO:182 (CDR-H1 VH.2a 38H12); residues 50-66 of SEQ ID NO:182 (CDR-H2 VH.2a 38H12); residues 99-107 of SEQ ID NO:182 (CDR-H3 VH.2a 38H12); residues 24-34 of SEQ ID NO:183 (CDR-L1 VL.1 38H12); residues 50-56 of SEQ ID NO:183 (CDR-L2 VL.1 38H12); residues 89-97 of SEQ ID NO:183 (CDR-L3 VL.1 38H12); residues 24-34 of SEQ ID NO:184 (CDR-L1 VL.1a 38H12); residues 50-56 of SEQ ID NO:184 (CDR-L2 VL.1a 38H12); residues 89-97 of SEQ ID NO:184 (CDR-L3 VL.1a 38H12); residues 24-34 of SEQ ID NO:185 (CDR-L1 VL.1b 38H12); residues 50-56 of SEQ ID NO:185 (CDR-L2 VL.1b 38H12); residues 89-97 of SEQ ID NO:185 (CDR-L3 VL.1b 38H12); residues 24-34 of SEQ ID NO:186 (CDR-L1 VL.2a 38H12); residues 50-56 of SEQ ID NO:186 (CDR-L2 VL.2a 38H12); residues 89-97 of SEQ ID NO:186 (CDR-L3 VL.2a 38H12); residues 31-35 of SEQ ID NO:187 (CDR-H1 h1A11VH.1), residues 50-66 of SEQ ID NO:187 (CDR-H2 h1A11VH.1); residues 99-107 of SEQ ID NO:187 (CDR-H3 h1A11VH.1); residues 31-35 of SEQ ID NO:188 (CDR-H1 h1A11.A6), residues 50-66 of SEQ ID NO:188 (CDR-H2 h1A11.A6); residues 99-107 of SEQ ID NO:188 (CDR-H3 h1A11.A6); residues 31-35 of SEQ ID NO:189 (CDR-H1 h1A11.A8), residues 50-66 of SEQ ID NO:189 (CDR-H2 h1A11.A8); residues 99-107 of SEQ ID NO:189 (CDR-H3 h1A11.A8); residues 31-35 of SEQ ID NO:190 (CDR-H1 h1A11.C6), residues 50-66 of SEQ ID NO:190 (CDR-H2 h1A11.C6); residues 99-107 of SEQ ID NO:190 (CDR-H3 h1A11.C6); residues 31-35 of SEQ ID NO:191 (CDR-H1 h1A11.A11), residues 50-66 of SEQ ID NO:191 (CDR-H2 h1A11.A11); residues 99-107 of SEQ ID NO:191 (CDR-H3 h1A11.A11); residues 31-35 of SEQ ID NO:192 (CDR-H1 h1A11.B5), residues 50-66 of SEQ ID NO:192 (CDR-H2 h1A11.B5); residues 99-107 of SEQ ID NO:192 (CDR-H3 h1A11.B5); residues 31-35 of SEQ ID NO:193 (CDR-H1 h1A11.E12), residues 50-66 of SEQ ID NO:193 (CDR-H2 h1A11.E12); residues 99-107 of SEQ ID NO:193 (CDR-H3 h1A11.E12); residues 31-35 of SEQ ID NO:194 (CDR-H1 h1A11.G3), residues 50-66 of SEQ ID NO:194 (CDR-H2 h1A11.G3); residues 99-107 of SEQ ID NO:194 (CDR-H3 h1A11.G3); residues 31-35 of SEQ ID NO:195 (CDR-H1 h1A11.F5), residues 50-66 of SEQ ID NO:195 (CDR-H2 h1A11.F5); residues 99-107 of SEQ ID NO:195 (CDR-H3 h1A11.F5); residues 31-35 of SEQ ID NO:196 (CDR-H1 h1A11.H2), residues 50-66 of SEQ ID NO:196 (CDR-H2 h1A11.H2); residues 99-107 of SEQ ID NO:196 (CDR-H3 h1A11.H2); residues 24-34 of SEQ ID NO:197 (CDR-L1 h1A11VL.1), residues 50-56 of SEQ ID NO:197 (CDR-L2 h1A11VL.1); residues 89-97 of SEQ ID NO:197 (CDR-L3 h1A11VL.1); residues 24-34 of SEQ ID NO:198 (CDR-L1 h1A11.A2), residues 50-56 of SEQ ID NO:198 (CDR-L2 h1A11.A2); residues 89-97 of SEQ ID NO:198 (CDR-L3 h1A11.A2); residues 24-34 of SEQ ID NO:199 (CDR-L1 h1A11.A12), residues 50-56 of SEQ ID NO:199 (CDR-L2 h1A11.A12); residues 89-97 of SEQ ID NO:199 (CDR-L3 h1A11.A12); residues 24-34 of SEQ ID NO:200 (CDR-L1 h1A11.A7), residues 50-56 of SEQ ID NO:200 (CDR-L2 h1A11.A7); residues 89-97 of SEQ ID NO:200 (CDR-L3 h1A11.A7); residues 24-34 of SEQ ID NO:201 (CDR-L1 h1A11.B4), residues 50-56 of SEQ ID NO:201 (CDR-L2 h1A11.B4); residues 89-97 of SEQ ID NO:201 (CDR-L3 h1A11.B4); residues 24-34 of SEQ ID NO:202 (CDR-L1 h1A11.B5), residues 50-56 of SEQ ID NO:202 (CDR-L2 h1A11.B5); residues 89-97 of SEQ ID NO:202 (CDR-L3 h1A11.B5); residues 24-34 of SEQ ID NO:203 (CDR-L1 h1A11.E12), residues 50-56 of SEQ ID NO:203 (CDR-L2 h1A11.E12); and residues 89-97 of SEQ ID NO:203 (CDR-L3 h1A11.E12).

In an embodiment, a DLL4 binding protein of the invention comprises at least three CDRs described herein (above or below). In a non-limiting example, a DLL4 binding protein of the invention comprises three CDRs described herein, wherein the three CDRs are a CDR-H1, a CDR-H2, and a CDR-H3 as described herein. In another non-limiting example, a DLL4 binding protein of the invention comprising three CDRs described herein, wherein the three CDRs are a CDR-L1, a CDR-L2, and a CDR-L3 as described herein.

In an embodiment, a DLL4 binding protein of the invention comprises one or more CDRs described herein (above or below), such as one, two, three, four, five, or six CDRs described herein. In a preferred embodiment, a DLL4 binding protein according to the invention comprises six CDRs described herein, e.g., a CDR-H1, a CDR-H2, a CDR-H3, a CDR-L1, a CDR-L2, and a CDR-L3 as described herein.

In another embodiment, a DLL4 binding protein of the invention comprises three CDRs selected from a set of variable domain CDRs, wherein the set of variable domain CDRs is selected from the group of variable domain CDR sets consisting of:

VH 38H12 CDR Set
CDR-H1: residues 31-35 of SEQ ID NO:157
CDR-H2: residues 50-66 of SEQ ID NO:157
CDR-H3 residues 99-107 of SEQ ID NO:157
VL 38H12 CDR Set
CDR-L1: residues 24-34 of SEQ ID NO:158
CDR-L2: residues 50-56 of SEQ ID NO:158
CDR-L3: residues 89-97 of SEQ ID NO:158
VH 1A11 CDR Set
CDR-H1: residues 31-35 of SEQ ID NO:159
CDR-H2: residues 50-66 of SEQ ID NO:159
CDR-H3: residues 99-107 of SEQ ID NO:159
VL 1A11 CDR Set
CDR-L1: residues 24-34 of SEQ ID NO:160
CDR-L2: residues 50-56 of SEQ ID NO:160
CDR-L3: residues 89-97 of SEQ ID NO:160
VH 37D10 CDR Set
CDR-H1: residues 31-35 of SEQ ID NO:161
CDR-H2: residues 50-68 of SEQ ID NO:161
CDR-H3: residues 101-111 of SEQ ID NO:161
VL 37D10 CDR Set
CDR-L1: residues 24-34 of SEQ ID NO:162
CDR-L2: residues 50-56 of SEQ ID NO:162
CDR-L3: residues 89-97 of SEQ ID NO:162
VH 32C7 CDR Set
CDR-H1: residues 31-35 of SEQ ID NO:163
CDR-H2: residues 50-66 of SEQ ID NO:163
CDR-H3: residues 99-105 of SEQ ID NO:163
VL 32C7 CDR Set
CDR-L1: residues 24-34 of SEQ ID NO:164
CDR-L2: residues 50-56 of SEQ ID NO:164
CDR-L3: residues 89-98 of SEQ ID NO:164
VH 14G1 CDR Set
CDR-H1: residues 31-35 of SEQ ID NO:165
CDR-H2: residues 50-66 of SEQ ID NO:165
CDR-H3: residues 99-105 of SEQ ID NO:165
VL 14G1 CDR Set
CDR-L1: residues 24-34 of SEQ ID NO:166
CDR-L2: residues 50-56 of SEQ ID NO:166
CDR-L3: residues 89-97 of SEQ ID NO:166
VH 14A11 CDR Set
CDR-H1: residues 31-35 of SEQ ID NO:167
CDR-H2: residues 50-66 of SEQ ID NO:167
CDR-H3: residues 99-110 of SEQ ID NO:167
VL 14A11 CDR Set
CDR-L1: residues 23-37 of SEQ ID NO:168
CDR-L2: residues 53-59 of SEQ ID NO:168
CDR-L3: residues 92-100 of SEQ ID NO:168
VH 15D6 CDR Set
CDR-H1: residues 31-35 of SEQ ID NO:169
CDR-H2: residues 50-66 of SEQ ID NO:169
CDR-H3: residues 99-110 of SEQ ID NO:169
VL 15D6 CDR Set
CDR-L1: residues 23-37 of SEQ ID NO:170
CDR-L2: residues 53-59 of SEQ ID NO:170
CDR-L3: residues 92-100 of SEQ ID NO:170
VH VH.1 1A11 CDR Set
CDR-H1: residues 31-35 of SEQ ID NO:171
CDR-H2: residues 50-66 of SEQ ID NO:171
CDR-H3: residues 99-107 of SEQ ID NO:171
VH VH.1a 1A11 CDR Set
CDR-H1: residues 31-35 of SEQ ID NO:172
CDR-H2: residues 50-66 of SEQ ID NO:172
CDR-H3: residues 99-107 of SEQ ID NO:172
VH VH.1b 1A11 CDR Set
CDR-H1: residues 31-35 of SEQ ID NO:173
CDR-H2: residues 50-66 of SEQ ID NO:173
CDR-H3: residues 99-107 of SEQ ID NO:173

VH VH.2a 1A11 CDR Set
CDR-H1: residues 31-35 of SEQ ID NO:174
CDR-H2: residues 50-66 of SEQ ID NO:174
CDR-H3: residues 99-107 of SEQ ID NO:174
VL VL.1 1A11 CDR Set
CDR-L1: residues 24-34 of SEQ ID NO:175
CDR-L2: residues 50-56 of SEQ ID NO:175
CDR-L3: residues 89-97 of SEQ ID NO:175
VL VL.1a 1A11 CDR Set
CDR-L1: residues 24-34 of SEQ ID NO:176
CDR-L2: residues 50-56 of SEQ ID NO:176
CDR-L3: residues 89-97 of SEQ ID NO:176
VL VL.1b 1A11 CDR Set
CDR-L1: residues 24-34 of SEQ ID NO:177
CDR-L2: residues 50-56 of SEQ ID NO:177
CDR-L3: residues 89-97 of SEQ ID NO:177
VL VL.2a 1A11 CDR Set
CDR-L1: residues 24-34 of SEQ ID NO:178
CDR-L2: residues 50-56 of SEQ ID NO:178
CDR-L3: residues 89-97 of SEQ ID NO:178
VH VH.1 38H12 CDR Set
CDR-H1: residues 31-35 of SEQ ID NO:179
CDR-H2: residues 50-66 of SEQ ID NO:179
CDR-H3: residues 99-107 of SEQ ID NO:179
VH VH.1a 38H12 CDR Set
CDR-H1: residues 31-35 of SEQ ID NO:180
CDR-H2: residues 50-66 of SEQ ID NO:180
CDR-H3: residues 99-107 of SEQ ID NO:180
VH VH.1b 38H12 CDR Set
CDR-H1: residues 31-35 of SEQ ID NO:181
CDR-H2: residues 50-66 of SEQ ID NO:181
CDR-H3: residues 99-107 of SEQ ID NO:181
VH VH.2a 38H12 CDR Set
CDR-H1: residues 31-35 of SEQ ID NO:182
CDR-H2: residues 50-66 of SEQ ID NO:182
CDR-H3: residues 99-107 of SEQ ID NO:182
VL VL.1 38H12 CDR Set
CDR-L1: residues 24-34 of SEQ ID NO:183
CDR-L2: residues 50-56 of SEQ ID NO:183
CDR-L3: residues 89-97 of SEQ ID NO:183
VL VL.1a 38H12 CDR Set
CDR-L1: residues 24-34 of SEQ ID NO:184
CDR-L2: residues 50-56 of SEQ ID NO:184
CDR-L3: residues 89-97 of SEQ ID NO:184
VL VL.1b 38H12 CDR Set
CDR-L1: residues 24-34 of SEQ ID NO:185
CDR-L2: residues 50-56 of SEQ ID NO:185
CDR-L3: residues 89-97 of SEQ ID NO:185
VL VL.2a 38H12 CDR Set
CDR-L1: residues 24-34 of SEQ ID NO:186
CDR-L2: residues 50-56 of SEQ ID NO:186
CDR-L3: residues 89-97 of SEQ ID NO:186
VH hA11VH.1 CDR Set
CDR-H1: residues 31-35 of SEQ ID NO:187
CDR-H2: residues 50-66 of SEQ ID NO:187
CDR-H3: residues 99-107 of SEQ ID NO:187
VH hA11.A6 CDR Set
CDR-H1: residues 31-35 of SEQ ID NO:188
CDR-H2: residues 50-66 of SEQ ID NO:188
CDR-H3: residues 99-107 of SEQ ID NO:188
VH hA11.A8 CDR Set
CDR-H1: residues 31-35 of SEQ ID NO:189
CDR-H2: residues 50-66 of SEQ ID NO:189
CDR-H3: residues 99-107 of SEQ ID NO:189
VH hA11.C6 CDR Set
CDR-H1: residues 31-35 of SEQ ID NO:190
CDR-H2: residues 50-66 of SEQ ID NO:190
CDR-H3: residues 99-107 of SEQ ID NO:190
VH hA11.A11 CDR Set
CDR-H1: residues 31-35 of SEQ ID NO:191
CDR-H2: residues 50-66 of SEQ ID NO:191
CDR-H3: residues 99-107 of SEQ ID NO:191
V hA11.B5 CDR Set
CDR-H1: residues 31-35 of SEQ ID NO:192
CDR-H2: residues 50-66 of SEQ ID NO:192
CDR-H3: residues 99-107 of SEQ ID NO:192
VH hA11.E12 CDR Set
CDR-H1: residues 31-35 of SEQ ID NO:193
CDR-H2: residues 50-66 of SEQ ID NO:193
CDR-H3: residues 99-107 of SEQ ID NO:193
VH hA11.G3 CDR Set
CDR-H1: residues 31-35 of SEQ ID NO:194
CDR-H2: residues 50-66 of SEQ ID NO:194
CDR-H3: residues 99-107 of SEQ ID NO:194
VH hA11.F5 CDR Set
CDR-H1: residues 31-35 of SEQ ID NO:195
CDR-H2: residues 50-66 of SEQ ID NO:195
CDR-H3: residues 99-107 of SEQ ID NO:195
VH hA11.H2 CDR Set
CDR-H1: residues 31-35 of SEQ ID NO:196
CDR-H2: residues 50-66 of SEQ ID NO:196
CDR-H3: residues 99-107 of SEQ ID NO:196
VL h1A11VL.1 CDR Set
CDR-L1: residues 24-34 of SEQ ID NO:197
CDR-L2: residues 50-56 of SEQ ID NO:197
CDR-L3: residues 89-97 of SEQ ID NO:197
VL h1A11.A2 CDR Set
CDR-L1: residues 24-34 of SEQ ID NO:198
CDR-L2: residues 50-56 of SEQ ID NO:198
CDR-L3: residues 89-97 of SEQ ID NO:198
VL h1A11.A12 CDR Set
CDR-L1: residues 24-34 of SEQ ID NO:199
CDR-L2: residues 50-56 of SEQ ID NO:199
CDR-L3: residues 89-97 of SEQ ID NO:199
VL h1A11.A7 CDR Set
CDR-L1: residues 24-34 of SEQ ID NO:200
CDR-L2: residues 50-56 of SEQ ID NO:200
CDR-L3: residues 89-97 of SEQ ID NO:200
VL h1A11.B4 CDR Set
CDR-L1: residues 24-34 of SEQ ID NO:201
CDR-L2: residues 50-56 of SEQ ID NO:201
CDR-L3: residues 89-97 of SEQ ID NO:201
VL h1A11.B5 CDR Set
CDR-L1: residues 24-34 of SEQ ID NO:202
CDR-L2: residues 50-56 of SEQ ID NO:202
CDR-L3: residues 89-97 of SEQ ID NO:202
and
VL h1A11.E12 CDR Set
CDR-L1: residues 24-34 of SEQ ID NO:203
CDR-L2: residues 50-56 of SEQ ID NO:203
CDR-L3: residues 89-97 of SEQ ID NO:203

In an embodiment, a DLL4 binding protein comprises CDRs from at least two sets of variable domain CDRs in the group above.

In another embodiment, a DLL4 binding protein of the invention comprises three CDRs selected from any VH set of three CDRs in the group above and three CDRs selected from any VL set of three CDRs in the group above.

In still another embodiment, a DLL4 binding protein of the invention comprises a VH set of three CDRs as described above and a VL set of three CDRs as described above from a pair of VH and VL sets of CDRs selected from the group consisting of:

VH 38H12 CDR Set and VL 38H12 CDR Set,
VH 1A11 CDR Set and VL 1A11 CDR Set,
VH 37D10 CDR Set and VL 37D10 CDR Set,
VH 32C7 CDR Set and VL 32C7 CDR Set,
VH 14G1 Set and VL 14G1 CDR Set,
VH 14A11 CDR Set and VL 14A11 CDR Set,
VH 15D6 CDR Set and VL 15D6 CDR Set,
VH VH.1 1A11 CDR Set and VL VL.1 1A11 CDR Set,
VH VH.1 1A11 CDR Set and VL VL.1a 1A11 CDR Set,
VH VH.1 1A11 CDR Set and VL VL.1b 1A11 CDR Set,
VH VH.1 1A11 CDR Set and VL VL.2a 1A11 CDR Set,
VH VH.1a 1A11 CDR Set and VL VL.1 1A11 CDR Set,
VH VH.1a 1A11 CDR Set and VL VL.1a 1A11 CDR Set,
VH VH.1a 1A11 CDR Set and VL VL.1b 1A11 CDR Set,
VH VH.1a 1A11 CDR Set and VL VL.2a 1A11 CDR Set,
VH VH.1b 1A11 CDR Set and VL VL.1 1A11 CDR Set,
VH VH.1b 1A11 CDR Set and VL VL.1a 1A11 CDR Set,
VH VH.1b 1A11 CDR Set and VL VL.1b 1A11 CDR Set,
VH VH.1b 1A11 CDR Set and VL VL.2a 1A11 CDR Set,
VH VH.2a 1A11 CDR Set and VL VL.1 1A11 CDR Set,
VH VH.2a 1A11 CDR Set and VL VL.1a 1A11 CDR Set,
VH VH.2a 1A11 CDR Set and VL VL.1b 1A11 CDR Set,
VH VH.2a 1A11 CDR Set and VL VL.2a 1A11 CDR Set,
VH VH.1 38H12 CDR Set and VL VL.1 38H12 CDR Set,
VH VH.1 38H12 CDR Set and VL VL.1a 38H12 CDR Set,
VH VH.1 38H12 CDR Set and VL VL.1b 38H12 CDR Set,
VH VH.1 38H12 CDR Set and VL VL.2a 38H12 CDR Set,
VH VH.1a 38H12 CDR Set and VL VL.1 38H12 CDR Set,
VH VH.1a 38H12 CDR Set and VL VL.1a 38H12 CDR Set,
VH VH.1a 38H12 CDR Set and VL VL.1b 38H12 CDR Set,
VH VH.1a 38H12 CDR Set and VL VL.2a 38H12 CDR Set,
VH VH.1b 38H12 CDR Set and VL VL.1 38H12 CDR Set,
VH VH.1b 38H12 CDR Set and VL VL.1a 38H12 CDR Set,
VH VH.1b 38H12 CDR Set and VL VL.1b 38H12 CDR Set,
VH VH.1b 38H12 CDR Set and VL VL.2a 38H12 CDR Set,
VH VH.2a 38H12 CDR Set and VL VL.1 38H12 CDR Set,
VH VH.2a 38H12 CDR Set and VL VL.1a 38H12 CDR Set,
VH VH.2a 38H12 CDR Set and VL VL.1b 38H12 CDR Set,
VH VH.2a 38H12 CDR Set and VL VL.2a 38H12 CDR Set,
VH h1A11.A6 CDR Set and VL h1A11VL.1 CDR Set,
VH h1A11.C6 CDR Set and VL h1A11VL.1 CDR Set,
VH h1A11.A11 CDR Set and VL h1A11VL.1 CDR Set,
VH h1A11.A8 CDR Set and VL h1A11VL.1 CDR Set,
VH h1A11VH.1 CDR Set and VL h1A11.B4 CDR Set,
VH h1A11VH.1 CDR Set and VL h1A11.A7 CDR Set,
VH h1A11VH.1 CDR Set and VL h1A11.A12 CDR Set,
VH h1A11VH.1 CDR Set and VL h1A11.A2 CDR Set,
VH h1A11.B5 CDR Set and VL h1A11.B5 CDR Set,
VH h1A11.E12 CDR Set and VL h1A11.E12 CDR Set,
VH h1A11.G3 CDR Set and VL h1A11.E12 CDR Set,
VH h1A11.F5 CDR Set and VL h1A11.E12 CDR Set, and
VH h1A 11.H2 CDR Set and VL h1A11.E12 CDR Set.

In a preferred embodiment, a DLL4 binding protein possess a DLL4 antigen binding domain (or binding site) comprising six CDRs, wherein a CDR-H1, CDR-H2, and CDR-H3 are located in a heavy chain variable region (VH) and a CDR-L1, CDR-L2, and CDR-L3 are located in a light chain variable region (VL), and wherein association of the VH and VL regions form a functional DLL4 antigen binding domain of the DLL4 binding protein. In a further non-limiting example of this embodiment, a DLL4 binding protein that possesses two DLL4 antigen binding domains comprises two sets of VH and VL regions and therefore comprises twelve CDRs.

In another embodiment, a DLL4 binding protein possesses a DLL4 antigen binding domain comprising six CDRs, wherein a CDR-H1, CDR-H2, and CDR-H3 are located in a heavy chain variable region (VH) and a CDR-L1, CDR-L2, and CDR-L3 are located in a light chain variable region (VL) and wherein the remaining sequences in each variable region constitute a framework (FR) region such that each CDR is positioned between two FR region sequences for a total of four FR sequences, i.e., FR1, FR2, FR3, and FR4. In this embodiment, the arrangement of FR and CDR sequences in a variable region is FR1-CDR1-FR2-CDR2-FR3-CDR3-FR4. In this embodiment, a binding domain formed by association of a VH region and a VL region comprises eight FR sequences and six CDRs.

DLL4 binding proteins of the invention include CDR-grafted antibodies, wherein one or more CDRs of VH and/or VL regions of an antibody of one species (donor species) are grafted into and replace the corresponding CDRs of the VH and/or VL of an antibody of another (acceptor) species using recombinant techniques available in the art. An example of a donor species is a rat anti-human DLL4 monoclonal antibody described herein and an example of an acceptor species is a human immunoglobulin gamma (IgG) molecule, wherein the human FR sequences of the VH and VL regions of the human IgG molecule are human acceptor framework sequences that receive the grafted in CDRs from the donor rat monoclonal antibody. The human acceptor framework sequences of the resulting CDR-grafted antibody may be further mutated to improve one or more properties of the CDR-grafted antibody. By way of non-limiting examples, one or more residues of one or more FR sequences of a CDR-grafted antibody may be mutated to improve DLL4 binding affinity or to lower immunogenicity of the CDR-grafted antibody in a human subject.

In an embodiment of the invention, a DLL4 binding protein comprising one or more CDRs described above further comprises a human acceptor framework sequence. Preferably, a DLL4 binding protein comprises one or more (e.g., one, two, three, four, five, six, seven, or eight) human acceptor framework sequences.

A human acceptor framework sequence present in a DLL4 binding protein of the invention may comprise one or more amino acid residues that have been back mutated to one or more corresponding amino acid residues present in a rat monoclonal antibody that binds DLL4 and/or that have been mutated to one or more amino acid residues that reduce or eliminate a site(s) for an undesirable reaction, for example, to reduce or eliminate a site for undesired glycosylation and/or a site for undesired N-terminal pyroglutamate formation and/or a site for potentially reduced immunogenicity risk.

In an embodiment, a DLL4 binding protein comprising one or more CDRs described above further comprises one or more (e.g., any one, two, three, four, five, six, seven, or eight) of the human acceptor framework sequences selected from the group of human acceptor framework sequences in Tables 3 and 4, below. One or more human acceptor framework sequences from Tables 3 and 4 present in a DLL4 binding protein of the invention may further comprise one or more amino acid residues that have been back mutated to one or more corresponding amino acid residues present in a rat monoclonal antibody that binds DLL4 and/or that have been mutated to one or more amino acids that reduce or eliminate a site(s) for an undesirable reaction, for example, to reduce or eliminate a site for undesired glycosylation and/or a site for undesired N-terminal pyroglutamate formation and/or a site for potentially reduced immunogenicity risk.

In another embodiment, the invention provides a DLL4 binding protein comprising one or more CDRs described above, wherein the binding protein also comprises one or more (e.g., any one, two, three, four, five, six, seven, or eight per binding domain) of the human acceptor framework sequences selected from any framework sequence present in a variable region sequence selected from the group consisting of:

SEQ ID NO: 171 VH.1 1A11
SEQ ID NO: 172 VH.1a 1A11
SEQ ID NO: 173 VH.1b 1A11
SEQ ID NO: 174 VH.2a 1A11
SEQ ID NO: 175 VL.1 1A11
SEQ ID NO: 176 VL.1a 1A11
SEQ ID NO: 177 VL.1b 1A11
SEQ ID NO: 178 VL.2a 1A11
SEQ ID NO: 179 VH.1 38H12
SEQ ID NO: 180 VH.1a 38H12
SEQ ID NO: 181 VH.1b 38H12
SEQ ID NO: 182 VH.2a 38H12
SEQ ID NO: 183 VL.1 38H12
SEQ ID NO: 184 VL.1a
SEQ ID NO: 185 VL.1b
SEQ ID NO: 186 VL.2a
SEQ ID NO: 187 VH h1A11VH.1
SEQ ID NO: 188 VH h1A11.A6
SEQ ID NO: 189 VH h1A11.A8
SEQ ID NO: 190 VH h1A11.C6
SEQ ID NO: 191 VH h1A11.A11
SEQ ID NO: 192 VH h1A11.B5
SEQ ID NO: 193 VH h1A11.E12
SEQ ID NO: 194 VH h1A11.G3
SEQ ID NO: 195 VH h1A11.F5
SEQ ID NO: 196 VH h1A11.H2
SEQ ID NO: 197 VL h1A11VL.1
SEQ ID NO: 198 VL h1A11.A2
SEQ ID NO: 199 VL h1A11.A12
SEQ ID NO: 200 VL h1A11.A7
SEQ ID NO: 201 VL h1A11.B4
SEQ ID NO: 202 VL h1A11.B5
SEQ ID NO: 203 VL h1A11.E12

In yet another embodiment of the invention, a DLL4 binding protein further comprises one or more (e.g., any one, two, three, four, five, six, seven, or eight) acceptor framework sequences selected from the group consisting of:

heavy chain framework-1 (H-FR1):
E-V-Q-L-V-E-S-G-G-G-L-V-Q-P-G-G-S-L-R-L-S-C-A-A-S-G-F-T-F-$X_{30}$(SEQ ID NO:143), wherein $X_{30}$ is S, R, or G;

heavy chain framework-2 (H-FR2): W-V-R-Q-A-P-G-K-G-L-E-W-V-A (SEQ ID NO:144);

heavy chain framework-3 (H-FR3):
R-F-T-I-S-R-D-N-A-K-$X_{11}$-S-L-Y-L-Q-M-N-S-L-R-A-E-D-T-A-V-Y-Y-C-$X_{31}$-R (SEQ ID NO:145), wherein;
$X_{11}$ is N or S; and
$X_{31}$ is A or S;

heavy chain framework-4 (H-FR4): W-G-Q-G-T-L-V-T-V-S-S (SEQ ID NO:146);

light chain framework-1 (L-FR1):
D-I-Q-M-T-QS-P-S-S-L-S-A-S-V-G-D-R-V-T-I-T-C (SEQ ID NO:147);

light chain framework-2 (L-FR2): W-Y-Q-Q-K-P-G-K-$X_9$-P-K-L-L-I-$X_{15}$ (SEQ ID NO:148), wherein;
$X_9$ is A or S; and
$X_{15}$ is F or Y;

light chain framework-3 (L-FR3):
G-V-P-S-R-F-S-G-S-G-S-G-T-D-$X_{15}$-T-L-T-I-S-S-L-Q-P-E-D-F-A-T-Y-Y-C (SEQ NO:149), wherein;
$X_{15}$ is F or S; and light chain framework-4 (L-FR4): F-G-Q-G-T-K-L-E-I-K (SEQ ID NO:150).

In another embodiment, a DLL4 binding protein comprising one or more CDRs described above also comprises a human acceptor framework sequence described above wherein the human acceptor framework sequence comprises at least one framework region amino acid substitution at a key residue, wherein the key residue is selected from the group consisting of a residue adjacent to a CDR, a glycosylation site residue, a rare residue, a residue capable of interacting with human DLL4, a residue capable of interacting with a CDR, a canonical residue, a contact residue between heavy chain variable region and light chain variable region, a residue within a Vernier zone, and a residue in a region that overlaps between a Chothia-defined variable heavy chain CDR1 and a Kabat-defined first heavy chain framework.

In another embodiment, a human acceptor framework sequence of a DLL4 binding protein described herein comprises at least one framework region amino acid substitution, wherein the amino acid sequence of the framework is at least 65% identical to a sequence of a human germline acceptor framework and comprises at least 70 amino acid residues identical to the human germline acceptor framework. In another embodiment, a DLL4 binding protein of the invention comprises a consensus human variable domain sequence.

In an embodiment, the invention provides a DLL4 binding protein comprises a human acceptor framework sequence, wherein the binding protein comprises at least one variable domain having an amino acid sequence selected from the group consisting of:

SEQ ID NO: 171
VH VH.1 1A11
SEQ ID NO: 172
VH VH.1a 1A11
SEQ ID NO: 173
VH VH.1b 1A11
SEQ ID NO: 174
VH VH.2a 1A11
SEQ ID NO: 175
VL VL.1 1A11
SEQ ID NO: 176
VL VL.1a 1A11
SEQ ID NO: 177
VL VL.1b
SEQ ID NO: 178
VL VL.2a 1A11
SEQ ID NO: 179
VH VH.1 38H12
SEQ ID NO: 180
VH VH.1a 38H12
SEQ ID NO: 181
VH VH.1b 38H12
SEQ ID NO: 182
VH VH.2a 38H12
SEQ ID NO: 183
VL VL.1 38H12
SEQ ID NO: 184
VL VL.1a 38H12
SEQ ID NO: 185
VL VL.1b 38H12
SEQ ID NO: 186
VL VL.2a 38H12
SEQ ID NO: 187
VH h1A11VH.1
SEQ ID NO: 188
VH h1A11.A6
SEQ ID NO: 189
VH h1A11.A8
SEQ ID NO: 190
VH h1A11.C6
SEQ ID NO: 191
VH h1A11.A11
SEQ ID NO: 192
VH h1A11.B5
SEQ ID NO: 193
VH h1A11.E12
SEQ ID NO: 194
VH h1A11.G3
SEQ ID NO: 195
VH h1A11.F5
SEQ ID NO: 196
VH h1A11.H2
SEQ ID NO: 197
VL h1A11VL.1
SEQ ID NO: 198
VL h1A11.A2
SEQ ID NO: 199
VL h1A11.A12
SEQ ID NO: 200
VL h1A11.A7
SEQ ID NO: 201
VL h1A11.B4
SEQ ID NO: 202
VL h1A11.B5
SEQ ID NO: 203
VL h1A11.E12

In another embodiment, a DLL4 binding protein of the invention comprises two or more variable domains described above. In a preferred embodiment, a DLL4 binding protein of the invention comprises two variable domains, wherein the two variable domains have amino acid sequences selected from the group consisting of:

SEQ ID NO: 171 and SEQ ID NO: 175
VH.1 and VL.1 1A11 (Table 12)
SEQ ID NO: 171 and SEQ ID NO: 176
VH.1 and VL.1a 1A11 (Table 12)
SEQ ID NO: 171 and SEQ ID NO: 177
VH.1 and VL.1b 1A11 (Table 12)
SEQ ID NO: 171 and SEQ ID NO: 178
VH.1 and VL.2a 1A11 (Table 12)
SEQ ID NO: 172 and SEQ ID NO: 175
VH.1a and VL.1 1A11 (Table 12)
SEQ ID NO: 172 and SEQ ID NO: 176
VH.1a and VL.1a 1A11 (Table 12)
SEQ ID NO: 172 and SEQ ID NO: 177
VH.1a and VL.1b 1A11 (Table 12)
SEQ ID NO: 172 and SEQ ID NO: 178
VH.1a and VL.2a 1A11 (Table 12)
SEQ ID NO: 173 and SEQ ID NO: 175
VH.1b and VL.1 1A11 (Table 12)
SEQ ID NO: 173 and SEQ ID NO: 176
VH.1b and VL.1a 1A11 (Table 12)
SEQ ID NO: 173 and SEQ ID NO: 177
VH.1b and VL.1b 1A11 (Table 12)
SEQ ID NO: 173 and SEQ ID NO: 178
VH.1b and VL.2a 1A11 (Table 12)
SEQ ID NO: 174 and SEQ ID NO: 175
VH.2a and VL.1 1A11 (Table 12)
EQ ID NO: 174 and SEQ ID NO: 176
VH.2a and VL.1a 1A11 (Table 12)
SEQ ID NO: 174 and SEQ ID NO: 177
VH.2a and VL.1b 1A11 (Table 12)
SEQ ID NO: 174 and SEQ ID NO: 178
VH.2a and VL.2a 1A11 (Table 12)
SEQ ID NO: 179 and SEQ ID NO: 183
VH.1 and VL.1 38H12 (Table 16)
SEQ ID NO: 179 and SEQ ID NO: 184
VH.1 and VL.1a 38H12 (Table 16)
SEQ ID NO: 179 and SEQ ID NO: 185
VH.1 and VL.1b 38H12 (Table 16)
SEQ ID NO: 179 and SEQ ID NO: 186
VH.1 and VL.2a 38H12 (Table 16)
SEQ ID NO: 180 and SEQ ID NO: 183
VH.1a and VL.1 38H12 (Table 16)
SEQ ID NO: 180 and SEQ ID NO: 184
VH.1a and VL.1a 38H12 (Table 16)
SEQ ID NO: 180 and SEQ ID NO: 185
VH.1a and VL.1b 38H12 (Table 16)
SEQ ID NO: 180 and SEQ ID NO: 186
VH.1a and VL.2a (Table 16)
SEQ ID NO: 181 and SEQ ID NO: 183
VH.1b and VL.1 (Table 16)
SEQ ID NO: 181 and SEQ ID NO: 184
VH.1b and VL.1a (Table 16)
SEQ ID NO: 181 and SEQ ID NO: 185
VH.1b and VL.1b (Table 16)
SEQ ID NO: 181 and SEQ ID NO: 186
VH.1b and VL.2a (Table 16)
SEQ ID NO: 182 and SEQ ID NO: 183
VH.2a and VL.1 (Table 16)
SEQ ID NO: 182 and SEQ ID NO: 184
VH.2a and VL.1a (Table 16)
SEQ ID NO: 182 and SEQ ID NO: 185
VH.2a and VL.1b (Table 16)
SEQ ID NO: 182 and SEQ ID NO: 186
VH.2a and VL.2a (Table 16)
SEQ ID NO: 188 and SEQ ID NO: 197
h1A11.A6 VH and h1A11VL.1
Tables 20/21
SEQ ID NO: 190 and SEQ ID NO: 197
h1A11.C6 VH and h1A11VL.1
Tables 20/21
SEQ ID NO: 191 and SEQ ID NO: 197
h1A11.A11 VH and h1A11VL.1
Tables 20/21
SEQ ID NO: 189 and SEQ ID NO: 197
h1A11.A8 VH and h1A11 VL.1
Tables 20/21
SEQ ID NO: 1878 and SEQ ID NO: 201
h1A11VH.1 and h1A11.B4 VL
Tables 20/21
SEQ ID NO: 187 and SEQ ID NO: 200
h1A11VH.1 and h1All.A7 VL
Tables 20/21

| | |
|---|---|
| SEQ ID NO: 187 and SEQ ID NO: 199 | |
| h1A11VH.1 and h1All.A12 VL | |
| Tables 20/21 | |
| SEQ ID NO: 187 and SEQ ID NO: 198 | |
| h1A11VH.1 VH and h1All.A2 VL | |
| Tables 20/21 | |
| SEQ ID NO: 192 and SEQ ID NO: 202 | |
| h1A11.B5 VH and h1All.B5 VL | |
| Tables 20/21 | |
| SEQ ID NO: 193 and SEQ ID NO: 203 | |
| h1A11.E12 VH and h1All.E12 VL | |
| Tables 20/21 | |
| SEQ ID NO: 194 and SEQ ID NO: 203 | |
| h1A11.G3 VH and h1All.E12 VL | |
| Tables 20/21 | |
| SEQ ID NO: 195 and SEQ ID NO: 203 | |
| h1A11.F5 VH and h1All.E12 VL | |
| Tables 20/21 | |
| SEQ ID NO: 196 and SEQ ID NO: 203 | |
| h1A11.H2 VH and h1All.E12 VL | |
| Tables 20/21 | |

In an embodiment, a DLL4 binding protein of the invention comprises at least one variable domain having an amino acid sequence selected from the group consisting of:

| | |
|---|---|
| SEQ ID NO: 157 | |
| VH 38H12 | |
| SEQ ID NO: 158 | |
| VL 38H12 | |
| SEQ ID NO: 159 | |
| VH 1A11 | |
| SEQ ID NO: 160 | |
| VL 1A11 | |
| SEQ ID NO: 161 | |
| VH 37D10 | |
| SEQ ID NO: 162 | |
| VL 37D10 | |
| SEQ ID NO: 163 | |
| VH 32C7 | |
| SEQ ID NO: 164 | |
| VL 32C7 | |
| SEQ ID NO: 165 | |
| VH 14G1 | |
| SEQ ID NO: 166 | |
| VL 14G1 | |
| SEQ ID NO: 167 | |
| VH 14A11 | |
| SEQ ID NO: 168 | |
| VL 14A11 | |
| SEQ ID NO: 169 | |
| VH 15D6 | |
| SEQ ID NO: 170 | |
| VL 15D6 | |
| SEQ ID NO: 171 | |
| VH VH.1 1A11 | |
| SEQ ID NO: 172 | |
| VH VH.1a 1A11 | |
| SEQ ID NO: 173 | |
| VH VH.1b 1A11 | |
| SEQ ID NO: 174 | |
| VH VH.2a 1A11 | |
| SEQ ID NO: 175 | |
| VL VL.1 1A11 | |
| SEQ ID NO: 176 | |
| VL VL.1a 1A11 | |
| SEQ ID NO: 177 | |
| VL VL.1b | |
| SEQ ID NO: 178 | |
| VL VL.2a 1A11 | |
| SEQ ID NO: 179 | |
| VH VH.1 38H12 | |
| SEQ ID NO: 180 | |
| VH VH.1a 38H12 | |
| SEQ ID NO: 181 | |
| VH VH.1b 38H12 | |
| SEQ ID NO: 182 | |
| VH VH.2a 38H12 | |
| SEQ ID NO: 182 | |
| VL VL.1 38H12 | |
| SEQ ID NO: 184 | |
| VL VL.1a 38H12 | |
| SEQ ID NO: 185 | |
| VL VL.1b 38H12 | |
| SEQ ID NO: 186 | |
| VL VL.2a 38H12 | |
| SEQ ID NO: 187 | |
| VH h1A11VH.1 | |
| SEQ ID NO: 188 | |
| VH h1A11.A6 | |
| SEQ ID NO: 189 | |
| VH h1A11.A8 | |
| SEQ ID NO: 190 | |
| VH h1A11.C6 | |
| SEQ ID NO: 191 | |
| VH h1A11.A11 | |
| SEQ ID NO: 192 | |
| VH h1A11.B5 | |
| SEQ ID NO: 193 | |
| VH h1A11.E12 | |
| SEQ ID NO: 194 | |
| VH h1A11.G3 | |
| SEQ ID NO: 195 | |
| VH h1A11.F5 | |
| SEQ ID NO: 196 | |
| VH h1A11.H2 | |
| SEQ ID NO: 197 | |
| VL h1A11VL.1 | |
| SEQ ID NO: 198 | |
| VL h1A11.A2 | |
| SEQ ID NO: 199 | |
| VL h1A11.A12 | |
| SEQ ID NO: 200 | |
| VL h1A11.A7 | |
| SEQ ID NO: 201 | |
| VL h1A11.B4 | |
| SEQ ID NO: 202 | |
| VL h1A11.B5 | |
| SEQ ID NO: 203 | |
| VL h1A11.E12 | |

In another embodiment, a DLL4 binding protein of the invention comprises two variable domains, wherein the two variable domains have the amino acid sequences selected from the group consisting of:

| | |
|---|---|
| SEQ ID NO: 157 and SEQ ID NO: 158 | |
| 38H12 | |
| SEQ ID NO: 159 and SEQ ID NO: 160 | |
| 1A11 | |
| SEQ ID NO: 161 and SEQ ID NO: 162 | |
| 37D10 | |
| SEQ ID NO: 163 and SEQ ID NO: 164 | |
| 32C7 | |
| SEQ ID NO: 165 and SEQ ID NO: 166 | |
| 14G1 | |
| SEQ ID NO: 167 and SEQ ID NO: 168 | |
| 14A11 | |
| SEQ ID NO: 169 and SEQ ID NO: 170 | |
| 15D6 | |
| SEQ ID NO: 171 and SEQ ID NO: 175 | |
| VH.1 and VL.1 1A11 (Table 11) | |
| SEQ ID NO: 171 and SEQ ID NO: 176 | |
| VH.1 and VL.1a 1A11 (Table 11) | |
| SEQ ID NO: 171 and SEQ ID NO: 177 | |
| VH.1 and VL.1b 1A11 (Table 11) | |
| SEQ ID NO: 171 and SEQ ID NO: 178 | |
| VH.1 and VL.2a (Table 11) | |
| SEQ ID NO: 172 and SEQ ID NO: 175 | |
| VH.1a and VL.1 (Table 11) | |
| SEQ ID NO: 172 and SEQ ID NO: 176 | |
| VH.1a and VL.1a (Table 11) | |

| -continued |
|---|
| SEQ ID NO: 172 and SEQ ID NO: 177 |
| VH.1a and VL.1b (Table 11) |
| SEQ ID NO: 172 and SEQ ID NO: 178 |
| VH.1a and VL.2a (Table 11) |
| SEQ ID NO: 173 and SEQ ID NO: 175 |
| VH.1b and VL.1 (Table 11) |
| SEQ ID NO: 173 and SEQ ID NO: 176 |
| VH.1b and VL.1a (Table 11) |
| SEQ ID NO: 173 and SEQ ID NO: 177 |
| VH.1b and VL.1b (Table 11) |
| SEQ ID NO: 173 and SEQ ID NO: 178 |
| VH.1b and VL.2a (Table 11) |
| SEQ ID NO: 174 and SEQ ID NO: 175 |
| VH.2a and VL.1 (Table 11) |
| SEQ ID NO: 174 and SEQ ID NO: 176 |
| VH.2a and VL.1a (Table 11) |
| SEQ ID NO: 174 and SEQ ID NO: 177 |
| VH.2a and VL.1b (Table 11) |
| SEQ ID NO: 174 and SEQ ID NO: 178 |
| VH.2a and VL.2a (Table 11) |
| SEQ ID NO: 179 and SEQ ID NO: 183 |
| VH.1 and VL.1 38H12 (Table 16) |
| SEQ ID NO: 179 and SEQ ID NO: 184 |
| VH.1 and VL.1a 38H12 (Table 16) |
| SEQ ID NO: 179 and SEQ ID NO: 185 |
| VH.1 and VL.1b 38H12 (Table 16) |
| SEQ ID NO: 179 and SEQ ID NO: 186 |
| VH.1 and VL.2a 38H12 (Table 16) |
| SEQ ID NO: 180 and SEQ ID NO: 183 |
| VH.1a and VL.1 38H12 (Table 16) |
| SEQ ID NO: 180 and SEQ ID NO: 184 |
| VH.1a and VL.1a 38H12 (Table 16) |
| SEQ ID NO: 180 and SEQ ID NO: 185 |
| VH.1a and VL.1b 38H12 (Table 16) |
| SEQ ID NO: 180 and SEQ ID NO: 186 |
| VH.1a and VL.2a (Table 16) |
| SEQ ID NO: 181 and SEQ ID NO: 183 |
| VH.1b and VL.1 (Table 16) |
| SEQ ID NO: 181 and SEQ ID NO: 184 |
| VH.1b and VL.1a (Table 16) |
| SEQ ID NO: 181 and SEQ ID NO: 185 |
| VH.1b and VL.1b (Table 16) |
| SEQ ID NO: 181 and SEQ ID NO: 186 |
| VH.1b and VL.2a (Table 16) |
| SEQ ID NO: 182 and SEQ ID NO: 183 |
| VH.2a and VL.1 (Table 16) |
| SEQ ID NO: 182 and SEQ ID NO: 184 |
| VH.2a and VL.1a (Table 16) |
| SEQ ID NO: 182 and SEQ ID NO: 185 |
| VH.2a and VL.1b (Table 16) |
| SEQ ID NO: 182 and SEQ ID NO: 186 |
| VH.2a and VL.2a (Table 16) |
| SEQ ID NO: 188 and SEQ ID NO: 197 |
| h1A11.A6 VH and h1A11VL.1 Tables 20/21 |
| SEQ ID NO: 190 and SEQ ID NO: 197 |
| h1A11.C6 VH and h1A11VL.1 Tables 20/21 |
| SEQ ID NO: 191 and SEQ ID NO: 197 |
| h1A11.All VH and h1A11VL.1 Tables 20/21 |
| SEQ ID NO: 189 and SEQ ID NO: 197 |
| h1A11.A8 VH and h1A11 VL.1 Tables 20/21 |
| SEQ ID NO: 187 and SEQ ID NO: 201 |
| h1A11VH.1 and h1A11.B4 VL Tables 20/21 |
| SEQ ID NO: 187 and SEQ ID NO: 200 |
| h1A11VH.1 and h1All.A7 VL Tables 20/21 |
| SEQ ID NO: 187 and SEQ ID NO: 199 |
| h1A11VH.1 and h1All.A12 VL Tables 20/21 |
| SEQ ID NO: 187 and SEQ ID NO: 198 |
| h1A11VH.1 VH and h1All.A2 VL Tables 20/21 |
| SEQ ID NO: 192 and SEQ ID NO: 202 |
| h1A11.B5 VH and h1All.B5 VL Tables 20/21 |
| SEQ ID NO: 193 and SEQ ID NO: 203 |
| h1A11.E12 VH and h1All.E12 VL Tables 20/21 |
| SEQ ID NO: 194 and SEQ ID NO: 203 |
| h1A11.G3 VH and h1All.E12 VL Tables 20/21 |
| SEQ ID NO: 195 and SEQ ID NO: 203 |
| h1A11.F5 VH and h1All.E12 VL Tables 20/21 |
| SEQ ID NO: 196 and SEQ ID NO: 203 |
| h1A11.H2 VH and h1All.E12 VL Tables 20/21 |

In an embodiment, a DLL4 binding protein of the invention comprises two variable domains having the amino acid sequences selected from the group consisting of:

SEQ ID NO:188 (h1A11.A6 VH) and SEQ ID NO:197 (h1A11VL.1),

SEQ ID NO:190 (h1A11.C6 VH) and SEQ ID NO:197 (h1A11VL.1), and

SEQ ID NO:191 (h1A11.A11 VH) and SEQ ID NO:197 (h1A11.VL1).

In an embodiment, a DLL4 binding protein of the invention comprises two variable domains having the amino acid sequences SEQ ID NO:181 (VH.1b 38H12) and SEQ ID NO:185 (VL.1b 38H12).

According to the invention, variable heavy (VH) domains and variable light (VL) domains of any of the DLL4 binding proteins described herein may also be shuffled using recombinant techniques available in the art to generate and select for additional DLL4 binding proteins that comprise various combinations of VH and VL domains described herein.

In an embodiment, a DLL4 binding protein according to the invention binds human DLL4 (hu DLL4) and at least one other species of DLL4. More preferably, a DLL4 binding protein described herein binds human DLL4 and a DLL4 selected from the group consisting of a cynomolgus monkey DLL4 (cynomolgus DLL4, cyno DLL4), a mouse DLL4 (mu DLL4), a rat DLL4, and combinations thereof.

In another embodiment, a DLL4 binding protein described herein is capable of blocking DLL4 interaction with a Notch protein. Preferably, the Notch protein is selected from the group consisting of Notch-1, Notch-2, Notch-3, Notch-4, and combinations thereof.

In an embodiment, a DLL4 binding protein described herein is capable of modulating, inhibiting, or neutralizing one or more biological functions of human DLL4. More preferably, a DLL4 binding protein of the invention is capable of modulating, inhibiting, or neutralizing an activity of a DLL4 selected from the group consisting of a human DLL4, a cynomolgus DLL4, a monkey DLL4, a rat DLL4, and combinations thereof.

In a further embodiment, a DLL4 binding protein described herein is capable of inhibiting VEGFR2 activity, VEGFR1 activity, or both VEGFR2 and VEGFR1 activities.

In an embodiment, a DLL4 binding protein described herein is capable of inhibiting normal angiogenesis.

In an embodiment, a DLL4 binding protein of the invention has an on rate constant ($K_{on}$) to DLL4 of at least about $10^2 M^{-1}s^{-1}$; at least about $10^3 M^{-1}s^{-1}$; at least about $10^4 M^{-1}s^{-1}$; at least about $10^5 M^{-1}s^{-1}$; or at least about $10^6 M^{-1}s^{-1}$, as measured by surface plasmon resonance. Preferably, the binding protein of the invention has an on rate constant ($K_{on}$) to DLL4 between $10^2 M^{-1}s^{-1}$ to $10^3 M^{-1}s^{-1}$; between $10^3 M^{-1}s^{-1}$ to $10^4 M^{-1}s^{-1}$; between $10^4 M^{-1}s^{-1}$ to $10^5 M^{-1}s^{-1}$; or between $10^5 M^{-1}s^{-1}$ to $10^6 M^{-1}s^{-1}$, as measured by surface plasmon resonance.

In another embodiment, a DLL4 binding protein of the invention has an off rate constant ($K_{off}$) for DLL4 of at most about $10^{-3} s^{-1}$; at most about $10^{-4} s^{-1}$; at most about $10^{-5} s^{-1}$; or at most about $10^{-6} s^{-1}$, as measured by surface plasmon resonance. Preferably, the binding protein of the invention has an off rate constant ($K_{off}$) to DLL4 of $10^{-3} s^{-1}$ to $10^{-4} s^{-1}$; of $10^{-4} s^{-1}$ to $10^{-5} s^{-1}$; or of $10^{-5} s^{-1}$ to $10^{-6} s^{-1}$, as measured by surface plasmon resonance.

In another embodiment, a DLL4 binding protein of the invention has a dissociation constant ($K_D$) to DLL4 of at most about $10^{-7}$ M; at most about $10^{-8}$ M; at most about $10^{-9}$ M; at most about $10^{-10}$ M; at most about $10^{-11}$ M; at most about $10^{-12}$ M; or at most $10^{-13}$ M. Preferably, the binding protein of the invention has a dissociation constant ($K_D$) to DLL4 of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of $10^{-11}$ M to $10^{-12}$ M; or of $10^{-12}$ to M $10^{-13}$ M.

In an embodiment, the invention provides an antibody construct comprising a DLL4 binding protein described above and a linker polypeptide or an immunoglobulin constant domain. In a preferred embodiment, an antibody construct according to the invention is selected from the group consisting of: an immunoglobulin molecule, a monoclonal antibody, a chimeric antibody, a CDR-grafted antibody, a humanized antibody, a Fab, a Fab', a F(ab')$_2$, an Fv, a disulfide linked Fv, a scFv, a single domain antibody, a diabody, a multispecific antibody, a dual specific antibody, and a bispecific antibody.

In a preferred embodiment, an antibody construct of the invention comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain.

In another embodiment, an antibody construct of the invention comprises an immunoglobulin constant region selected from the group consisting of an immunoglobulin gamma-1 (IgG-1) heavy chain constant region (such as SEQ ID NO:3), a mutant IgG-1 heavy chain constant region (such as SEQ ID NO:4), an immunoglobulin kappa light chain constant region (such as SEQ ID NO:5), an immunoglobulin lambda light chain constant region (such as SEQ ID NO:6), and combinations thereof.

In another embodiment, an antibody construct is glycosylated. Preferably, the glycosylation is a human glycosylation pattern.

In an embodiment, the invention provides an antibody conjugate comprising an antibody construct described herein conjugated to an agent. Preferably, the agent is selected from the group consisting of: an imaging agent, a therapeutic agent, a cytotoxic agent, and an immunoadhesin molecule. In a preferred embodiment, an imaging agents is selected from the group consisting of: a radiolabel, an enzyme, a fluorescent label, a luminescent label, a bioluminescent label, a magnetic label, and biotin. More preferably the imaging agent is a radiolabel selected from the group consisting of: $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm. In a preferred embodiment, the therapeutic or cytotoxic agent is selected from the group consisting of: an anti-metabolite, an alkylating agent, an antibiotic, a growth factor, a cytokine, an anti-angiogenic agent, an anti-mitotic agent, an anthracycline, toxin, and an apoptotic agent.

In another embodiment, a DLL4 binding protein, an antibody construct, or antibody conjugate described above exists as a crystal. Preferably, the crystal is a carrier-free pharmaceutical controlled release crystal. In another embodiment, such a crystallized binding protein, crystallized antibody construct, or crystallized antibody conjugate has a greater half life in vivo than its soluble counterpart. In a preferred embodiment, a crystallized binding protein, crystallized antibody construct, or crystallized antibody conjugate retains the biological activity of the soluble or non-crystal form of the binding protein, antibody construct, or antibody conjugate after crystallization.

In an embodiment, the invention provides an isolated nucleic acid encoding one or more amino acid sequences of a DLL4 binding protein (including any antibody construct or antibody conjugate) described herein In a preferred embodiment, the invention provides an isolated nucleic acid encoding a polypeptide selected from the group consisting of: a polypeptide comprising a heavy chain variable domain, wherein the heavy chain variable domain comprises one or more of a CDR-H1, a CDR-H2, and a CDR-H3 as described above; a polypeptide comprising a light chain variable domain, wherein the light chain variable domain comprises one or more of a CDR-L1, a CDR-L2, and a CDR-L3 as described above; and a combination of both polypeptides.

One aspect of the invention pertains to an isolated nucleic acid encoding a DLL4 binding protein, an antibody construct, a DLL4 binding antibody conjugate, or DLL4 binding portion thereof. Particularly preferred is an isolated nucleic acid that encodes a polypeptide selected from the group consisting of: a polypeptide comprising a heavy chain variable domain, wherein the heavy chain variable domain comprises a CDR-H1, a CDR-H2, or a CDR-H3 described above; a polypeptide comprising a light chain variable domain, wherein the light chain variable domain comprises a CDR-L1, a CDR-L2, or a CDR-L3 as described above; or a combination of both polypeptides.

A further embodiment provides a vector comprising an isolated nucleic acid described herein. In a preferred embodiment, the vector is selected from the group consisting of: pcDNA, pTT (Durocher et al., Nucl. Acids Res., 30(2e9): 1-9 (2002)), pTT3 (pTT with additional multiple cloning sites), pEFBOS (Mizushima et al., Nucl. Acids. Res., 18 (17): 5322 (1990)), pBV, pJV, and pBJ.

In another aspect of the invention there is provided a host cell transformed with the vector described above. The host cell can be a prokaryotic or eukaryotic cell. A preferred prokaryotic host cell is *Escherichia coli*. Preferably, the eukaryotic cell is selected from the group consisting of: a protist cell, an animal cell, a plant cell, and a fungal cell. More preferably, the host cell is a mammalian cell including, but not limited to, CHO and COS cells. A preferred fungal cell is *Saccharomyces cerevisiae*. A preferred insect cell is an Sf9 cell.

In another aspect of the invention there is provided a method of producing a binding protein that binds human DLL4 comprising the step of culturing any one of the host cells described above in a culture medium under conditions sufficient to produce a binding protein that binds human DLL4.

One embodiment provides a composition for the release of a DLL4 binding protein according to the invention wherein the composition comprises a formulation that comprises a crystallized DLL4 binding protein, a crystallized antibody construct, or a crystallized antibody conjugate as described above and an ingredient, and further at least one polymeric carrier. Preferably, the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutyrate), poly (caprolactone), poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. Preferably, the ingredient is selected from the group consisting of albumin, sucrose, trehalose, lactitol, gelatin, hydroxypropyl-β-cyclodextrin, methoxypolyethylene glycol and polyethylene glycol.

Another embodiment provides a method for treating a mammal comprising the step of administering to the mammal an effective amount of a composition comprising a crystallized DLL4 binding protein, a crystallized antibody construct, or a crystallized antibody conjugates described above.

The invention also provides a pharmaceutical composition comprising a DLL4 binding protein as described above (including an antibody construct or an antibody conjugate as described above) and a pharmaceutically acceptable carrier. In a further embodiment, the pharmaceutical composition comprises at least one additional agent. The additional agent may be a therapeutic agent for treating a disorder in which DLL4 is detrimental. Preferably, a pharmaceutical composition of the invention comprises an additional agent selected from the group consisting of: a therapeutic agent; an imaging agent; an antineoplastic agent; a chemotherapeutic agent; an angiogenesis inhibitor; an anti-VEGF antibody; an anti-EGFR antibody; an anti-cMet antibody; an anti-ErbB3 antibody; an anti-HER2 antibody; an anti-CD20 antibody; a VEGF-trap molecule; a kinase inhibitor; a co-stimulation molecule blocker; an anti-B7.2 antibody; a CTLA4-Ig; an adhesion molecule blocker; an anti-E selectin antibody; an anti-L selectin antibody; an anti-cytokine antibody or functional fragment thereof; an anti-IL-18 antibody; an anti-TNF antibody; anti-IL-6 antibody; methotrexate; a corticosteroid; a cyclosporin; a rapamycin; FK506; a DNA alkylating agent; cisplatin; carboplatin; an anti-tubulin agent; paclitaxel; docetaxel; doxorubicin; gemcitabine; gemzar; an anthracycline; adriamycin; a topoisiomersase I inhibitor; a topoisomerase II inhibitor; 5-fluorouracil (5-FU); leucovorin; irinotecan; a receptor tyrosine kinase inhibitor; an apoptosis inhibitor; a Bcl2/Bclx inhibitor; erlotinib; gefitinib; a COX-2 inhibitor; celecoxib; cyclosporin; rapamycin; a detectable label or reporter molecule; a TNF antagonist; an antirheumatic; a muscle relaxant; a narcotic; an analgesic; an anesthetic; a sedative; a local anesthetic; a neuromuscular blocker; an antimicrobial agent; an antipsoriatic agent; a corticosteroid; an anabolic steroid; an erythropoietin; an immunization; an immunoglobulin; an immunosuppressive agent; a growth hormone; a hormone replacement drug; a radiopharmaceutical drug; an antidepressant; an antipsychotic drug; a stimulant; an asthma medication; a beta agonist; an inhaled steroid; an epinephrine; an epinephrine analog thereof; a cytokine; and a cytokine antagonist.

In another aspect, the invention provides a method for inhibiting human DLL4 activity comprising contacting human DLL4 with a binding protein disclosed above such that human DLL4 is inhibited or neutralized. In a related aspect, the invention provides a method for inhibiting DLL4 activity in a human subject suffering from a disorder in which DLL4 is detrimental, comprising administering to the human subject a binding protein disclosed above such that human DLL4 in the human subject is inhibited and treatment is achieved. Preferably, the disorder is selected from the group comprising primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder, and urothelium), female genital tract (including cervix, uterus, and ovaries as well as choriocarcinoma and gestational trophoblastic disease), male genital tract (including prostate, seminal vesicles, testes, and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias and lymphomas (both Hodgkin's and non-Hodgkin's lymphomas), tumor metastases, ocular neovascularization (including diabetic blindness, retinopathies, age-induced macular degeneration and rubeosis), edema, rheumatoid arthritis, atherosclerotic plaques, refractory ascites, psoriasis, pancreatitis, polycystic ovarian disease (POD), endometriosis, uterine fibroids, benign prostate hypertrophy, T-cell acute lymphoblastic leukemia (T-ALL), cerebral autosomal dominant arteriopathy with subcortical infarcts and leukoencephalopathy (CADASIL), multiple sclerosis (MS), tetralogy of Fallot (TOF), Alagille syndrome (AS), macular degeneration and age-related macular degeneration diseases, and other angiogenesis independent and dependent diseases characterized by aberrant DLL4 expression or activity.

In another aspect, the invention provides a method of treating a patient suffering from a disorder in which human DLL4 is detrimental comprising the step of administering any one of the binding proteins disclosed above before, concurrent, or after the administration of a therapeutically effective amount of a second agent. In a preferred embodiment, the second agent is selected from the group consisting of: a radiotherapeutic agent; an antineoplastic agent; a chemotherapeutic agent; a DNA alkylating agent; cisplatin; carboplatin; an anti-tubulin agent; paclitaxel; docetaxel; taxol; doxorubicin; gemcitabine; gemzar; an anthracycline; adriamycin; a topoisomerase I inhibitor; a topoisomerase II inhibitor; 5-fluorouracil (5-FU); leucovorin; irinotecan; a receptor tyrosine kinase inhibitor; an apoptosis inhibitor; a Bcl2/Blx inhibitor; erlotinib; gefitinib; a COX-2 inhibitor; celecoxib; a kinase inhibitor; an angiogenesis inhibitor; an anti-VEGF antibody; anti-EGFR antibody; an anti-cMet antibody; an anti-ErbB3 antibody; an anti-HER2 antibody; an anti-CD20 antibody; VEGF-Trap (aflibercept); a co-stimulation molecule blocker; an anti-B7.1 antibody; an anti-B7.2 antibody; CTLA4-Ig; an adhesion molecule blocker; an anti-LFA-1 antibody; an anti-E selectin antibody; an anti-L selectin antibody; a small molecule inhibitor; an anti-cytokine antibody or functional fragment thereof; an anti-IL-18 antibody; an anti-TNF antibody; an anti-IL-6 antibody; an anti-cytokine receptor antibody; methotrexate; cyclosporin; rapamycin; FK506; a detectable label or reporter; a TNF antagonist; an antirheumatic; a muscle relaxant; a narcotic; a non-steroid anti-inflammatory drug (NSAID); an analgesic; an anesthetic; a sedative; a local anesthetic; a neuromuscular blocker; an antimicrobial agent; an antipsoriatic drug; a corticosteroid; an anabolic steroid; an erythropoietin; an immunization; an immunoglobulin; an immunosuppressive agent; a growth hormone; a hormone replacement drug; a radiopharmaceutical drug; an antidepressant; an antipsychotic drug; a stimulant; an asthma medication; a beta agonist; an inhaled steroid; an epinephrine; an epinephrine analog; a cytokine; and a cytokine antagonist.

In a preferred embodiment, the pharmaceutical compositions disclosed above are administered to the subject by at least one mode selected from the group consisting of: parenteral, subcutaneous, intramuscular, intravenous, intraarterial, intraarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

Another aspect of the invention provides at least one DLL4 anti-idiotype antibody to at least one DLL4 binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, and any portion thereof, that can be incorporated into a binding protein of the present invention.

Any of a variety of immunodetection assay formats may be adapted to employ a DLL4 binding protein of the invention to detect or measure DLL4 in a mixture, solution, or biological sample. Such immunodetection assay formats include but are not limited to radioimmunoassay (RIA), immunoprecipitation, enzyme-linked immunosorbent assay ELISA), immunoblot (e.g., Western), immunostrips (e.g., immunodipsticks) comprising a DLL4 binding protein of the invention adsorbed or immobilized to substrate, FACS, and the like. Detection of DLL4 using a DLL4 binding protein of the invention may be conducted in vitro on a mixture, solution, or in biological sample. A biological sample that may be contacted with a binding protein of the invention to detect or measure DLL4 in the sample includes, but is not limited to, urine, saliva, oral swab (buccal, lingual, or throat swab), dermal swab, dermal scrape, rectal swab, vaginal swab, whole blood sample, plasma sample, serum sample, tissue biopsy, and any other sample obtained from an individual by a procedure known in the art. In another embodiment, a DLL4 binding protein may be employed to detect DLL4 in vivo such as various tomography and scanning methods, including but not limited to X-ray computer assisted tomography (CT), magnetic resonance imaging (MRI), and positron emission tomography (PET).

DETAILED DESCRIPTION OF THE INVENTION

This invention pertains to DLL4 binding proteins, particularly anti-DLL4 antibodies, or antigen-binding portions thereof that bind DLL4. An amino acid sequence (SEQ ID NO:1) for human DLL4 is shown in Table 1 along with a corresponding DLL4 nucleotide coding sequence (SEQ ID NO:2). Various aspects of the invention relate to antibodies and antibody fragments, and pharmaceutical compositions thereof, as well as nucleic acids, recombinant expression vectors, and host cells for making such antibodies and fragments. Methods of using the antibodies of the invention to detect human DLL4 or murine DLL4, methods to inhibit human or mouse DLL4 and/or human or mouse VEGFR2 or VEGFR1 activity, either in vitro or in vivo, and methods to regulate gene expression are also encompassed by the invention.

TABLE 1

| Amino acid and nucleotide coding sequences for human DLL4. | | |
|---|---|---|
| Kind of Sequence | Sequence Identifier | Sequence 12345678901234567890123456789 0 |
| Human DLL4 Amino Acid Sequence | SEQ ID NO: 1 | MAAASRSASGWALLLLVALWQQR AAGSGVF QLQLQEFINERGVLASGRPCEPGCR TFFRV CLKHFQAVVSPGPCTFGTVSTPVLG TNSFA VRDDSSGGGRNPLQLPFNFTWPGTF SLIIE AWHAPGDDLRPEALPPDALISKIAIQ GSLA VGQNWLLDEQTSTLTRLRYSYRVIC SDNYY GDNCSRLCKKRNDHFGHYVCQPDG NLSCLP GWTGEYCQQPICLSGCHEQNGYCS KPAECL CRPGWQGRLCNECIPHNGCRHGTC STPWQC |

TABLE 1-continued

Amino acid and nucleotide coding sequences for human DLL4.

| Kind of Sequence | Sequence Identifier | Sequence<br>12345678901234567890123456789 0 |
|---|---|---|
|  |  | TCDEGWGGLFCDQDLNYCTHHSPC<br>KNGATC<br>SNSGQRSYTCTCRPGYTGVDCELEL<br>SECDS<br>NPCRNGGSCKDQEDGYHCLCPPGY<br>YGLHCE<br>HSTLSCADSPCFNGGSCRERNQGAN<br>YACEC<br>PPNFTGSNCEKKVDRCTSNPCANGG<br>QCLNR<br>GPSRMCRCRPGFTGTYCELHVSDCA<br>RNPCA<br>HGGTCHDLENGLMCTCPAGFSGRR<br>CEVRTS<br>IDACASSPCFNRATCYTDLSTDTFVC<br>NCPY<br>GFVGSRCEFPVGLPPSFPWVAVSLG<br>VGLAV<br>LLVLLGMVAVAVRQLRLRRPDDGS<br>REAMNN<br>LSDFQKDNLIPAAQLKNTNQKKELE<br>VDCGL<br>DKSNCGKQQNHTLDYNLAPGPLGR<br>GTMPGK<br>FPHSDKSLGEKAPLRLHSEKPECRIS<br>AICS<br>PRDSMYQSVCLISEERNECVIATEV |
| Human DLL4<br>Nucleotide Coding<br>Sequence | SEQ ID<br>NO:2 | atggcggcagcgtcccggagcgcctctggctgggcgc<br>tactgctgctggtggcactttggcagcagcgcgcggcc<br>ggctccggcgtcttccagctgcagctgcaggagttcatc<br>aacgagcgcggcgtactggccagtgggcggccttgcg<br>agcccggctgccggactttcttccgcgtctgccttaagc<br>acttccaggcggtcgtctcgcccggaccctgcaccttcg<br>ggaccgtctccacgccggtattgggcaccaactccttcg<br>ctgtccgggacgacagtagcggcgggggcgcaacc<br>ctctccaactgcccttcaatttcacctggccgggtaccttc<br>tcgctcatcatcgaagcttggcacgcgccaggagacga<br>cctgcggccagaggccttgccaccagatgcactcatca<br>gcaagatcgccatccagggctccctagctgtgggtcag<br>aactggttattggatgagcaaaccagcaccctcacaag<br>gctgcgctactcttaccgggtcatctgcagtgacaactac<br>tatggagacaactgctcccgcctgtgcaagaagcgcaa<br>tgaccacttcggccactatgtgtgccagccagatggcaa<br>cttgtcctgcctgcccggttggactggggaatattgcca<br>acagcctatctgtctttcgggctgtcatgaacagaatggc<br>tactgcagcaagccagcagagtgcctctgccgcccag<br>gctggcagggccggctgtgtaacgaatgcatcccccac<br>aatggctgtcgccacggcacctgcagcactccctggca<br>atgtacttgtgatgagggctggggaggcctgttttgtgac<br>caagatctcaactactgcacccactcccatgcaag<br>aatggggcaacgtgctccaacagtgggcagcaagct<br>acacctgcacctgtcgcccaggctacactggtgtggact<br>gtgagctggagctcagcgagtgtgacagcaaccccctgt<br>cgcaatggaggcagctgtaaggaccaggaggatggct<br>accactgcctgtgtcctccgggctactatggcctgcattg<br>tgaacacagcaccttgagctgcgccgactcccctgctt<br>caatggggctcctgccgggagcgcaaccaggggc<br>caactatgcttgtgaatgtccccccaacttcaccggctcc<br>aactgcgagaagaaagtggacaggtgcaccagcaacc<br>cctgtgccaacgggggacagtgcctgaaccgaggtcc<br>aagccgcatgtgccgctgccgtcctggattcacgggca<br>cctactgtgaactccacgtcagcgactgtgcccgtaacc<br>cttgcgcccacggtggcactttgccatgacctggagaat<br>gggctcatgtgcacctgccctgccggcttctctggccga<br>cgctgtgaggtgcggacatccatcgatgcctgtgcctcg<br>agtccctgcttcaacagggccacctgctacaccgacctc<br>tccacagacacctttgtgtgcaactgcccttatggctttgt<br>gggcagccgctgcgagttcccgtgggcttgccgcc<br>agcttcccctgggtggccgtctcgctgggtgtggggct<br>ggcagtgctgctggtactgctgggcatggtggcagtgg<br>ctgtgcggcagctgcggcttcgacggccggacgacgg<br>cagcagggaagccatgaacaacttgtcggacttccaga<br>aggacaacctgattcctgccgcccagataaaaacaca<br>aaccagaagaaggagctggaagtggactgtggcctgg |

TABLE 1-continued

Amino acid and nucleotide coding sequences for human DLL4.

| Kind of Sequence | Sequence Identifier | Sequence 12345678901234567890123 4567890 |
|---|---|---|
| | | acaagtccaactgtggcaaacagcaaaaccacacattg gactataatctggccccagggcccctggggcggggga ccatgccaggaaagtttccccacagtgacaagagctta ggagagaaggcgccactgcggttacacagtgaaaagc cagagtgtcggatatcagcgatatgctcccccagggact ccatgtaccagtctgtgtgtttgatatcagaggagagga atgaatgtgtcattgccacggaggtataa |

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric. Use of "polypeptide" herein is intended to encompass polypeptide and fragments and variants (including fragments of variants) thereof, unless otherwise stated. For an antigenic polypeptide, a fragment of polypeptide optionally contains at least one contiguous or nonlinear epitope of polypeptide. The precise boundaries of the at least one epitope fragment can be confirmed using ordinary skill in the art. The fragment comprises at least about 5 contiguous amino acids, such as at least about 10 contiguous amino acids, at least about 15 contiguous amino acids, or at least about 20 contiguous amino acids. A variant of polypeptide is as described herein.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The term "human DLL4" (abbreviated herein as "hDLL4" or "huDLL4"), as used herein, includes several EGF-like domains and a DSL domain that is required for receptor binding. The term includes a protein comprising about 74-75 kDa. The structure and deduced DNA and protein sequences of human DLL4 is described further in, for example, Shutter et al., Genes & Dev., 4: 1313-1318 (2000). The term "human DLL4" is intended to include recombinant human DLL4 (rh DLL4), which can be prepared by standard recombinant expression methods.

"Biological activity", as used herein with respect to DLL4, refers to all inherent biological properties of DLL4. Biological properties of DLL4 include, but are not limited to, binding a Notch receptor, activating a Notch receptor, negatively regulating VEGF signaling, repressing VEGFR2, and inducing VEGR1.

The terms "specific binding" or "specifically binding", as used herein, in reference to the interaction of an antibody, a protein, or a peptide with a second chemical species, means that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "binding protein" is a monomeric or multimeric protein that binds to and forms a complex with a binding partner, which may be a polypeptide, an antigen, a chemical compound or other molecule, or a substrate of any kind. A binding protein specifically binds a binding partner. Binding proteins include antibodies and other molecules comprising one or more antigen-binding domains that bind to an antigen molecule or a particular site (epitope) on the antigen molecule. A binding protein includes an antibody or any of its antigen-binding fragments, and various forms and derivatives of antibodies known in the art and described below. Accordingly, a binding protein includes, but is not limited to, an antibody, a tetrameric immunoglobulin, an IgG molecule, an $IgG_1$ molecule, a monoclonal antibody, a chimeric antibody, a CDR-grafted antibody, a humanized antibody, an affinity matured antibody, and fragments of any such antibodies that retain the ability to bind to an antigen.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1 CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4 Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 portion. Replacements of amino acid residues in the Fc portion to alter antibody effector function are known in the art (U.S. Pat. Nos. 5,648,260 and 5,624,821). The Fc portion of an antibody mediates several important effector functions, e.g., cytokine induction, ADCC, phagocytosis, complement dependent cytotoxicity (CDC), and half-life/clearance rate of antibody and antigen-antibody complexes. In some cases these effector functions are desirable for a therapeutic antibody but in other cases might be unnecessary or even deleterious, depending on the therapeutic objectives. Certain human IgG isotypes, particularly IgG1 and IgG3, mediate ADCC and CDC via binding to Fcγi and complement C1q, respectively. Neonatal Fc receptors (FcRn) are the critical components determining the circulating half-life of antibodies. In still another embodiment, at least one amino acid residue is replaced in the constant region of the antibody, for example the Fc region of the antibody, such that effector functions of the antibody are altered. The dimerization of two identical heavy chains of an immunoglobulin is mediated by the dimerization of CH3 domains and is stabilized by the disulfide bonds within the hinge region (Huber et al., Nature, 264: 415-420 (1976); Thies et al., J. Mol. Biol., 293: 67-79 (1999)). Mutation of cysteine residues within the hinge regions to prevent heavy chain-heavy chain disulfide bonds will destabilize dimerization of CH3 domains. Residues responsible for CH3 dimerization have been identified (Dall' Acqua, Biochem., 37: 9266-9273 (1998)). Therefore, it is possible to generate a monovalent half-Ig. Interestingly, these monovalent half Ig molecules have been found in nature for both IgG and IgA subclasses (Seligman, Ann. Immunol., 129: 855-70 (1978); Biewenga et al., Clin. Exp. Immunol., 51: 395-400 (1983)). The stoichiometry of FcRn: Ig Fc region has been determined to be 2:1 (West et al., Biochem., 39: 9698-9708 (2000)), and half Fc is sufficient for mediating FcRn binding (Kim et al., Eur. J. Immunol., 24: 542-548 (1994)). Mutations to disrupt the dimerization of CH3 domain may not have greater adverse effect on its FcRn binding as the residues important for CH3 dimerization are located on the inner interface of CH3 b sheet structure, whereas the region responsible for FcRn binding is located on the outside interface of $CH_2$-CH3 domains. However, the half Ig molecule may have certain advantages in tissue penetration due to its smaller size in comparison to that of a regular antibody. In one embodiment, at least one amino acid residue is replaced in the constant region of a binding protein of the invention, for example the Fc region, such that the dimerization of the heavy chains is disrupted, resulting in half Ig molecules. The anti-inflammatory activity of IgG is completely dependent on sialylation of the N-linked glycan of the IgG Fc fragment. The precise glycan requirements for anti-inflammatory activity has been determined, such that an appropriate IgG1 Fc fragment can be created, thereby generating a fully recombinant, sialylated IgG1 Fc with greatly enhanced potency (Anthony et al., Science, 320: 373-376 (2008)).

The term "antigen-binding portion" of an antibody (or simply "antibody portion"), as used herein, refers to one or more fragments of an antibody that retains the ability to bind specifically to an antigen (i.e., to a particular epitope of an antigen, such as an epitope of DLL4). It has been shown that the antigen-binding function of an antibody can be performed by fragments of a full-length antibody. Such antibody embodiments may also be bispecific, dual specific, or multi-specific formats; specifically binding to two or more different antigens (or two or more different epitopes of the same antigen). Examples of binding fragments encompassed within the term "antigen-binding portion" of an antibody include (i) a Fab fragment, a monovalent fragment consisting of the VL, VH, CL, and CH1 domains; (ii) a $F(ab')_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody; (v) a dAb fragment (Ward et al., Nature, 341:544-546 (1989); PCT Publication No. WO 90/05144 A1), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al., Science, 242: 423-426 (1988); Huston et al., Proc. Natl. Acad. Sci. USA, 85: 5879-5883 (1988)). Such single chain antibodies are also intended to be encompassed within the term "antigen-binding portion" of an antibody. Other forms of single chain antibodies, such as diabodies, are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., Proc. Natl. Acad. Sci. USA, 90: 6444-6448 (1993); Poljak, R. J., Structure, 2: 1121-1123 (1994)). Such antibody binding portions are known in the art (see, Kontermann and Dubel eds., *Antibody Engineering* (Springer-Verlag. New York, 2001), p. 790 (ISBN 3-540-41354-5)). In addition, single chain antibodies also include "linear antibodies" comprising a pair of tandem Fv segments (VH-CH1-VH-CH1) which, together with complementary light chain polypeptides, form a pair of antigen binding regions (Zapata et al. Protein Eng., 8(10): 1057-1062 (1995); and U.S. Pat. No. 5,641,870).

The term "antibody construct" (or "DLL4 antibody construct") as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger et al., Proc. Natl. Acad. Sci. USA, 90: 6444-6448 (1993); Poljak, R. J., Structure, 2: 1121-1123 (1994)). An immunoglobulin constant domain refers to a heavy or light chain constant domain. Human IgG heavy chain and light chain constant domain amino acid sequences are known in the art and represented in Table 2.

TABLE 2

Sequence of human IgG heavy chain constant domain and light chain constant domain

| Protein | Sequence Identifier | Sequence 123456789012345678901234567890012 |
|---|---|---|
| Ig gamma-1 constant region | SEQ ID NO: 3 | ASTKGPSVFFLAPSSKSTSGGTAALGCL VKDYFPEPVTVSWNSGALTSGVHTFPA VLQSSGLYSLSSVVTVPSSSLGTQTYIC NVNHKPSNTKVDKKVEPKSCDKTHTC PPCPAPELLGGPSVFLFPPKPKDTLMISR TPEVTCVVVDVSHEDPEVKFNWYVDG VEVHNAKTKPREEQYNSTYRVVSVLT VLHQDWLNGKEYKCKVSNKALPAPIE KTISKAKGQPREPQVYTLPPSREEMTK NQVSLTCLVKGFYPSDIAVEWESNGQP ENNYKTTPPVLDSDGSFFLYSKLTVDK SRWQQGNVFSCSVMHEALHNHYTQKS LSLSPGK |
| Ig gamma-1 constant region mutant | SEQ ID NO: 4 | ASTKGPSVFPLAPSSKSTSGGTAALGCL VKDYFPEPVTVSWNSGALTSGVHTFPA VLQSSGLYSLSSVVTVPSSSLGTQTYIC NVNHKPSNTKVDKKVEPKSCDKTHTC PPCPAPEAAGGPSVFLFPPKPKDTLMIS RTPEVTCVVVDVSHEDPEVKFNWYVD GVEVHNAKTKPREEQYNSTYRVVSVL TVLHQDWLNGKEYKCKVSNKALPAPI EKTISKAKGQPREPQVYTLPPSREEMTK NQVSLTCLVKGFYPSDIAVEWESNGQP ENNYKTTPPVLDSDGSFFLYSKLTVDK SRWQQGNVFSCSVMHEALHNHYTQKS LSLSPGK |
| Ig Kappa constant region | SEQ ID NO: 5 | TVAAPSVFIFPPSDEQLKSGTASVVCLL NNFYPREAKVQWKVDNALQSGNSQES VTEQDSKDSTYSLSSTLTLSKADYEKH KVYACEVTHQGLSSPVTKSFNRGEC |
| Ig Lambda constant region | SEQ ID NO: 6 | QPKAAPSVTLFPPSSEELQANKATLVCL ISDFYPGAVTVAWKADSSPVKAGVETT TPSKQSNNKYAASSYLSLTPEQWKSHR SYSCQVTHEGSTVEKTVAPTECS |

Still further, an antibody or antigen-binding portion thereof may be part of a larger immunoadhesin molecule, formed by covalent or noncovalent association of the antibody or antibody portion with one or more other proteins or peptides. Examples of such immunoadhesin molecules include use of the streptavidin core region to make a tetrameric scFv molecule (Kipriyanov et al., Human Antibodies and Hybridomas, 6: 93-101 (1995)) and use of a cysteine residue, a marker peptide, and a C-terminal polyhistidine tag to make bivalent and biotinylated scFv molecules (Kipriyanov et al., Mol. Immunol., 31: 1047-1058 (1994)). Antibody portions, such as Fab and F(ab')2 fragments, can be prepared from whole antibodies using conventional techniques, such as papain or pepsin digestion, respectively, of whole antibodies. Moreover, antibodies, antibody portions, and immunoadhesin molecules can be obtained using standard recombinant DNA techniques, as described herein and known in the art.

An "isolated antibody", as used herein, is intended to refer to an antibody that is substantially free of other antibodies having different antigenic specificities (e.g., an isolated antibody that specifically binds hDLL4 is substantially free of antibodies that specifically bind antigens other than hDLL4). An isolated antibody that specifically binds hDLL4 may, however, have cross-reactivity to other antigens, such as DLL4 molecules from other species (e.g., muDLL4). Moreover, an isolated antibody may be substantially free of other cellular material and/or chemicals.

The term "monoclonal antibody" and abbreviations "MAb" and "mAb", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created, or isolated by recombinant means, such as antibodies expressed using a recombinant expression vector transfected into a host cell, antibodies isolated from a recombinant, combinatorial human antibody library (Hoogenboom, Trends Biotechnol., 15:62-70 (1997); Azzazy and Highsmith, Clin. Biochem., 35: 425-445 (2002); Gavilondo and Larrick, BioTechniques, 29: 128-145 (2000); Hoogenboom and Chames, Immunol. Today, 21: 371-378 (2000)), antibodies isolated from an animal (e.g., a mouse) that is transgenic for human immunoglobulin genes (see, Taylor et al., Nucl. Acids Res., 20: 6287-6295 (1992); Kellermann and Green, Curr. Opin. Biotechnol., 13: 593-597 (2002); Little et al., Immunol. Today, 21: 364-370 (2000)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species, such as antibodies having murine heavy and light chain variable regions linked to human constant regions.

As used herein, the term "CDR" refers to a complementarity determining region within antibody variable sequences. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995) and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs.

The terms "Kabat numbering," "Kabat definitions", and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., Ann. NY Acad. Sci., 190: 382-391 (1971) and Kabat et al., *Sequences of Proteins of Immunological Interest, Fifth Edition*, U.S. Department of Health and Human Services, NIH Publication No. 91-3242 (1991)). For the heavy chain variable region (VH), the hypervariable region ranges from amino acid positions 31 to 35 for CDR1, amino acid positions 50 to 65 for CDR2, and amino acid positions 95 to 102 for CDR3. For the light chain variable region (VL), the hypervariable region ranges from amino acid positions 24 to 34 for CDR1, amino acid positions 50 to 56 for CDR2, and amino acid positions 89 to 97 for CDR3.

The growth and analysis of extensive public databases of amino acid sequences of variable heavy and light regions over the past twenty years have led to the understanding of the typical boundaries between framework regions (FR) and CDR sequences within variable region sequences and enabled persons skilled in this art to accurately determine the CDRs according to Kabat numbering, Chothia numbering, or other systems. See, e.g., Martin, "Protein Sequence and Structure Analysis of Antibody Variable Domains," In Kontermann and Dübel, eds., *Antibody Engineering* (Springer-Verlag, Berlin, 2001), chapter 31, pages 432-433. A useful method of determining the amino acid sequences of Kabat CDRs, and thereby sequences of Kabat FRs as well, within the amino acid sequences of variable heavy (VH) and variable light (VL) regions is provided below:

To identify a CDR-L1 amino acid sequence:
Starts approximately 24 amino acid residues from the amino terminus of the VL region;
Residue before the CDR-L1 sequence is always cysteine (C);
Residue after the CDR-L1 sequence is always tryptophan (W), typically Trp-Tyr-Gln (W-Y-Q), but also Trp-Leu-Gln (W-L-Q), Trp-Phe-Gln (W-F-Q), and Trp-Tyr-Leu (W-Y-L);
Length is typically 10 to 17 amino acid residues.
To identify a CDR-L2 amino acid sequence:
Starts always 16 residues after the end of CDR-L1;
Residues before the CDR-L2 sequence are generally Ile-Tyr (I-Y), but also Val-Tyr (V-Y), Ile-Lys (I-K), and Ile-Phe (I-F);
Length is always 7 amino acid residues.
To identify a CDR-L3 amino acid sequence:
Starts always 33 amino acids after the end of CDR-L2;
Residue before the CDR-L3 amino acid sequence is always a cysteine (C);
Residues after are always Phe-Gly-X-Gly (F-G-X-G) (SEQ ID NO:7),
where X is any amino acid;
Length is typically 7 to 11 amino acid residues.
To identify a CDR-H1 amino acid sequence:
Starts approximately 31 amino acid residues from amino terminus of VH region and always 9 residues after a cysteine (C);
Residues before are always Cys-X-X-X-X-X-X-X-X (SEQ ID NO:8), where X is any amino acid;
Residue after is always a Trp (W), typically Trp-Val (W-V), but also Trp-Ile (W-I), and Trp-Ala (W-A);
Length is typically 5 to 7 amino acid residues.
To identify a CDR-H2 amino acid sequence:
Starts always 15 amino acid residues after the end of CDR-H1;
Residues before are typically Leu-Glu-Trp-Ile-Gly (L-E-W-I-G) (SEQ ID NO:9), but other variations also;
Residues after are Lys/Arg-Leu/Ile/Val/Phe/Thr/Ala-Thr/Ser/Ile/Ala (K/R-L/I/V/F/T/A-T/S/I/A);
Length is typically 16 to 19 amino acid residues.
To identify a CDR-H3 amino acid sequence:
Starts always 33 amino acid residues after the end of CDR-H2 and always 3 after a cysteine (C)
Residues before are always Cys-X-X (C—X-X), where X is any amino acid, typically Cys-Ala-Arg (C-A-R);
Residues after are always Trp-Gly-X-Gly (W-G-X-G) (SEQ ID NO:10), where X is any amino acid;
Length is typically 3 to 25 amino acid residues.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See, e.g., Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

An "affinity matured" antibody is an antibody with one or more alterations in one or more CDRs thereof which result in an improvement in the affinity of the antibody for a target antigen, compared to a parent antibody which does not possess the alteration(s). Exemplary affinity matured antibodies will have nanomolar or even picomolar affinities for the target antigen. A variety of procedures for producing affinity matured antibodies are known in the art. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); Hawkins et al, J. Mol. Biol., 226: 889-896 (1992). Selective mutation at selective mutagenesis positions and at contact or hypermutation positions with an activity enhancing amino acid residue is described in U.S. Pat. No. 6,914,128 B1.

The term "multivalent binding protein" denotes a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein capable of binding two or more related or unrelated targets, including a binding protein capable of binding two or more different epitopes of the same target molecule.

The term "bispecific antibody", as used herein, refers to full-length antibodies that are generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches which introduces mutations in the Fc region (see Holliger et al., Proc. Natl. Acad. Sci. USA, 90(14): 6444-6448 (1993)), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is monovalent for each antigen it binds to.

The term "dual-specific antibody", as used herein, refers to full-length antibodies that can bind two different antigens (or epitopes) in each of its two binding arms (a pair of HC/LC) (see PCT publication WO 02/02773). Accordingly a dual-specific binding protein has two identical antigen binding arms, with identical specificity and identical CDR sequences, and is bivalent for each antigen to which it binds.

"Dual variable domain" ("DVD") binding proteins of the invention comprise two or more antigen binding sites and may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides is referred to as a "DVD immunoglobulin" or "DVD-Ig". Such a DVD-Ig binding protein is thus tetrameric and reminiscent of an IgG molecule, but provides more antigen binding site than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provide a single antigen binding domain, a pair of heavy and light chains of a DVD-Ig provide two or more antigen binding sites.

Each antigen binding site of a DVD-Ig binding protein is derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., Nature Biotech., 25: 1290-1297 (2007). A preferred example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein according to the invention not only binds the same target molecules bound by its parental monoclonal antibodies, but also possesses one or more desirable properties of one or more of its parental monoclonal antibodies. Preferably, such an additional property is an improved parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein according to the invention binds at least one epitope of a human DLL4 protein. Non-limiting examples of a DVD-Ig binding protein according to the invention include a DVD-Ig binding protein that binds one or more epitopes of human DLL4, a DVD-Ig binding protein that binds an epitope of a human DLL4 and an epitope of a DLL4 of another species (for example, mouse), and a DVD-Ig binding protein that binds an epitope of a human DLL4 and an epitope of another target molecule (for example, VEGFR2 or VEGFR1).

A "functional antigen binding site" of a binding protein is one that is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

As used herein, the terms "acceptor" and "acceptor antibody" refer to an antibody or nucleic acid sequence providing or encoding at least 80%, at least 85%, at least 90%, at least 95%, at least 98%, or 100% of the amino acid sequences of one or more of the framework regions (FRs). In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "canonical" residue refers to a residue in a CDR or framework that defines a particular canonical CDR structure as defined by Chothia et al. (J. Mol. Biol., 196: 901-917 (1987); Chothia et al., J. Mol. Biol., 227: 799-817 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain framework (FR) sequences are known in the art that can be used as heavy chain and light chain "acceptor" framework sequences (or simply, "acceptor" sequences) to humanize a non-human antibody using techniques known in the art. In an embodiment of the invention, human heavy chain and light chain acceptor sequences are selected from the framework sequences listed in publicly available databases such as V-base (hypertext transfer protocol://vbase.mrc-cpe.cam.ac.uk/) or in the international ImMunoGeneTics® (IMGT®) information system (hypertext transfer protocol://imgt.cines.fr/texts/IMGTrepertoire/LocusGenes/). Table 3, below, provides a non-limiting list of examples of human heavy chain acceptor sequences known in the art. Table 4, below, provides a non-limiting list of examples of human light chain acceptor sequences known in the art. In an embodiment of the invention, human heavy chain and light chain acceptor sequences are selected from the amino acid sequences described in Table 3 and Table 4, below, however, other human heavy chain and light acceptors sequences not listed in Tables 3 and 4 may also be used to humanize an antibody according to the invention.

TABLE 3

Heavy Chain Acceptor Sequences.

| SEQ ID NO: | Protein region/ Closest Germline Family | Amino Acid Sequence 123456789012345678901234567890 12 |
|---|---|---|
| 11 | VH3-7 FR1 | EVQLVESGGGLVQPGGSLRLSCAASGF TFS |
| 12 | VH3-7 FR2 | WVRQAPGKGLEWVA |
| 13 | VH3-7 FR3 | RFTISRDNAKNSLYLQMNSLRAEDTAV YYCAR |
| 14 | JH4 FR4 | WGQGTLVTVSS |
| 15 | VH3 CONSENUSUS FR1 | EVQLVESGGGLVQPGGSLRLSCAASGF TFS |
| 16 | VH3 CONSENUSUS FR2 | WVRQAPGKGLEWVS |
| 17 | VH3 CONSENUSUS FR3 | RFTISRDNSKNTLYLQMNSLRAEDTAV YYCAR |
| 18 | JH4 FR4 | WGQGTLVTVSS |

TABLE 3-continued

Heavy Chain Acceptor Sequences.

| SEQ ID NO: | Protein region/ Closest Germline Family | Amino Acid Sequence 123456789012345678901234567890 12 |
|---|---|---|
| 19 | VH1-46 FR1 | QVQLVQSGAEVKKPGASVKVSCKASG YTFT |
| 20 | VH1-46 FR2 | WVRQAPGQGLEWMG |
| 21 | VH1-46 FR3 | RVTMTRDTSTSTVYMELSSLRSEDTAV YYCAR |
| 22 | JH4 FR4 | WGQGTLVTVSS |
| 23 | VH3-30 FR1 | QVQLVESGGGVVQPGRSLRLSCAASGF TFS |
| 24 | VH3-30 FR2 | WVRQAPGKGLEWVA |
| 25 | VH3-30 FR3 | RFTISRDNSKNTLYLQMNSLRAEDTAV YYCAR |
| 26 | JH3 FR4 | WGQGTMVTVSS |
| 27 | VH3 CONSENUSUS FR1 | EVQLVESGGGLVQPGGSLRLSCAASGF TFS |
| 28 | VH3 CONSENUSUS FR2 | WVRQAPGKGLEWVS |
| 29 | VH3 CONSENUSUS FR3 | RFTISRDNSKNTLYLQMNSLRAEDTAV YYCAR |
| 30 | JH3 FR4 | WGQGTMVTVSS |
| 31 | VH2-70/JH6 FR1 | EVTLRESGPALVKPTQTLTLTCTFSGFS LS |
| 32 | VH2-70/JH6 FR2 | WIRQPPGKALEWLA |
| 33 | VH2-70/JH6 FR3 | RLTISKDTSKNQVVLTMTNMDPVDTAT YYCAR |
| 34 | VH2-70/JH6 FR4 | WGQGTTVTVSS |
| 35 | VH2-26/JH6 FR1 | EVTLKESGPVLVKPTETLTLTCTVSGFS LS |
| 36 | VH2-26/JH6 FR2 | WIRQPPGKALEWLA |
| 37 | VH2-26/JH6 FR3 | RLTISKDTSKSQVVLTMTNMDPVDTAT YYCAR |
| 38 | VH2-26/JH6 FR4 | WGQGTTVTVSS |
| 39 | VH3-72/JH6 FR1 | EVQLVESGGGLVQPGGSLRLSCAASGF TFS |
| 40 | VH3-72/JH6 FR2 | WVRQAPGKGLEWVG |
| 41 | VH3-72/JH6 FR3 | RFTISRDDSKNSLYLQMNSLKTEDTAV YYCAR |
| 42 | VH3-72/JH6 FR4 | WGQGTTVTVSS |
| 43 | VH3-21/JH6 FR1 | EVQLVESGGGLVKPGGSLRLSCAASGF TFS |
| 44 | VH3-21/JH6 FR2 | WVRQAPGKGLEWVS |
| 45 | VH3-21/JH6 FR3 | RFTISRDNAKNSLYLQMNSLRAEDTAV YYCAR |

TABLE 3-continued

Heavy Chain Acceptor Sequences.

| SEQ ID NO: | Protein region/ Closest Germline Family | Amino Acid Sequence |
|---|---|---|
| 46 | VH3-21/JH6 FR4 | WGQGTTVTVSS |
| 47 | VH1-69/JH6 FR1 | EVQLVQSGAEVKKPGSSVKVSCKASGGTFS |
| 48 | VH1-69/JH6 FR2 | WVRQAPGQGLEWMG |
| 49 | VH1-69/JH6 FR3 | RVTITADKSTSTAYMELSSLRSEDTAVYYCAR |
| 50 | VH1-69/JH6 FR4 | WGQGTTVTVSS |
| 51 | VH1-18/JH6 FR1 | EVQLVQSGAEVKKPGASVKVSCKASGYTFT |
| 52 | VH1-18/JH6 FR2 | WVRQAPGQGLEWMG |
| 53 | VH1-18/JH6 FR3 | RVTMTTDTSTSTAYMELRSLRSDDTAVYYCAR |
| 54 | VH1-18/JH6 FR4 | WGQGTTVTVSS |
| 55 | IGHV4-59 FR1 | EVQLQESGPGLVKPSETLSLTCTVSGGSIS |
| 56 | IGHV4-59 FR2 | WIRQPPGKGLEWIG |
| 57 | IGHV4-59 FR3 | RVTISVDTSKNQFSLKLSSVTAADTAVYYCAR |
| 58 | IGHV4-59/JH FR4 | WGQGTLVTVSS |
| 59 | IGHV3-66 FR1 | EVQLVESGGGLVQPGGSLRLSCAVSGGSIS |
| 60 | IGHV3-66 FR2 | WIRQAPGKGLEWIG |
| 61 | IGHV3-66 FR3 | RVTISVDTSKNSFYLQMNSLRAEDTAVYYCAR |
| 62 | IGHV3-66/JH FR4 | WGQGTLVTVSS |
| 63 | IGHV4-59 FR1 | EVQLQESGPGLVKPGETLSLTCTVSGGSIS |
| 64 | IGHV4-59 FR2 | WIRQAPGKGLEWIG |
| 65 | IGHV4-59 FR3 | RVTISVDTSKNQFYLKLSSVRAEDTAVYYCAR |
| 66 | IGHV4-59/JH FR4 | WGQGTLVTVSS |
| 67 | IGHV5-51 FR1 | EVQLVQSGTEVKKPGESLKISCKVSGGSIS |
| 68 | IGHV5-51 FR2 | WIRQMPGKGLEWIG |
| 69 | IGHV5-51 FR3 | QVTISVDTSFNTFFLQWSSLKASDTAMYYCAR |
| 70 | IGHV5-51/JH FR4 | WGQGTMVTVSS |
| 71 | IGHV2-70 FR1 | EVTLRESGPALVKPTQTLTLTCTVSGGSIS |
| 72 | IGHV2-70 FR2 | WIRQPPGKGLEWIG |
| 73 | IGHV2-70 FR3 | RVTISVDTSKNQFVLTMTNMDPVDTATYYCAR |
| 74 | IGHV2-70/JH FR4 | WGQGTTVTVSS |
| 75 | IGHV3-15 FR1 | EVQLLESGGGLVKSGGSLRLSCAASGFTFR |
| 76 | IGHV3-15 FR2 | WVRQAPGKGLEWVA |
| 77 | IGHV3-15 FR3 | RFTISRDNSKNTLYLQLNSLRAEDTAVYYCAK |
| 78 | IGHV3-15/JH FR4 | WGQGTMVTVSS |
| 79 | IGHV3-43 FR1 | EVQLVESGGGVVQPGGSLRLSCAASGFTFG |
| 80 | IGHV3-43 FR2 | WVRQAPGKGLEWVA |
| 81 | IGHV3-43 FR3 | RFTISRDNSKNTLYLQLNSLRAEDTAVYYCAK |
| 82 | IGHV3-43/JH FR4 | WGQGTMVTVSS |

TABLE 4

Light Chain Acceptor Sequences

| SEQ ID NO.: | Protein region/ Closest Germline Family | Sequence |
|---|---|---|
| 83 | O2 FR1 | DIQMTQSPSSLSASVGDRVTITC |
| 84 | O2 FR2 | WYQQKPGKAPKLLIY |
| 85 | O2 FR3 | GVPSRFSGSGSGTDFTLTISSLQPEDFATYYC |
| 86 | JK2 FR4 | FGQGTKLEIK |
| 87 | L2 FR1 | EIVMTQSPATLSVSPGERATLSC |
| 88 | L2 FR2 | WYQQKPGQAPRLLIY |
| 89 | L2 FR3 | GIPARFSGSGSGTEFTLTISSLQSEDFAVYYC |
| 90 | JK2 FR4 | FGQGTKLEIK |
| 91 | B3/JK4 FR1 | DIVMTQSPDSLAVSLGERATINC |
| 92 | B3/JK4 FR2 | WYQQKPGQPPKLLIY |
| 93 | B3/JK4 FR3 | GVPDRFSGSGSGTDFTLTISSLQAEDVAVYYC |
| 94 | B3/JK4 FR4 | FGGGTKVEIKR |
| 95 | L2/JK4 FR1 | EIVMTQSPATLSVSPGERATLSC |
| 96 | L2/JK4 FR2 | WYQQKPGQAPRLLIY |
| 97 | L2/JK4 FR3 | GIPARFSGSGSGTEFTLTISSLQSEDFAVYYC |
| 98 | L2/JK4 FR4 | FGGGTKVEIKR |

TABLE 4-continued

Light Chain Acceptor Sequences

| SEQ ID NO.: | Protein region/ Closest Germline Family | Sequence 123456789012345678901234567890123456789012 |
|---|---|---|
| 99 | L15/JK4 FR1 | DIQMTQSPSSLSASVGDRVTITC |
| 100 | L15/JK4 FR2 | WYQQKPEKAPKSLIY |
| 101 | L15/JK4 FR3 | GVPSRFSGSGSGTDFTLTISSLQPEDFATYYC |
| 102 | L15/JK4 FR4 | FGGGTKVEIKR |
| 103 | L5/JK4 FR1 | DIQMTQSPSSVSASVGDRVTITC |
| 104 | L5/JK4 FR2 | WYQQKPGKAPKLLIY |
| 105 | L5/JK4 FR3 | GVPSRFSGSGSGTDFTLTISSLQPEDFATYYC |
| 106 | L5/JK4 FR4 | FGGGTKVEIKR |
| 107 | IGLV3-1 FR1 | SYELTQPPSVSVSPGQTASITC |
| 108 | IGLV3-1 FR2 | WYQQKPGQSPVLVIY |
| 109 | IGLV3-1 FR3 | GIPERFSGSNSGDTATLTISGTQPMDEADYYC |
| 110 | IGLV3-1/JL FR4 | FGYGTKVTVL |
| 111 | IGLV3-1 FR1 | SYELTQPPSVSVSPGQTASITC |
| 112 | IGLV3-1 FR2 | WYQQKPGQSPVLVIY |
| 113 | IGLV3-1 FR3 | GIPERFSGSNSGDTATLTISGTQPMDEADYYC |
| 114 | IGLV3-1/JL FR4 | GGGTKLTVLG |
| 115 | IGLV3-1 FR1 | YELTQPPSVSVSPGQTASITC |
| 116 | IGLV3-1 FR2 | WYQQKPGQSPVLVIY |
| 117 | IGLV3-1 FR3 | GIPERFSGSNSGDTATLTISGTQPMDEADYYC |
| 118 | IGLV3-1/JL FR4 | GGGTKLTVLG |
| 119 | IGLV3-1 FR1 | LYVLTQPPSVSVSPGQTASITC |
| 120 | IGLV3-1 FR2 | WYQQKPGQSPVLVIY |
| 121 | IGLV3-1 FR3 | GIPERFSGSNSGDTATLTISGTQTMDEADYLC |
| 122 | IGLV3-1/JL FR4 | FGGGTKVTVLG |
| 123 | IGKV6D-21 FR1 | EYVLTQSPDFQSVTPKEKVTITC |
| 124 | IGKV6D-21 FR2 | WYQQKPDQSPKLVIY |
| 125 | IGKV6D-21 FR3 | GVPSRFSGSGSNSGDDATLTINSLEAEDAATYYC |
| 126 | IGKV6D-21/JK FR4 | FGQGTKVEIKR |
| 127 | IGKV3D-15 FR1 | EYVLTQSPATLSVSPGERATLSC |
| 128 | IGKV3D-15 FR2 | WYQQKPGQSPRLVIY |
| 129 | IGKV3D-15 FR3 | DIPARFSGSNSGDEATLTISSLQSEDFAVYYC |
| 130 | IGKV3D-15/JK FR4 | FGQGTRLEIKR |
| 131 | IGKV4-1 FR1 | DYVLTQSPDSLAVSLGERATINC |
| 132 | IGKV4-1 FR2 | WYQQKPGQSPKLVIY |
| 133 | IGKV4-1 FR3 | GIPDRFSGSNSGDDATLTISSLQAEDVAVYYC |
| 134 | IGKV4-1/JK FR4 | FGGGTKVEIKR |
| 135 | IGLV3-1 FR1 | LPVLTQPPSVSVSPGQTASITC |
| 136 | IGLV3-1 FR2 | WYQQKPGQSPVLVIY |
| 137 | IGLV3-1 FR3 | GIPERFSGSNSGNTATLTISGTQTMDEADYLC |
| 138 | IGLV3-1/JL FR4 | FGGGTKVTVL |
| 139 | IGLV3-1 FR1 | SYELTQPPSVSVSPGQTASITC |
| 140 | IGLV3-1 FR2 | WYQQKPGQSPVLVIY |
| 141 | IGLV3-1 FR3 | GIPERFSGSNSGNTATLTISGTQTMDEADYLC |
| 142 | IGLV3-1/JL FR4 | FGGGTKLTVL |

In an embodiment, heavy chain human acceptor framework sequences from Table 3 for use in generating humanized antibodies that bind DLL4 according to the invention include a set consisting of the VH3-7 FR1, the VH3-7 FR2, the VH3-7 FR3, and the JH4 FR4 acceptor sequences; a set consisting of the VH3 consensus FR1, the VH3 consensus FR2, the VH3 consensus FR3, and the JH4 FR4 acceptor sequences; a set consisting of the VH1-46 FR1, the VH1-46 FR2, the VH1-46 FR3, and the JH4 FR4 acceptor sequences; a set consisting of the VH3-30 FR1, the VH3-30 FR2, the VH3-30 FR3, and the JH3 FR4 acceptor sequences; and a set consisting of the VH3 consensus FR1, the VH3 consensus FR2, the VH3 consensus FR3, and the JH3 FR4 acceptor sequences.

In an embodiment, light chain human acceptor framework sequences from Table 4 for use in generating humanized antibodies that bind DLL4 according to the invention include a set consisting of the O2 FR1, O2 FR2, O2 FR3, and JK2 FR4 acceptors sequences and a set a consisting of the L2 FR1, L2 FR2, L2 FR3, and JK2 FR4 acceptor sequences.

In an embodiment, a set of human acceptor framework sequences for use in generating a humanized antibody that binds DLL4 according to the invention comprises one or more (e.g., any one, two, three, four, five, six, seven, or eight per binding domain) of the acceptor framework sequences selected from the group consisting of:

heavy chain framework-1 (H-FR1):
E-V-Q-L-V-E-S-G-G-G-L-V-Q-P-G-G-S-L-R-L-S-C-A-A-S-G-F-T-F-$X_{30}$(SEQ ID NO:143), wherein $X_{30}$ is S, R, or G;

heavy chain framework-2 (H-FR2): W-V-R-Q-A-P-G-K-G-L-E-W-V-A (SEQ ID NO:144);

heavy chain framework-3 (H-FR3):
R-F-T-I-S-R-D-N-A-K-$X_{11}$-S-L-Y-L-Q-N-S-L-R-A-E-D-T-A-V-Y-Y-C-$X_{31}$-R (SEQ ID NO:145), wherein;
$X_{11}$ is N or S; and
$X_{31}$ is A or S;

heavy chain framework-4 (H-FR4): W-G-Q-G-T-L-V-T-V-S-S (SEQ ID NO:146);

light chain framework-1 (L-FR1):
D-I-Q-M-T-Q-S-P-S-S-L-S-A-S-V-G-D-R-V-T-I-T-C (SEQ ID NO:147);
light chain framework-2 (L-FR2): W-Y-Q-Q-K-P-G-K-$X_9$-P-K-L-L-I-$X_{15}$ (SEQ ID NO:148), wherein;
$X_9$ is A or S; and
$X_{15}$ is F or Y;
light chain framework-3 (L-FR3):
G-V-P-S-R-F-S-G-S-G-S-G-T-D-$X_{15}$-T-L-T-I-S-S-L-Q-P-E-D-F-A-T-Y-Y-C (SEQ ID NO:149), wherein;
$X_{15}$ is F or S; and
light chain framework-4 (L-FR4): F-G-Q-G-T-K-L-E-I-K (SEQ ID NO:150).

In a preferred embodiment, an antibody that binds DLL4 according to the invention is humanized using a set of human acceptor sequences consisting of an H-FR1, H-FR2, H-FR3, H-FR-4, L-FR1, L-FR2, L-FR3, and L-FR4 acceptor sequence described above.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol., 22(3): 183-200 (2002); Marchalonis et al., Adv. Exp. Med. Biol., 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key residue" refers to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, "Vernier" zone refers to a subset of framework residues that may adjust CDR structure and fine-tune the fit to antigen as described by Foote and Winter (J. Mol. Biol., 224: 487-499 (1992)). Vernier zone residues form a layer underlying the CDRs and may impact on the structure of CDRs and the affinity of the antibody.

As used herein, the term "neutralizing" refers to counteracting the biological activity of an antigen when a binding protein specifically binds the antigen. In an embodiment, the neutralizing binding protein binds an antigen and reduces its biological activity by at least about 20%, 40%, 60%, 80%, 85%, 90%, 95%, or more.

The term "activity" includes activities such as the binding specificity/affinity of an antibody for an antigen, for example, an anti-hDLL4 antibody that binds to an DLL4 antigen and/or the neutralizing potency of an antibody, or an anti-hDLL4 antibody whose binding to hDLL4 inhibits the biological activity of hDLL4, e.g. inhibition of PHA blast proliferation or inhibition of receptor binding in a human Notch receptor binding assay, or PHA blast interferon-gamma induction assay.

The term "epitope" includes any polypeptide determinant that specifically binds to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. An epitope thus consists of the amino acid residues of a region of an antigen (or fragment thereof) known to bind to the complementary site on the specific binding partner. An antigen or antigenic fragment can contain more than one epitope. Thus, it is understood by persons skilled in this art that every "antigen binding site" of an antibody molecule binds an epitope of an antigen molecule and every antigen molecule may have one, two, several, or many epitopes. Moreover, it is understood by persons skilled in this art that two independently isolated antibodies to an antigen molecule may bind at the same epitope or at two different epitopes on the antigen molecule.

In certain embodiments, an antibody is said to specifically bind an antigen when it recognizes its target antigen in a complex mixture of proteins and/or macromolecules. Antibodies are said to "bind to the same epitope" if the antibodies cross-compete (one prevents the binding or modulating effect of the other). In addition, structural definitions of epitopes (overlapping, similar, identical) are informative, but functional definitions are often more relevant as they encompass structural (binding) and functional (modulation, competition) parameters.

The term "surface plasmon resonance," as used herein, refers to an optical phenomenon that allows for the analysis of real-time biospecific interactions by detection of alterations in protein concentrations within a biosensor matrix, for example using the BIAcore® system (BIAcore International AB, a GE Healthcare company, Uppsala, Sweden and Piscataway, N.J., US). For further descriptions, see Jönsson et al., Ann. Biol. Clin., 51: 19-26 (1993); Jönsson et al. BioTechniques, 11: 620-627 (1991); Johnsson et al., J. Mol. Recognit., 8: 125-131 (1995); and Johnsson et al., Anal. Biochem., 198: 268-277 (1991).

The term "$K_{on}$", as used herein, is intended to refer to the on rate constant for association of a binding protein (e.g., an antibody) to a cognate partner (e.g., an antigen) to form a binding partner/cognate partner (e.g., antibody/antigen) complex as is known in the art. The "$K_{on}$" also is known by the terms "association rate constant," or "$k_a$," as used interchangeably herein. This value indicating the binding rate of an antibody to its target antigen or the rate of complex formation between an antibody and antigen also is shown by the equation:

Antibody("Ab")+Antigen("Ag")→Ab–Ag.

The term "$K_{off}$," as used herein, is intended to refer to the off rate constant for dissociation of a binding protein (e.g., an antibody) from the, e.g., antibody/antigen complex as is known in the art. The "$K_{off}$" also is known by the terms "dissociation rate constant" or "$k_d$" as used interchangeably herein. This value indicates the dissociation rate of an antibody from its target antigen or separation of Ab-Ag complex over time into free antibody and antigen as shown by the equation below:

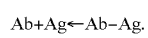

Ab+Ag←Ab–Ag.

The terms "equilibrium dissociation constant" or "$K_D$", as used interchangeably herein, refer to the value obtained in a titration measurement at equilibrium, or by dividing the dissociation rate constant ($K_{off}$) by the association rate constant ($K_{on}$). The association rate constant, the dissociation rate constant, and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® surface plasmon resonance (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

"Label" and "detectable label" mean a moiety attached to a specific binding partner, such as an antibody or an analyte bound by the antibody, e.g., to render the reaction between members of a specific binding pair, such as an antibody and an analyte, detectable. The specific binding partner, e.g., antibody or analyte, so labeled is referred to as "detectably labeled". Thus, the term "labeled binding protein" as used herein, refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by a marked avidin (e.g., an avidin or a streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm); chromogens, fluorescent labels (e.g., FITC, rhodamine, and lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, and epitope tags); and magnetic agents, such as gadolinium chelates. Representative examples of labels commonly employed for immunoassays include moieties that produce light, e.g., acridinium compounds, and moieties that produce fluorescence, e.g., fluorescein. Other labels are known in the art or described herein. In this regard, the moiety itself may not be detectably labeled but may become detectable upon reaction with yet another moiety. Use of "detectably labeled" is intended to encompass the latter type of detectable labeling.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal" and "crystallized" as used herein, refer to a binding protein (e.g., an antibody), or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes, including Fab/antigen complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See, Giegé et al., In *Crystallization of Nucleic Acids and Proteins, a Practical Approach,* 2nd ed., (Ducruix and Giegé, eds.) (Oxford University Press, New York, 1999), chapter 1, pages 1-16.

The term "polynucleotide" means a polymeric form of two or more nucleotides, either ribonucleotides or deoxyribonucleotides or a modified form of either type of nucleotide. The term includes single and double stranded forms of DNA.

The term "isolated polynucleotide" shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector," is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. RNA versions of vectors (including RNA viral vectors) may also find use in the invention.

The term "operably linked" refers to a juxtaposition wherein the components described are in a relationship permitting them to function in their intended manner A control sequence "operably linked" to a coding sequence is ligated in such a way that expression of the coding sequence is achieved under conditions compatible with the control sequences. "Operably linked" sequences include expression control sequences that are contiguous with a gene of interest, expression control sequences that act in trans, i.e., located on a different nucleic acid molecule than a gene of interest, as well as expression control sequences that are located on the same nucleic acid molecule as, but at a distance from, a gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include a promoter, a ribosomal binding site, and a transcription termination sequence; in eukaryotes, generally, such control sequences include a promoter and a transcription termination sequence. The term "control sequences" is intended to include components whose presence is essential for expression and processing, and can also include additional components whose presence is advantageous, for example, leader sequences and fusion partner sequences.

"Transformation," refers to any process by which exogenous nucleic acid (e.g., a DNA molecule) enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, plasmid uptake across a cellular membrane, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), is intended to refer to a cell into which exogenous DNA has been introduced. In an embodiment, the host cell comprises two or more (e.g., multiple) nucleic acids encoding antibodies, such as, by way of non-limiting example, the host cells described in U.S. Pat. No. 7,262,028. Such terms are intended to refer not only to the particular subject cell, but, also to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the Kingdoms of life. In another embodiment, eukaryotic cells include protist, fungal, plant and animal cells. In another embodiment, host cells include but are not limited to prokaryotic species, such *Escherichia coli*; mammalian cell lines, such as CHO, HEK 293, COS, NS0, SP2, and PER.C6; the insect cell line Sf9; and fungal cell species, such as *Saccharomyces cerevisiae.*

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See, e.g., Sambrook et al., *Molecular Cloning: A Laboratory Manual, second ed.* (Cold Spring Harbor Laboratory Press, Cold Spring Harbor, 1989).

"Transgenic organism," as known in the art, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of hDLL4). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hDLL4). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies have been described. See, e.g., PCT Publication No. WO01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, members of the Notch-signaling pathway, DLL4 polypeptides and nucleic acids, carbohydrates, or any other molecules that bind to DLL4.

The term "antagonist" or "inhibitor", as used herein, refers to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of DLL4, especially human DLL4 (hDLL4). Antagonists and inhibitors of hDLL4 may include, but are not limited to, proteins, nucleic acids, carbohydrates, or any other molecule, which binds to hDLL4 and/or rodent DLL4.

As used herein, the term "effective amount" refers to the amount of a therapy that is sufficient to reduce or ameliorate the severity and/or duration of a disorder or one or more symptoms thereof; inhibit or prevent the advancement of a disorder; cause regression of a disorder; inhibit or prevent the recurrence, development, onset, or progression of one or more symptoms associated with a disorder; detect a disorder; or enhance or improve the prophylactic or therapeutic effect(s) of another therapy (e.g., prophylactic or therapeutic agent).

"Patient" and "subject" may be used interchangeably herein to refer to an animal, such as a mammal, including a primate (for example, a human, a monkey, and a chimpanzee), a non-primate (for example, a cow, a pig, a camel, a llama, a horse, a goat, a rabbit, a sheep, a hamster, a guinea pig, a cat, a dog, a rat, a mouse, and a whale), a bird (e.g., a duck or a goose), and a shark. Preferably, a patient or subject is a human, such as a human being treated or assessed for a disease, disorder, or condition; a human at risk for a disease, disorder, or condition; a human having a disease, disorder, or condition; and/or human being treated for a disease, disorder, or condition. More preferably, a patient or subject is being treated or assessed for cancer or other disease in which the existing aberrant DLL4 expression supports the cancer or other disease and inhibition or disruption of DLL4 activity is desirable to treat the cancer or other disease.

The term "sample," as used herein, is used in its broadest sense. A "biological sample," as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, (e.g., whole blood), plasma, serum, urine, amniotic fluid, synovial fluid, endothelial cells, leukocytes, monocytes, other cells, organs, tissues, bone marrow, lymph nodes and spleen.

"Component," "components," and "at least one component," refer generally to a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide or other analyte as above, such as a composition comprising an analyte such as a polypeptide, which is optionally immobilized on a solid support, such as by binding to an anti-analyte (e.g., anti-polypeptide) antibody. Some components can be in solution or lyophilized for reconstitution for use in an assay.

"Risk" refers to the possibility or probability of a particular event occurring either presently or at some point in the future. "Risk stratification" refers to an array of known clinical risk factors that allows physicians to classify patients into a low, moderate, high or highest risk of developing a particular disease, disorder or condition.

"Specific" and "specificity" in the context of an interaction between members of a specific binding pair (e.g., an antigen or fragment thereof and an antibody or antigen binding fragment thereof) refer to the selective reactivity of the interaction. The phrase "specifically binds to" and analogous phrases refer to the ability of binding proteins, such as antibodies (or antigen binding fragments thereof), to bind specifically to a molecule of interest (or a fragment thereof) and not bind specifically to other entities.

"Specific binding partner" is a member of a specific binding pair. A specific binding pair comprises two different molecules, which specifically bind to each other through chemical or physical means. Therefore, in addition to antigen and antibody specific binding pairs, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

"Variant" as used herein means a polypeptide that differs from a given polypeptide (e.g., DLL4 polypeptide or anti-DLL4 antibody) in amino acid sequence by the addition (e.g., insertion), deletion, or conservative substitution of amino acids, but that retains the biological activity of the given polypeptide (e.g., a variant DLL4 may compete with a wild-type DLL4 for binding with an anti-DLL4 antibody if the variant DLL4 retains the original antibody binding site (epitope) of the wildtype DLL4). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol., 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity, e.g., the ability to bind to DLL4. Use of "variant" herein is intended to encompass fragments of a variant unless otherwise contradicted by context.

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes, and spleen.

I. Antibodies That Bind Human DLL4.

One aspect of the present invention provides isolated rat monoclonal antibodies, or antigen-binding portions thereof, that bind to DLL4 with high affinity, a slow off rate, and/or high neutralizing capacity. Another aspect of the invention provides chimeric antibodies that bind DLL4. In another aspect, the invention provides CDR grafted antibodies, or antigen-binding portions thereof, that DLL4. Another aspect of the invention provides humanized antibodies, or antigen-binding portions thereof, that bind DLL4. In an embodiment, the antibodies, or portions thereof, are isolated antibodies or isolated portions thereof. In another embodiment, the antibodies, or antigen-binding portions thereof, of the invention are neutralizing anti-DLL antibodies. Advantageously, such antibodies or antigen-binding portions thereof that bind DLL4 find use as therapeutic agents that can be administered to an individual (human or other mammal). Preferably, the antibodies or antigen-binding portions thereof of the invention are neutralizing anti-DLL4 and/or anti-VEGFR2 antibodies.

A. Method of Making Anti-DLL4 Antibodies.

Antibodies of the present invention may be made by any of a number of techniques known in the art. Aspects of various techniques that may be employed to obtain DLL4 monoclonal antibodies according to the invention are described below.

1. Anti-DLL4 Monoclonal Antibodies Using Hybridoma Technology.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual, second edition*, (Cold Spring Harbor Laboratory Press, Cold Spring Harbor, 1988); Hammerling, et al., In *Monoclonal Antibodies and T-Cell Hybridomas*, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In an embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from an animal, e.g., a rat or a mouse, immunized with DLL4 with myeloma cells and then screening the hybridomas resulting from the fusion for hybridoma clones that secrete an antibody able to bind a polypeptide of the invention. Briefly, rats can be immunized with a DLL4 antigen (see, Examples, below). In a preferred embodiment, the DLL4 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a DLL4 antigen, antibodies and/or antibody-producing cells may be obtained from the animal. An anti-DLL4 antibody-containing serum is obtained from the animal by bleeding or sacrificing the animal. The serum may be used as it is obtained from the animal, an immunoglobulin fraction may be obtained from the serum, or the anti-DLL4 antibodies may be purified from the serum. Serum or immunoglobulins obtained in this manner are polyclonal, thus having a heterogeneous array of properties.

Once an immune response is detected, e.g., antibodies specific for the antigen DLL4 are detected in the rat serum, the rat spleen is harvested and splenocytes isolated. The splenocytes are then fused by well-known techniques to any suitable myeloma cells, for example cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding DLL4. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using DLL4, or a portion thereof, or a cell expressing DLL4. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-DLL4 antibody-producing hybridomas are selected, cloned, and further screened for desirable characteristics, including robust hybridoma growth, high antibody production, and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas, as described herein. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-DLL4 antibody.

Antibody fragments that recognize specific epitopes may be generated by known techniques. For example, Fab and F(ab')$_2$ fragments of the invention may be produced by proteolytic cleavage of immunoglobulin molecules, using enzymes such as papain (to produce two identical Fab fragments) or pepsin (to produce a F(ab')$_2$ fragment). A F(ab')$_2$ fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, a F(ab')$_2$ fragment is still capable of crosslinking antigen molecules like the parent IgG molecule.

2. Anti-DLL4 Monoclonal Antibodies Using SLAM.

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., Proc. Natl. Acad. Sci. USA, 93: 7843-7848 (1996). In this method, single cells secreting antibodies of interest, e.g., lymphocytes derived from any one of the immunized animals described in Section I.A.1 (above), are screened using an antigen-specific hemolytic plaque assay, wherein the antigen DLL4, a subunit of DLL4, or a fragment thereof, is coupled to sheep red blood cells using a linker, such as biotin, and used to identify single cells that secrete antibodies with specificity for DLL4. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to DLL4. The amplified immunoglobulin sequences further can be manipulated in vitro, such as by in vitro affinity maturation method. See, for example, PCT Publication No. WO 97/29131 and PCT Publication No. WO 00/56772.

3. Anti-DLL4 Monoclonal Antibodies Using Transgenic Animals.

In another embodiment of the instant invention, antibodies are produced by immunizing a non-human animal comprising some, or all, of the human immunoglobulin locus with a DLL4 antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., Nature Genetics, 7: 13-21 (1994) and U.S. Pat. Nos. 5,916,771; 5,939,598; 5,985,615; 5,998,209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., Nature Genetics, 15: 146-156 (1997), Green and Jakobovits, J. Exp. Med., 188: 483-495 (1998), the disclosures of which are hereby incorporated by reference.

4. Anti-DLL4 Monoclonal Antibodies Using Recombinant Antibody Libraries.

In vitro methods also can be used to make the antibodies of the invention, wherein an antibody library is screened to identify an antibody having the desired DLL4-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., Bio/Technology, 9: 1369-1372 (1991); Hay et al., Hum. Antibod. Hybridomas, 3: 81-85 (1992); Huse et al., Science, 246: 1275-1281 (1989); McCafferty et al., Nature, 348: 552-554 (1990); Griffiths et al., EMBO J., 12: 725-734 (1993); Hawkins et al., J. Mol. Biol., 226: 889-896 (1992); Clackson et al., Nature, 352: 624-628 (1991); Gram et al., Proc. Natl. Acad. Sci. USA, 89: 3576-3580 (1992); Garrard et al., Bio/Technology, 9: 1373-1377 (1991); Hoogenboom et al., Nucl. Acids Res., 19: 4133-4137 (1991); Barbas et al., Proc. Natl. Acad. Sci. USA, 88: 7978-7982 (1991); US Patent Application Publication No. 2003/0186374; and PCT Publication No. WO 97/29131, the contents of each of which are incorporated herein by reference.

The recombinant antibody library may be from a subject immunized with DLL4, or a portion of DLL4. Alternatively, the recombinant antibody library may be from a naïve subject, i.e., one who has not been immunized with DLL4, such as a human antibody library from a human subject who has not been immunized with human DLL4. Antibodies of the invention are selected by screening the recombinant antibody library with the peptide comprising human DLL4 to thereby select those antibodies that recognize DLL4. Methods for conducting such screening and selection are well known in the art, such as described in the references in the preceding paragraph. To select antibodies of the invention having particular binding affinities for DLL4, such as those that dissociate from human DLL4 with a particular $K_{off}$ rate constant, the art-known method of surface plasmon resonance can be used to select antibodies having the desired $K_{off}$ rate constant. To select antibodies of the invention having a particular neutralizing activity for hDLL4, such as those with a particular $IC_{50}$, standard methods known in the art for assessing the inhibition of DLL4 activity may be used.

In one aspect, the invention pertains to an isolated antibody, or an antigen-binding portion thereof, that binds human DLL4. Preferably, the antibody is a neutralizing antibody. In various embodiments, the antibody is a recombinant antibody or a monoclonal antibody.

For example, antibodies of the present invention can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies of the present invention include those disclosed in Brinkmann et al., J. Immunol. Methods, 182: 41-50 (1995); Ames et al., J. Immunol. Methods, 184:177-186 (1995); Kettleborough et al., Eur. J. Immunol., 24: 952-958 (1994); Persic et al., Gene, 187: 9-18 (1997); Burton et al., Advances in Immunology, 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., BioTechniques, 12(6): 864-869 (1992); Sawai et al., Am. J. Reprod. Immunol., 34: 26-34 (1995); and Better et al., Science, 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., Proc. Natl. Acad. Sci. USA, 90: 7995-7999 (1993); and Skerra et al., Science, 240: 1038-1041 (1988).

Alternative to screening of recombinant antibody libraries by phage display, other methodologies known in the art for screening large combinatorial libraries can be applied to the identification of antibodies of the invention. One type of alternative expression system is one in which the recombinant antibody library is expressed as RNA-protein fusions, as described in PCT Publication No. WO 98/31700 (Szostak and Roberts), and in Roberts and Szostak, Proc. Natl. Acad. Sci. USA, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology, is the PROfusion display technology employed in the Examples (infra).

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in U.S. Pat. No. 6,699,658 (Wittrup et al.) incorporated herein by reference.

B. Production of Recombinant DLL4 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human DLL4) and the other heavy and light chain are specific for an antigen other than human DLL4 by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Anti-DLL4 Antibodies.

Amino acid sequences of VH and VL regions of isolated rat monoclonal antibodies that bind human DLL4 are shown for clones 38H12, 1A11, 37D10, 32C7, 14G1, 14A11, and 15D6 in Table 9 (See, Example 4, below). The isolated anti-DLL4 antibody CDR sequences described herein establish a family of DLL4 binding proteins, isolated in accordance with this invention, and comprising polypeptides that include the CDR sequences derived therefrom and affinity matured clones thereof. Sequences of variable regions and CDRs of the monoclonal antibodies and affinity matured derivatives thereof are listed in Tables 9, 11, 16, 20, and 21. To generate and to select CDRs for binding proteins according to the invention having preferred DLL4 binding and/or neutralizing activity with respect to human DLL4, standard methods known in the art for generating binding proteins of the present invention and assessing the DLL4 binding and/or neutralizing characteristics of those binding protein may be used, including but not limited to those specifically described herein.

Based on an alignment of the amino acid sequences of the CDRs of the heavy chain variable regions (VH) and the light chain variable regions (VL) of the anti-DLL4 antibody clones described herein, the invention provides a DLL4 binding protein comprising an antigen binding domain capable of binding human DLL4, said antigen binding domain comprising at least one or more of the six CDRs, i.e., CDR-H1, CDR-H2, CDR-H3, CDR-L1, CDR-L2, and CDRL-3, defined below:

CDR-H1 is selected from the group consisting of:
$X_1$-$X_2$-$X_3$-$X_4$-$X_5$ (SEQ ID NO:151), wherein;
  $X_1$ is N, H, or Y;
  $X_2$ is F;
  $X_3$ is P;
  $X_4$ is M; and
  $X_5$ is A or S;
residues 31-35 of SEQ ID NO:157 (CDR-H1 38H12);
residues 31-35 of SEQ ID NO:161 (CDR-H1 37D10);
residues 31-35 of SEQ ID NO:163 (CDR-H1 32C7);
residues 31-35 of SEQ ID NO:165 (CDR-H1 14G1);
residues 31-35 of SEQ ID NO:167 (CDR-H1 14A11);
residues 31-35 of SEQ ID NO:169 (CDR-H1 15D6);
residues 31-35 of SEQ ID NO:171 (CDR-H1 VH.1 1A11);
residues 31-35 of SEQ ID NO:172 (CDR-H1 VH.1a 1A11);
residues 31-35 of SEQ ID NO:173 (CDR-H1 VH.1b 1A11);
residues 31-35 of SEQ ID NO:174 (CDR-H1 VH.2a 1A11);
residues 31-35 of SEQ ID NO:179 (CDR-H1 VH.1 38H12);
residues 31-35 of SEQ ID NO:180 (CDR-H1 VH.1A 38H12);
residues 31-35 of SEQ ID NO:181 (CDR-H1 VH.1b 38H12);
residues 31-35 of SEQ ID NO:182 (CDR-H1 VH.2a 38H12);
residues 31-35 of SEQ ID NO:187 (CDR-H1 h1A11VH.1);
residues 31-35 of SEQ ID NO:188 (CDR-H1 h1A11.A6);
residues 31-35 of SEQ ID NO:189 (CDR-H1 h1A11.A8);
residues 31-35 of SEQ ID NO:190 (CDR-H1 h1A11.C6);
residues 31-35 of SEQ ID NO:191 (CDR-H1 h1A11.A11);
residues 31-35 of SEQ ID NO:192 (CDR-H1 h1A11.B5);
residues 31-35 of SEQ ID NO:193 (CDR-H1 h1A11.E12);
residues 31-35 of SEQ ID NO:194 (CDR-H1 h1A11.G3);
residues 31-35 of SEQ ID NO:195 (CDR-H1 h1A11.F5); and
residues 31-35 of SEQ ID NO:196 (CDR-H1 h1A11.H2);

CDR-H2 is selected from the group consisting of:
$X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$ (SEQ ID NO:152), wherein;
  $X_1$ is T or S;
  $X_2$ is I;
  $X_3$ is S;
  $X_4$ is S or G;
  $X_5$ is S;
  $X_6$ is D;
  $X_7$ is G, A, D, S, or E;
  $X_8$ is T or W;
  $X_9$ is T, P, or A;
  $X_{10}$ is Y, S, T, or N;
  $X_{11}$ is Y or I;
  $X_{12}$ is R or G;
  $X_{13}$ is D;
  $X_{14}$ is S;
  $X_{15}$ is V;
  $X_{16}$ is K; and
  $X_{17}$ is G;
residues 50-66 of SEQ ID NO:157 (CDR-H2 38H12);
residues 50-68 of SEQ ID NO:161 (CDR-H2 37D10);
residues 50-66 of SEQ ID NO:163 (CDR-H2 32C7);
residues 50-66 of SEQ ID NO:165 (CDR-H2 14G1);
residues 50-66 of SEQ ID NO:167 (CDR-H2 14A11);
residues 50-66 of SEQ ID NO:169 (CDR-H2 15D6);
residues 50-66 of SEQ ID NO:171 (CDR-H2 VH.1 1A11);
residues 50-66 of SEQ ID NO:172 (CDR-H2 VH.1a 1A11);
residues 50-66 of SEQ ID NO:173 (CDR-H2 VH.1b 1A11);
residues 50-66 of SEQ ID NO:174 (CDR-H2 VH.2a 1A11);
residues 50-66 of SEQ ID NO:179 (CDR-H2 VH.1 38H12);
residues 50-66 of SEQ ID NO:180 (CDR-H2 VH.1A 38H12);
residues 50-66 of SEQ ID NO:181 (CDR-H2 VH.1b 38H12);
residues 31-35 of SEQ ID NO:182 (CDR-H1 VH.2a 38H12);
residues 50-66 of SEQ ID NO:187 (CDR-H2 h1A11VH.1);
residues 50-66 of SEQ ID NO:188 (CDR-H2 h1A11.A6);
residues 50-66 of SEQ ID NO:189 (CDR-H2 h1A11.A8);
residues 50-66 of SEQ ID NO:190 (CDR-H2 h1A11.C6);
residues 50-66 of SEQ ID NO:191 (CDR-H2 h1A11.A11);
residues 50-66 of SEQ ID NO:192 (CDR-H2 h1A11.B5);
residues 50-66 of SEQ ID NO:193 (CDR-H2 h1A11.E12);
residues 50-66 of SEQ ID NO:194 (CDR-H2 h1A11.G3);
residues 50-66 of SEQ ID NO:195 (CDR-H2 h1A11.F5); and
residues 50-66 of SEQ ID NO:196 (CDR-H2 h1A11.H2);

CDR-H3 is selected from the group consisting of:
$X_1$-$X_2$-$X_3$-$X_4$-$X_5$-$X_6$-$X_7$-$X_8$-$X_9$ (SEQ ID NO:153), wherein;
  $X_1$ is G;
  $X_2$ is Y;

$X_3$ is Y;
$X_4$ is N;
$X_5$ is S;
$X_6$ is P;
$X_7$ is F;
$X_8$ is A; and
$X_9$ is Y, F, or S;
residues 99-107 of SEQ ID NO:157 (CDR-H3 38H12);
residues 101-111 of SEQ ID NO:161 (CDR-H3 37D10);
residues 99-105 of SEQ ID NO:163 (CDR-H3 32C7);
residues 99-105 of SEQ ID NO:165 (CDR-H3 14G1);
residues 99-110 of SEQ ID NO:167 (CDR-H3 14A11);
residues 99-110 of SEQ ID NO:169 (CDR-H3 15D6);
residues 99-107 of SEQ ID NO:171 (CDR-H3 VH.1 1A11);
residues 99-107 of SEQ ID NO:172 (CDR-H3 VH.1a 1A11);
residues 99-107 of SEQ ID NO:173 (CDR-H3 VH.1b 1A11);
residues 99-107 of SEQ ID NO:174 (CDR-H3 VH.2a 1A11);
residues 99-107 of SEQ ID NO:179 (CDR-H3 VH.1 38H12);
residues 99-107 of SEQ ID NO:180 (CDR-H3 VH.1A 38H12);
residues 99-107 of SEQ ID NO:181 (CDR-H2 VH.1b 38H12);
residues 99-107 of SEQ ID NO:182 (CDR-H1 VH.2a 38H12);
residues 99-107 of SEQ ID NO:187 (CDR-H3 h1A11VH.1);
residues 99-107 of SEQ ID NO:188 (CDR-H3 h1A11.A6);
residues 99-107 of SEQ ID NO:189 (CDR-H3 h1A11.A8);
residues 99-107 of SEQ ID NO:190 (CDR-H3 h1A11.C6);
residues 99-107 of SEQ ID NO:191 (CDR-H3 h1A11.A11);
residues 99-107 of SEQ ID NO:192 (CDR-H3 h1A11.B5);
residues 99-107 of SEQ ID NO:193 (CDR-H3 h1A11.E12);
residues 99-107 of SEQ ID NO:194 (CDR-H3 h1A11.G3);
residues 99-107 of SEQ ID NO:195 (CDR-H3 h1A11.F5); and
residues 99-107 of SEQ ID NO:196 (CDR-H3 h1A11.H2);
CDR-L1 is selected from the group consisting of:
$X_1$-$X_2$-$X_3$-$X_4$-$X_5$-$X_6$-$X_7$-$X_8$-$X_9$-$X_{10}$-$X_{11}$ (SEQ ID NO:154), wherein;
$X_1$ is R;
$X_2$ is A;
$X_3$ is S;
$X_4$ is E or Q;
$X_5$ is D or E;
$X_6$ is I;
$X_7$ is Y or W;
$X_8$ is S, I, Y, N, or R;
$X_9$ is N;
$X_{10}$ is L; and
$X_{11}$ is A;
residues 24-34 of SEQ ID NO:158 (CDR-L1 38H12);
residues 24-34 of SEQ ID NO:162 (CDR-L1 37D10);
residues 24-34 of SEQ ID NO:164 (CDR-L1 32C7);
residues 24-34 of SEQ ID NO:166 (CDR-L1 14G1);
residues 23-37 of SEQ ID NO:168 (CDR-L1 14A11);
residues 23-37 of SEQ ID NO:170 (CDR-L1 15D6);
residues 24-34 of SEQ ID NO:175 (CDR-L1 VL.1 1A11);
residues 24-34 of SEQ ID NO:176 (CDR-L1 VL.1a 1A11);
residues 24-34 of SEQ ID NO:177 (CDR-L1 VL.1b 1A11);
residues 24-34 of SEQ ID NO:178 (CDR-L1 VL.2a 1A11);
residues 24-34 of SEQ ID NO:183 (CDR-L1 VL.1 38H12);
residues 24-34 of SEQ ID NO:184 (CDR-L1 VL.1a 38H12);
residues 24-34 of SEQ ID NO:185 (CDR-L1 VL.1b 38H12);
residues 24-34 of SEQ ID NO:186 (CDR-L1 VL.2a 38H12);
residues 24-34 of SEQ ID NO:197 (CDR-L1 h1A11VL.1);
residues 24-34 of SEQ ID NO:198 (CDR-L1 h1A11.A2);
residues 24-34 of SEQ ID NO:199 (CDR-L1 h1A11.A12);
residues 24-34 of SEQ ID NO:200 (CDR-L1 h1A11.A7);
residues 24-34 of SEQ ID NO:201 (CDR-L1 h1A11.B4);
residues 24-34 of SEQ ID NO:202 (CDR-L1 h1A11.B5); and
residues 24-34 of SEQ ID NO:203 (CDR-L1 h1A11.E12);
CDR-L2 is selected from group consisting of:
$X_1$-$X_2$-$X_3$-$X_4$-$X_5$-$X_6$-$X_7$ (SEQ ID NO:155), wherein;
$X_1$ is D;
$X_2$ is T;
$X_3$ is N or S;
$X_4$ is N, D, S, I, Y, or V;
$X_5$ is L;
$X_6$ is A; and
$X_7$ is D;
residues 50-56 of SEQ ID NO:158 (CDR-L2 38H12);
residues 50-56 of SEQ ID NO:162 (CDR-L2 37D10);
residues 50-56 of SEQ ID NO:164 (CDR-L2 32C7);
residues 50-56 of SEQ ID NO:166 (CDR-L2 14G1);
residues 53-59 of SEQ ID NO:168 (CDR-L2 14A11);
residues 53-59 of SEQ ID NO:170 (CDR-L2 15D6);
residues 50-56 of SEQ ID NO:175 (CDR-L2 VL.1 1A11);
residues 50-56 of SEQ ID NO:176 (CDR-L2 VL.1a 1A11);
residues 50-56 of SEQ ID NO:177 (CDR-L2 VL.1b 1A11);
residues 50-56 of SEQ ID NO:178 (CDR-L2 VL.2a 1A11);
residues 50-56 of SEQ ID NO:183 (CDR-L2 VL.1 38H12);
residues 50-56 of SEQ ID NO:184 (CDR-L2 VL.1a 38H12);
residues 50-56 of SEQ ID NO:185 (CDR-L2 VL.1b 38H12);
residues 50-56 of SEQ ID NO:186 (CDR-L2 VL.2a 38H12);
residues 50-56 of SEQ ID NO:197 (CDR-L2 h1A11VL.1);
residues 50-56 of SEQ ID NO:198 (CDR-L2 h1A11.A2);

residues 50-56 of SEQ ID NO:199 (CDR-L2 h1A11.A12);
residues 50-56 of SEQ ID NO:200 (CDR-L2 h1A11.A7);
residues 50-56 of SEQ ID NO:201 (CDR-L2 h1A11.B4);
residues 50-56 of SEQ ID NO:202 (CDR-L2 h1A11.B5); and
residues 50-56 of SEQ ID NO:203 (CDR-L2 h1A11.E12); and CDR-L3 is selected from the group consisting of:
$X_1$-$X_2$-$X_3$-$X_4$-$X_5$-$X_6$-$X_7$-$X_8$-$X_9$ (SEQ ID NO:156), wherein;
$X_1$ is Q;
$X_2$ is Q;
$X_3$ is Y;
$X_4$ is N, D, or T;
$X_5$ is N, Y, or W;
$X_6$ is Y or V;
$X_7$ is P;
$X_8$ is P; and
$X_9$ is T;
residues 89-97 of SEQ ID NO:158 (CDR-L3 38H12);
residues 89-97 of SEQ ID NO:162 (CDR-L3 37D10);
residues 89-97 of SEQ ID NO:164 (CDR-L3 32C7);
residues 89-98 of SEQ ID NO:166 (CDR-L3 14G1);
residues 92-100 of SEQ ID NO:168 (CDR-L3 14A11);
residues 92-100 of SEQ ID NO:170 (CDR-L3 15D6);
residues 89-97 of SEQ ID NO:175 (CDR-L3 VL.1 1A11);
residues 89-97 of SEQ ID NO:176 (CDR-L3 VL.1a 1A11);
residues 89-97 of SEQ ID NO:177 (CDR-L3 VL.1b 1A11);
residues 89-97 of SEQ ID NO:178 (CDR-L3 VL.2a 1A11);
residues 89-97 of SEQ ID NO:183 (CDR-L3 VL.1 38H12);
residues 89-97 of SEQ ID NO:184 (CDR-L3 VL.1a 38H12);
residues 89-97 of SEQ ID NO:185 (CDR-L3 VL.1b 38H12);
residues 89-97 of SEQ ID NO:186 (CDR-L3 VL.2a 38H12);
residues 89-97 of SEQ ID NO:197 (CDR-L3 h1A11VL.1);
residues 89-97 of SEQ ID NO:198 (CDR-L3 h1A11.A2);
residues 89-97 of SEQ ID NO:199 (CDR-L3 h1A11.A12);
residues 89-97 of SEQ ID NO:200 (CDR-L3 h1A11.A7);
residues 89-97 of SEQ ID NO:201 (CDR-L3 h1A11.B4);
residues 89-97 of SEQ ID NO:202 (CDR-L3 h1A11.B5); and
residues 89-97 of SEQ ID NO:203 (CDR-L3 h1A11.E12).

Preferably, a DLL4 binding protein comprises at least one CDR described above, more preferably any two CDRs described above, more preferably any three CDRs described above, even more preferably any four CDRs described above, still more preferably any five CDRs described above, and most preferably any six CDRs described above (i.e., CDR-H1, CDR-H2, CDR-H3, CDR-L1, CDR-L2, and CDR-L3 as described above). A particularly preferred DLL4 binding protein comprising three CDRs comprises CDR-H1, CDR-H2, and CDR-H3 as described above.

Preferably, a DLL4 binding protein comprising one or more CDRs described above binds human ("hu", "h") DLL4 and also one or more DLL4 proteins selected from the group consisting of: mouse ("murine", "mu") DLL4, cynomolgus monkey ("cynomolgus", "cyno") DLL4, and rat DLL4.

Preferably, a DLL4 binding protein comprising one or more CDRs described above binds human ("hu") DLL4 and also cynomolgus monkey ("cynomolgus", "cyno") DLL4.

2. Anti-DLL4 Chimeric Antibodies.

A chimeric antibody is a molecule in which different portions of the antibody are derived from different animal species, such as antibodies having a variable region derived from a murine monoclonal antibody and a human immunoglobulin constant region. See e.g., Morrison, Science, 229: 1202-1207 (1985); Oi et al., BioTechniques, 4: 214 (1986); Gillies et al., J. Immunol. Methods, 125: 191-202 (1989); U.S. Pat. Nos. 5,807,715; 4,816,567; and 4,816,397. In addition, techniques developed for the production of "chimeric antibodies" by splicing genes from a mouse antibody molecule of appropriate antigen specificity together with genes from a human antibody molecule of appropriate biological activity can be used. See, for example, Morrison et al., Proc. Natl. Acad. Sci. USA, 81: 6851-6855 (1984); Neuberger et al., Nature, 312: 604-608 (1984); Takeda et al., Nature, 314: 452-454 (1985), which are incorporated herein by reference in their entireties.

3. Anti-DLL4 CDR Grafted antibodies.

The isolated anti-DLL4 antibody CDR sequences of the invention may be used to make CDR-grafted antibodies to modulate the properties of the original antibody. Such properties include but are not limited to binding kinetics, affinity, biological activities, species cross-reactivity, molecule cross-reactivity, epitope, physicochemical properties, pharmacokinetic properties, pharmacodynamic properties, or pharmacological properties. CDR-grafted antibodies comprise heavy and light chain variable region sequences from a human antibody or a non-human primate antibody wherein one or more of the CDR regions of VH and/or VL are replaced with CDR sequences of the original anti-DLL4 antibody. A framework sequence from any human or non-human primate antibody may serve as the template for CDR grafting. However, straight chain replacement onto such a framework often leads to some loss of binding affinity to the antigen. The more homologous a human, or other species, antibody is to the original human antibody, the less likely the possibility that combining the CDRs with the new human framework or non-human primate framework will introduce distortions in the CDRs that could reduce affinity or other properties. Therefore, it is preferable that the variable framework that is chosen to replace the human variable region framework apart from the CDRs has at least a 30% sequence identity with the human antibody variable region framework. It is more preferable that the variable region framework that is chosen to replace the human variable region framework apart from the CDRs has at least a 40% sequence identity with the human antibody variable region framework. It is more preferable that the variable region framework that is chosen to replace the human variable framework apart from the CDRs has at least a 50% sequence identity with the human antibody variable region framework. It is more preferable that the variable region framework that is chosen to replace the human variable framework apart from the CDRs has at least a 60% sequence identity with the human antibody variable region framework. It is more preferable that the new human or non-human primate and the original human variable region framework apart from the CDRs has at least 70% sequence identity. It is even more preferable that the new human or non-human primate and the original human variable region framework apart from the CDRs has at least 75% sequence identity. It is most preferable that the new human or non-human primate and the original human variable region framework apart from the CDRs has at least 80% sequence identity. Even using a highly homologous human or non-human primate framework to graft CDRs of the original human anti-DLL4 antibody, the resulting grafted antibody may still lose binding affinity to antigen to some degree. In this case, to regain the affinity it is necessary to include at least one or more key framework residue(s) substitution of the original antibody to the corresponding position of the newly grafted antibody. Such a key residue may be selected from the group consisting of:

- a residue adjacent to a CDR;
- a glycosylation site residue;
- a rare residue;
- a residue capable of interacting with human DLL4
- a canonical residue;
- a contact residue between heavy chain variable region and light chain variable region;
- a residue within a Vernier zone; and
- a residue in a region that overlaps between a Chothia-defined variable heavy chain CDR1 and a Kabat-defined first heavy chain framework.

4. Anti-DLL4 Humanized Antibodies.

While the compositions of the present invention eliminate the requirement to make humanized antibodies, humanized DLL4 antibodies may be prepared using compositions of the invention. Humanized antibodies are antibody molecules from non-human species antibody that binds the desired antigen having one or more complementarity determining regions (CDRs) from the non-human species and framework regions from a human immunoglobulin molecule. Known human Ig sequences are disclosed at web sites available via the world wide web (www.), e.g., ncbi.nlm.nih.gov/entrez/query.fcgi; atcc.org/phage/hdb.html; sciquest.com/; abcam.com/; antibodyresource.com/onlinecomp.html; public.iastate.eduLabout.pedro-/research_tools.html; mgen.uniheidelberg.de/SD/IT/IT.html; whfreeman.com/immunology-/CH05/kuby05.htm; library.thinkquest.org/12429/Immune/Antibody.html; hhmi.org/grants/lectures/1996/vlab/; path.-cam.ac.uk/.about.mrc7/mikeimages.html; antibodyresource.com/; mcb.harvard.edu/BioLinks-/Immunology.html; immunologylink.com/; pathbox.wustl.eduLabout.hcenter/index.html; bio-tech.ufl.edu/.about.hcl/; pebio-.com/pa/340913-/340913.html; nal.usda.gov/awic/pubs/antibody/; m.ehimeu.acjp/.about.yasuhito-/Elisa.html; biodesign.com/table.asp; icnet.uk/axp/facs/davies/lin-ks.html; biotech.ufl.edu-/.about.fccl/protocol.html; isac-net.org/sites_geo.html; aximtl.imt.uni-marburg.de/.about.rek/AEP-Start.html; baserv.uci.kun.nl/.about.jraats/linksl.html; recab.uni-hd.de/immuno.bme.nwu.edu/; mrc-cpe.cam.ac.uk/imt-doc/public/INTRO.html; ibt.unam.mx/-virN_mice.html; imgt.cnusc.fr:8104/; biochem.ucl.ac.uk/.about.martin/abs/index.html; anti-body.bath.ac.uk/; abgen.cvm.tamu.edu/lab/wwwabgen.html; unizh.ch/.about.honegger/AHO-seminar/Slide01.html; cryst.bbk.ac.uk/.about.ubcg07s/; nimr.mrc.ac.uk/CC/ccaewg/ccaewg.htm; path.cam.ac.uk/.about.mrc7/humanisation/TAHHP.html; ibt.unam.mx/vir/structure/stat_aim.-html; biosci.missouri.edu/smithgp/index.html; cryst.bioc.cam.ac.uk/.about.fmolina/Webpages-/Pept/spottech.html; jerini.de/frroducts.htm; patents.ibm.com/ibm.html. Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089 (Queen et al.); Riechmann et al., Nature, 332: 323-327 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature, 321: 522-525 (1986); Verhoeyen et al., Science, 239: 1534-1536 (1988), Sims et al., J. Immunol., 151: 2296-2308 (1993); Chothia and Lesk, J. Mol. Biol., 196: 901-917 (1987), Carter et al., Proc. Natl. Acad. Sci. USA, 89: 4285-4289 (1992); Presta et al., J. Immunol., 151: 2623-2632 (1993), Padlan, E. A., Molecular Immunology, 28(4/5): 489-498 (1991); Studnicka et al., Protein Engineering, 7(6): 805-814 (1994); Roguska. et al., Proc. Natl. Acad. Sci. USA, 91:969-973 (1994); PCT Publication Nos. WO 91/09967, WO 99/06834 (PCT/US98/16280), WO 97/20032 (PCT/US96/18978), WO 92/11272 (PCT/US91/09630), WO 92/03461 (PCT/US91/05939), WO 94/18219 (PCT/US94/01234), WO 92/01047 (PCT/GB91/01134), WO 93/06213 (PCT/GB92/01755), WO90/14443, WO90/14424, and WO90/14430; European Publication Nos. EP 0 592 106, EP 0 519 596, and EP 0 239 400; U.S. Pat. Nos. 5,565,332; 5,723,323; 5,976, 862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567, each entirely incorporated herein by reference, included references cited therein.

C. Production of Antibodies and Antibody-Producing Cell Lines.

Preferably, anti-DLL4 antibodies of the present invention exhibit a high capacity to reduce or to neutralize tumor angiogenesis activity, e.g., as assessed by any one of several in vitro and in vivo assays known in the art. For example, these antibodies neutralize DLL4 interaction in the Notch-signaling pathway with $IC_{50}$ values in DLL4 in the range of at least about $10^{-7}$ M, or about $10^{-8}$ M. Preferably, anti-DLL4 antibodies of the present invention also exhibit a high capacity to reduce or to neutralize DLL4 activity.

In preferred embodiments, an isolated antibody, or antigen-binding portion thereof, binds human DLL4, wherein the antibody, or antigen-binding portion thereof, dissociates from human DLL4 with a $K_{off}$ rate constant of about 0.1 s$^{-1}$ or less, as determined by surface plasmon resonance, or which inhibits DLL4 and/or human DLL4 activity with an $IC_{50}$ of about $1\times10^{-6}$ M or less. Alternatively, the antibody, or an antigen-binding portion thereof, may dissociate from human DLL4 with a $K_{off}$ rate constant of about $1\times10^{-2}$ s$^{-1}$ or less, as determined by surface plasmon resonance, or may inhibit human DLL4 and/or human DLL4 activity with an $IC_{50}$ of about $1\times10^{-7}$ M or less. Alternatively, the antibody, or an antigen-binding portion thereof, may dissociate from human DLL4 with a $K_{off}$ rate constant of about $1\times10^{-3}$ s$^{-1}$ or less, as determined by surface plasmon resonance, or may inhibit human DLL4 with an $IC_{50}$ of about $1\times10^{-8}$ M or less. Alternatively, the antibody, or an antigen-binding portion thereof, may dissociate from human DLL4 with a $K_{off}$ rate constant of about $1\times10^{4}$ s$^{-1}$ or less, as determined by surface plasmon resonance, or may inhibit DLL4 activity with an $IC_{50}$ of about $1\times10^{-9}$ M or less. Alternatively, the antibody, or an antigen-binding portion thereof, may dissociate from human DLL4 with a $K_{off}$ rate constant of about $1\times10^{-5}$ s$^{-1}$ or less, as determined by surface plasmon resonance, or may inhibit DLL4 and/or human DLL4 activity with an $IC_{50}$ of about $1\times10^{-10}$ M or less. Alternatively, the antibody, or an antigen-binding portion thereof, may dissociate from human DLL4 with a $K_{off}$ rate constant of about $1\times10^{-5}$ s$^{-1}$ or less, as determined by surface plasmon resonance, or may inhibit DLL4 and/or human DLL4 activity with an $IC_{50}$ of about $1\times10^{-11}$ M or less.

In certain embodiments, the antibody comprises a heavy chain constant region, such as an IgG1, IgG2, IgG3, IgG4, IgA, IgE, IgM, or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (see, U.S. Pat. Nos. 5,648,260 and 5,624,821 (Winter et al.)). The Fc portion of an antibody mediates several important effector functions e.g. cytokine induction, ADCC, phagocytosis, complement dependent cytotoxicity (CDC), and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized DLL4 binding protein. Preferably, the invention relates to crystals of DLL4 binding proteins described herein, including whole anti-DLL4 antibodies, fragments thereof, as well as antibody constructs and binding protein conjugates (including antibody conjugates) as disclosed herein, and formulations and compositions comprising such crystals. In one embodiment, the crystallized binding protein has a greater half-life in vivo than the soluble counterpart of the binding protein. In another embodiment the binding protein retains biological activity after crystallization. Crystallized binding proteins of the invention may be produced according methods known in the art and as disclosed in PCT Publication No. WO 02/72636, incorporated herein by reference.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (US Patent Application Publication Nos. 2004/0018590 and 2002/0137134).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

D. Uses of DLL4 Binding Proteins.

Given their ability to bind to human DLL4 and murine DLL4, the DLL4 binding proteins described herein, including antibodies and portions thereof, can be used to detect or measure DLL4 in a sample (e.g., in a mixture, solution, or biological sample, such as blood, serum, or plasma), using any of the conventional immunoassays known in the art, such as an enzyme linked immunosorbent assays (ELISA), a radioimmunoassay (RIA), or a tissue immunohistochemistry. The invention provides a method for detecting human DLL4 and/or murine DLL4 in a sample comprising contacting a sample with a DLL4 binding protein and detecting either the DLL4 binding protein bound to human DLL4 and/or murine DLL4 or the unbound binding protein to thereby detect human DLL4 and/or murine DLL4 in the sample. A DLL4 binding protein described herein can be directly or indirectly labeled with a detectable substance to facilitate detection of the bound or unbound DLL4 binding protein. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Biological samples that can be assayed for DLL4 include urine, feces, blood, serum, plasma, perspiration, saliva, oral swab (cheek, tongue, throat), vaginal swab, rectal swab, dermal swab, dermal scrape, tissue biopsy, as well as any other tissue sample that can be obtained by methods available in the art.

Alternative to labeling the binding protein, human DLL4 can be assayed in biological fluids by a competition immunoassay utilizing recombinant human (rh) DLL4 standards labeled with a detectable substance and an unlabeled DLL4 binding protein described herein. In this assay, the biological sample, the labeled rhDLL4 standards, and the DLL4 binding protein are combined and the amount of labeled rhDLL4 standard bound to the unlabeled binding protein is determined. The amount of human DLL4 in the biological sample is inversely proportional to the amount of labeled rhDLL4 standard bound to the DLL4 binding protein. Similarly, human DLL4 can also be assayed in biological fluids by a competition immunoassay utilizing rhDLL4 standards labeled with a detectable substance and an unlabeled DLL4 binding protein described herein.

The DLL4 binding proteins of the invention preferably are capable of neutralizing DLL4 activity, in particular hDLL4 activity, both in vitro and in vivo. Accordingly, such binding proteins of the invention can be used to inhibit DLL4 activity, e.g., in a cell culture containing DLL4, in human subjects, or in other mammalian subjects expressing a DLL4 with which a binding protein of the invention cross-reacts. In one embodiment, the invention provides a method for inhibiting DLL4 activity comprising contacting a DLL4 with a DLL4 antibody or antibody portion of the invention such that DLL4 activity is inhibited. For example, in a cell culture containing or suspected of containing DLL4, an antibody or antibody portion of the invention can be added to the culture medium to inhibit DLL4 activity in the culture.

In another embodiment, the invention provides a method for reducing DLL4 activity in a subject, advantageously from a subject suffering from a disease or disorder in which DLL4 or DLL4 activity is detrimental. The invention provides methods for reducing DLL4 or DLL4 activity in a subject suffering from such a disease or disorder, which method comprises administering to the subject a DLL4 binding protein of the invention such that DLL4 or DLL4 activity in the subject is reduced. Preferably, the DLL4 is human DLL4, and the subject is a human subject. Alternatively, the subject can be a mammal expressing a DLL4 to which a DLL4 binding protein of the invention is capable of binding. Still further, the subject can be a mammal into which DLL4 has been introduced (e.g., by administration of DLL4 or by expression of a DLL4 transgene). An antibody or other DLL4 binding protein of the invention can be administered to a human subject for therapeutic purposes. Moreover, a DLL4 binding protein of the invention can be administered to a non-human mammal expressing a DLL4 with which the binding protein is capable of binding for veterinary purposes or as an animal model of human disease. Regarding the latter, such animal models may be useful for evaluating the therapeutic efficacy of antibodies and other DLL4 binding proteins of the invention (e.g., testing of dosages and time courses of administration).

As used herein, the term "a disorder in which DLL4 and/or Notch signaling activity is detrimental" is intended to include diseases, such as cancer, and other disorders in which the presence of DLL4 and/or Notch signaling activity in a subject suffering from the disorder has been shown to be or is suspected of being either responsible for the pathophysiology of the disorder or a factor that contributes to a worsening of the disorder. Accordingly, a disorder in which DLL4 and/or Notch signaling activity is detrimental is a disorder in which reduction of DLL4 and/or Notch signaling activity is expected to alleviate the symptoms and/or progression of the disorder (e.g., tumor growth). Such disorders may be evidenced, for example, by an increase in angiogenesis in a subject suffering from the disorder (e.g., an increase in the concentration of various proteins known in the art to increase in serum, plasma, synovial fluid, etc., of the subject during tumor growth and formation), which can be detected, for example, using an anti-DLL4 antibody as described above. Non-limiting examples of disorders that can be treated with the antibodies of the invention include those disorders discussed in the section below pertaining to pharmaceutical compositions of the antibodies of the invention.

II. Pharmaceutical Compositions and Therapeutic Uses.

The invention also provides pharmaceutical compositions comprising a DLL4 binding protein of the invention and a pharmaceutically acceptable carrier. The pharmaceutical compositions comprising DLL4 binding proteins of the invention are for use in, but not limited to, diagnosing, detecting, or monitoring a disorder; in preventing, treating, managing, or ameliorating a disorder or one or more symptoms thereof; and/or in research. In a specific embodiment, a composition comprises one or more DLL4 binding proteins of the invention.

In another embodiment, the pharmaceutical composition comprises one or more binding proteins of the invention and one or more prophylactic or therapeutic agents other than binding proteins of the invention for treating a disorder in which DLL4 and/or DLL4 activity is detrimental. Preferably, the prophylactic or therapeutic agents known to be useful for or having been or currently being used in the prevention, treatment, management, or amelioration of a disorder, such as cancer or a tumor, or one or more symptoms thereof. In accordance with these embodiments, the composition may further comprise of a carrier, diluent, or excipient.

The binding proteins of the invention can be incorporated into pharmaceutical compositions suitable for administration to a subject. Typically, the pharmaceutical composition comprises a DLL4 binding protein (or DLL4 binding portion thereof) of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more DLL4 binding proteins of the invention or the combination of one or more binding proteins of the invention and a prophylactic agent or therapeutic agent useful for preventing, managing, treating, or ameliorating a disorder or one or more symptoms thereof, e.g., reducing tumor angiogenesis, encapsulation in liposomes, microparticles, microcapsules, recombinant cells capable of expressing the DLL4 binding protein, receptor-mediated endocytosis (see, e.g., Wu and Wu, J. Biol. Chem., 262: 4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934, 272; 5,874,064; 5,855,913; 5,290,540; and 4,880,078; and PCT Publication Nos. WO 92/19244, WO 97/32572, WO 97/44013, WO 98/31346, and WO 99/66903, each of which is incorporated herein by reference their entireties. In one embodiment, a DLL4 binding protein of the invention, combination therapy, or a composition of the invention is administered using Alkermes AIR® pulmonary drug delivery technology (Alkermes, Inc., Cambridge, Mass., US). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more DLL4 binding proteins of the invention antagonists is administered locally to the affected area to a subject to prevent, treat, manage, and/or ameliorate a disorder or a symptom thereof. In another embodiment, an effective amount of one or more DLL4 binding proteins of the invention is administered locally to the affected area in combination with an effective amount of one or more therapies (e.g., one or more prophylactic or therapeutic agents) other than a binding protein of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see, Langer (Science, 249: 1527-1533 (1990)); Sefton, CRC Crit. Ref. Biomed. Eng., 14: 201-240 (1987); Buchwald et al., Surgery, 88: 507-516 (1980); Saudek et al., N. Engl. J. Med., 321: 574-579 (1989)). In another embodiment, polymeric materials can be used to achieve controlled or sustained release of the therapies of the invention. See, e.g., Goodson, J. M, *In Medical Applications of Controlled Release, Vol. II, Applications and Evaluations*, (Langer and Wise, eds.), (CRC Press Inc., Boca Raton, 1984), chapter 6, pages 115-138; *Controlled Drug Bioavailability, Drug Product Design and Performance*, Smolen and Ball (eds.) (Wiley, New York, 1984); Langer and Peppas, J. Macromol. Sci. Rev. Macromol. Chem. Phys., C23: 61-126 (1983); see also, Levy et al., Science, 228: 190-192 (1985); During et al., Ann. Neurol., 25: 351-356 (1989); Howard et al., J. Neurosurg., 71: 105-112 (1989); U.S. Pat. Nos. 5,679,377; 5,916,597; 5,912,015; 5,989,463; and 5,128,326; and PCT Publication Nos. WO 99/15154 and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, In *Medical Applications of Controlled Release*, (1984), pages 115-138).

Controlled release systems are discussed in the review by Langer (Science, 249: 1527-1533 (1990)). Any technique known to one of skill in the art can be used to produce sustained release formulations comprising one or more therapeutic agents of the invention. See, e.g., U.S. Pat. No. 4,526,938; PCT Publication Nos. WO 91/05548 and WO 96/20698; Ning et al., "Intratumoral Radioimmunotherapy of a Human Colon Cancer Xenograft Using a Sustained-Release Gel," Radiother. Oncol., 39: 179-189 (1996); Song et al., "Antibody Mediated Lung Targeting of Long-Circulating Emulsions," PDA J. Pharm. Sci.Tech., 50: 372-377 (1996); Cleek et al., "Biodegradable Polymeric Carriers for a bFGF Antibody for Cardiovascular Application," Proceed. Intl. Symp. Control. Rel. Bioact. Mater., 24: 853-854 (1997), and Lam et al., "Microencapsulation of Recombinant Humanized Monoclonal Antibody for Local Delivery," Proceed. Intl. Symp. Control Rel. Bioact. Mater.: 24: 759-760 (1997), each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, DuPont), or coating with lipids or cell-surface receptors or transfecting agents, or by administering it in linkage to a homeobox-like peptide which is known to enter the nucleus (see, e.g., Joliot et al., Proc. Natl. Acad. Sci. USA, 88: 1864-1868 (1991)). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral (e.g., intravenous), intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., *Remington's Pharmaceutical Sciences and Introduction to Pharmaceutical Dosage Forms*, 19th ed., (Mack Publishing Co., Easton, Pa., 1995). For non-sprayable topical dosage forms, viscous to semisolid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well known in the art.

If a method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If a method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

A method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass., US).

A method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

A method of the invention may additionally comprise administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

Methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, a composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml, or at least 100 mg/ml. The liquid form should be stored at between 2° C. and 8° C. in its original container.

The binding proteins of the invention can be incorporated into a pharmaceutical composition suitable for parenteral administration. Preferably, the binding protein will be prepared as an injectable solution containing 0.1-250 mg/ml antibody. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, a DLL4 binding protein described herein is administered by intravenous infusion or injection. In another preferred embodiment, a DLL4 binding protein is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The DLL4 binding proteins of the present invention can be administered by a variety of methods known in the art, although for many therapeutic applications, the preferred route/mode of administration is subcutaneous injection, intravenous injection, or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., (Marcel Dekker, Inc., New York, 1978).

In certain embodiments, a binding protein of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, a binding protein of the invention is coformulated with and/or coadministered with one or more additional therapeutic agents that are useful for treating disorders in which DLL4 activity is detrimental. For example, an anti-huDLL4 antibody or antibody portion of the invention may be coformulated and/or coadministered with one or more additional antibodies that bind other targets (e.g., antibodies that bind other cytokines or that bind cell surface molecules). Furthermore, one or more binding proteins of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, a DLL4 binding protein of the invention is linked to a half-life extending vehicle known in the art. Such vehicles include, but are not limited to, the Fc domain, polyethylene glycol, and dextran. Such vehicles are described, e.g., in U.S. Pat. No. 6,660,843 B1 and published PCT Publication No. WO 99/25044, which are hereby incorporated by reference.

In a specific embodiment, nucleic acid sequences comprising nucleotide sequences encoding a binding protein of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded binding protein or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., Clin. Pharmacy, 12: 488-505 (1993); Wu and Wu, Biotherapy, 3: 87-95 (1991); Tolstoshev, Ann. Rev. Pharmacol. Toxicol., 32: 573-596 (1993); Mulligan, Science, 260: 926-932 (1993); and Morgan and Anderson, Ann. Rev. Biochem., 62: 191-217 (1993); Robinson, C., Trends Biotechnol., 11(5):155 (1993). Methods commonly known in the art of recombinant DNA technology which can be used are described in Ausubel et al. (eds.), *Current Protocols in Molecular Biology* (John Wiley & Sons, New York, 1993); and Kriegler, *Gene Transfer and Expression, A Laboratory Manual*, (Stockton Press, New York, 1990). Detailed descriptions of various methods of gene therapy are disclosed in US Patent Application Publication No. 20050042664 A1, which is incorporated herein by reference.

In another aspect, this invention provides a method of treating (e.g. curing, suppressing, ameliorating, delaying, or preventing the onset of, or preventing recurrence or relapse of) or preventing a DLL4-associated tumor in a subject. The method includes administering to a subject a DLL4 binding protein, e.g., an anti-DLL4 antibody or fragment thereof as described herein, in an amount sufficient to treat or prevent the DLL-associated tumor or cancer. The DLL4 antagonist, i.e., the anti-DLL4 antibody or fragment thereof, may be administered to a subject alone or in combination with other therapeutic modalities as described herein.

DLL4 plays a critical role in the pathology associated with a variety of diseases involving immune and inflammatory elements, in particular cancer and tumor angiogenesis. Examples of DLL4-associated disorders include, but are not limited to, those disorders that adversely affect the following biological processes: neuronal function and development; stabilization of arterial endothelial fate and angiogenesis; regulation of crucial cell communication events between endocardium and myocardium during both the formation of the valve primordial and ventricular development and differentiation; cardiac valve homeostasis, as well as implications in other human disorders involving the cardiovascular system; timely cell lineage specification of both endocrine and exocrine pancreas; influencing of binary fate decisions of cells that must choose between the secretory and absorptive lineages in the gut; expansion of the hematopoietic stem cell compartment during bone development and participation in commitment to the osteoblastic lineage such as osteoporosis; regulation of cell-fate decision in mammary glands at several distinct development stages; and certain non-nuclear mechanisms, such as control of the actin cytoskeleton through the tyrosine kinase Abl. More specifically, DLL4-associated disorders include, but are not limited to, cancers, T-ALL (T-cell acute lymphoblastic leukemia), CADASIL (cerebral autosomal dominant arteriopathy with subcortical infarcts and leukoencephalopathy), MS (multiple sclerosis), tetralogy of Fallot (TOF), and Alagille syndrome (AS), macular degeneration and age-related macular degeneration diseases, and other angiogenesis independent and dependent diseases characterized by aberrant DLL4 expression or activity.

Preferably, DLL4 binding proteins, such as antibodies and antigen-binding portions thereof as described herein, are used to treat cancers and tumors.

Binding proteins according to the invention can be used alone or in combination, i.e., more than one DLL4-binding protein described herein, to treat a cancer, a tumor, or other disorder in which binding to, inhibition of, and/or neutralization of DLL4 is considered desirable or otherwise beneficial to the health of an individual.

It should be understood that DLL4 binding proteins of the invention can also be used alone or in combination with an additional agent, e.g., a therapeutic agent, said additional agent being selected by the skilled practitioner for its intended purpose. For example, the additional agent can be a therapeutic agent that is recognized in the art as being useful to treat a cancer, tumor, or other disease or condition in which binding to or inhibition of DLL4 is considered to be desirable or advantageous for treating the cancer, tumor, or other disease or condition. The additional agent also can be an agent that imparts a beneficial attribute to the therapeutic composition, e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents, if the combination is such that the formed composition can perform its intended function.

Preferred combinations of therapeutic agents may interfere at different points in the pro-tumorigenic or pro-angiogenic signaling pathways. Preferred examples of therapeutic agents useful in the methods and compositions of the invention include antineoplastic agents, radiotherapy, and chemotherapy such as DNA alkylating agents, cisplatin, carboplatin, anti-tubulin agents, paclitaxel, docetaxel, taxol, doxorubicin, gemcitabine, gemzar, anthracyclines, adriamycin, topoisomerase I inhibitors, topoisomerase II inhibitors, 5-fluorouracil (5-FU), leucovorin, irinotecan, receptor tyrosine kinase inhibitors (e.g., erlotinib, gefitinib), COX-2 inhibitors (e.g., celecoxib), and kinase inhibitors.

The DLL4 binding proteins of the invention may also be administered in combination with agents, such as methotrexate, 6-MP, azathioprine sulphasalazine, mesalazine, olsalazine chloroquinine/hydroxychloroquine, penicillamine, aurothiomalate (intramuscular and oral), azathioprine, colchicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g. IRAK, NIK, IKK, p38 or MAP kinase inhibitors), IL-1β converting enzyme inhibitors, TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™) and p55TNFRIgG (Lenercept), sIL-1RI, sIL-1RII, sIL-6R), antiinflammatory cytokines (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone hcl, hydrocodone bitartrate/apap, diclofenac sodium/misoprostol, fentanyl, anakinra, human recombinant, tramadol hcl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine hcl, misoprostol, naproxen sodium, omeprazole, cyclophosphamide, rituximab, IL-1 TRAP, MRA, CTLA4-IG, IL-18 BP, anti-IL-18, anti-IL15, BIRB-796, SCIO-469, VX-702, AMG-548, VX-740, Roflumilast, IC-485, CDC-801, and Mesopram.

Non-limiting examples of therapeutic agents for cancers with which a DLL4 binding protein of the invention can be co-administered or used in combination include the following: budenoside; epidermal growth factor; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; and antibodies to or antagonists of other human cytokines or growth factors, for example, TNF, LT, IL-1, IL-2, IL-6, IL-7, IL-8, IL-15, IL-16, IL-17, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90, or their ligands.

Other examples of therapeutic agents with which a DLL4 binding protein of the invention can be combined include the following: TNF antagonists, for example, anti-TNF antibodies, D2E7 (PCT Publication No. WO 97/29131; HUMIRA®), CA2 (REMICADE®), CDP 571, TNFR-Ig constructs (p75TNFRIgG (ENBREL®) and p55TNFRIgG (LENERCEPT)), and PDE4 inhibitors. Binding proteins of the invention can be combined with mesalamine, prednisone, azathioprine, mercaptopurine, infliximab, methylprednisolone sodium succinate, diphenoxylate/atrop sulfate, loperamide hydrochloride, methotrexate, omeprazole, folate, ciprofloxacin/dextrose-water, hydrocodone bitartrate/apap, tetracycline hydrochloride, fluocinonide, metronidazole, thimerosal/boric acid, cholestyramine/sucrose, ciprofloxacin hydrochloride, hyoscyamine sulfate, meperidine hydrochloride, midazolam hydrochloride, oxycodone hcl/acetaminophen, promethazine hydrochloride, sodium phosphate, sulfamethoxazole/trimethoprim, celecoxib, polycarbophil, propoxyphene napsylate, hydrocortisone, multivitamins, balsalazide disodium, codeine phosphate/apap, colesevelam hcl, cyanocobalamin, folic acid, levofloxacin, methylprednisolone, natalizumab, and interferon-gamma Non-limiting examples of therapeutic agents with which a binding protein of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil hcl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, and bisoprolol fumarate.

The pharmaceutical compositions of the invention may include a "therapeutically effective amount" or a "prophylactically effective amount" of a binding protein of the invention. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the binding protein are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a DLL4 binding protein of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

III. Use in Immunotechniques.

Any of a variety of immunodetection assay formats may be adapted to employ a DLL4 binding protein of the invention for use in detecting DLL4 present in a mixture, solution, or biological sample. Such immunodetection assay formats include but are not limited to radioimmunoassay (RIA), immunoprecipitation, enzyme-linked immunosorbent assay (ELISA), immunoblot (e.g., Western blot), immunostrips (e.g., immunodipsticks) that comprise a DLL4 binding protein of the invention adsorbed or immobilized to substrate, fluorescence activated cell sorting (FACS), and the like. A DLL4 binding protein described herein can be adsorbed or immobilized to a substrate, e.g., a resin particle or other material, for use in an affinity column or any other affinity format available in the art to purify DLL4 from a sample. Detection of DLL4 using a DLL4 binding protein of the invention can be conducted in vitro on a mixture, solution, or in biological sample. A biological sample that can be contacted with a DLL4 binding protein of the invention to detect or measure DLL4 in the sample includes, but is not limited to, urine, saliva, oral swab (buccal, lingual, or throat swab), dermal swab, dermal scrape, rectal swab, vaginal swab, whole blood sample, plasma sample, serum sample, tissue biopsy, and any other sample obtained from an individual by a procedure known in the art. In another embodiment, a DLL4 binding protein may be employed to detect DLL4 in vivo such as various tomography and scanning methods, including but not limited to X-ray computer assisted tomography (CT), magnetic resonance imaging (MRI), and positron emission tomography (PET).

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

In vitro Assays Used to Determine the Functional Activity of DLL4 Antibodies

Example 1.1

Affinity Determination Using BIACORE® Surface Plasmon Resonance Technology

The BIACORE® surface plasmon resonance assay (Biacore, Inc., Piscataway, N.J., US) determines the affinity of antibodies with kinetic measurements of on-rate and off-rate constants. Binding of DLL4 antibodies to a purified recombinant DLL4 extracellular domain (ECD) was determined by surface plasmon resonance-based measurements with a Biacore® instrument (either a Biacore 2000, Biacore 3000, or Biacore T100; GE Healthcare, Piscataway, N.J., US) using running buffer HBS-EPB (10 mM HEPES [pH 7.4], 150 mM NaCl, 3 mM EDTA, 0.1 mg/ml BSA and 0.005% surfactant P20) at 25° C. For example, approximately 9000 RU of goat anti-human Fc specific polyclonal antibody (Thermo Fisher Scientific Inc., Rockford, Ill., US) diluted in 10 mM sodium acetate (pH 4.5) is directly immobilized across a CM5 research grade biosensor chip using a standard amine coupling kit according to manufacturer's instructions and procedures at 25 µg/ml. Unreacted moieties on the biosensor surface were blocked with ethanolamine. For kinetic analysis, rate equations derived from the 1:1 Langmuir binding model were fitted simultaneously to multiple antigen injections (using global fit analysis) with the use of Scrubber 2 (BioLogic Software), Biacore Biaevaluation 4.0.1 software or Biacore T100 Evaluation software. Purified antibodies were diluted in running buffer for capture across goat anti-human Fc reaction surfaces. Antibodies to be captured as a ligand (1 µg/ml) were injected over reaction matrices at a flow rate of 10 µl/min. During the assay, all measurements were referenced against the capture surface alone (i.e., with no captured anti-DLL4 antibody). The association and dissociation rate constants, $K_{on}$ ($M^{-1}s^{-1}$) and $K_{off}$ ($s^{-1}$) were determined under a continuous flow rate of 80 µl/min. Rate constants were derived by making kinetic binding measurements at different antigen concentrations ranging from 1.23-900 nM, as a 3-fold dilution series, and included buffer-only injections (to be used for double referencing). The equilibrium dissociation constant $K_D$ (M) of the reaction between antibodies and the target antigen was then calculated from the kinetic rate constants by the following formula: $K_D=K_{off}/K_{on}$. Binding was recorded as a function of time and kinetic rate constants were calculated. In this assay, on-rates as fast as $10^6 M^{-1}s^{-1}$ and off-rates as slow as $10^{-6} s^{-1}$ could be measured.

Example 1.2

Binding of DLL4 Antibodies to Soluble DLL4 Extracellular Domain as Determined by ELISA Method 1 (Capture ELISA).

96-well Nunc-Immuno plates (#439454) were coated with 5 µg/ml antibody against human IgG (Fcg fragment specific, Jackson ImmunoResearch, #109-005-098, 100 µl/well) in D-PBS (Gibco #14190) and incubated overnight at 4° C. ELISA plates were washed 3 times with wash buffer (PBS, 0.05% Tween-20) and then blocked with 200 ml/well blocking buffer (D-PBS, 1% BSA, 1 mM CaCl$_2$, 0.05% Tween-20) for 1 hour at 25° C. Plates were washed 3 times and incubated with 100 µl/well DLL4 antibodies (0.0001-100 nM, 10-fold serial dilution in blocking buffer) for 1 hour at 25° C., and then washed again 3 times. Plates containing captured DLL4 antibody were incubated with biotin-labeled human DLL4 extracellular domain (10 nM in blocking buffer, 100 µl/well) for 1 hour at 25° C., washed 3 times, and incubated with streptavidin conjugated with HRP (KPL #474-3000, 1:10,000 dilution in blocking buffer, 100 µl/well) for 1 hour at 25° C. After the final wash, plates were incubated with 100 µl/well ELISA substrate (1-Step Ultra TMB-ELISA, Pierce #340280). The reaction was stopped after 2 minutes at 25° C. with 100 µl/well 2 N H$_2$SO$_4$ and the absorbance was read at 450 nm. Data were analyzed using Graphpad Prism software and EC$_{50}$ values were reported.

Method 2 (Copper Coated Plate).

96-well copper-coated plates (Thermo Scientific #15143) were washed 3 times with wash buffer (PBS, 0.05% Tween-20) before use and then incubated with 100 µl/well of 6×His-tagged recombinant DLL4 extracellular domain (ECD) ("6×His" disclosed as SEQ ID NO: 206) at 1 µg/ml in PBS, 1 hour at 25° C. with shaking. Plates were then washed 3 times. 100 µl/well of recombinant rat/human chimeric or recombinant human anti-DLL4 antibodies were then added to the plate (0.00164-27 nM, 4-fold serial dilution in ELISA buffer=PBST, 10% Superblock (Pierce #37515)) for 1 hour at 25° C. with shaking and then washed again 3 times. Plates were incubated with goat anti-human HRP (Pierce #31412) (1:40,000 dilution in ELISA buffer, 100 µl/well) for 1 hour at 25° C. with shaking, then washed 3 times. After the final wash, plates were incubated with 100 µl/well ELISA substrate (Sigma #T8665). The reaction was stopped after 8 minutes at 25° C. with 100 µl/well 1N HCl and the absorbance was read at 450 nm. Data were analyzed using Graphpad Prism software, and EC50 values were reported.

Example 1.3

Binding of DLL4 Monoclonal Antibodies to the Surface of Human Tumor Cell Lines as Assessed by Flow Cytometry (FACS)

Stable cell lines overexpressing cell-surface DLL4 were harvested from tissue culture flasks, washed four times and resuspended in phosphate buffered saline (PBS) containing 1% bovine serum albumin and 1 mM CaCl$_2$ (FACS buffer). 1.5×10$^5$ cells were incubated with antibodies at various concentrations in FACS buffer for 60 minutes on ice. Cells were washed twice and 50 µL of R-phycoerythrin-conjugated anti-rat IgG, F(ab')$_2$ fragment (1:200 dilution in FACS buffer) (Jackson ImmunoResearch, West Grove, Pa., Cat.#112-116-072) were added. Following an incubation on ice (4° C., 60 minutes), cells were washed three times and resuspended in FACS buffer. Fluorescence was measured using a Becton Dickinson FACSCalibur-HTS (Becton Dickinson, San Jose, Calif., US). Data were analyzed using Graphpad Prism software and EC$_{50}$ values were reported as the concentration of antibody to achieve 50% of maximal DLL4 antibodies binding to DLL4 expressing cells.

Example 1.4

Inhibition of Notch-1 Interaction with Soluble DLL4 Extracellular Domain by DLL4 Antibodies (Competition ELISA)

96-well Nunc-Immuno plates (#439454 for huDLL4 ELISA) and 96-well Costar plates (#9018 for muDLL4 ELISA) were coated with 16 nM human Notch-1 (R&D Systems #3647-TK, 100 µl/well in D-PBS) and incubated overnight at 4° C. Plates were then washed 3 times with wash buffer (PBS, 0.05% Tween-20) and blocked with 200 µl/well blocking buffer (D-PBS, 1% BSA, 1 mM CaCl$_2$, 0.05% Tween-20) for 1 hour at 25° C. While blocking, biotin labeled DLL4 extracellular domain (14 nM) was mixed with antibody (30 pM-66 nM, 3-fold serial dilution in blocking buffer) for 1 hour at 25° C. with shaking. Assay plates were washed after blocking, and incubated with DLL4/antibody mixtures (100 µl/well, 1 hour at 25° C. with shaking). Plates were washed again and 100 µl/well streptavidin conjugated with HRP (Fitzgerald #65R-S104PHRPx, diluted 1:5,000 in blocking buffer) was added for 1 hour at 25° C. with shaking. After a final wash, plates were developed using 100 µl/well substrate (TMB Sigma #T8665), and the reaction was stopped using 100 µl/well 1N HCl, and the absorbance was read at 450 nm. Data were analyzed using Graphpad Prism software and IC$_{50}$ values were reported as the concentration of antibody to achieve 50% reduction of DLL4 bound to Notch1.

Example 1.5

Blocking of Soluble Notch Binding to DLL4-Overexpressing 293G Cells by Anti-DLL4 Monoclonal Antibodies as Assessed by Flow Cytometry (Competition FACS)

Notch blocking assay: Briefly, stable cell lines overexpressing cell-surface DLL4 were harvested from tissue culture flasks and re-suspended in phosphate buffered saline (PBS) containing 1% bovine serum albumin and 1 mM CaCl$_2$ (FACS buffer). HEK293G-DLL4 cells were dispensed into 96-well plate (v-bottom) at 1.5×10$^5$ cells/well in FACS buffer. After spinning down cells and discarding the supernatant, 50 µL of purified IgG with appropriate dilution were added to each well, and incubated on ice at 4° C. for 60 minutes, followed by addition of 50 µL/well of Notch1-biotin at 0.2 µg/mL for human DLL4-293G or 2.0 µg/mL for mouse DLL4-293G (1.0 or 0.1 µg/mL final) for an additional 1 hour incubation ice at 4° C. After washing the cells two times with FACS buffer, 50 µL of R-phycoerythrin-conjugated streptavidin (1:150 dilution in FACS buffer) (Jackson ImmunoResearch, West Grove, Pa., Cat.#016-110-084) were added. Following an incubation on ice (4° C., 60 minutes), cells were washed three times and resuspended in FACS buffer. Fluorescence was measured using a Becton Dickinson FACSCalibur-HTS (Becton Dickinson, San Jose, Calif.). Data were analyzed using Graphpad Prism software, and $IC_{50}$ values were reported as the concentration of antibody to achieve 50% reduction of Notch1 bound to DLL4 expressing cells.

Example 1.6

Inhibition of DLL4-Dependent Notch Activation in EA.hy926 Cells by DLL4 Antibodies using Notch Reporter Assay 96-well black clear-bottom tissue culture plates were seeded overnight with 7,000 cells/well engineered EA.hy926 cells expressing luciferase driven by a Notch-responsive promoter. Antibodies serially diluted from 200 nM were mixed for 15 minutes with equal volume of 5,000 HEK293G cells/well expressing full-length DLL4. The 293G/DLL4 cells were co-cultured with EA.hy926 Notch reporter cells for 24 hours in the presence of testing antibodies. Luciferase activity was analyzed by Promega's substrate (Promega #E2940). Data was analyzed using Graphpad Prism software, and $IC_{50}$ values were reported as the concentration of antibody to achieve 50% reduction of DLL4-induced Notch activation.

Example 1.7

Analytical Methods and Techniques for Physicochemical Property Characterizations PEG Precipitation Method.

The use of PEG for inducing phase separation of a solid protein according to principles of volume exclusion represents a feasible approach to assess the solubility of a protein. PEG has several advantages over other precipitants, including minimal denaturation of proteins at ambient temperatures (does not affect tertiary structure of proteins) and within the range of 4° C. to 30° C. temperature control is not required, i.e., precipitation studies can be performed at ambient temperature at the laboratory bench.

Generally, the precipitation of proteins by PEGs is explained on the basis of volume exclusion effects. According to this theory, proteins are sterically excluded from the regions of solvent that are occupied by PEG linear chains. As a result, proteins are concentrated and eventually precipitated when their solubility is exceeded. In thermodynamic terms, the steric exclusion leads to an increase in the chemical potential of the protein until it exceeds that of the pure solid state, resulting in protein precipitation. This happens mainly because of a large unfavorable free energy of interaction between PEG and proteins, reducing the preferential hydration of protein due to steric exclusion effects. In aqueous solutions, preferential hydration helps to maintain the native structure of proteins. Generally, volume exclusion has been shown to become more effective with increasing molecular weight of the PEG, i.e., less PEG is needed to precipitate proteins with increasing PEG molecular weight.

A PEG molecular weight of 3000 was chosen for estimating the solubility of the antibodies covered by this patent. A 50% PEG solution was made by dissolving PEG in deionized water in the ratio of one gram of PEG to 1 mL of water. The PEG solution was then added to a solution of antibody which was initially at a concentration of less than or equal to 0.5 mg/ml and a volume of 0.5 mL. The PEG solution was continually added and mixed until the first instance of cloudiness persists. The percentage of PEG 3000 needed to cause this precipitation is calculated as (50)×(volume of PEG 3000 solution added)/(initial volume of antibody solution before PEG addition).

The percentage of PEG 3000 needed for precipitation was compared to the percentage needed for precipitation of protein with known water solubility. For example, the water solubility of adalimumab exceeds 200 mg/mL. Consequently, if the percentage of PEG 3000 required to precipitate a protein of interest is similar to the percentage needed to precipitate adalimumab, then the predicted solubility of that protein will be similar to the solubility adalimumab.

Real Solubility Method.

Real solubility is determined by using Amicon centrifugal filters to concentrate a protein in solution until the protein is observed to precipitate out of solution or until the minimum volume to which the protein can be concentrated within the filter unit is reached. For the latter, 15 mL Amicon centrifugal filters have a minimum volume of ~50 µl while 4 mL Amicon centrifugal filters have a minimum volume of ~15 µl.

First, a protein was dialyzed into a specific formulation(s). For these studies, the antibody amount was 10 mg or much less. Then the protein solution was inserted into the Amicon centrifugal filter retentate chamber. The chamber was lined with a nitrocellulose membrane with pores that permitted molecules of less than 10 to 30 kilodaltons to pass when subjected to centrifugal force. Antibodies, which were typically above 140 kilodaltons, were retained while water, buffer molecules, small excipients, and salts passed through. The centrifugal filter was then centrifuged according to manufacturer specifications until the protein was observed to precipitate out of solution or until the minimum volume to which the protein can be concentrated within the filter unit was reached.

After centrifugation, the protein solution was removed from the retentate chamber, and the concentration was measured by ultraviolet absorbance. The solution was then kept at 25° C. and 5° C. for 1 to 2 days and was monitored for signs of precipitation.

Near UV-CD Technique.

Near UV-CD spectroscopy provides important information about the tertiary structure of proteins and was one of the most used techniques in this regards. CD refers to the differential absorption of the left and right circularly polarized components of plane polarized radiation. For proteins, the chromophores in the near UVCD region (250-320 nm) are the aromatic amino acids (i.e., tryptophan, tyrosine, and phenylalanine) and the disulfide bonds, and the CD effect occurs when the chromophores are present in an asymmetric (buried) environment. Signals in the region from 250-270 nm are attributable to phenylalanine residues, signals from 270-290 nm are attributable to tyrosine, and those from 280-300 nm are attributable to tryptophan. Disulfide bonds give rise to broad weak signals throughout the near-UV spectrum. The near-UV CD spectrum can be sensitive to small changes in tertiary structure such as those due to protein-protein interactions and/or changes in formulation conditions.

There are a number of other factors that can influence the CD spectra of aromatic amino acids. Among these are (1) the rigidity of the protein, (2) the nature of hydrogen bonding, and (3) interactions between various aromatic amino acids. Additionally, proteins with large number of such amino acids can have smaller CD bands due to the cancellation of the positive and negative bands.

Briefly, a protein dialyzed into the desired formulation(s) at 1 mg/ml and was scanned from 250-320 nm or 240-320 nm with a Jasco 800 CD spectrometer. The corresponding formulation without protein was also scanned, and the readings subtracted from that of the scan of the protein solution. A near UV-CD spectra was a plot of molar ellipticities versus wavelength from 250 or 240 to 320 nm.

For antibodies in general, a near UV-CD spectrum with a semi-sigmoidal profile indicates good tertiary structure folding while a flatter and less featured profile indicates a greater tendency to unfold. Compact folding is associated with good stability while poor folding exposes the hydrophobic interior which may lead to hydrophobic interactions among protein molecules resulting in the formation of undesired aggregates.
DSC Technique.

The thermal stability of the antibodies was assessed using a differential scanning calorimetry (DSC) instrument. The DSC instrument used was an automated VP-DSC equipment with Capillary Cell (Microcal, GE Healthcare Ltd./Microcal, Buckinghamshire, UK). Unfolding of molecules was studied applying a 1° C./minute scan rate over a 25° C.-95° C. temperature range for samples at 1 mg/mL. Additional measurement parameters applied were a fitting period of 16 seconds, a pre-scan wait time of 10 minutes, and measurements were performed in none-feedback mode. Per individual measurement, 420 µL of sample/blank were filled into the DSC measurement sample holder, with a plate fill scheme as provided below. The thermograms obtained were fitted to a non two state model to obtain the midpoint temperatures and enthalpies of the different transitions.

An additional requirement for successful biologics development candidate is that the protein remains in its native state and conformation. A protein in aqueous solution is in equilibrium between the native (folded) conformation and its denatured (unfolded) conformation. The stability of the native state is based on the magnitude of the Gibbs free energy (DG) of the system and the thermodynamic relationship between enthalpy (DH) and entropy (DS) changes. A positive DG indicates the native state is more stable than the denatured state—the more positive the DG, the greater the stability. For a protein to unfold, stabilizing forces need to be broken. Conformational entropy overcomes stabilizing forces allowing the protein to unfold at temperatures where entropy becomes dominant. DSC measures DH of protein unfolding due to heat denaturation. As a general rule, it can be stated that the higher the transition midpoint (the Tm), the more stable the protein at lower temperatures. During the same experiment, DSC also measures the change in heat capacity (DCp) for protein denaturation. Heat capacity changes associated with protein unfolding are primarily due to changes in hydration of side chains that were buries in the native state, but become solvent exposed in the denatured state. DSC has been shown to be a valuable predictor of liquid formulation stability for proteins and other biological macromolecules (Remmele, R. L. Jr., Gombotz, W. R., BioPharm 13, 36-46, 2000, and; Remmele, R. L. Jr., Nightlinger, N. S., Srinivasen, S., Gombotz, W. R., Pharm. Res. 15, 200-208, 1998).
SEC Technique.

Size exclusion chromatography (SEC) was used to separate proteins based on size. Proteins are carried in an aqueous mobile phase and through a porous stationary phase resin packed in a column. The retention time in the column is a function of the hydrodynamic size of the protein and the size of the pores in the packed resin bed. Smaller molecules can penetrate into smaller pores in the resin and are retained longer than larger molecules. Upon elution from the column, the proteins are detected by UV absorbance. The SEC method used a TSK gel guard (TOSOH Biosciences, Montgomeryville, Pa., cat. no. 08543) and a TSK gel G3000SWxL (TOSOH Biosciences, Montgomeryville, Pa., cat. no. 08541). The mobile phase was 100 mM $Na_2HPO_4$, 200 mM $Na_2SO_4$, pH 6.8. The flow rate was 0.25 mL/minute. Injection volume was 20 µL of 1 mg/mL sample. The column temperature was room temperature. The autosampler temperature was 2-8° C. The total run time was 55 minutes. The detection was based on UV absorbance at 214 nm wavelength, with band width set at 8 nm, using reference wavelength at 360 nm with band width 100 nm.
Freeze-Thaw Method.

Antibody solutions at 1 mg/ml in the desired formulation (s) were frozen at −80° C. for at least 4 hours and then thawed at 30° C. in a water bath. The solutions were then refrozen at −80° C. This was repeated for 5 cycles. After certain freeze-thaw cycles, e.g., second and fourth, a portion of the solution was withdrawn for analysis by SEC before refreezing. Freeze-thaw stability testing was done at low protein concentration in order obtain a "worse-case scenario" due to greater exposure of protein molecules to the denaturing ice-water interfaces. At higher concentrations, proportionally less protein encounters the ice-water interface, instead interacting with other protein molecules.
Accelerated Stability Method.

Antibody solutions at 1 mg/ml in the desired formulation (s) were passed through 0.22 µm PVDF filters under sterile conditions and incubated at 40° C. and/or 50° C. for at least 21 days. At 7 days and 21 days, aliquots were withdrawn under sterile conditions and subjected to analysis by SEC. Solutions were then returned to incubation.

Example 2

Generation of Rat Anti-DLL4 Monoclonal Antibodies by Rat Hybridoma Technology

Rats were immunized according to the methods known in the art (for example, E Harlow, D. Lane, Antibody: *A Laboratory Manual*, (Cold Spring Harbor Laboratory Press, Cold Spring Harbor, N.Y., 1998). A human cell line expressing full-length human DLL4 as well as recombinant mouse DLL4-ECD (DLL4 extracellular domain) proteins was used as immunogen. Mouse cell lines expressing either human DLL4 or mouse DLL4 were used for determining anti-sera titer and for screening hybridomas secreting antigen-specific antibodies Immunizing dosages contained $1 \times 10^6$ cells/rat/injection for both primary and boost immunizations. To increase immune response to mouse DLL4, the rats were further boosted with recombinant mouse DLL4-ECD in emulsion form with an incomplete Freud's adjuvant (Sigma, St. Louis, Mo., US). Briefly, adjuvant-antigen mixture was prepared by first gently mixing the adjuvant in a vial using a vortex. The desired amount of adjuvant was removed from the vial and put into an autoclaved 1.5 mL microcentrifuge tube. The antigen was prepared in PBS or saline with concentration ranging from 0.5-1.0 mg/ml. The calculated amount of antigen was then added to the microcentrifuge tube with the adjuvant, and the solution was mixed by gently vortexing for 2 minutes to generate water-in-oil emulsion. The adjuvant-antigen solution was then drawn into the proper syringe for animal injection. A total of 50 µg of antigen was injected in a volume of 50-100 µl. Each animal was immunized, and then boosted for 2 to 3 times depending on the titer. Animals with good titers were given a final subcutaneous boost with cell line expressing human DLL4 before fusion.
Hybridoma Fusion and Screening.

Cells of murine myeloma cell line (SP2/0-Ag14, ATCC CRL-1581) were cultured to reach the log phase stage right before fusion. Immunized rat spleen cells were prepared sterilely and fused with myeloma cells according to the methods known in the art (for example, E Harlow, D. Lane, *Antibody: A Laboratory Manual*, (Cold Spring Harbor Laboratory Press, Cold Spring Harbor, N.Y., 1998); Kohler G, and Milstein C., "Continuous cultures of fused cell secreting antibody of predefined specificity," Nature, 256: 495-497 (1975)). Fused "hybrid cells" were subsequently dispensed into 96-well plates in DMEM/20% FCS/HAT media. Surviving hybridoma colonies were observed under the microscope seven to ten days post-fusion. After two weeks, the supernatant from each well was subjected to cell-based binding screening using mouse cell lines expressing either recombinant human DLL4 or mouse DLL4. Briefly, the mixture (1:1 ratio) of mouse cell lines expressing either human or mouse DLL4 was dispensed into a 96-well (round bottom) plate at 1×10$^6$ cells/well and incubated with hybridoma supernatant (50 µl) at 4° C. for 1 hour. Cells were then washed 3 times with FACS buffer (PBS+2% BSA), HRP-goat anti-rat Ig-PE (phycoerythrin) was used for detection in FACS machine. Hybridomas were screened using ELISA format according the following procedure. ELISA plates were coated with 50 µl of either human DLL4 or mouse DLL4 (2.0 µg/ml in PBS) overnight at 4° C. Plates were washed 3 times with 250 µl PBS/0.5% Tween$_{20}$ and blocked with 200 µl blocking buffer (2% BSA in PBS with 0.5% Tween$_{20}$). Diluted sera or hybridoma supernatant (100 µl) was added to each well, and incubated at room temperature for 1 hour. Plates were then washed 3 times with PBS/0.5% Tween$_{20}$, HRP-goat anti-rat-IgG was used for detection, and binding ODs were observed at 450 nm. Positive hybridoma secreting antibody that binds to either human DLL4 or mouse DLL4 or both were then selected and transferred to 24-well plates and subcloned by limiting dilution to ensure the clonality of the cell line. The isotype of each monoclonal antibody was determined using the Zymed's Mouse MonoAb-ID Kit. Hybridoma clones producing antibodies that showed high specific binding activity were subcloned and purified (Table 5), and affinity (Biacore) and potency (Notch blocking FACS and reporter assay) of the antibodies were characterized as follows.

TABLE 5

A List of Anti-DLL4 Antibodies Generated Using Rat Hybridoma Technology

|  |  | FACS binding | |
| --- | --- | --- | --- |
| Hybridoma | Isotype | Human DLL4 | Mouse DLL4 |
| MC10-37D10.1C2 | IgG2a/k | + | + |
| MC10-40B10.3C3 | IgG2a/k | + | + |
| MC10-32C7.5A4 | IgG2a/k | + | + |
| MC10-38H12.2G8 | IgG2a/k | + | − |
| MC13-14A11.3A4 | IgG2a/K | + | + |
| MC13-14G1.1B4 | IgG2a/K | + | − |
| MC13-1A11.2E1 | IgG1/K | + | + |
| MC13-13E4.4A3 | IgG1/K | + | + |
| MC13-15D6.1G7 | IgG2a/K | + | + |

"+" indicates antibody bound to cells;
"−" indicates antibody did not bind to cells Example 3

In Vitro Characterization of Anti-DLL4 Rat Monoclonal Antibodies

The antigen binding affinities of these rat monoclonal antibodies (mAbs) were determined by the BIACORE technology as described in Example 1.1, and are shown in Tables 6 and 7, below. Their in vitro activities were further examined using other methods described in Example 1, and are summarized in Table 8. Further characterization determined 37D10 and 40B10 were identical rat mAbs.

TABLE 6

Biacore Kinetics of Anti-DLL4 Rat Hybridoma Antibodies Binding to Human and Cynomolgus Monkey DLL4.

| | Kinetics on Biacore | | | | | |
| --- | --- | --- | --- | --- | --- | --- |
| | huDLL4 ECD | | | cynoDLL4 ECD | | |
| Clone | $k_a$ (M$^{-1}$s$^{-1}$) | $k_d$ (s$^{-1}$) | $K_D$ (nM) | $k_a$ (M$^{-1}$s$^{-1}$) | $k_d$ (s$^{-1}$) | $K_D$ (nM) |
| 38H12 | 4.0 × 10$^{+5}$ | 1.1 × 10$^{-4}$ | 0.3 | 2.6 × 10$^{+5}$ | 9.8 × 10$^{-5}$ | 0.4 |
| 1A11 | 1.9 × 10$^{+5}$ | 1.1 × 10$^{-3}$ | 5.8 | 1.1 × 10$^{+5}$ | 9.3 × 10$^{-4}$ | 8.1 |
| 37D10 = 40B10 | 1.4 × 10$^{+5}$ | 7.0 × 10$^{-2}$ | 484 | 4.0 × 10$^{+4}$ | Too fast* | <617 |
| 32C7 | 2.8 × 10$^{+5}$ | 7.0 × 10$^{-6}$ | 0.03 | 2.2 × 10$^{+5}$ | 6.3 × 10$^{-6}$ | 0.03 |
| 15D6 | 1.1 × 10$^{+5}$ | 1.0 × 10$^{-3}$ | 9.2 | 5.6 × 10$^{+4}$ | 8.3 × 10$^{-4}$ | 14.9 |
| 14A11 | 1.2 × 10$^{+5}$ | 1.2 × 10$^{-3}$ | 10.3 | 1.1 × 10$^{+5}$ | 1.2 × 10$^{-3}$ | 11.6 |
| 14G1 | 5.4 × 10$^{+4}$ | 3.9 × 10$^{-4}$ | 7.2 | 3.9 × 10$^{+4}$ | 4.1 × 10$^{-4}$ | 10.5 |
| 13E4 | 2.3 × 10$^{+5}$ | 3.9 × 10$^{-4}$ | 1.7 | 1.5 × 10$^{+5}$ | 4.2 × 10$^{-4}$ | 2.8 | hu = human;
cyno = cynomolgus monkey;
*= falls out of measurement range

TABLE 7

Biacore Kinetics of Anti-DLL4 Rat Hybridoma Antibodies Binding Murine and Rat DLL4.

| | Kinetics on Biacore | | | | | |
|---|---|---|---|---|---|---|
| | muDLL4 ECD | | | ratDLL4 ECD | | |
| Clone | $k_a$ ($M^{-1}s^{-1}$) | $k_d$ ($s^{-1}$) | $K_D$ (nM) | $k_a$ ($M^{-1}s^{-1}$) | $k_d$ ($s^{-1}$) | $K_D$ (nM) |
| 38H12 | N/B | N/B | N/B | N/B | N/B | N/B |
| 1A11 | $1.3 \times 10^{+5}$ | $2.9 \times 10^{-3}$ | 23 | N/B | N/B | N/B |
| 37D10 = 40B10 | $1.0 \times 10^{+5}$ | $1.35 \times 10^{-2}$ | 135 | N/D | N/D | N/D |
| 32C7 | $4.8 \times 10^{+4}$ | $4.1 \times 10^{-3}$ | 88 | N/D | N/D | N/D |
| 15D6 | $7.4 \times 10^{+4}$ | $5.1 \times 10^{-5}$ | 0.7 | N/B | N/B | N/B |
| 14A11 | $7.0 \times 10^{-4}$ | $9.0 \times 10^{-5}$ | 1.3 | N/B | N/B | N/B |
| 14G1 | N/B | N/B | N/B | N/B | N/B | N/B |
| 13E4 | $1.8 \times 10^{+5}$ | $1.9 \times 10^{-4}$ | 1.1 | N/B | N/B | N/B |

N/B = no significant binding;
N/D = not determined,
mu = mouse significant binding; N/D=not determined, mu=mouse

TABLE 8

In Vitro Characterization of Rat Hybridoma Derived Anti-DLL4 Antibodies.

| | Direct Binding Assays | | Functional Blockade Assays | | | | Notch activation |
| | | | Competition | Competition | | | |
| | Binding ELISA ($EC_{50}$, nM) DLL4 ECD | FACS ($EC_{50}$, nM) DLL4 Cells | ELISA ($IC_{50}$, nM) DLL4 ECD/ huNotch-1 | | FACS ($IC_{50}$, nM) huNotch-1/ DLL4 cells | | Inhibition ($IC^{50}$, nM) huDLL4 cell/Notch |
| Rat mAb | hu | mu | hu | mu | hu | mu | hu | mu | reporter cells |
|---|---|---|---|---|---|---|---|---|---|
| 1A11 | 0.06 | 0.11 | 34.8 | 0.8 | 0.78 | 0.79 | 8.4 | 0.8 | 2.9 |
| 38H12 | 0.06 | — | 1.2 | — | 3.63 | — | 1.7 | — | 0.5 |
| 37D10 = 40B10 | 0.12 | 0.14 | 2.3 | 0.7 | 5.39 | 3.36 | 5.5 | 3.8 | — |
| 32C7 | 0.08 | 0.15 | 3.1 | 0.8 | — | — | — | — | Agonist |
| 14G1 | N/D | N/D | 8.6 | >50 | N/D | N/D | 4.2 | — | 6.1 |
| 14A11 | N/D | N/D | >50 | 2.1 | — | 19.8 | 205 | 1.6 | 2.7 |
| 15D6 | N/D | N/D | 15 | 1.6 | — | — | 25 | 1.5 | 3.2 |
| 13E4 | N/D | N/D | 26 | 1.3 | — | — | 5.2 | >200 | — |

"—" = no activity or under detection limit of the assays used; "N/D" = not determined; hu = human; cyno = cynomolgus monkey; mu = mouse.

Example 4

Deduction of Variable Region Protein Sequences of Anti-DLL4 Rat Monoclonal Antibodies by DNA Cloning and Sequencing Total RNA was extracted from hybridoma cell pellets using RNeasy mini kit (Qiagen, catalog #74104) using the following protocol. 600 µl of buffer RLT were added to disrupt cells by pipetting up and down several times. The cell lysate was homogenized by passing it 10 times through a 20-gauge needle fitted to an RNase-free syringe. One volume of 70% ethanol was added to the homogenized lysate and mixed well by pipetting. Up to 700 µl at a time of the sample were added to an RNeasy spin column and spun for 15 seconds at 10,000 rpm, discarding flow through. 700 µl of buffer RW1 were added to the column and spun for 15 seconds at 10,000 rpm, discarding flow through. 500 µl of buffer RPE were added to wash the column membrane and spun for 15 seconds at 10,000 rpm, discarding flow through. The same step was repeated one more time, but the column was centrifuged for 2 minutes. Sample was then centrifuged for 1 minute at 10,000 rpm to eliminate any carryover of buffer RPE. RNA was eluted with 30 µl of RNase-free water by centrifuging for 1 minute at 10,000 rpm. Subsequently, 2 µg of total RNA were used to synthesize first-strand cDNA using SuperScript First-Strand Synthesis System for RT-PCR (Invitrogen, catalog #11904-018) according to following protocol: 2 µg of RNA+2 µl dNTP+2 µl Oligo (dT)+DEPC-$H_2O$ (to 20 µl) were incubated at 65° C. for 5 minutes, then transferred to ice for at least 1 minute. The sample was then added to the following mixture: 4 µl of 10× RT buffer+8 µl 25 mM $MgCl_2$+4 µl 0.1 M DTT+2 µl RNase OUT and incubated at 42° C. for 2 minutes. Then, 2 µl of SuperScript II RT were added to the sample and incubated at 42° C. for 50 minutes. Sample was then incubated at 70° C. for 15 minutes and chilled on ice. 2 µl of RNase H were then added and the sample was incubated at 37° C. for 20 minutes. cDNA was then used as template for PCR amplification of variable regions of antibodies. PCR was performed using first-strand cDNA, primers from Mouse Ig-Primer Set (Novagen, catalog #69831-3) and Platinum Super Mix High Fidelity (Invitrogen, catalog #12532-016). To amplify heavy chain variable regions, PCR samples were assembled as follows: 22.5 µl PCR Super Mix+0.25 µl reverse primer MuIgG $V_H3'$-2+1 µl cDNA+1.25 µl of one the forward primers (VH-A, VH-B) or 0.5 µl of one of the forward primers (VH-C, VH-D, VH-E, VH-F). To amplify light chain variable regions PCR samples were assembled as follows: 22.5 µl PCR Super Mix+0.25 µl reverse primer MuIgK$V_L$-3'-1+1 µl cDNA+1.25 µl of one the forward primers (VL-A, VL-B) or 0.5 µl of one of the forward primers (VL-C, VL-D, VL-E, VL-F, VL-G).

For samples with primers VH-A, VH-B, VL-A and VL-B, the following PCR cycles were used (40-45 cycles, steps 2 through 4):

1-Denature 94° C. 2 min.

2-Denature 94° C. 30 sec.

3-Anneal 50° C. 30 sec.

4-Extend 68° C. 1 min.

5-Final extension 68° C. 5 min.

6-Cool 4° C. forever

For samples with primers VH-C through VH-F, and VL-C through VL-G, the following PCR cycles were used (40-45 cycles, steps 2 through 4):
1-Denature 94° C. 2 min.
2-Denature 94° C. 30 sec.
3-Anneal 60° C. 30 sec.
4-Extend 68° C. 1 min.
5-Final extension 68° C. 5 min.
6-Cool 4° C. forever PCR products were run on 1.2% agarose gel, and bands migrating at the expected size (400-500 bp) were excised for DNA extraction. DNA was purified using QIAquick Gel Extraction Kit (Qiagen, catalog #28704) according to the following protocol: gel slices were weighed. 3 volumes of buffer QG to 1 volume of gel were added to each gel slice. Samples were incubated at 50° C. for 10 minutes until gel slices were completely dissolved, mixing every 2-3 minutes. One gel volume of isopropanol was then added to each sample and mixed. Samples were then applied to QIAquick column and centrifuged for 1 minute at 13000 rpm. To wash, 750 µl of buffer PE were added to samples and spun for 1 minute at 13000 rpm. Columns were then centrifuged for an additional minute at 13,000 rpm to completely remove residual ethanol. DNA was eluted by adding 30 µl of $H_2O$ to each column and by spinning 1 minute at 13,000 rpm. Purified PCR products were then sequenced to identify variable region sequences (Table 9, below).

TABLE 9

VH and VL Amino Acid Sequences of Rat Anti-DLL4 Monoclonal Antibodies.

| SEQ ID NO: | Protein region | | Sequence |
|---|---|---|---|
| | | | 123456789012345678901234567890 |
| 157 | VH 38H12 | | EVQLVESGGGLVQPGRSLKLSC AASGFTFS NYGMYWIRQAPTKGLQWVAFIS HGGGITYY RDSVKGRFTISRDNAKSTLYLQ MDSLRSED TATYHCAALNWELGIDYWGQG VMVTVSS |
| | VH 38H12 CDR-H1 | Residues 31-35 of SEQ ID NO: 157 | NYGMY |
| | VH 38H12 CDR-H2 | Residues 50-66 of SEQ ID NO: 157 | FISHGGGITYYRDSVKG |
| | VH 38H12 CDR-H3 | Residues 99-107 of SEQ ID NO: 157 | LNWELGIDY |
| | | | 123456789012345678901234567890 123456789012345678901234567890 |
| 158 | VH 38H12 | | DIQMTQSPASLSASLGETISIECR ASEDIY SNLAWYQKKSGKSPQLLIYAAN RLQDGVPS RFSGSGSGTQYSLKISGMQPEDE GDYFCLQ GSKFPLTFGSGTKLEIKR |
| | VH 38H12 CDR-L1 | Residues 24-34 of SEQ ID NO: 158 | RASEDIYSNLA |
| | VH 38H12 CDR-L2 | Residues 50-56 of SEQ ID NO: 158 | AANRLDQ |
| | VH 38H12 CDR-L3 | Residues 89-97 of SEQ ID NO: 158 | LQGSKFPLT |

TABLE 9-continued

VH and VL Amino Acid Sequences of Rat Anti-DLL4 Monoclonal Antibodies.

| SEQ ID NO | Name | Residues | Sequence |
|---|---|---|---|
| | | | 123456789012345678901234567890 |
| 159 | VH 1A11 | | EVQLVESGGGLVQPGRSMKLSC |
| | | | AASGFTFR |
| | | | NFPMAWVRQAPTRGLEWVATIS |
| | | | SSDGTTYY |
| | | | RDSVKGRFTISRDNAKSTLYLQV |
| | | | NSLRSED |
| | | | TATYYCSRGYYNSPFAYWGQGT |
| | | | LVTVSS |
| | | | 123456789012345678901234567890 |
| | VH 1A11 CDR-H1 | Residues 31-35 of SEQ ID NO: 159 | NFPMA |
| | VH 1A11 CDR-H2 | Residues 50-66 of SEQ ID NO: 159 | TISSSDGTTYYRDSVKG |
| | VH 1A11 CDR-H3 | Residues 99-107 of SEQ ID NO: 159 | GYYNSPFAY |
| | | | 123456789012345678901234567890 |
| 160 | VL 1A11 | | DIQMTQSPASLSASLGETVTIECR |
| | | | ASEDIY |
| | | | SNLAWYQQKPGNSPQLLIFDTN |
| | | | NLADGVPS |
| | | | RFSGSGSGTQSSLKINSLQSEDV |
| | | | ASYFCQQ |
| | | | YNNYPPTFGGGTKLELKR |
| | VL 1A11 CDR-L1 | Residues 24-34 of SEQ ID NO: 160 | RASEDIYSNLA |
| | VH 1A11 CDR-L2 | Residues 50-56 of SEQ ID NO: 160 | DTNNLAD |
| | VH 1A11 CDR-L3 | Residues 89-97 of SEQ ID NO: 160 | QQYNNYPPT |
| | | | 123456789012345678901234567890 |
| | | | 123456789012345678901234567890 |
| 161 | VH 37D10 | | AVQLVESSGGGLVQPKESLKISCA |
| | | | ASGFTFS |
| | | | NAAMYWVRLAPGKGLEWVARI |
| | | | RTKPNNYAT |
| | | | YYAESVKGRFTISRDDSKSMVY |
| | | | VQMDNLKT |
| | | | EDTAMYYCTAAPWRDSYAHVY |
| | | | WGQHVMVTV |
| | | | SS |
| | VH 37D10 CDR-H1 | Residues 31-35 of SEQ ID NO: 161 | NAAMY |
| | VH 37D10 CDR-H2 | Residues 50-68 of SEQ ID NO: 161 | RIRTKPNNYATYYAESVKG |
| | VH 37D10 CDR-H3 | Residues 101-111 of SEQ ID NO: 161 | APWRDSYAHVY |

TABLE 9-continued

VH and VL Amino Acid Sequences of Rat Anti-DLL4 Monoclonal Antibodies.

| | | | |
|---|---|---|---|
| 162 | VL 37D10 | | 123456789012345678901234567890<br>DIQMTQSPPVLSASVGDRVTLSC<br>KASQNIH<br>KNLDWYQQKHGDAPKLLIYYT<br>DHLQTGVPS<br>RFSGSGSATDYTLTISSLQPEDVA<br>TYYCYQ<br>YNGGPFTFGSGTKLEIKR |
| | | | 123456789012345678901234567890 |
| | VL 37D10<br>CDR-L1 | Residues 24-34<br>of SEQ ID<br>NO: 162 | KASQNIHKNLD |
| | VL 37D10<br>CDR-L2 | Residues 50-56<br>of SEQ ID<br>NO: 162 | YTDHLQT |
| | VL 37D10<br>CDR-L3 | Residues 89-97<br>of SEQ ID<br>NO: 162 | YQYNGGPFT |
| 163 | VH 32C7 | | 123456789012345678901234567890<br>EVQLVESGGGLVQPGRSLKLSCL<br>ASGFPFS<br>SVWMTWIRQAPGKGLEWIATIT<br>NSGASTYY<br>SASVKGRFTISRDNVKSTLYLQM<br>TSLGSED<br>TATYYCTRVGTSFDYWGQGVM<br>VTVSS |
| | VH 32C7<br>CDR-H1 | Residues 31-35<br>of SEQ ID<br>NO: 163 | SVWMT |
| | VH 32C7<br>CDR-H2 | Residues 50-66<br>of SEQ ID<br>NO: 163 | TITNSGASTYYSASVKG |
| | | | 123456789012345678901234567890 |
| | VH 32C7<br>CDR-H3 | Residues 99-105<br>of SEQ ID<br>NO: 163 | VGTSFDY |
| 164 | VL 32C7 | | 123456789012345678901234567890<br>DIQMTQSPASLSASLGETVTIECR<br>ASDDIY<br>NGLAWFQQKPGKSPQLLIYDAN<br>TLHTGVPS<br>RFSGSGSGTQFSLKINSLQSEDV<br>ASYFCQQ<br>FYDYPPYTFGAGTKLELKR |
| | VL 32C7<br>CDR-L1 | Residues 24-34<br>of SEQ ID<br>NO: 164 | RASDDIYNGLA |
| | VL 32C7<br>CDR-L2 | Residues 50-56<br>of SEQ ID<br>NO: 164 | DANTLHT |
| | VL 32C7<br>CDR-L3 | Residues 89-98<br>of SEQ ID<br>NO: 164 | QQFYDYPPYT |
| | | | 123456789012345678901234567890 |

TABLE 9-continued

VH and VL Amino Acid Sequences of Rat Anti-DLL4 Monoclonal Antibodies.

| | | | 123456789012345678901234567890 |
|---|---|---|---|
| 165 | VH 14G1 | | EVQLQQSGAELAKPGSSVKISCK ASGYTFT NYDISWIKQTNGQGLEYLGYINT GSGGIYS NEKFKGKATLTVDKSSNTAFMQ LSSLTPED TAVYYCVREGNNFDHWGQGVK VTVSS |
| | VH 14G1 CDR-H1 | Residues 31-35 of SEQ ID NO: 165 | NYDIS |
| | VH 14G1 CDR-H2 | Residues 50-66 of SEQ ID NO: 165 | YINTGSGGIYSNEKFKG |
| | VH 14G1 CDR-H3 | Residues 99-105 of SEQ ID NO: 165 | EGNNFDH |

| | | | 123456789012345678901234567890 |
|---|---|---|---|
| 166 | VL 14G1 | | DTVMTQSPASMSTSVGERVTVN CKASQSVG TIVAWFQQKPGQSPKRLIYLATY RHTGVPD RFIGSGFGRDFTLTISNVEAEDLA VYYCLQ YGSRPFTFGAGTKLEIKR |
| | | | 123456789012345678901234567890 |
| | VL 14G1 CDR-L1 | Residues 24-34 of SEQ ID NO: 166 | KASQSVGTIVA |
| | VL 14G1 CDR-L2 | Residues 50-56 of SEQ ID NO: 166 | LATYRHT |
| | VL 14G1 CDR-L3 | Residues 89-97 of SEQ ID NO: 166 | LQYGSRPFT |

| | | | 123456789012345678901234567890 |
|---|---|---|---|
| 167 | VH 14A11 | | EVQLQQSGPELAKPGSSVKISCK ASGYTFY NSYISWIKQTTGQGLEYVGYINT GSGGADY NEKFKGKATLTVDKSSRTAFMQ LSSLTPGD SAVYYCAKSILLGSTCYFDYWG QGVLVTVSS |
| | VH 14A11 CDR-H1 | Residues 31-35 of SEQ ID NO: 167 | NSYIS |
| | VH 14A11 CDR-H2 | Residues 50-66 of SEQ ID NO: 167 | YINTGSGGADYYNEKFKG |
| | | | 123456789012345678901234567890 |

TABLE 9-continued

VH and VL Amino Acid Sequences of Rat Anti-DLL4 Monoclonal Antibodies.

| | | | |
|---|---|---|---|
| | VH 14A11 CDR-H3 | Residues 99-110 of SEQ ID NO: 167 | SILLGSTCYFDY |
| 168 | VL 14A11 | | 12345678901234567890123456789<br>NTVLTQSPALAVSLGQRVTISCK<br>ASRSVSS<br>PMYSYIYWYQQKPGQQPKLLIY<br>RASTLASG<br>VPARFSGSGSGTDFTLNIDPVEA<br>DDIATYF<br>CQQSWSDPFTFGSGTKLEIKR |
| | VL 14A11 CDR-L1 | Residues 23-37 of SEQ ID NO: 168 | KASRSVSSPMYSYIY |
| | VL 14A11 CDR-L2 | Residues 53-59 of SEQ ID NO: 168 | RASTLAS |
| | VL 14A11 CDR-L3 | Residues 92-100 of SEQ ID NO: 168 | QQSWSDPFT |
| | | | 12345678901234567890123456789 |
| 169 | VH 15D6 | | 12345678901234567890123456789<br>EVQLQQSGPELAKPGSSVKISCK<br>ASGYTFT<br>SSYISWIKQTTGQGLEYIGYINTG<br>SGGTDY<br>NEKFKDKATLTVDKSSRTVFMQ<br>LSSLTPGD<br>SAVYYCAKSILLGSTYYLDYWG<br>QGVMVTVSS |
| | VH 15D6 CDR-H1 | Residues 31-35 of SEQ ID NO: 169 | SSYIS |
| | VH 15D6 CDR-H2 | Residues 50-66 of SEQ ID NO: 169 | YINTGSGGTDYNEKFKD |
| | VH 15D6 CDR-H3 | Residues 99-110 of SEQ ID NO: 169 | SILLGSTYYLDY |
| 170 | VL 15D6 | | 12345678901234567890123456789<br>DTVLTQSPALAVSLGQRVTISCK<br>ASRSLSS<br>PMYSYIYWYQQKLGQQPRLLIY<br>RASTLASG<br>VPARFSGSGSGTDFTLNIDPVEA<br>DDIATYF<br>CQQSWSDPFTFGSGTKLEIKR |
| | | | 12345678901234567890123456789 |
| | VL 15D6 CDR-L1 | Residues 23-37 of SEQ ID NO: 170 | KASRSLSSPMYSYIY |
| | VL 15D6 CDR-L2 | Residues 53-59 of SEQ ID NO: 170 | RASTLAS |
| | VL 15D6 CDR-L3 | Residues 92-100 of SEQ ID NO: 170 | QQSWSDPFT |

Example 5

Generation of Chimeric Antibodies

The variable domains of the heavy and light chain of the anti-DLL4 rat mAbs (Table 9, above) were cloned in-frame to mutant human IgG1 (L234, 235A) heavy-chain and kappa light-chain constant regions, respectively. The activities of the resulting chimeric antibodies were confirmed in FACS-based binding and competition assays (Table 10, below), and were comparable to their parental rat mAbs.

TABLE 10

FACS-Based Binding and Neutralizing Activity of Recombinant Chimeric Antibodies Containing the Variable Domains of the Anti-DLL4 Rat mAbs.

| Chimera of | FACS binding ($EC_{50}$ nM) DLL4 cells | | Competition FACS ($IC_{50}$ nM) huNotch-1/DLL4 cells | |
|---|---|---|---|---|
| | Human DLL4 | Mouse DLL4 | Human DLL4 | Mouse DLL4 |
| 1A11 | 19.59 | 0.74 | 2.338 | 0.682 |
| 38H12 | 1.468 | N/D | 1.443 | N/D |
| 32C7 | 3.706 | 4.114 | ND | ND |
| 37D10 | 2.32 | 0.99 | 5.951 | 4.395 |
| 14G1 | 0.994 | N/D | 4.11 | N/D |
| 14A11 | 1.613 | 2.139 | 4.025 | 1.391 |
| 15D6 | 1.715 | 1.817 | 10.48 | 1.49 |

N/D = not determined.

Example 6

Humanization of Anti-DLL4 Rat Monoclonal Antibody 1A11

1A11 rat anti-DLL4 antibody (Table 9, above) was humanized. Humanized variant amino acid sequences VH.1, VH.1a, VH.1b, VH.2a, VL.1, VL.1a, VL.1b, and VL.2a (Table 11, below) were converted to DNA sequence based on the most homologous human germlines and synthesized. For the heavy chain variants, human germline heavy chain acceptor sequences VH3-7 FR1, VH3-7 FR2, VH3-7 FR 3, and JH4 FR4 were used (see, Table 3, above). For light chain variants VL.1, VL.1a, and VL.1b, human germline light chain acceptor sequences O2 FR1, O2 FR2, O2 FR3, and JK2 FR4 were used (see, Table 3, above). For light chain variant VL.2a, human germline light chain acceptor sequences L2 FR1, L2 FR2, L2 FR3, and JK2 FR4 were used (see, Table 4, above). Individual constructs were sequence verified to check for accuracy. Positive variants were then inoculated into 250 mls Luria broth plus ampicillin and cultured overnight at 37° C. DNA was extracted from variant cultures using the Qiagen Hi speed maxi prep kit (12662).

TABLE 11

VH and VL Amino Acid Sequences of Humanized Versions of Rat Anti-DLL4 Monoclonal Antibody 1A11.

| SEQ ID NO: | Protein region | Sequence 12345678901234567890123456 7890 |
|---|---|---|
| 171 | VH.1 1A11 | EVQLVESGGGLVQPGGSLRLSCAASGFTFS NFPMAWVRQAPGKGLEWVATISSSDGTTYY RDSVKGRFTISRDNAKNSLYLQMNSLRAED TAVYYCARGYYNSPFAYWGQGTLVTVSS |
| | VH.1 1A11 CDR-H1 | Residues 31-35 of SEQ ID NO: 171 NFPMA |
| | VH.1 1A11 CDR-H2 | Residues 50-66 of SEQ ID NO: 171 TISSSDGTTYYRDSVKG |
| | VH.1 1A11 CDR-H3 | Residues 99-107 of SEQ ID NO: 171 GYYNSPFAY |
| 172 | VH.1a 1A11 | EVQLVESGGGLVQPGGSLRLSCAASGFTFS NFPMAWVRQAPGKGLEWVATISSSDGTTYY RDSVKGRFTISRDNAKSSLYLQMNSLRAED TAVYYCSRGYYNSPFAYWGQGTLVTVSS |
| | VH.1a 1A11 CDR-H1 | Residues 31-35 of SEQ ID NO: 172 NFPMA |
| | VH.1a 1A11 CDR-H2 | Residues 50-66 of SEQ ID NO: 172 TISSSDGTTYYRDSVKG |
| | VH.1a 1A11 CDR-H3 | Residues 99-107 of SEQ ID NO: 172 GYYNSPFAY |
| 173 | VH.1b 1A11 | EVQLVESGGGLVQPGGSLRLSCAASGFTFS NFPMAWVRQAPGKGLEWVATISSSDGTTYY RDSVKGRFTISRDNAKNSLYLQMNSLRAED TAVYYCSRGYYNSPFAYWGQGTLVTVSS |
| | VH.1b 1A11 CDR-H1 | Residues 31-35 of SEQ ID NO: 173 NFPMA |
| | VH.1b 1A11 CDR-H2 | Residues 50-66 of SEQ ID NO: 173 TISSSDGTTYYRDSVKG |
| | VH.1b 1A11 CDR-H3 | Residues 99-107 of SEQ ID NO: 173 GYYNSPFAY |
| 174 | VH.2a 1A11 | EVQLVESGGGLVQPGGSLRLSCAASGFTFS NFPMAWVRQAPGKGLEWVATISSSDGTTYY RDSVKGRFTISRDNSKSTLYLQMNSLRAED TAVYYCSRGYYNSPFAYWGQGTLVTVSS |
| | VH.2a 1A11 CDR-H1 | Residues 31-35 of SEQ ID NO: 174 NFPMA |

TABLE 11-continued

VH and VL Amino Acid Sequences of Humanized Versions of Rat Anti-DLL4 Monoclonal Antibody 1A11.

| SEQ ID NO: | Protein region | Sequence<br>123456789012345678901234567890 |
|---|---|---|
| | VH.2a 1A11 CDR-H2 | Residues 50-66 of SEQ ID NO: 174 TISSSDGTTYYRDSVKG |
| | VH.2a 1A11 CDR-H3 | Residues 99-107 of SEQ ID NO: 174 GYYNSPFAY |
| 175 | VL.1 1A11 | DIQMTQSPSSLSASVGDRVTITCRASEDIY SNLAWYQQKPGKAPKLLIYDTNNLADGVPS RFSGSGSGTDFTLTISSLQPEDFATYYCQQ YNNYPPTFGQGTKLEIKR |
| | VL.1 1A11 CDR-L1 | Residues 24-34 of SEQ ID NO: 175 RASEDIYSNLA |
| | VL.1 1A11 CDR-L2 | Residues 50-56 of SEQ ID NO: 175 DTNNLAD |
| | VL.1 1A11 CDR-L3 | Residues 89-97 of SEQ ID NO: 175 QQYNNYPPT |
| 176 | VL.1a 1A11 | DIQMTQSPSSLSASVGDRVTITCRASEDIY SNLAWYQQKPGKSPKLLIFDTNNLADGVPS RFSGSGSGTDSTLTISSLQPEDFATYFCQQ YNNYPPTFGQGTKLEIKR |
| | VL.1a 1A11 CDR-L1 | Residues 24-34 of SEQ ID NO: 176 RASEDIYSNLA |
| | VL.1a 1A11 CDR-L2 | Residues 50-56 of SEQ ID NO: 176 DTNNLAD |
| | VL.1a 1A11 CDR-L3 | Residues 89-97 of SEQ ID NO: 176 QQYNNYPPT |
| 177 | VL.1b 1A11 | DIQMTQSPSSLSASVGDRVTITCRASEDIY SNLAWYQQKPGKAPKLLIFDTNNLADGVPS RFSGSGSGTDFTLTISSLQPEDFATYYCQQ YNNYPPTFGQGTKLEIKR |
| | VL.1b 1A11 CDR-L1 | Residues 24-34 of SEQ ID NO: 177 RASEDIYSNLA |
| | VL.1b 1A11 CDR-L2 | Residues 50-56 of SEQ ID NO: 177 DTNNLAD |
| | VL.1b 1A11 CDR-L3 | Residues 89-97 of SEQ ID NO: 177 QQYNNYPPT |
| 178 | VL.2A 1A11 | EIVMTQSPATLSVSPGERATLSCRASEDIY SNLAWYQQKPGQSPRLLIFDTNNLADGVPA RFSGSGSGTESTLTISSLQSEDFAVYFCQQ YNNYPPTFGQGTKLEIKR |
| | VL.2a 1A11 CDR-L1 | Residues 24-34 of SEQ ID NO: 178 RASEDIYSNLA |
| | VL.2a 1A11 CDR-L2 | Residues 50-56 of SEQ ID NO: 178 DTNNLAD |
| | VL.2a 1A11 CDR-L3 | Residues 89-97 of SEQ ID NO: 178 QQYNNYPPT |

Humanized antibodies were generated by combining each heavy chain variant with each light chain variant for a total of 16 variants (Table 12, below). Variants 1-4 each contained VH.1 paired with each VL variant: VL.1: 0 back mutations, VL.1a: 4 back mutations, VL.1b: 1 back mutation, and VL.2a: 5 back mutations. Variants 5-8 each contained VH.1a paired with each VL variant: VL.1: 2 back mutations, VL.1a: 6 back mutations, VL.1b:3 back mutations, and VL.2a: 7 back mutations. Variants 9-12 each contained VH.1b paired with each VL variant: VL.1: 1 back mutation, VL.1a: 5 back mutations, VL.1b: 2 back mutations, and VL.2a: 6 back mutations. Variants 13-16 each contained VH.2a paired with each VL variant: VL.1: 3 back mutations, VL.1a: 7 back mutations, VL.1b: 4 back mutations, VL.2a: 8 back mutations.

TABLE 12

Summary of Humanized 1A11 Antibodies Generated and Back Mutations.

| Name | VH/VL Combination | Back Mutations in Variable Regions[†] (VH/VL) |
|---|---|---|
| h1A11.1 | VH.1/VL.1 | 0/0 |
| h1A11.2 | VH.1/VL.1a | 0/A43S, Y49F, F71S, Y87F |
| h1A11.3 | VH.1/VL.1b | 0/Y49F |
| h1A11.4 | VH.1/VL.2a | 0/A43S, Y49F, I58V, F71S, Y87F |
| h1A11.5 | VH.1a/VL.1 | N76S, A93S/0 |
| h1A11.6 | VH.1a/VL.1a | N76S, A93S/A43S, Y49F, F71S, Y87F |
| h1A11.7 | VH.1a/VL.1b | N76S, A93S/Y49F |
| h1A11.8 | VH.1a/VL.2a | N76S, A93S/A43S, Y49F, I58V, F71S, Y87F |
| h1A11.9 | VH.1b/VL.1 | A93S/0 |
| h1A11.10 | VH.1b/VL.1a | A93S/A43S, Y49F, F71S, Y87F |
| h1A11.11 | VH.1b/VL.1b | A93S/Y49F |
| h1A11.12 | VH.1b/VL.2a | A93S/A43S, Y49F, I58V, F71S, Y87F |
| h1A11.13 | VH.2a/VL.1 | S49A, N76S, A93S/0 |
| h1A11.14 | VH.2a/VL.1a | S49A, N76S, A93S,/A43S, Y49F, F71S, Y87F |
| h1A11.15 | VH.2a/VL.1b | S49A, N76S, A93S/Y49F |
| h1A11.16 | VH.2a/VL.2a | S49A, N76S, A93S/A43S, Y49F, I58V, F71S, Y87F |

[†]Kabat numbering used.

All 16 variants were transiently transfected into 50 mls of HEK 293 6e suspension cell cultures in a ratio of 60% to 40% light to heavy chain construct. 1 mg/ml PEI was used to transfect the cells. Cell supernatants were harvested after six days in shaking flasks, spun down to pellet cells, and filtered through 0.22 μm filters to separate IgG from culture contaminates. Variant binding to human DLL4 was initially assessed through a capture binding ELISA (Example 1.2), which utilized a goat anti human-Fc capture antibody (Jackson ImmunoResearch, 109-005-008) to capture IgG within filtered 293 6e cell supernatants (Table 13, below). All 16 variants had very comparable affinities and were purified for further characterization.

All 16 variants (h1A11.1-h1A11.16) were batch purified by adding 1 supernatant volume of protein A IgG binding buffer (Thermo Scientific 21001) and 1 ml of rProteinA sepharose fast flow beads (GE Healthcare, 17-1279-04). Supernatants, with beads and buffer added, were rocked overnight at 4° C., and the day after beads were collected by gravity over poly prep chromatography columns (Bio Rad, 731-1550). Once supernatants had passed through the columns the beads were washed with 10 column volumes of binding buffer, and IgG was eluted with Immunopure IgG elution buffer (Pierce, 185 1520) and collected in 1 ml aliquots. Fractions containing IgG were pooled and dialyzed in PBS overnight at 4° C.

Purified variants were further characterized for their affinities for human, murine and cynomolgus DLL4 by binding ELISA (Example 1.2, Method 2), by Biacore (Example 1.1), and by Flow Cytometry (FACS). All 16 variants showed comparable affinities to the parent recombinant antibody 1A11 in all the three assays (Table 13). The humanized variants were then tested for their functionality with human and murine DLL4 by competition ELISA (Example 1.3) and by Notch reporter assay (Example 1.6). All 16 variants showed comparable potencies to the parent recombinant antibody 1A11 in both assays (Table 14, below).

TABLE 14

Summary of In Vitro Functional Potency of Humanized 1A11 mAbs.
Functional Data

| mAb | Human DLL4 Competition ELISA (IC50, nM) | Human DLL4 Reporter Assay (EC50, nM) | Mouse DLL4 Competition ELISA (IC50, nM) |
|---|---|---|---|
| h1A11-1 | 0.4 | 2.53 | 1.3 |
| h1A11-2 | 0.3 | 3.92 | 0.9 |
| h1A11-3 | 0.2 | 2.53 | 0.9 |
| h1A11-4 | 0.3 | 3.28 | 0.9 |
| h1A11-5 | 0.3 | 3.8 | 0.8 |
| h1A11-6 | 0.4 | 1.45 | 0.8 |
| h1A11-7 | 0.5 | 4.84 | 0.9 |
| h1A11-8 | 0.35 | 4.24 | 0.9 |
| h1A11-9 | 0.3 | 3.18 | 0.9 |
| h1A11-10 | 0.35 | 5.88 | 0.9 |
| h1A11-11 | 0.4 | 3.73 | 0.8 |
| h1A11-12 | 0.4 | 2.89 | 0.9 |
| h1A11-13 | 0.3 | 10.42 | 1 |
| h1A11-14 | 0.25 | 4.1 | 0.7 |
| h1A11-15 | 0.2 | 5.4 | 0.7 |
| h1A11-16 | 0.3 | 2.61 | 0.7 |
| 1A11 (chimera) | 1.8 | 5.98 | 3.5 |
| 1A11 (rat hybridoma mAb) | 0.5 | | 1.1 |

TABLE 13

Summary of Binding Activities of Humanized 1A11 mAbs.
Binding Data

| mAb | Human DLL4 Binding ELISA (EC50, nM) | Human DLL4 Biacore (KD, M) | Human DLL4 Binding FACS (EC50, nM) | Mouse DLL4 Binding ELISA (EC50, nM) | Mouse DLL4 Biacore (KD, M) | Mouse DLL4 Binding FACS (EC50, nM) | Cyno DLL4 Binding ELISA (EC50, nM) |
|---|---|---|---|---|---|---|---|
| h1A11-1 | 0.08 | $1.5 \times 10^{-8}$ | 3.13 | 0.09 | $3.8 \times 10^{-8}$ | 0.21 | 0.13 |
| h1A11-2 | 0.08 | $1.0 \times 10^{-8}$ | 2.85 | 0.09 | $1.9 \times 10^{-8}$* | 0.21 | 0.13 |
| h1A11-3 | 0.07 | $1.5 \times 10^{-8}$ | 3.51 | 0.08 | $3.7 \times 10^{-8}$ | 0.24 | 0.16 |
| h1A11-4 | 0.08 | $1.6 \times 10^{-8}$ | 3.61 | 0.09 | $3.9 \times 10^{-8}$ | 0.22 | 0.17 |
| h1A11-5 | 0.07 | $0.96 \times 10^{-8}$ | 3.61 | 0.08 | $2.2 \times 10^{-8}$ | 0.21 | 0.16 |
| h1A11-6 | 0.08 | $1.13 \times 10^{-8}$ | 3.74 | 0.10 | $3.1 \times 10^{-8}$ | 0.15 | 0.13 |
| h1A11-7 | 0.06 | $1.3 \times 10^{-8}$ | 3.71 | 0.09 | $3.5 \times 10^{-8}$ | 0.18 | 0.14 |
| h1A11-8 | 0.06 | $1.1 \times 10^{-8}$ | 3.34 | 0.09 | $2.4 \times 10^{-8}$ | 0.18 | 0.17 |
| h1A11-9 | 0.07 | $1.3 \times 10^{-8}$ | 3.28 | 0.09 | $3.4 \times 10^{-8}$ | 0.18 | 0.15 |
| h1A11-10 | 0.06 | $1.3 \times 10^{-8}$ | nt | 0.09 | $3.5 \times 10^{-8}$ | nt | 0.15 |
| h1A11-11 | 0.07 | $1.2 \times 10^{-8}$ | nt | 0.09 | $2.7 \times 10^{-8}$ | nt | 0.15 |
| h1A11-12 | 0.06 | $1.4 \times 10^{-8}$ | nt | 0.08 | $3.5 \times 10^{-8}$ | nt | 0.16 |
| h1A11-13 | 0.06 | $1.4 \times 10^{-8}$ | nt | 0.09 | $3.7 \times 10^{-8}$ | nt | 0.16 |
| h1A11-14 | 0.055 | $1.3 \times 10^{-8}$ | nt | 0.07 | $2.8 \times 10^{-8}$ | nt | 0.14 |
| h1A11-15 | 0.07 | $1.4 \times 10^{-8}$ | nt | 0.09 | $3.7 \times 10^{-8}$ | nt | 0.13 |
| h1A11-16 | 0.06 | $1.5 \times 10^{-8}$ | nt | 0.09 | $3.9 \times 10^{-8}$ | nt | 0.12 |
| 1A11 (chimeric) | 0.2 | $0.9 \times 10^{-8}$ | 6.29 | 0.3 | $2.4 \times 10^{-8}$ | 0.53 | 0.33 |
| 1A11 (rat mAb) | | $0.6 \times 10^{-8}$ | | | | | | nt = not tested

Additional Designs for Humanizing Anti-DLL4 1A11 Antibodies.

Additional VH and VL designs for humanizing anti-DLL4 rat monoclonal antibody 1A11 are shown in the table below.

TABLE 15

Additional VH and VL Designs for Humanizing 1A11 Antibodies.

| VH or VL Design | Acceptor Framework Sequence | Back Mutations† |
|---|---|---|
| h1A11VH.2 | VH3 CONSENSUS + JH4 | 0 |
| h1A11VH.2b | VH3 CONSENSUS + JH4 | S49A, A93S |
| h1A11VH.3 | VH1-46 + JH4 (with Q1E to prevent N-terminal pyroglutamate formation) | 0 |
| h1A11VH.3b | VH1-46 + JH4 (Q1E) | Y27F, M48V, G49A, A93S |
| h1A11VH.3c | VH1-46 + JH4 (Q1E) | Y27F, M48V, G49A, V67F, M69I, T73N, V78L, A93S, and T75I (to avoid undesirable N-glycosylation signal) |
| h1A11VH.3d | VH1-46 + JH4 (Q1E) | Y27F, M48V, G49A, V67F, M69I, V78L, A93S (T73N omitted to avoid undesirable N-glycosylation signal) |
| h1A11VL.1c | O2 + JK2 | Y49F, F71S |
| h1A11VL.2 | 3-15/L2 + JK2 | 0 |

TABLE 15-continued

Additional VH and VL Designs for Humanizing 1A11 Antibodies.

| VH or VL Design | Acceptor Framework Sequence | Back Mutations† |
|---|---|---|
| h1A11VL.2b | 3-15/L2 + JK2 | Y49F |
| h1A11VL.2c | 3-15/L2 + JK2 | Y49F, F71S |

†Kabat numbering used.

Example 7

Humanization of Anti-DLL4 Rat mAb 38H12

The 38H12 rat anti-DLL4 antibody (Table 9, above) was humanized. Humanized variant amino acid sequences VH.1, VH.1a, VH.1b, VH.2a, VL.1, VL.1a, VL.1b, and VL.2a (Table 16, below) were converted to DNA sequence, based on the most homologous human germlines, and synthesized. Human germline heavy chain acceptor sequences VH3-30 FR1, VH3-30 FR2, VH3-30 FR3, and JH3 FR4 (see, Table 3) were used for generating the humanized heavy chain variants shown in Table 16. Human germline light chain acceptor sequences O2 FR1, O2 FR2, O2 FR3, and JK2 FR4 (see, Table 4) were used for generating the humanized light chain variants shown in Table 16. Individual constructs were sequence verified to check for accuracy. Positive variants were then inoculated into 150 mls Luria broth plus ampicillin and cultured overnight at 37° C. DNA was extracted from variant cultures using the Qiagen Hi speed maxi prep kit (12662).

Table 16. VH and VL Amino Acid Sequences of Humanized Rat Anti-DLL4 Monoclonal Antibody 38H12.

| SEQ ID NO: | Protein region | | Sequence 123456789012345678901234567890 |
|---|---|---|---|
| 179 | VH.1 38H12 | | EVQLVESGGGVVQPGRSLRLSC AASGFTFS NYGMYWVRQAPGKGLEWVAFI SHGGGITYY RDSVKGRFTISRDNSKNTLYLQ MNSLRAED TAVYYCARLNWELGIDYWGQG TMVTVSS |
| | VH.1 38H12 CDR-H1 | Residues 31-35 of SEQ ID NO: 179 | NYGMY |
| | VH.1 38H12 CDR-H2 | Residue 50-66 of SEQ ID NO: 179 | FISHGGGITYYRDSVKG |
| | VH.1 38H12 CDR-H3 | Residues 99-107 of SEQ ID NO: 179 | LNWELGIDY |
| 180 | VH.1a 38H12 | | EVQLVESGGGVVQPGRSLRLSC AASGFTFS NYGMYWIRQAPGKGLEWVAFIS HGGGITYY RDSVKGRETISRDNSKSTLYLQM NSLRAED TAVYHCAALNWELGIDYWGQG TMVTVSS |
| | VH.1a 8H12 CDR-H1 | Residues 31-35 of SEQ ID NO: 180 | NYGMY |

-continued

| SEQ ID NO: | Protein region | | Sequence 12345678901234567890123456 7890 |
|---|---|---|---|
| | VH.1a 38H12 CDR-H2 | Residue 50-66 of SEQ ID NO: 180 | FISHGGGITYYRDSVKG |
| | VH.1a 38H12 CDR-H3 | Residues 99-107 of SEQ ID NO: 180 | LNWELGIDY |
| 181 | VH.1b 38H12 | | EVQLVESGGGVVQPGRSLRLSC AASGFTFS NYGMYWVRQAPGKGLEWVAFI SHGGGITYY RDSVKGRFTISRDNSKNTLYLQ MNSLRAED TAVYYCAALNWELGIDYWGQG TMVTVSS |
| | VH.1b 38H12 CDR-H1 | Residues 31-35 of SEQ ID NO: 181 | NYGMY |
| | VH.1b 38H12 CDR-H2 | Residues 50-66 of SEQ ID NO: 181 | FISHGGGITYYRDSVKG |
| | VH.1b 38H12 CDR-H3 | Residues 99-107 of SEQ ID NO: 181 | LNWELGIDY |
| 182 | VH.2a 38H12 | | EVQLVESGGGLVQPGGSLRLSC AASGFTFS NYGMYWIRQAPGKGLEWVAFIS HGGGITYY RDSVKGRFTISRDNSKSTLYLQM NSLRAED TAVYHCAALNWELGIDYWGQG TMVTVSS |
| | VH.2a 38H12 CDR-H1 | Residues 31-35 of SEQ ID NO: 182 | NYGMY |
| | VH.2a 38H12 CDR-H2 | Residues 50-66 of SEQ ID NO: 182 | FISHGGGITYYRDSVKG |
| | VH.2a 38H12 CDR-H3 | Residues 99-107 of SEQ ID NO: 182 | LNWELGIDY |
| 183 | VL.1 38H12 | | DIQMTQSPSSLSASVGDRVTITC RASEDIY SNLAWYQQKPGKAPKLLIYAAN RLQDGVPS RFSGSGSGTDFTLTISSLQPEDFA TYYCLQ GSKFPLTFGQGTKLEIKR |
| | VL.1 38H12 CDR-L1 | Residues 24-34 of SEQ ID NO: 183 | RASEDIYSNLA |
| | VL.1 38H12 CDR-L2 | Residues 50-56 of SEQ ID NO: 183 | AANRLQD |
| | VL.1 38H12 CDR-L3 | Residues 89-97 of SEQ ID NO: 183 | LQGSKFPLT |
| 184 | VL.1a 38H12 | | DIQMTQSPSSLSASVGDRVTITC RASEDIY SNLAWYQKKPGKSPKLLIYAAN RLQDGVPS RFSGSGSGTDYTLTISSLQPEDFA TYFCLQ GSKFPLTFGQGTKLEIKR |
| | VL.1a 38H12 CDR-L1 | Residues 24-34 of SEQ ID NO: 184 | RASEDIYSNLA |
| | VL.1a 38H12 CDR-L2 | Residues 50-56 of SEQ ID NO: 184 | AANRLQD |

```
SEQ
ID  Protein                    Sequence
NO: region                     12345678901234567890123456789O VL.1a 38H12 Residues 89-97 of  LQGSKFPLT
    CDR-L3      SEQ ID NO: 184

185 VL.1b 38H12                    DIQMTQSPSSLSASVGDRVTITC
                                   RASEDIY
                                   SNLAWYQQKPGKAPKLLIYAAN
                                   RLQDGVPS
                                   RFSGSGSGTDYTLTISSLQPEDFA
                                   TYYCLQ
                                   GSKFPLTFGQGTKLEIKR

VL.1b 38h12 Residues 24-34 of  RASEDIYSNLA
    CDR-L1      SEQ ID NO: 185

VL.1b 38H12 Residues 50-56 of  AANRLQD
    CDR-L2      SEQ ID NO: 185

VL.1b 38H12 Residues 89-97 of  LQGSKFPLT
    CDR-L3      SEQ ID NO: 185

186 VL.2a 38H12                    EIVMTQSPATLSVSPGERATLSC
                                   RASEDIY
                                   SNLAWYQKKPGQSPRLLIYAAN
                                   RLQDGVPA
                                   RFSGSGSGTEYTLTISSLQSEDFA
                                   VYFCLQ
                                   GSKFPLTFGQGTKLEIKR

VL.2a 38H12 Residues 24-34 of  RASEDIYSNLA
    CDR-L1      SEQ ID NO: 186

VL.2a 38H12 Residues 50-56 of  AANRLQD
    CDR-L2      SEQ ID NO: 186

VL.2a 38H12 Residues 89-97 of  LQGSKFPLT
    CDR-L3      SEQ ID NO: 186
```

Humanized antibodies were generated by combining each heavy chain variant with each light chain variant for a total of 16 variants (Table 17, below). Variants 1-4 each contained VH.1 paired with each VL variant: VL.1: 0 back mutations, VL.1a: 4 back mutations, VL.1b: 1 back mutation, and VL.2a: 5 back mutations. Variants 5-8 each contained VH.1a paired with each VL variant: VL.1: 4 back mutations, VL.1a: 8 back mutations, VL.1b: 5 back mutations, and VL.2a: 9 back mutations. Variants 9-12 each contained VH.1b paired with each VL variant: VL.1: 1 back mutation, VL.1a: 5 back mutations, VL.1b: 2 back mutations, and VL.2a: 5 back mutations. Variants 13-16 each contained VH.2a paired with each VL variant: VL.1: 5 back mutations, VL.1a: 9 back mutations, VL.1b: 6 back mutations, VL.2a: 10 back mutations.

TABLE 17

Summary of Humanized 38H12 Antibodies Generated and Back Mutations.

| Name | VH/VL Combination | Back Mutations in Variable Regions† (VH/VL) |
|---|---|---|
| h38H12.1 | VH.1/VL.1 | 0/0 (Q1E in VH to prevent N-terminal pyroglutamate formation) |
| h38H12.2 | VH.1/VL.1a | 0/Q38K, A43S, F71Y, Y87F (Q1E in VH as noted above) |
| h38H12.3 | VH.1/VL.1b | 0/F71Y (Q1E in VH as noted above) |
| h38H12.4 | VH.1/VL.2a | 0/Q38K, A43S, I58V, F71Y, Y87F (Q1E in VH as noted above) |
| h38H12.5 | VH.1a/VL.1 | V37I, N76S, Y91H, R94A/0 |
| h38H12.6 | VH.1a/VL.1a | V37I, N76S, Y91H, R94A/Q38K, A43S, F71Y, Y87F |
| h38H12.7 | VH.1a/VL.1b | V37I, N76S, Y91H, R94A/F71Y |
| h38H12.8 | VH.1a/VL.2a | V37I, N76S, Y91H, R94A/Q38K, A43S, I58V, F71Y, Y87F |
| h38H12.9 | VH.1b/VL.1 | R94A/0 |
| h38H12.10 | VH.1b/VL.1a | R94A/Q38K, A43S, F71Y, Y87F |
| h38H12.11 | VH.1b/VL.1b | R94A/F71Y |
| h38H12.12 | VH.1b/VL.2a | R94A/Q38K, A43S, I58V, F71Y, Y87F |
| h38H12.13 | VH.2a/VL.1 | V37I, S49A, N76S, Y91H, R94A/0 |

TABLE 17-continued

Summary of Humanized 38H12 Antibodies Generated and Back Mutations.

| Name | VH/VL Combination | Back Mutations in Variable Regions† (VH/VL) |
|---|---|---|
| h38H12.14 | VH.2a/VL.1a | V37I, S49A, N76S, Y91H, R94A/Q38K, A43S, F71Y, Y87F |
| h38H12.15 | VH.2a/VL.1b | V37I, S49A, N76S, Y91H, R94A/F71Y |
| h38H12.16 | VH.2a/VL.2a | V37I, S49A, N76S, Y91H, R94A/Q38K, A43S, I58V, F71Y, Y87F |

†Kabat numbering used.

All 16 variants were transiently transfected into 50 mls of HEK 293 6e suspension cell cultures in a ratio of 60% to 40% light to heavy chain construct. 1 mg/ml PEI was used to transfect the cells. Cell supernatants were harvested after seven days in shaking flasks, spun down to pellet cells, and filtered through 0.22 μm filters to separate IgG from culture contaminates. Variant binding to human DLL4 was initially assessed through a capture binding ELISA (Example 1.2), which utilized a goat anti human-Fc capture antibody (Jackson immuno research, 109-005-008) to capture IgG within filtered 293 6e cell supernatants (see, ELISA binding $EC_{50}$, Table 18, below). Variants containing VH.1 exhibited the lowest binding affinities as compared to the other variants and were considered out of the screening. VH.1 is CDR-grafted with no framework back mutations.

Good binders (h38H12.5-h38H12.16) were then batch purified by adding 1 supernatant volume of protein A IgG binding buffer (Thermo Scientific 21001) and 800 μl of rProteinA sepharose fast flow beads (GE Healthcare, 17-1279-04). Supernatants, with beads and buffer added, were stirred at room temperature for 4 hours, and beads were collected by gravity over poly prep chromatography columns (Bio Rad, 731-1550). Once supernatants had passed through the columns the beads were washed with 10 mls binding buffer and IgG was eluted with Immunopure IgG elution buffer (Pierce, 185 1520) and collected in 1 ml aliquots neutralized with 100 μl 1M Tris, pH 8.

Purified variants were further characterized in human Notch-1 competition ELISAs (Example 1.4), which used a format of plating Notch-1 Fc onto ELISA plates and pre-incubating biotinylated human DLL4 plus titrated antibody. Signal was assessed by free biotinylated DLL4 binding to Notch-1 Fc. Strong binders inhibited signal at low antibody concentration. h38H12.5 through h38H12.7 exhibited lower competition potencies as compared to the other variants (see, Notch Competition ELISA $EC_{50}$, Table 18, below).

The good binder variants, as determined by binding ELISA, were assessed by Biacore (Example 1.1) concurrently with cell based assay screens. The $K_D$ for human DLL4 was similar for all variants (see, Biacore, $K_D$ in Table 18, below). Variants were screened in cell-based assays that examined direct binding to human DLL4 (Example 1.3; FACS binding $EC_{50}$ in Table 18, below) and inhibition of Notch-1 signaling (Example 1.6; Notch Reporter Assay $EC_{50}$ in Table 18, below).

TABLE 18

Summary of In Vitro Activities Against Human DLL4 of Humanized 38H12 mAbs.

| Name | ELISA binding $EC_{50}$ (nM) | Notch Competition ELISA $EC_{50}$ (nM) | FACS binding $EC_{50}$ (nM) | Notch Reporter Assay $EC_{50}$ (nM) | Biacore, $K_D$ (nM) |
|---|---|---|---|---|---|
| h38H12.1 | 21.5 | | 17.84 | | |
| h38H12.2 | 26.88 | | | | |
| h38H12.3 | 5.57 | | | | |
| h38H12.4 | 20.65 | | | | |
| h38H12.5 | 0.2015 | 14.81 | 77.15 | 7.307 | 0.401 |
| h38H12.6 | 0.1584 | 26.96 | 12.29 | 6.317 | 0.434 |
| h38H12.7 | 0.1798 | 12.49 | 19.06 | 2.598 | 0.34 |
| h38H12.8 | 0.1972 | 8.315 | 20.02 | 5.557 | 0.397 |
| h38H12.9 | 0.1155 | 4.158 | 3.71 | 1.436 | 0.986 |
| h38H12.10 | 0.1226 | 3.902 | 2.489 | 0.7861 | 0.578 |
| h38H12.11 | 0.1264 | 3.8 | 2.477 | 0.6572 | 0.554 |
| h38H12.12 | 0.1651 | 3.228 | 1.478 | 1.062 | 0.819 |
| h38H12.13 | 0.1534 | 5.287 | 2.556 | 0.7943 | 0.507 |
| h38H12.14 | 0.146 | 5.839 | 1.04 | 1.014 | 0.303 |
| h38H12.15 | 0.0904 | 5.714 | 2.369 | 0.837 | 0.355 |
| h38H12.16 | 0.1696 | 3.766 | 2.914 | 1.185 | 0.392 |

Additional Designs for Humanizing Anti-DLL4 38H12 Antibodies.

Additional VH and VL designs for humanizing anti-DLL4 rat monoclonal antibody 38H12 are shown in the table below.

TABLE 19

Additional VH and VL Designs for Humanizing 38H12 Antibodies.

| VH or VL Design | Germline Acceptor Framework Sequences | Back Mutations† |
|---|---|---|
| h38H12VH.2 | VH3 CONSENSUS + JH3 | 0 |
| h38H12VH.2b | VH3 CONSENSUS + JH3 | S49A, R94A |
| h38H12VH.3 | VH1-46 + JH3 | 0 (Q1E in VH to prevent N-terminal pyroglutamate formation) |
| h38H12VH.3b | VH1-46 + JH3 | Y27F, M48V, G49A, R94A (Q1E in VH as noted above) |
| h38H12VH.3c | VH1-46 + JH3 | Y27F, Y37I, M48V, G49A, V67F, M69I, T73N, V78L, Y91H, R94A (T75I to eliminate undesirable N-glycosylation signal, Q1E in VH as noted above) |
| h38H12VH.3d | VH1-46 + JH3 | Y27F, Y37I, M48V, G49A, V67F, M69I, V78L, Y91H, R94A (Q1E in VH as noted above) |
| h38H12VL.2 | 3-15/L2 + JK2 | 0 |
| h38H12VL.2b | 3-15/L2 + JK2 | F71Y |

†Kabat numbering used.

Example 8

Affinity Maturation of h1A11.1

Humanized antibody h1A11.1 was used as a template for affinity maturation. A description of the design of the library is provided below. Numbering of variable region sequences of monoclonal antibodies was annotated with Kabat numbering (as described above; or see worldwide website bioinf.org.uk/abs/#kabatnum) and was used in generating the libraries described below.

Three libraries were made as described below.

H1+H2 library (doping: 76080808):

Doped 11 residues at 30, 31, 32, 35, 50, 52, 52a, 55, 56, 57, and 58.

Toggle between germline and h1A11 sequence at position 76(V/I).

A $10^9$ library sampled mutants with 4 or fewer mutated residues at least 3.7 times.

The majority of the library with mutants carrying 4 to 6 residues was mutated by doping.

H3 library (doping: 70101010)

Doped 8 residues @ 95, 96, 97, 98, 99, 100, 100a, and 102.

Toggle between germline and h1A11 sequence at position 93(A/S) and 101 (D/A).

A $10^9$ library sampled mutants with 4 or fewer mutated residues at least 4.7 times.

The majority of the library with mutants carrying 4 to 5 residues was mutated by doping.

LC library (doping: 70101010):

Doped 9 residues at 28, 30, 31, 50, 53, 92, 93, 94, and 96.

Toggle between germline and h1A11 sequence at 7 positions 27(Q/E), 43(A/S), 49(Y/F), 52(S/N), 71(F/S), 87(Y/F), and 91(S/Y).

A $10^9$ library sampled mutants with 4 or fewer mutated residues at least 1 time.

The majority of the library with mutants carrying 4 to 6 residues was mutated by doping.

rHC library: recombine outputs of H1+H2 and H3 libraries.

rHCLC library: recombine outputs of H1+H2, H3, and LC libraries.

Both VH and VL framework germlining reduced predicted immunogenicity. The most desirable germlining mutation in the h1A11VL.1a was the S43A and S71F Used codons specified here for residues that were doped:

If a proline is to be doped, the doping oligo will have $C_{(5-85-5-5)}C_{(5-85-5-5)}S$ codon regardless of the original codon in the antibody sequence. These codons were selected based on the following criteria:
1. increase non-synonymous mutation
2. increase coverage of more amino acids when mutated
3. uses high frequency codons
4. avoid SSS and WWW codons.

Doping order was A-C-G-T $A_{(85-5-5-5)}$, $A_{(70-10-10-10)}$
$C_{(5-85-5-5)}$, $C_{(10-70-10-10)}$
$G_{(5-5-85-5)}$, $G_{(10-10-70-10)}$
$T_{(5-5-5-85)}$, $T_{(10-10-10-70)}$

| | | |
|---|---|---|
| Alanine (A): | | |
| GCN | $G_{(10-10-70-10)}C_{(10-70-10-10)}S$ | $G_{(5-5-85-5)}C_{(5-85-5-5)}S$ |
| Threonine (T): | | |
| ACN | $A_{(70-10-10-10)}C_{(10-70-10-10)}S$ | $A_{(85-5-5-5)}C_{(5-85-5-5)}S$ |
| Proline (P): | | |
| CCN | $C_{(10-70-10-10)}C_{(10-70-10-10)}S$ | $C_{(5-85-5-5)}C_{(5-85-5-5)}S$ |
| Serine (S): | | |
| If TCN | $T_{(10-10-10-70)}C_{(10-70-10-10)}S$ | $T_{(5-5-5-85)}C_{(5-85-5-5)}S$ |
| If AGY | $A_{(70-10-10-10)}G_{(10-10-70-10)}C_{(10-70-10-10)}$ | $A_{(85-5-5-5)}G_{(5-5-85-5)}C_{(5-85-5-5)}$ |
| Valine (V): | | |
| GTN | $G_{(10-10-70-10)}T_{(10-10-10-70)}S$ | $G_{(5-5-85-5)}T_{(5-5-5-85)}S$ |
| Glycine (G): | | |
| GGN | $G_{(10-10-70-10)}G_{(10-10-70-10)}S$ | $G_{(5-5-85-5)}G_{(5-5-85-5)}S$ |
| Leucine (L): | | |
| If CTN | $C_{(10-70-10-10)}T_{(10-10-10-70)}S$ | $C_{(5-85-5-5)}T_{(5-5-5-85)}S$ |
| If TTR | $T_{(10-10-10-70)}T_{(10-10-10-70)}G_{(10-10-70-10)}$ | $T_{(5-5-5-85)}T_{(5-5-5-85)}G_{(5-5-85-5)}$ |
| Arginine (R): | | |
| If CGN | $C_{(10-70-10-10)}G_{(10-10-70-10)}S$ | $C_{(5-85-5-5)}G_{(5-5-85-5)}S$ |
| If AGR | $A_{(70-10-10-10)}G_{(10-10-70-10)}G_{(10-10-70-10)}$ | $A_{(85-5-5-5)}G_{(5-5-85-5)}G_{(5-5-85-5)}$ |
| Methionine (M): | | |
| ATG | $A_{(70-10-10-10)}T_{(10-10-10-70)}G_{(10-10-70-10)}$ | $A_{(85-5-5-5)}T_{(5-5-5-85)}G_{(5-5-85-5)}$ |
| Tryptophan (W): | | |
| TGG | $T_{(10-10-10-70)}G_{(10-10-70-10)}G_{(10-10-70-10)}$ | $T_{(5-5-5-85)}G_{(5-5-85-5)}G_{(5-5-85-5)}$ |
| Pheylalanine (F): | | |
| TTY | $T_{(10-10-10-70)}T_{(10-10-10-70)}C_{(10-70-10-10)}$ | $T_{(5-5-5-85)}T_{(5-5-5-85)}C_{(5-85-5-5)}$ |
| Isoleucine (I): need two oligos | | |
| 50% ATY | $A_{(70-10-10-10)}T_{(10-10-10-70)}C_{(10-70-10-10)}$ | $A_{(85-5-5-5)}T_{(5-5-5-85)}C_{(5-85-5-5)}$ |
| 50% ATA | $A_{(70-10-10-10)}T_{(10-10-10-70)}A_{(70-10-10-10)}$ | $A_{(85-5-5-5)}T_{(5-5-5-85)}A_{(85-5-5-5)}$ |
| Tyrosine (Y): | | |
| TAY | $T_{(10-10-10-70)}A_{(70-10-10-10)}C_{(10-70-10-10)}$ | $T_{(5-5-5-85)}A_{(85-5-5-5)}C_{(5-85-5-5)}$ |
| Histidine (H): | | |
| CAY | $C_{(10-70-10-10)}A_{(70-10-10-10)}C_{(10-70-10-10)}$ | $C_{(5-85-5-5)}A_{(85-5-5-5)}C_{(5-85-5-5)}$ |

-continued

| | |
|---|---|
| Glutamine (Q): | |
| CAR Asparagines (N): | $C_{(10\text{-}70\text{-}10\text{-}10)}A_{(70\text{-}10\text{-}10\text{-}10)}G_{(10\text{-}10\text{-}70\text{-}10)}$ $C_{(5\text{-}85\text{-}5\text{-}5)}A_{(85\text{-}5\text{-}5\text{-}5)}G_{(5\text{-}5\text{-}85\text{-}5)}$ |
| AAY Lysine (K): | $A_{(70\text{-}10\text{-}10\text{-}10)}A_{(70\text{-}10\text{-}10\text{-}10)}C_{(10\text{-}70\text{-}10\text{-}10)}$ $A_{(85\text{-}5\text{-}5\text{-}5)}A_{(85\text{-}5\text{-}5\text{-}5)}C_{(5\text{-}85\text{-}5\text{-}5)}$ |
| AAR Aspartic Acid (D): | $A_{(70\text{-}10\text{-}10\text{-}10)}A_{(70\text{-}10\text{-}10\text{-}10)}G_{(10\text{-}10\text{-}70\text{-}10)}$ $A_{(85\text{-}5\text{-}5\text{-}5)}A_{(85\text{-}5\text{-}5\text{-}5)}G_{(5\text{-}5\text{-}85\text{-}5)}$ |
| GAY Glutamic acid (E): | $G_{(10\text{-}10\text{-}70\text{-}10)}A_{(70\text{-}10\text{-}10\text{-}10)}C_{(10\text{-}70\text{-}10\text{-}10)}$ $G_{(5\text{-}5\text{-}85\text{-}5)}A_{(85\text{-}5\text{-}5\text{-}5)}C_{(5\text{-}85\text{-}5\text{-}5)}$ |
| GAR Cysteine (C): | $G_{(10\text{-}10\text{-}70\text{-}10)}A_{(70\text{-}10\text{-}10\text{-}10)}G_{(10\text{-}10\text{-}70\text{-}10)}$ $G_{(5\text{-}5\text{-}85\text{-}5)}A_{(85\text{-}5\text{-}5\text{-}5)}G_{(5\text{-}5\text{-}85\text{-}5)}$ |
| TGY | always NNS |

The h1A11.1 libraries were transformed into yeast cells and displayed on the cell surface to be selected against low concentration of biotinylated DLL4 extracellular domain by magnetic then fluorescence activated cell sorting. Selection for improved on-rate or off-rate or both were carried out, and antibody protein sequences of affinity-modulated hu1A11 clones (Tables 20 and 21, below) were recovered from yeast cells for converting back to IgG format for further characterization (see, summary of clones in Table 22). Table 23 lists the amino acids observed during the affinity maturation selection in both framework regions (FR) and CDRs.

TABLE 20

VH sequences of Affinity Matured Humanized 1A11.1 Clones

| SEQ ID NO: | Protein region | | | Sequence 12345678901234567890 1234567890 |
|---|---|---|---|---|
| 187 | h1A11VH.1 VH | | | EVQLVESGGGLVQPGGSLRLSC AASGFTFSNFPMAWVRQAPGKG LEWVATISSSDGTTYYRDSVKG RFTISRDNAKNSLYLQMNSLRAE DTAVYYCARGYYNSPFAYWGQ GTLVTVSS |
| | h1A11VH.1 VH | CDR-H1 | Residues 31-35 of SEQ ID NO: 187 | NFPMA |
| | h1A11VH.1 VH | CDR-H2 | Residues 50-66 of SEQ ID NO: 187 | TISSSDGTTYYRDSVKG |
| | h1A11VH.1 VH | CDR-H3 | Residues 99-107 of SEQ ID NO: 187 | GYYNSPFAY |
| 188 | h1A11.A6 VH | | | EVQLVESGGGLVQPGGSLRLSC AASGFTFRHFPMAWVRQAPGKG LEWVATISSSDAWPSYRDSVKG RFTISRDNAKNSLYLQMNSLRAE DTAVYYCSRGYYNSPFAYWGQ GTLVTVSS |
| | h1A11.A6 VH | CDR-H1 | Residues 31-35 of SEQ ID NO: 188 | HFPMA |
| | h1A11.A6 VH | CDR-H2 | Residues 50-66 of SEQ ID NO: 188 | TISSSDAWPSYRDSVKG |

TABLE 20-continued

VH sequences of Affinity Matured Humanized 1A11.1 Clones

| SEQ ID NO: | Protein region | | | Sequence 123456789012345678901234567890 |
|---|---|---|---|---|
| | h1A11.A6 VH | CDR-H3 | Residues 99-107 of SEQ ID NO: 188 | GYYNSPFAY |
| 189 | h1A11.A8 VH | | | EVQLVESGGGLVQPGGSLRLSCAASGFTFGNFPMSWVRQAPGKGLEWVASISSSDSWATIGDSVKGRFTISRDNAKNSLYLQMNSLRAEDTAVYYCSRGYYNSPFAYWGQGTLVTVSS |
| | h1A11.A8 VH | CDR-H1 | Residues 31-35 of SEQ ID NO: 189 | NFPMS |
| | h1A11.A8 VH | CDR-H2 | Residues 50-66 of SEQ ID NO: 189 | SISSSDSWATIGDSVKG |
| | h1A11.A8 VH | CDR-H3 | Residues 99-107 of SEQ ID NO: 189 | GYYNSPFAY |
| 190 | h1A11.C6 VH | | | EVQLVESGGGLVQPGGSLRLSCAASGFTFRNFPMAWVRQAPGKGLEWVATISSSDGWPTYRDSVKGRFTISRDNAKSSLYLQMNSLRAEDTAVYYCSRGYYNSPFAYWGQGTLVTVSS |
| | h1A11.C6 VH | CDR-H1 | Residues 31-35 of SEQ ID NO: 190 | NFPMA |
| | h1A11.C6 VH | CDR-H2 | Residues 50-66 of SEQ ID NO: 190 | TISSSDGWPTYRDSVKG |
| | h1A11.C6 VH | CDR-H3 | Residues 99-107 of SEQ ID NO: 190 | GYYNSPFAY |
| 191 | h1A11.A11 VH | | | EVQLNESGGGLVQPGGSLRLSCAASGFTFRHFPMAWVRQAPGKGLEWVATISSSDDWPNYRDSVKGRFTISRDNAKSSLYLQMNSLRAEDTAVYYCSRGYYNSPFAYWGQGTLVTVSS |
| | h1A11.A11 VH | CDR-H1 | Residues 31-35 of SEQ ID NO: 191 | HFPMA |
| | h1A11.A11 VH | CDR-H2 | Residues 50-66 of SEQ ID NO: 191 | TISSSDDWPNYRDSVKG |
| | h1A11.A11 VH | CDR-H3 | Residues 99-107 of SEQ ID NO: 191 | GYYNSPFAY |

TABLE 20-continued

VH sequences of Affinity Matured Humanized 1A11.1 Clones

| SEQ ID NO: | Protein region | | | Sequence 123456789012345678901234567890 |
|---|---|---|---|---|
| 192 | h1A11.B5 VH | | | EVQLVESGGGLVQPGGSLRLSC AASGFTFRYFPMSWVRQAPGKG LEWVASISGSDGWASVKG RFTISRDNAKNSLYLQMNSLRAE DTAVYYCARGYYNSPFASWGQ GTLVTVSS |
| | h1A11.B5 VH | CDR-H1 | Residues 31-35 of SEQ ID NO: 192 | YFPMS |
| | h1A11.B5 VH | CDR-H2 | Residues 50-66 of SEQ ID NO: 192 | SISGSDGWASYRDSVKG |
| | h1A11.B5 VH | CDR-H3 | Residues 99-107 of SEQ ID NO: 192 | GYYNSPFAS |
| 193 | h1A11.E12 VH | | | EVQLVESGGGLVQPGGSLRLSC AASGFTFRYFPMAWVRQAPGKG LEWVATISGSDEWPNYRDSVKG RFTISRDNAKNSLYLQMNSLRAE DTAVYYCARGYYNSPFAFWGQ GTLVTVSS |
| | H1A11.E12 VH | CDR-H1 | Residues 31-35 of SEQ ID NO: 193 | YFPMA |
| | h1A11.E12 VH | CDR-H2 | Residues 50-66 of SEQ ID NO: 193 | TISGSDEWPNYRDSVKG |
| | h1A11.E12 VH | CDR-H3 | Residues 99-107 of SEQ ID NO: 193 | GYYNSPFAF |
| 194 | h1A11.G3 VH | | | EVQLNESGGGLVQPGGSLRLSC AASGFTFRYFPMSWVRQAPGKG LEWVASISGSDGWASYRDSVKG RFTISRDNAKNSLYLQMNSLRAE DTAVYYCARGYYNSPFAYWGQ GTLVTVSS |
| | h1A11.G3 VH | CDR-H1 | Residues 31-35 of SEQ ID NO: 194 | YFPMS |
| | h1A11.G3 VH | CDR-H2 | Residues 50-66 of SEQ ID NO: 194 | SISGSDGWASYRDSVKG |
| | h1A11.G3 VH | CDR-H3 | Residues 99-107 of SEQ ID NO: 194 | GYYNSPFAY |

TABLE 20-continued

VH sequences of Affinity Matured Humanized 1A11.1 Clones

| SEQ ID NO: | Protein region | | | Sequence 123456789012345678901234567890 |
|---|---|---|---|---|
| 195 | h1A11.F5 VH | | | EVQLVESGGGLVQPGGSLRLSC AASGFTFRHFPMAWVRQAPGKG LEWVATISSSDAWPSYRDSVKG RFTISRDNAKNSLYLQMNSLRAE DTAVYYCARGYYNSPFAYWGQ GTLVTVSS |
| | h1A11.F5 VH | CDR-H1 | Residues 31-35 of SEQ ID NO: 195 | HFPMA |
| | h1A11.F5 VH | CDR-H2 | Residues 50-66 of SEQ ID NO: 195 | TISSSDAWPSYRDSVKG |
| | h1A11.F5 VH | CDR-H3 | Residues 99-107 of SEQ ID NO: 195 | GYYNSPFAY |
| 196 | h1A11.H2 VH | | | EVQLVESGGGLVQPGGSLRLSC AASGFTFGNFPMSWVRQAPGKG LEWVASISSSDSWATIGDSVKGR FTISRDNAKNSLYLQMNSLRAED TAVYYCARGYYNSPFAFWGQG TLVTVSS |
| | h1A11.H2 VH | CDR-H1 | Residues 31-35 of SEQ ID NO: 196 | NFPMS |
| | h1A11.H2 VH | CDR-H2 | Residues 50-66 of SEQ ID NO: 196 | SISSSDSWATIGDSVKG |
| | h1A11.H2 VH | CDR-H3 | Residues 99-107 of SEQ ID NO: 196 | GYYNSPFAF |

TABLE 21

VL Sequences of Affinity Matured Humanized 1A11.1 Clones.

| SEQ ID NO: | Protein region | | | Sequence 123456789012345678901234567890 |
|---|---|---|---|---|
| 197 | h1A11VL.1 VL | | | DIQMTQSPSSLSASVGDRVTITC RASEDIYSNLAWYQQKPGKAPK LLIYDTNNLADGVPSRFSGSGSG TDFTLTISSLQPEDFATYYCQQY NNYPPTFGQGTKLEIK |
| | h1A11VL.1 VL | CDR-L1 | Residues 24-34 of SEQ ID NO: 197 | RASEDIYSNLA |
| | h1A11VL.1 VL | CDR-L2 | Residues 50-56 of SEQ ID NO: 197 | DTNNLAD |

TABLE 21-continued

VL Sequences of Affinity Matured Humanized 1A11.1 Clones.

| SEQ ID NO: | Protein region | | | Sequence 12345678901234567890123456789 0 |
|---|---|---|---|---|
| | h1A11VL.1 VL | CDR-L3 | Residues 89-97 of SEQ ID NO: 197 | QQYNNYPPT |
| 198 | h1A11.A2 VL | | | DIQMTQSPSSLSASVGDRVTITC RASQDIYINLAWYQQKPGKSPK LLIFDTNDLADGVPSRFSGSGSG TDFTLTISSLQPEDFATYYCQQY DYVPPTFGQGTKLEIK |
| | h1A11.A2 VL | CDR-L1 | Residues 24-34 of SEQ ID NO: 198 | RASQDIYINLA |
| | h1A11.A2 VL | CDR-L2 | Residues 50-56 of SEQ ID NO: 198 | DTNDLAD |
| | h1A11.A2 VL | CDR-L3 | Residues 89-97 of SEQ ID NO: 198 | QQYDYVPPT |
| 199 | h1A11.A12 VL | | | DIQMTQSPSSLSASVGDRVTITC RASQDIYYNLAWYQQKPGKSPK LLIFDTSSLADGVPSRFSGSGSGT DFTLTISSLQPEDPATYFCQQYD WYPPTFGQGTKLEIK |
| | h1A11.A12 VL | CDR-L1 | Residues 24-34 of SEQ ID NO: 199 | RASQDIYYNLA |
| | h1A11.A12 VL | CDR-L2 | Residues 50-56 of SEQ ID NO: 199 | DTSSLAD |
| | h1A11.A12 VL | CDR-L3 | Residues 89-97 of SEQ ID NO: 199 | QQYDWYPPT |
| 200 | h1A11.A7 VL | | | DIQMTQSPSSLSASVGDRVTITC RASQDIYINLAWYQQKPGKAPK LLIFDTSDLADGVPSRFSGSGSGT DFTLTISSLQPEDFATYYCQQYD YYPPTFGQGTKLEIK |
| | h1A11.A7 VL | CDR-L1 | Residues 24-34 of SEQ ID NO: 200 | RASQDIYINLA |
| | h1A11.A7 VL | CDR-L2 | Residues 50-56 of SEQ ID NO: 200 | DTSDLAD |
| | h1A11.A7 VL | CDR-L3 | Residues 89-97 of SEQ ID NO: 200 | QQYDYYPPT |
| 201 | h1A11.B4 VL | | | DIQMTQSPSSLSASVGDRVTITC RASQDIYYNLAWYQQKPGKAPK LLIFDTNILADGVPSRFSGSGSGT DFTLTISSLQPEDFATYFCQQYD YVPPTFGQGTKLEIK |

TABLE 21-continued

VL Sequences of Affinity Matured Humanized 1A11.1 Clones.

| SEQ ID NO: | Protein region | | | Sequence<br>12345678901234567890123456789 0 |
|---|---|---|---|---|
| | h1A11.B4 VL | CDR-L1 | Residues 24-34 of SEQ ID NO: 201 | RASQDIYYNLA |
| | h1A11.B4 VL | CDR-L2 | Residues 50-56 of SEQ ID NO: 201 | DTNILAD |
| | h1A11.B4 VL | CDR-L3 | Residues 89-97 of SEQ ID NO: 201 | QQYDYVPPT |
| 202 | h1A11.B5 VL | | | DIQMTQSPSSLSASVGDRVTITC RASQDIWNNLAWYQQKPGKSP KLLIFDTSYLADGVPSRFSGSGS GTDFTLTISSLQPEDFATYYCQQ YDWYPPTFGQGTKLEIK |
| | h1A11.B5 VL | CDR-L1 | Residues 24-34 of SEQ ID NO: 202 | RASQDIWNNLA |
| | h1A11.B5 VL | CDR-L2 | Residues 50-56 of SEQ ID NO: 202 | DTSYLAD |
| | h1A11.B5 VL | CDR-L3 | Residues 89-97 of SEQ ID NO: 202 | QQYDWYPPT |
| 203 | h1A11.E12 VL | | | DIQMTQSPSSLSASVGDRVTITC RASQEIYRNLAWYQQKPGKSPK LLIFDTSVLADGVPSRFSGSGSGT DSTLTISSLQPEDFATYYCQQYT YYPPTFGQGTKLEIK |
| | h1A11.E12 VL | CDR-L1 | Residues 24-34 of SEQ ID NO: 203 | RASQEIYRNLA |
| | h1A11.E12 VL | CDR-L2 | Residues 50-56 of SEQ ID NO: 203 | DTSVLAD |
| | h1A11.E12 VL | CDR-L3 | Residues 89-97 of SEQ ID NO: 203 | QQYTYYPPT |

TABLE 22

Summary of Affinity Matured h1A11.1 Converted Clones.

| Clone name | VH | VL |
|---|---|---|
| h1A11.A6 | h1A11.A6 VH | h1A11VL.1 |
| h1A11.C6 | h1A11.C6 VH | h1A11VL.1 |
| h1A11.A11 | h1A11.A11 VH | h1A11VL.1 |
| h1A11.A8 | h1A11.A8 VH | h1A11VL.1 |
| h1A11.B4 | h1A11VH.1 | h1A11.B4 VL |
| h1A11.A7 | h1A11VH.1 | h1A11.A7 VL |
| h1A11.A12 | h1A11VH.1 | h1A11.A12 VL |
| h1A11.A2 | h1A11VH.1 | h1A11.A2 VL |
| h1A11.B5 | h1A11.B5 VH | h1A11.B5 VL |
| h1A11.E12 | h1A11.E12 VH | h1A11.E12 VL |
| h1A11.G3 | h1A11.G3 VH | h1A11.E12 VL |
| h1A11.F5 | h1A11.F5 VH | h1A11.E12 VL |
| h1A11.H2 | h1A11.H2 VH | h1A11.E12 VL |

TABLE 23

Amino acids observed during affinity maturation selections of h1A11.1 in framework regions (FRs) and each of the CDRs for VH (SEQ ID NO: 204) and VL (SEQ ID NO: 205) regions.

SEQ ID NO: 204

VH
EVQLVESGGGLVQPGGSLRLSCAASGFTFSNFPMAWVRQAPGKGLEWVATISSSDGTTYYRDSVKG
```
                              RYY  S           S   G   SSASIG
                              NH   T           A       AFDN
                              GS                       EWST
                              KA                       D  PA
                              T                        F  D
                              L                        Q
                                                       C
```

RFTISRDNAKNSLYLQMNSLRAEDTAVYYCARGYYNSPFAYWGQGTLVTVSS
```
        SL           D              DF
                                    S
```

SEQ ID NO: 205

VL
DIQMTQSPSSLSASVGDRVTITCRASEDIYSNLAWYQQKPGKAPKLLIYDTNNLAD
```
                       TQE  WN           S      F   NS
                       T    EI                      D
                            DT                      Q
                            NR                      T
                            M                       V
                            G                       E
```

GYPSRFSGSGSGTDFTLTISSLQPEDFATYYCQQYNNYPPTFGQGTKLEIK
```
         S                       F    SDWV  P
                                      TY
                                      YI
                                      F
                                      P
```

The hu1A11.1 affinity matured clones (Table 22) were expressed, purified, and further characterized in vitro. Their antigen binding affinities were determined by Biacore technology as described in Example 1.1, and are shown in Tables 24 and 25 (below). Their activities of binding to cell-bound DLL4 and inhibiting cell-bound DLL4-induced Notch activation were further examined using methods described in Examples 1.3 and 1.6, and are summarized in Table 26 (below).

TABLE 24

Biacore Kinetics of Affinity-Matured Humanized 1A11.1 Antibodies Binding to Human and Cynomolgus Monkey DLL4.

| | Kinetics on Biacore | | | | | |
|---|---|---|---|---|---|---|
| | Human DLL4 | | | Cyno DLL4 | | |
| Clone | $k_a$ ($M^{-1}s^{-1}$) | $k_d$ ($s^{-1}$) | $K_D$ (nM) | $k_a$ ($M^{-1}s^{-1}$) | $k_d$ ($s^{-1}$) | $K_D$ (nM) |
| h1A11.A6 | $1.82 \times 10^{+5}$ | $6.62 \times 10^{-6}$ | $3.6 \times 10^{-11}$ | $1.71 \times 10^{+5}$ | $2.10 \times 10^{-5}$ | $1.2 \times 10^{-10}$ |
| h1A11.C6 | $1.78 \times 10^{+5}$ | $7.18 \times 10^{-6}$ | $4.0 \times 10^{-11}$ | $1.71 \times 10^{+5}$ | $3.12 \times 10^{-5}$ | $1.8 \times 10^{-10}$ |
| h1A11.G3 | $1.09 \times 10^{+5}$ | $9.39 \times 10^{-6}$ | $8.7 \times 10^{-11}$ | $9.90 \times 10^{+4}$ | $1.73 \times 10^{-5}$ | $1.7 \times 10^{-10}$ |
| h1A11-F5 | $1.31 \times 10^{+5}$ | $9.82 \times 10^{-6}$ | $7.5 \times 10^{-11}$ | $1.18 \times 10^{+5}$ | $2.00 \times 10^{-5}$ | $1.7 \times 10^{-10}$ |
| h1A11.A8 | $1.74 \times 10^{+5}$ | $1.08 \times 10^{-5}$ | $6.2 \times 10^{-11}$ | $1.60 \times 10^{+5}$ | $2.40 \times 10^{-5}$ | $1.5 \times 10^{-10}$ |
| h1A11.A11 | $1.83 \times 10^{+5}$ | $2.66 \times 10^{-5}$ | $1.5 \times 10^{-10}$ | $1.70 \times 10^{+5}$ | $3.35 \times 10^{-5}$ | $2.0 \times 10^{-10}$ |
| h1A11.E12 | $1.49 \times 10^{+5}$ | $3.26 \times 10^{-5}$ | $2.2 \times 10^{-10}$ | $1.37 \times 10^{+5}$ | $3.84 \times 10^{-5}$ | $2.8 \times 10^{-10}$ |
| h1A11.H2 | $1.43 \times 10^{+5}$ | $3.85 \times 10^{-5}$ | $2.7 \times 10^{-10}$ | $1.31 \times 10^{+5}$ | $4.60 \times 10^{-5}$ | $3.5 \times 10^{-10}$ |
| h1A11.B5 | $1.30 \times 10^{+5}$ | $1.34 \times 10^{-4}$ | $1.0 \times 10^{-9}$ | $1.17 \times 10^{+5}$ | $1.78 \times 10^{-4}$ | $1.5 \times 10^{-9}$ |
| h1A11.A2 | $1.42 \times 10^{+5}$ | $4.21 \times 10^{-4}$ | $3.0 \times 10^{-9}$ | $1.34 \times 10^{+5}$ | $5.27 \times 10^{-4}$ | $3.9 \times 10^{-9}$ |
| h1A11.B4 | $1.57 \times 10^{+5}$ | $8.23 \times 10^{-4}$ | $5.2 \times 10^{-9}$ | $1.43 \times 10^{+5}$ | $9.90 \times 10^{-4}$ | $6.9 \times 10^{-9}$ |
| h1A11.A7 | $1.70 \times 10^{+5}$ | $9.73 \times 10^{-4}$ | $5.7 \times 10^{-9}$ | $1.58 \times 10^{+5}$ | $1.24 \times 10^{-3}$ | $7.8 \times 10^{-9}$ |
| h1A11.A12 | $1.73 \times 10^{+5}$ | $1.32 \times 10^{-3}$ | $7.6 \times 10^{-9}$ | $1.58 \times 10^{+5}$ | $1.62 \times 10^{-3}$ | $1.0 \times 10^{-8}$ |
| h1A11.1 | $1.58 \times 10^{+5}$ | $2.12 \times 10^{-3}$ | $1.3 \times 10^{-8}$ | $1.44 \times 10^{+5}$ | $2.55 \times 10^{-3}$ | $1.8 \times 10^{-8}$ |

TABLE 25

Biacore Kinetics of Affinity-Matured Humanized 1A11.1 Antibodies Binding to Mouse and Rat DLL4.

| | Kinetics on Biacore | | | | | |
|---|---|---|---|---|---|---|
| | Mouse DLL4 | | | Rat DLL4 | | |
| Clone | $k_a$ ($M^{-1}s^{-1}$) | $k_d$ ($s^{-1}$) | $K_D$ (nM) | $k_a$ ($M^{-1}s^{-1}$) | $k_d$ ($s^{-1}$) | $K_D$ (nM) |
| h1A11.A6 | $1.98 \times 10^{+5}$ | $3.12 \times 10^{-5}$ | $1.6 \times 10^{-10}$ | $1.29 \times 10^{+5}$ | $7.72 \times 10^{-4}$ | $6.0 \times 10^{-9}$ |
| h1A11.C6 | $2.03 \times 10^{+5}$ | $2.34 \times 10^{-5}$ | $1.2 \times 10^{-10}$ | $1.69 \times 10^{+5}$ | $3.05 \times 10^{-3}$ | $1.8 \times 10^{-8}$ |
| h1A11-G3 | $1.17 \times 10^{+5}$ | $4.04 \times 10^{-5}$ | $3.5 \times 10^{-10}$ | $1.18 \times 10^{+5}$ | $1.01 \times 10^{-3}$ | $8.6 \times 10^{-9}$ |
| h1A11-F5 | $1.43 \times 10^{+5}$ | $3.97 \times 10^{-5}$ | $2.8 \times 10^{-10}$ | $1.16 \times 10^{+5}$ | $6.79 \times 10^{-4}$ | $5.8 \times 10^{-9}$ |
| h1A11.A8 | $1.87 \times 10^{+5}$ | $3.27 \times 10^{-5}$ | $1.8 \times 10^{-10}$ | $1.39 \times 10^{+5}$ | $6.50 \times 10^{-3}$ | $4.7 \times 10^{-8}$ |
| h1A11.A11 | $1.98 \times 10^{+5}$ | $3.54 \times 10^{-5}$ | $1.8 \times 10^{-10}$ | $1.16 \times 10^{+5}$ | $1.02 \times 10^{-3}$ | $8.8 \times 10^{-9}$ |
| h1A11-E12 | $1.56 \times 10^{+5}$ | $5.44 \times 10^{-5}$ | $3.5 \times 10^{-10}$ | $1.08 \times 10^{+5}$ | $1.75 \times 10^{-4}$ | $1.6 \times 10^{-9}$ |
| h1A11-H2 | $1.54 \times 10^{+5}$ | $5.07 \times 10^{-5}$ | $3.3 \times 10^{-10}$ | $1.78 \times 10^{+5}$ | $2.83 \times 10^{-3}$ | $1.6 \times 10^{-8}$ |
| h1A11-B5 | $1.45 \times 10^{+5}$ | $1.66 \times 10^{-4}$ | $1.2 \times 10^{-9}$ | $9.82 \times 10^{+4}$ | $3.97 \times 10^{-2}$ | $4.1 \times 10^{-7}$ |
| h1A11.A2 | $1.81 \times 10^{+5}$ | $9.04 \times 10^{-4}$ | $5.0 \times 10^{-9}$ | NB | NB | NB |
| h1A11-B4 | $4.79 \times 10^{+5}$ | $2.5 \times 10^{-3}$ | $5.2 \times 10^{-9}$ | NB | NB | NB |
| h1A11.A7 | poor binding | | $1.3 \times 10^{-8}$ | NB | NB | NB |
| h1A11.A12 | poor binding | | $1.6 \times 10^{-8}$ | NB | NB | NB |
| h1A11.1 | $1.56 \times 10^{+5}$ | $4.98 \times 10^{-3}$ | $3.2 \times 10^{-8}$ | NB | NB | NB |

NB = no observable binding

TABLE 26

In Vitro Activities Against Cell-Bound DLL4 of Affinity-Matured Humanized 1A11.1 Antibodies.

| | Direct Binding to DLL4 cells, FACS (nM) | | Inhibition of Notch Activation via DLL4 cells, Notch reporter assay (nM) | |
|---|---|---|---|---|
| | Human DLL4 | Mouse DLL4 | Human DLL4 | Mouse DLL4 |
| h1A11.A6 | 2.227 | 0.636 | 0.746 | 1.168 |
| h1A11.C6 | 2.452 | 0.517 | 0.894 | 1.188 |
| h1A11-G3 | 3.592 | 1.397 | 1.845 | 2.353 |
| h1A11-F5 | 1.171 | 0.460 | 0.484 | 0.649 |
| h1A11.A8 | 3.160 | 0.744 | 1.331 | 1.247 |
| h1A11.A11 | 2.480 | 0.500 | 0.904 | 1.175 |
| h1A11-E12 | 0.996 | 1.615 | 0.208 | 0.266 |
| h1A11-H2 | 1.977 | 0.420 | 0.856 | 0.586 |
| h1A11.A2 | 2.375 | 0.634 | 3.681 | 0.854 |
| h1A11-B4 | 2.145 | 0.665 | 3.280 | 1.079 |
| h1A11.A7 | 2.174 | 0.625 | 2.920 | 1.788 |
| h1A11.A12 | 1.768 | 0.568 | 1.662 | 0.832 |

Example 9

Molecular Identity and Physicochemical Properties of Rat Hybridoma Antibodies

The identity of monoclonal antibodies specific to DLL4 was determined by mass spectrometry as described below.

Mass Spectrometry Analysis of h1A11.1

The light chain molecular weight of 23,501 Daltons matched well with the theoretical value. The heavy chain molecular weights matched well with the theoretical values. The observed molecular weights were 50,190 Daltons; 50,352 Daltons; and 50,514 Daltons, with the difference corresponding to 162 Daltons as the result of different glycosylation.

Mass Spectrometry Analysis of h38H12.11

The light chain molecular weight of 23,408 Daltons matched well with the theoretical value. The heavy chain molecular weights matched well with the theoretical values. The observed molecular weights were 50,368 Dalton; 50,530 Daltons; and 50,692 Daltons; with the difference corresponding to 162 Daltons as the result of different glycosylation.

The solubilities of the antibodies were estimated by polyethylene glycol (PEG) 3000 precipitation. They were also directly determined, i.e., real solubility, by concentrating the antibodies in a specific solution and/or buffer with Amicon centrifugal filters and then observed for any precipitation at 25° C. and 5° C. Stability was inferred by near ultra-violet circular (UV-CD) and differential scanning calorimetry (DSC). Stability to freezing and thawing and at elevated temperatures (accelerated stability) was assessed by size exclusion chromatography (SEC). The details of the techniques were described in Example 1.7, and the results are described below.

Real Solubility Screening Results for 1A11

For a series of 1A11 clones, including hu1A11.1, hu1A11.3, hu1A11.9, hu1A11.11, and 1A11 recombinant, 2 mg of each were concentrated with Amicon centrifugal filters to above 60 mg/ml. No precipitation or cloudiness was observed at 25° C. or after storage for 1 day at 5° C. The concentrations of each were 63 mg/ml for 1A11.1, 76 mg/ml for 1A11.3, 63 mg/ml for 1A11.9, 69 mg/ml for 1A11.11, and 76 mg/ml for chimeric 1A11.

Example 10

Anti-DLL4 Antibody Epitope Grouping by Biacore Technology

Epitope grouping was performed with the use of Biacore 2000, 3000, and T100 instruments. Antibodies of interest were directly immobilized on the CM5 chip surface via amino coupling. Flow cell one with similarly immobilized irrelevant IgG served as a reference surface. First, immobilized monoclonal antibodies (mAbs) were allowed to bind recombinant antigen (at concentrations of at least 200 nM) for 120 seconds at 50 μl/min. Then, another antibody was injected at 50 μl/ml for 120-240 seconds to monitor its ability to bind to the antigen that is already bound to the immobilized mAbs. The absence of additional binding response on the sensogram constituted overlap in the epitopes of the two mAbs (the one immobilized on the chip and the one introduced in liquid phase). Orientation of the assay was then switched in such a way that the antibody that was in a liquid phase was immobilized and vice versa. The pairs of mAbs that did not allow for additional antibody binding in both orientations of the assay were grouped as truly overlapping in these experiments. The resulting grouping of mAbs with overlapping epitopes is shown in Table 27, below.

TABLE 27

Anti-DLL4 Antibody Epitope Grouping By BIAcore Technology.

| Immobilized antibody | 1st Injection huDLL4 | 2nd Injection | | | | | | |
|---|---|---|---|---|---|---|---|---|
| | | 38H12 | 15D6 | 13E4 | 1A11 | 14G1 | 14A11 | 37D10 |
| 38H12 | + | − | + | + | + | + | + | + |
| 15D6  | + | + | − | − | − | − | − | |
| 13E4  | + | + | − | − | − | + | − | |
| 1A11  | + | + | − | − | − | − | − | |
| 14G1  | + | + | + | + | + | − | − | − |
| 14A11 | + | + | − | − | − | − | − | |

"+" indicates binding;
"−" indicates no binding

Example 11

Activities of DLL4 Antibodies in Endothelial Cell Sprouting Assay In Vitro

Fibrin gel beads sprouting assay was carried out to examine the in vitro angiogenesis activity of HUVEC (passage 2-3, Lonza) as described (Nakatsu, M. N. et al. 2003 Microvasc. Res. 66, 102-112). Briefly, fibrinogen solution was reconstituted with aprotinin (4 units/ml) and thrombin (50 units/ml). Cytodex 3 beads (Amersham Pharmacia Biotech) were coated with 350-400 HUVECs per bead for over night. About 20 HUVEC-coated beads were imbedded in the fibrin clot per well of a 96-well tissue culture plate. Conditioned medium derived from normal human fibroblasts (NHLF, Lonza) at 80% confluence was plated on top of the gel. DLL4 antibody and control antibody KLH at 15 µg/ml were added onto the well. At day 10 and 12, images were taken with inverted microscope and Nikon CCD camera. Table 28 summarizes the activities of some DLL4 antibodies to enhance endothelial cell sprouting in vitro. (Nakatsu et al., "Angiogenic sprouting and capillary lumen formation modeled by human umbilical vein endothelial cells (HUVEC) in fibrin gels: the role of fibroblasts and Angiopoietin-1," Microvasc. Res. 66, 102-112 (2003)).

TABLE 28

Activities of DLL4 antibodies to stimulate endothelial cell sprouting.

| Tested antibody | Stimulate HUVEC sprouting |
|---|---|
| 38H12 rat mAb | Yes |
| 1A11 rat mAb | Yes |
| h1A11.1 | Yes |
| 40B10 rat mAb | Not observed |
| 32C7 rat mAb | Not observed |

Example 12

Rodent PK Assessment of Hybridoma-Derived Antibodies

To assess pharmacokinetics properties of anti-DLL4 antibodies, SCID-Beige mice (n=3 per antibody) were administered a single intraperitoneal (IP) dose of antibody at either 1, 5, 10, or 30 mg/kg concentration, depending on cross-reactivity of antibody to murine DLL4. Longitudinal serum samples (5 µl of whole blood diluted 1:50 in HBS-EP+buffer per time point) were collected from each animal over 21 days. Serum concentrations were determined using a DLL4-specific Biacore platform. Briefly, human DLL4 was immobilized to a sensorchip and samples were injected over the flowcell at 5 µl per minute for 5 minutes with the resulting binding levels measured and compared to standards. Serum concentration time profiles were used to estimate the pharmacokinetic parameters of $C_{max}$ (peak serum concentration), CL (clearance), and $t_{1/2}$ (antibody half-life), summarized in Table 29, below.

TABLE 29

Pharmacokinetic Parameters of Anti-DLL4 Antibodies in SCID-Beige Mice Following a Single IP Dose.

| Antibody | Dose (mg/kg) | Cmax (µg/mL) | CL (mL/hr/kg) | $t_{1/2}$ (d) |
|---|---|---|---|---|
| 38H12 rat mAb | 5 | 30.2 | 0.3 | 20-29 |
| h1A11.1 | 30 | 163 | 0.44 | 11.3 |
| h1A11.1 | 10 | 49.9 | 0.50 | 9.9 |
| h1A11.1 | 5 | 11.0 | 1.78 | 6.3 |
| h1A11.1 | 1 | 3.1 | 2.16 | 4.4 |

Example 13

DLL4 Antibody Treatment Inhibited Tumor Growth In Vivo

The effect of anti-DLL4 antibodies on tumor growth was evaluated on subcutaneous Calu-6 xenograft tumors implanted in SCID-Beige mice. Briefly, $2 \times 10^6$ cells were inoculated subcutaneously into the right hind flank of female SCID-Beige mice. Tumors were allowed to establish for 14-18 days, at which point tumor volume was determined using electronic caliper measurements. Tumor size was calculated using the formula: $L \times W^2/2$. Mice were allocated into treatment groups (n=10 per group) so that each cohort of animals had equivalent mean tumor volume prior to initiation of therapy (typically between 180 and 250 mm³). Animals were then dosed intraperitoneally either twice a week for two weeks (total of 4 doses) or weekly for four weeks (total of 4 doses) with anti-DLL4 antibodies. Tumor volume was measured on average twice a week for the duration of the experiment until the mean tumor volume in each group reached an endpoint of ≥2,000 mm³. Results are shown in Table 30, below.

TABLE 30

Efficacy of Anti-DLL4 Antibodies in the Calu-6 Human Non-Small Cell Lung Cancer Subcutaneous Xenograft Model.

| Treatment | Dose, Route, Regimen | % T/C[a] | % ILS[b] |
|---|---|---|---|
| 1A11 rat mAb | 30 mg/kg, IP, 2X/weekX2 | 37** | 89** |
| 1A11 rat mAb | 10 mg/kg, IP, 2X/weekX2 | 47** | 39** |
| 1A11 rat mAb | 5 mg/kg, IP, 2X/weekX2 | 43** | 57** |
| 14A11 rat mAb | 10 mg/kg, IP, 2X/weekX2 | 37** | 57** |
| 40B10 rat mAb | 30 mg/kg, IP, 2X/weekX2 | 29** | 89** |
| 32C7 rat mAb | 30 mg/kg, IP, 2X/weekX2 | 65* | 28* |
| 14A11 chimera | 10 mg/kg, IP, q7dX4 | 32** | 114** |
| 15D6 chimera | 10 mg/kg, IP, q7dX4 | 47** | 57** |
| 40B10 chimera | 10 mg/kg, IP, q7dX4 | 43** | 73** |
| 32C7 chimera | 10 mg/kg, IP, q7dX4 | 71* | 18* |
| h1A11.1 | 10 mg/kg, IP, q7dX4 | 34** | 75** |
| h1A11.1 | 5 mg/kg, IP, q7dX4 | 31** | 80** |
| h1A11.1 | 1 mg/kg, IP, q7dX4 | 43** | 36** |
| h1A11.1 | 0.5 mg/kg, IP, q7dX4 | 62** | 25* |

[a]% T/C = mean tumor volume of treatment group/tumor volume of treatment control group x 100. P values (as indicated by asterisks) were derived from Student's T test comparison of treatment group versus treatment control group. Based on day 25/26/27 measurements.
[b]% ILS = (T − C)/C x 100, where T = median time to endpoint of treatment group and C = median time to endpoint of treatment control group. P values (as indicated by asterisks) were derived from Kaplan Meier log-rank comparison of treatment group versus treatment control group. Based on an endpoint of 2000 mm³.
*p < 0.05;
**p < 0.001

INCORPORATION BY REFERENCE

The contents of all cited references (including literature references, patents, patent applications, and websites) that maybe cited throughout this application are hereby expressly incorporated by reference in their entirety for any purpose, as are the references cited therein.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

What is claimed is:

1. A binding protein comprising an antigen-binding domain capable of binding DLL4, wherein the antigen-binding domain comprises a set of six complementarity determining region (CDR) sequences: CDR-H1, CDR-H2, CDR-H3, CDR-L1, CDR-L2, and CDR-L3, wherein:

(a) CDR-H1 is selected from the group consisting of:
  residues 31-35 of SEQ ID NO:171 (CDR-H1 VH.1 1A11);
  residues 31-35 of SEQ ID NO:172 (CDR-H1 VH.1a 1A11);
  residues 31-35 of SEQ ID NO:173 (CDR-H1 VH.1b 1A11);
  residues 31-35 of SEQ ID NO:174 (CDR-H1 VH.2a 1A11);
  residues 31-35 of SEQ ID NO:187 (CDR-H1 h1A11VH.1);
  residues 31-35 of SEQ ID NO:188 (CDR-H1 h1A11.A6);
  residues 31-35 of SEQ ID NO:189 (CDR-H1 h1A11.A8);
  residues 31-35 of SEQ ID NO:190 (CDR-H1 h1A11.C6);
  residues 31-35 of SEQ ID NO:191 (CDR-H1 h1A11.A11);
  residues 31-35 of SEQ ID NO:192 (CDR-H1 h1A11.B5);
  residues 31-35 of SEQ ID NO:193 (CDR-H1 h1A11.E12);
  residues 31-35 of SEQ ID NO:194 (CDR-H1 h1A11.G3);
  residues 31-35 of SEQ ID NO:195 (CDR-H1 h1A11.F5); and
  residues 31-35 of SEQ ID NO:196 (CDR-H1 h1A11.H2);

(b) CDR-H2 is selected from the group consisting of:
  residues 50-66 of SEQ ID NO:171 (CDR-H2 VH.1 1A11);
  residues 50-66 of SEQ ID NO:172 (CDR-H2 VH.1a 1A11);
  residues 50-66 of SEQ ID NO:173 (CDR-H2 VH.1b 1A11);

residues 50-66 of SEQ ID NO:174 (CDR-H2 VH.2a 1A11);
residues 50-66 of SEQ ID NO:187 (CDR-H2 h1A11VH.1);
residues 50-66 of SEQ ID NO:188 (CDR-H2 h1A11.A6);
residues 50-66 of SEQ ID NO:189 (CDR-H2 h1A11.A8);
residues 50-66 of SEQ ID NO:190 (CDR-H2 h1A11.C6);
residues 50-66 of SEQ ID NO:191 (CDR-H2 h1A11.A11);
residues 50-66 of SEQ ID NO:192 (CDR-H2 h1A11.B5);
residues 50-66 of SEQ ID NO:193 (CDR-H2 h1A11.E12);
residues 50-66 of SEQ ID NO:194 (CDR-H2 h1A11.G3);
residues 50-66 of SEQ ID NO:195 (CDR-H2 h1A11.F5); and
residues 50-66 of SEQ ID NO:196 (CDR-H2 h1A11.H2);
(c) CDR-H3 is selected from the group consisting of:
residues 99-107 of SEQ ID NO:171 (CDR-H3 VH.1 1A11);
residues 99-107 of SEQ ID NO:172 (CDR-H3 VH.1a 1A11);
residues 99-107 of SEQ ID NO:173 (CDR-H3 VH.1b 1A11);
residues 99-107 of SEQ ID NO:174 (CDR-H3 VH.2a 1A11);
residues 99-107 of SEQ ID NO:187 (CDR-H3 h1A11VH.1);
residues 99-107 of SEQ ID NO:188 (CDR-H3 h1A11.A6);
residues 99-107 of SEQ ID NO:189 (CDR-H3 h1A11.A8);
residues 99-107 of SEQ ID NO:190 (CDR-H3 h1A11.C6);
residues 99-107 of SEQ ID NO:191 (CDR-H3 h1A11.A11);
residues 99-107 of SEQ ID NO:192 (CDR-H3 h1A11.B5);
residues 99-107 of SEQ ID NO:193 (CDR-H3 h1A11.E12);
residues 99-107 of SEQ ID NO:194 (CDR-H3 h1A11.G3);
residues 99-107 of SEQ ID NO:195 (CDR-H3 h1A11.F5); and
residues 99-107 of SEQ ID NO:196 (CDR-H3 h1A11.H2);
(d) CDR-L1 is selected from the group consisting of:
residues 24-34 of SEQ ID NO:175 (CDR-L1 VL.1 1A11);
residues 24-34 of SEQ ID NO:176 (CDR-L1 VL.1a 1A11);
residues 24-34 of SEQ ID NO:177 (CDR-L1 VL.1b 1A11);
residues 24-34 of SEQ ID NO:178 (CDR-L1 VL.2a 1A11);
residues 24-34 of SEQ ID NO:197 (CDR-L1 h1A11VL.1);
residues 24-34 of SEQ ID NO:198 (CDR-L1 h1A11.A2);
residues 24-34 of SEQ ID NO:199 (CDR-L1 h1A11.A12);
residues 24-34 of SEQ ID NO:200 (CDR-L1 h1A11.A7);
residues 24-34 of SEQ ID NO:201 (CDR-L1 h1A11.B4);
residues 24-34 of SEQ ID NO:202 (CDR-L1 h1A11.B5); and
residues 24-34 of SEQ ID NO:203 (CDR-L1 h1A11.E12);
(e) CDR-L2 is selected from group consisting of:
residues 50-56 of SEQ ID NO:175 (CDR-L2 VL.1 1A11);
residues 50-56 of SEQ ID NO:176 (CDR-L2 VL.1a 1A11);
residues 50-56 of SEQ ID NO:177 (CDR-L2 VL.1b 1A11);
residues 50-56 of SEQ ID NO:178 (CDR-L2 VL.2a 1A11);
residues 50-56 of SEQ ID NO:197 (CDR-L2 h1A11VL.1);
residues 50-56 of SEQ ID NO:198 (CDR-L2 h1A11.A2);
residues 50-56 of SEQ ID NO:199 (CDR-L2 h1A11.A12);
residues 50-56 of SEQ ID NO:200 (CDR-L2 h1A11.A7);
residues 50-56 of SEQ ID NO:201 (CDR-L2 h1A11.B4);
residues 50-56 of SEQ ID NO:202 (CDR-L2 h1A11.B5); and
residues 50-56 of SEQ ID NO:203 (CDR-L2 h1A11.E12); and
(f) CDR-L3 is selected from the group consisting of:
residues 89-97 of SEQ ID NO:175 (CDR-L3 VL.1 1A11);
residues 89-97 of SEQ ID NO:176 (CDR-L3 VL.1a 1A11);
residues 89-97 of SEQ ID NO:177 (CDR-L3 VL.1b 1A11);
residues 89-97 of SEQ ID NO:178 (CDR-L3 VL.2a 1A11);
residues 89-97 of SEQ ID NO:197 (CDR-L3 h1A11VL.1);
residues 89-97 of SEQ ID NO:198 (CDR-L3 h1A11.A2);
residues 89-97 of SEQ ID NO:199 (CDR-L3 h1A11.A12);
residues 89-97 of SEQ ID NO:200 (CDR-L3 h1A11.A7);
residues 89-97 of SEQ ID NO:201 (CDR-L3 h1A11.B4);
residues 89-97 of SEQ ID NO:202 (CDR-L3 h1A11.B5); and
residues 89-97 of SEQ ID NO:203 (CDR-L3 h1A11.E12).

2. The binding protein according to claim 1, wherein the binding protein comprises a CDR set of three CDRs selected from the group of variable domain CDR sets consisting of:
VH1A11 CDR Set, comprising:
CDR-H1: residues 31-35 of SEQ ID NO:159
CDR-H2: residues 50-66 of SEQ ID NO:159
CDR-H3: residues 99-107 of SEQ ID NO:159
VL 1A11 CDR Set, comprising:
CDR-L1: residues 24-34 of SEQ ID NO:160
CDR-L2: residues 50-56 of SEQ ID NO:160 and
CDR-L3: residues 89-97 of SEQ ID NO:160

VH.1 1A11 CDR Set, comprising:
 CDR-H1: residues 31-35 of SEQ ID NO:171
 CDR-H2: residues 50-66 of SEQ ID NO:171 and
 CDR-H3: residues 99-107 of SEQ ID NO:171
VH.1a 1A11 CDR Set, comprising:
 CDR-H1: residues 31-35 of SEQ ID NO:172
 CDR-H2: residues 50-66 of SEQ ID NO:172 and
 CDR-H3: residues 99-107 of SEQ ID NO:172
VH.1b 1A11 CDR Set, comprising:
 CDR-H1: residues 31-35 of SEQ ID NO:173
 CDR-H2: residues 50-66 of SEQ ID NO:173 and
 CDR-H3: residues 99-107 of SEQ ID NO:173
VH.2a 1A11 CDR Set, comprising:
 CDR-H1: residues 31-35 of SEQ ID NO:174
 CDR-H2: residues 50-66 of SEQ ID NO:174 and
 CDR-H3: residues 99-107 of SEQ ID NO:174
VL.1 1A11 CDR Set, comprising:
 CDR-L1: residues 24-34 of SEQ ID NO:175
 CDR-L2: residues 50-56 of SEQ ID NO:175 and
 CDR-L3: residues 89-97 of SEQ ID NO:175
VL.1a 1A11 CDR Set, comprising:
 CDR-L1: residues 24-34 of SEQ ID NO:176
 CDR-L2: residues 50-56 of SEQ ID NO:176 and
 CDR-L3: residues 89-97 of SEQ ID NO:176
VL.1b 1A11 CDR Set, comprising:
 CDR-L1: residues 24-34 of SEQ ID NO:177
 CDR-L2: residues 50-56 of SEQ ID NO:177 and
 CDR-L3: residues 89-97 of SEQ ID NO:177
VL.2a 1A11 CDR Set, comprising:
 CDR-L1: residues 24-34 of SEQ ID NO:178
 CDR-L2: residues 50-56 of SEQ ID NO:178 and
 CDR-L3: residues 89-97 of SEQ ID NO:178
VH h1A11VH.1 CDR Set, comprising:
 CDR-H1: residues 31-35 of SEQ ID NO:187
 CDR-H2: residues 50-66 of SEQ ID NO:187 and
 CDR-H3: residues 99-107 of SEQ ID NO:187
VH h1A11.A6 CDR Set, comprising:
 CDR-H1: residues 31-35 of SEQ ID NO:188
 CDR-H2: residues 50-66 of SEQ ID NO:188 and
 CDR-H3: residues 99-107 of SEQ ID NO:188
VH h1A11.A8 CDR Set, comprising:
 CDR-H1: residues 31-35 of SEQ ID NO:189
 CDR-H2: residues 50-66 of SEQ ID NO:189 and
 CDR-H3: residues 99-107 of SEQ ID NO:189
VH h1A11.C6 CDR Set, comprising:
 CDR-H1: residues 31-35 of SEQ ID NO:190
 CDR-H2: residues 50-66 of SEQ ID NO:190 and
 CDR-H3: residues 99-107 of SEQ ID NO:190
VH h1A11.A11 CDR Set, comprising:
 CDR-H1: residues 31-35 of SEQ ID NO:191
 CDR-H2: residues 50-66 of SEQ ID NO:191 and
 CDR-H3: residues 99-107 of SEQ ID NO:191
VH h1A11.B5 CDR Set, comprising:
 CDR-H1: residues 31-35 of SEQ ID NO:192
 CDR-H2: residues 50-66 of SEQ ID NO:192 and
 CDR-H3: residues 99-107 of SEQ ID NO:192
VH h1A11.E12 CDR Set, comprising:
 CDR-H1: residues 31-35 of SEQ ID NO:193
 CDR-H2: residues 50-66 of SEQ ID NO:193 and
 CDR-H3: residues 99-107 of SEQ ID NO:193
VH h1A11.G3 CDR Set, comprising:
 CDR-H1: residues 31-35 of SEQ ID NO:194
 CDR-H2: residues 50-66 of SEQ ID NO:194 and
 CDR-H3: residues 99-107 of SEQ ID NO:194
VH h1A11.F5 CDR Set, comprising:
 CDR-H1: residues 31-35 of SEQ ID NO:195
 CDR-H2: residues 50-66 of SEQ ID NO:195 and
 CDR-H3: residues 99-107 of SEQ ID NO:195
VH h1A11.H2 CDR Set, comprising:
 CDR-H1: residues 31-35 of SEQ ID NO:196
 CDR-H2: residues 50-66 of SEQ ID NO:196 and
 CDR-H3: residues 99-107 of SEQ ID NO:196
VL h1A11VL.1 CDR Set, comprising:
 CDR-L1: residues 24-34 of SEQ ID NO:197
 CDR-L2: residues 50-56 of SEQ ID NO:197 and
 CDR-L3: residues 89-97 of SEQ ID NO:197
VL h1A11.A2 CDR Set, comprising:
 CDR-L1: residues 24-34 of SEQ ID NO:198
 CDR-L2: residues 50-56 of SEQ ID NO:198 and
 CDR-L3: residues 89-97 of SEQ ID NO:198
VL h1A11.A12 CDR Set, comprising:
 CDR-L1: residues 24-34 of SEQ ID NO:199
 CDR-L2: residues 50-56 of SEQ ID NO:199 and
 CDR-L3: residues 89-97 of SEQ ID NO:199
VL h1A11.A7 CDR Set, comprising:
 CDR-L1: residues 24-34 of SEQ ID NO:200
 CDR-L2: residues 50-56 of SEQ ID NO:200 and
 CDR-L3: residues 89-97 of SEQ ID NO:200
VL h1A11.B4 CDR Set, comprising:
 CDR-L1: residues 24-34 of SEQ ID NO:201
 CDR-L2: residues 50-56 of SEQ ID NO:201 and
 CDR-L3: residues 89-97 of SEQ ID NO:201
VL h1A11.B5 CDR Set, comprising:
 CDR-L1: residues 24-34 of SEQ ID NO:202
 CDR-L2: residues 50-56 of SEQ ID NO:202 and
 CDR-L3: residues 89-97 of SEQ ID NO:202 and
VL h1A11.E12 CDR Set, comprising:
 CDR-L1: residues 24-34 of SEQ ID NO:203
 CDR-L2: residues 50-56 of SEQ ID NO:203 and
 CDR-L3: residues 89-97 of SEQ ID NO:203.

3. The binding protein according to claim 2, comprising at least two variable domain CDR sets.

4. The binding protein according to claim 3, wherein the at least two variable domain CDR sets are selected from the group consisting of:
 VH1A11 CDR Set and VL 1A11 CDR Set,
 VH.1 1A11 CDR Set and VL.1 1A11 CDR Set,
 VH.1 1A11 CDR Set and VL.1a 1A11 CDR Set,
 VH.1 1A11 CDR Set and VL.1b 1A11 CDR Set,
 VH.1 1A11 CDR Set and VL.2a 1A11 CDR Set,
 VH.1a 1A11 CDR Set and VL.1 1A11 CDR Set,
 VH.1a 1A11 CDR Set and VL.1a 1A11 CDR Set,
 VH.1a 1A11 CDR Set and VL.1b 1A11 CDR Set,
 VH.1a 1A11 CDR Set and VL.2a 1A11 CDR Set,
 VH.1b 1A11 CDR Set and VL.1 1A11 CDR Set,
 VH.1b 1A11 CDR Set and VL.1a 1A11 CDR Set,
 VH.1b 1A11 CDR Set and VL.1b 1A11 CDR Set,
 VH.1b 1A11 CDR Set and VL.2a 1A11 CDR Set,
 VH.2a 1A11 CDR Set and VL.1 1A11 CDR Set,
 VH.2a 1A11 CDR Set and VL.1a 1A11 CDR Set,
 VH.2a 1A11 CDR Set and VL.1b 1A11 CDR Set,
 VH.2a 1A11 CDR Set and VL.2a 1A11 CDR Set,
 VH h1A11.A6 CDR Set and VL h1A11VL.1 CDR Set,
 VH h1A11.C6 CDR Set and VL h1A11VL.1 CDR Set,
 VH h1A11.A11 CDR Set and VL h1A11VL.1 CDR Set,
 VH h1A11.A8 CDR Set and VL h1A11VL.1 CDR Set,
 VH h1A11VH.1 CDR Set and VL h1A11.B4 CDR Set,
 VH h1A11VH.1 CDR Set and VL h1A11.A7 CDR Set,
 VH h1A11VH.1 CDR Set and VL h1A11.A12 CDR Set,
 VH h1A11VH.1 CDR Set and VL h1A11.A2 CDR Set,
 VH h1A11.B5 CDR Set and VL h1A11.B5 CDR Set, VH h1A11.E12 CDR Set and VL h1A11.E12 CDR Set,
VH h1A11.G3 CDR Set and VL h1A11.E12 CDR Set,
VH h1A11.F5 CDR Set and VL h1A11.E12 CDR Set, and
VH h1A11.H2 CDR Set and VL h1A11.E12 CDR Set.

5. The binding protein according to claim 1, further comprising a human acceptor framework sequence.

6. The binding protein according to claim 5, wherein the human acceptor framework comprises an amino acid sequence selected from the group consisting of SEQ ID NOs: 6-34 and SEQ ID NOs: 35-98.

7. The binding protein according to claim 5, wherein the binding protein comprises at least one acceptor framework sequence selected from the group consisting of:
   (a) heavy chain framework-1 (H-FR1): E-V-Q-L-V-E-S-G-G-G-L-V-Q-P-G-G-S-L-R-L-S-C-A-A-S-G-F-T-F-X30 (SEQ ID NO:143), wherein X30 is S, R, or G;
   (b) heavy chain framework-2 (H-FR2): W-V-R-Q-A-P-G-K-G-L-E-W-V-A (SEQ ID NO:144);
   (c) heavy chain framework-3 (H-FR3): R-F-T-I-S-R-D-N-A-K-X11-S-L-Y-L-Q-M-N-S-L-R-A-E-D-T-A-V-Y-Y-C-X31-R (SEQ ID NO:145), wherein;
       X11 is N or S; and
       X31 is A or S;
   (d) heavy chain framework-4 (H-FR4): W-G-Q-G-T-L-V-T-V-S-S (SEQ ID NO:146);
   (e) light chain framework-1 (L-FR1): D-I-Q-M-T-Q-S-P-S-S-L-S-A-S-V-G-D-R-V-T-I-T-C (SEQ ID NO:147);
   (f) light chain framework-2 (L-FR2): W-Y-Q-Q-K-P-G-K-X9-P-K-L-L-I-X15 (SEQ ID NO:148), wherein;
       X9 is A or S; and
       X15 is F or Y;
   (g) light chain framework-3 (L-FR3): G-V-P-S-R-F-S-G-S-G-S-G-T-D-X15-T-L-T-I-S-S-L-Q-P-E-D-F-A-T-Y-Y-C (SEQ ID NO:149), wherein;
       X15 is F or S; and
   (h) light chain framework-4 (L-FR4): F-G-Q-G-T-K-L-E-I-K (SEQ ID NO:150).

8. The binding protein of claim 2, wherein the antigen-binding domain comprises variable domain sequences selected from the group consisting of:
   SEQ ID NOs: 159 and 160;
   SEQ ID NOs: 171 and 175;
   SEQ ID NOs: 171 and 176;
   SEQ ID NOs: 171 and 177;
   SEQ ID NOs: 171 and 178;
   SEQ ID NOs: 172 and 175;
   SEQ ID NOs: 172 and 176;
   SEQ ID NOs: 172 and 177;
   SEQ ID NOs: 172 and 178;
   SEQ ID NOs: 173 and 175;
   SEQ ID NOs: 173 and 176;
   SEQ ID NOs: 173 and 178;
   SEQ ID NOs: 174 and 175;
   SEQ ID NOs: 174 and 176;
   SEQ ID NOs: 174 and 177;
   SEQ ID NOs: 174 and 178;
   SEQ ID NOs: 188 and 197;
   SEQ ID NOs: 190 and 197;
   SEQ ID NOs: 189 and 197;
   SEQ ID NOs: 187 and 197;
   SEQ ID NOs: 187 and 201;
   SEQ ID NOs: 187 and 200;
   SEQ ID NOs: 187 and 199;
   SEQ ID NOs: 187 and 198;
   SEQ ID NOs: 192 and 202;
   SEQ ID NOs: 193 and 203;
   SEQ ID NOs: 194 and 203;
   SEQ ID NOs: 195 and 203; and
   SEQ ID NOs: 196 and 203.

9. The binding protein according to claim 5, wherein the framework sequence of the binding protein comprises at least one amino acid substitution relative to a human germline acceptor framework at a key residue selected from the group consisting of:
   a residue adjacent to a CDR;
   a glycosylation site residue;
   a rare residue;
   a residue capable of interacting with human DLL4;
   a residue capable of interacting with a CDR;
   a canonical residue;
   a contact residue between heavy chain variable region and light chain variable region;
   a residue within a Vernier zone; and
   a residue in a region that overlaps between a Chothia-defined variable heavy Chain CDR1 and a Kabat-defined first heavy chain framework.

10. The binding protein according to claim 5, wherein said human acceptor framework comprises at least one framework region amino acid substitution, wherein the amino acid sequence of the framework is at least 65% identical to a sequence of a human germline acceptor framework and comprises at least 70 amino acid residues identical to the human germline acceptor framework.

11. The binding protein of claim 1, wherein the antigen-binding domain comprises variable domain sequences selected from the group consisting of:
   SEQ ID NOs: 159 and 160;
   SEQ ID NOs: 171 and 175;
   SEQ ID NOs: 171 and 176;
   SEQ ID NOs: 171 and 177;
   SEQ ID NOs; 171 and 178;
   SEQ ID NOs: 172 and 175:
   SEQ ID NOs: 172 and 176;
   SEQ ID NOs: 172 and 177;
   SEQ ID NOs: 172 and 178;
   SEQ ID NOs: 173 and 175;
   SEQ ID NOs: 173 and 176;
   SEQ ID NOs: 173 and 177;
   SEQ ID NOs: 173 and 178;
   SEQ ID NOs: 174 and 175;
   SEQ ID NOs: 174 and 176;
   SEQ ID NOs: 174 and 177:
   SEQ ID NOs: 174 and 178; and
   SEQ ID NOs: 187 and 197.

12. The binding protein according to claim 1, wherein the binding protein is capable of blocking DLL4 interaction with a Notch protein.

13. The binding protein according to claim 1, wherein the binding protein is capable of blocking DLL4 interaction with a Notch protein selected from the group consisting of Notch-1, Notch-2, Notch-3, Notch-4, and combinations thereof.

14. The binding protein according to claim 1, wherein the binding protein is capable of modulating a biological function of DLL4.

15. The binding protein according to claim 1, wherein the binding protein is capable of neutralizing a biological function of DLL4.

16. The binding protein according to claim 1, wherein the binding protein is capable of inhibiting VEGFR2 activity, VEGFR1 activity, or both.

17. The binding protein according to claim 1, wherein the binding protein is capable of diminishing the ability of DLL4 to bind to its receptor.

18. The binding protein according to claim 1, wherein the binding protein is capable of inhibiting normal angiogenesis.

19. The binding protein according to claim 1, wherein the binding protein has an on rate constant ($K_{on}$) to DLL4 selected from the group consisting of: at least about $10^2 M^{-1}s^{-1}$; at least about $10^3 M^{-1}s^{-1}$; at least about $10^4 M^{-1}s^{-1}$; at least about $10^5 M^{-1}s^{-1}$; and at least about $10^6 M^{-1}s^{-1}$, as measured by surface plasmon resonance.

20. The binding protein according to claim 1, wherein the binding protein has an off rate constant ($K_{off}$) to DLL4 selected from the group consisting of: at most about $10^{-3} s^{-1}$; at most about $10^{-4} s^{-1}$; at most about $10^{-5} s^{-1}$; and at most about $10^{-6} s^{-1}$, as measured by surface plasmon resonance.

21. The binding protein according to claim 1, wherein the binding protein has a dissociation constant ($K_D$) to DLL4 selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most about $10^{-13}$ M.

22. A binding protein construct comprising the binding protein of claim 1, the binding protein construct further comprising a linker polypeptide or an immunoglobulin constant domain.

23. The binding protein construct according to claim 22, wherein the binding protein is selected from the group consisting of:
an immunoglobulin molecule,
a monoclonal antibody,
a chimeric antibody,
a CDR-grafted antibody,
a Fab,
a Fab',
a F(ab')$_2$,
an Fv,
a disulfide-linked Fv,
an scFv,
a single domain antibody,
a diabody,
a multispecific antibody,
a dual specific antibody,
a dual variable domain immunoglobulin (DVD-Ig) binding protein, and
a bispecific antibody.

24. The binding protein construct according to claim 22, wherein the binding protein construct comprises a heavy chain immunoglobulin constant domain selected from the group consisting of:
a human IgM constant domain,
a human IgG1 constant domain,
a human IgG2 constant domain,
a human IgG3 constant domain,
a human IgG4 constant domain,
a human IgE constant domain, and
a human IgA constant domain.

25. The binding protein construct according to claim 22, comprising an immunoglobulin constant domain having an amino acid sequence selected from the group consisting of: SEQ ID NO:3, SEQ ID NO:4, SEQ ID NO:5, SEQ ID NO:6, and combinations thereof.

26. A binding protein conjugate comprising the binding protein construct of claim 22, binding protein conjugate further comprising an agent selected from the group consisting of: an imaging agent, a therapeutic agent, a cytotoxic agent, and an immunoadhesion molecule.

27. The binding protein conjugate according to claim 26, wherein the agent is an imaging agent selected from the group consisting of a radiolabel, an enzyme, a fluorescent label, a luminescent label, a bioluminescent label, a magnetic label, and biotin.

28. The binding protein conjugate according to claim 26, wherein the imaging agent is a radiolabel selected from the group consisting of: $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm.

29. The binding protein conjugate according to claim 26, wherein the agent is a therapeutic or cytotoxic agent selected from the group consisting of: an anti-metabolite, an alkylating agent, an antibiotic, a growth factor, a cytokine, an anti-angiogenic agent, an anti-mitotic agent, an anthracycline, a toxin, and an apoptotic agent.

30. The binding protein construct according to claim 22, wherein the binding protein possesses a human glycosylation pattern.

31. The binding protein conjugate according to claim 26, wherein the binding protein possesses a human glycosylation pattern.

32. The binding protein according to claim 1, wherein the binding protein exists as a crystal.

33. The binding protein construct according to claim 22, wherein the binding protein construct exists as a crystal.

34. The binding protein conjugate according to claim 26, wherein the binding protein construct exists as a crystal.

35. The binding protein according to claim 32, wherein the crystal is a carrier-free pharmaceutical controlled release crystal.

36. The binding protein construct according to claim 33, wherein the crystal is a carrier-free pharmaceutical controlled release crystal.

37. The binding protein conjugate according to claim 34, wherein the crystal is a carrier-free pharmaceutical controlled release crystal.

38. The binding protein according to claim 32, wherein the binding protein crystal has a greater half-life in vivo than the soluble counterpart of the binding protein.

39. The binding protein construct according to claim 33, wherein the binding protein construct crystal has a greater half-life in vivo than the soluble counterpart of the binding protein construct.

40. The binding protein conjugate according to claim 34, wherein the binding protein conjugate crystal has a greater half-life in vivo than the soluble counterpart of the binding protein conjugate.

41. The binding protein according to claim 32, wherein the binding protein crystal retains biological activity of the non-crystal form of the binding protein.

42. The binding protein construct according to claim 33, wherein the binding protein construct crystal retains biological activity of the non-crystal form of the binding protein construct.

43. The binding protein conjugate according to claim 34, wherein the binding protein conjugate crystal retains biological activity of the non-crystal form of the binding protein conjugate.

44. An isolated nucleic acid encoding the binding protein amino acid sequence of claim 1.

45. A vector comprising the isolated nucleic acid according to claim 44.

46. The vector according to claim 45, wherein the vector is selected from the group consisting of: pcDNA, pTT, pTT3, pEFBOS, pBV, NV, and pBJ.

47. A host cell comprising the vector of claim 45.

48. The host cell according to claim 47, wherein said host cell is a prokaryotic cell.

49. The host cell according to claim 48, wherein the host cell is an *Escherichia coli* cell.

50. The host cell according to claim 47, wherein said host cell is a eukaryotic cell.

51. The host cell according to claim 50, wherein said eukaryotic cell is selected from the group consisting of: a protist cell, an animal cell, a plant cell, and a fungal cell.

52. The host cell according to claim 51, wherein said eukaryotic cell is an animal cell selected from the group consisting of: a mammalian cell, an avian cell, and an insect cell.

53. The host cell according to claim 52, wherein said mammalian cell is a CHO cell.

54. The host cell according to claim 52, wherein said mammalian cell is a COS cell.

55. The host cell according to claim 51, wherein the fungal cell is a *Saccharomyces cerevisiae* cell.

56. The host cell according to claim 52, wherein said insect cell is an Sf9 cell, 57. A method of producing a binding protein that binds human DLL4, comprising culturing the host cell of claim 47 in a culture medium under conditions sufficient to produce a binding protein that binds human DLL4.

58. A binding protein produced according to the method of claim 57.

59. A composition for the release of a binding protein, the composition comprising:
(a) a formulation, wherein said formulation comprises a crystallized binding protein of claim 32, and an ingredient; and
(b) at least one polymeric carrier.

60. The composition according to claim 59, wherein said polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone), poly (ethylene glycol), poly ((hydroxypropyl) methacrylamide, poly [(organo)phosphazene], poly (ortho esters), poly (vinyl alcohol), poly (vinylpyrrolidone), maleic anhydride- alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

61. The composition according to claim 59, wherein said ingredient is selected from the group consisting of albumin, sucrose, trehalose, lactitol, gelatin, hydroxypropyl-β-cyclodextrin, methoxypolyethylene glycol and polyethylene glycol.

62. A method for treating a mammal comprising the step of administering to the mammal an effective amount of the composition of claim 59.

63. A pharmaceutical composition comprising the binding protein of claim 1, and a pharmaceutically acceptable carrier.

64. The pharmaceutical composition of claim 63, further comprising at least one additional agent for treating a disorder in which DLL4 activity is detrimental.

65. The pharmaceutical composition of claim 64, wherein said additional agent is selected from the group consisting of: a therapeutic agent; an imaging agent; an antineoplastic agent; a chemotherapeutic agent; an angiogenesis inhibitor; an anti-VEGF antibody; an anti-EGFR antibody; an anti-cMet antibody; an anti-ErbB3 antibody; an anti-HER2 antibody; an anti-CD20 antibody; aflibercept; a kinase inhibitor; a co-stimulation molecule blocker; an anti-B7.2 antibody; a CTLA4-Ig; an adhesion molecule blocker; an anti-E selectin antibody; an anti-L selectin antibody; an anti-cytokine antibody or functional fragment thereof; an anti-IL-18 antibody; an anti-TNF antibody; anti-IL-6 antibody; methotrexate; a corticosteroid; a cyclosporin; a rapamycin; FK506; a DNA alkylating agent; cisplatin; carboplatin; an anti-tubulin agent; paclitaxel; docetaxel; doxorubicin; gemcitabine; gemzar; an anthracycline; adriamycin; a topoisomersase I inhibitor; a topoisomerase II inhibitor; 5-fluorouracil (5-FU); leucovorin; irinotecan; a receptor tyrosine kinase inhibitor, an apoptosis inhibitor; a Bcl2/Bclx inhibitor; erlotinib, gefitinib, a COX-2 inhibitor, celecoxib, cyclosporin; rapamycin; a detectable label or reporter molecule; a TNF antagonist; an antirheumatic; a muscle relaxant; a narcotic; an analgesic; an anesthetic; a sedative; a local anesthetic; a neuromuscular blocker; an antimicrobial agent; an antipsoriatic agent; a corticosteroid; an anabolic steroid; an erythropoietin; an immunization; an immunoglobulin; an immunosuppressive agent; a growth hormone; a hormone replacement drug; a radiopharmaceutical drug; an antidepressant; an antipsychotic drug; a stimulant; an asthma medication; a beta agonist; an inhaled steroid; an epinephrine; an epinephrine analog thereof; a cytokine; and a cytokine antagonist.

66. A method for reducing human DLL4 activity comprising contacting human DLL4 with the binding protein of claim 1 such that human DLL4 activity is reduced.

67. A method for reducing human DLL4 activity in a human subject suffering from a disorder in which DLL4 activity is detrimental, comprising administering to the human subject the binding protein of claim 1 such that human DLL4 activity in the human subject is reduced.

68. A method for treating a subject for a disease or a disorder in which DLL4 activity is detrimental by administering to the subject the binding protein of claim 2 such that treatment is achieved.

69. The method of claim 68, wherein said disorder is selected from the group consisting of: breast cancer, colon cancer, rectal cancer, lung cancer, oropharynx cancer, hypopharynx cancer, esophageal cancer, stomach cancer, pancreas cancer, liver cancer, gallbladder cancer, bile duct cancer, small intestine cancer, urinary tract cancer, female genital tract cancer, male genital tract cancer, endocrine gland cancer, skin cancer, hemangioma, melanoma, sarcoma, brain tumor, nerve cancer, eye tumor, meninges cancer, solid tumors from hematopoietic malignancy, tumor metastases, ocular neovascularization, edema, rheumatoid arthritis, atherosclerotic plaques, Crohn's disease, inflammatory bowel disease, refractory ascites, psoriasis, sarcoidosis, arterial arteriosclerosis, sepsis, peptic ulcers, burns, pancreatitis, polycystic ovarian disease (POD), endometriosis, uterine fibroid, benign prostate hypertrophy, T-cell acute lymphoblastic leukemia (T-ALL), cerebral autosomal dominant arteriopathy with subcortical infarcts and leukoencephalopathy (CADASIL), multiple sclerosis (MS), tetralogy of Fallot (TOF), Alagille syndrome (AS), macular degeneration and age-related macular degeneration diseases, and other angiogenesis independent and dependent diseases characterized by aberrant DLL4 activity.

70. The method according to claim 69, wherein the disorder is a primary and metastatic cancer.

71. The method according to claim 69, wherein the urinary tract cancer is selected from the group consisting of renal cancer, bladder cancer, and urothelium cancer.

72. The method according to claim 69, wherein the female genital tract cancer is selected from the group consisting of cervical cancer, uterine cancer, ovarian cancer, choriocarcinoma, and gestational trophoblastic disease.

73. The method according to claim 69, wherein the male genital tract cancer is selected from the group consisting of prostate cancer, seminal vesicles cancer, testicular cancer, and germ cell tumor.

74. The method according to claim 69, wherein the endocrine gland cancer is selected from the group consisting of thyroid cancer, adrenal cancer, and pituitary gland cancer.

75. The method according to claim 69, wherein the sarcoma is selected from the group consisting of a bone sarcoma, a soft tissue sarcoma, and Kaposi's sarcoma.

76. The method according to claim 69, wherein the meninges cancer is selected from the group consisting of an astrocytoma, a glioma, a glioblastoma, a retinoblastoma, a neuroma, a neuroblastoma, a Schwannoma, and a meningioma.

77. The method according to claim 69, wherein the solid tumor from a hematopoietic malignancy is a leukemia, a Hodgkin's leukemia, a non-Hodgkin's leukemia, a lymphoma, a Hodgkin's lymphoma, and a non-Hodgkin's lymphomas.

78. The method according to claim 69, wherein the ocular neovascularization is selected from the group consisting of diabetic blindness, a retinopathy, an age-related macular degeneration, and a rubeosis.

79. The method according to claim 68, wherein said administering to the subject is by at least one mode selected from the group consisting of: parenteral, subcutaneous, intramuscular, intravenous, intraarterial, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

80. A method of treating a patient suffering from a disorder in which DLL4 is detrimental comprising the step of administering the DLL4 binding protein of claim 1 before, concurrent with, or after the administration of a therapeutically effective amount of a second agent, wherein the second agent is selected from the group consisting of an antibody or fragment thereof capable of binding human VEGFR2; methotrexate; an antibody or fragment thereof capable of binding human TNF; a corticosteroid; a cyclosporine; a rapamycin; FK506; a non-steroidal anti-inflammatory agent (NSAID); a radiotherapeutic agent; an antineoplastic agent; a chemotherapeutic agent; a DNA alkylating agent; cisplatin; carboplatin; an anti-tubulin agent; paclitaxel; docetaxel; taxol; doxorubicin; gemcitabine; gemzar; an anthracycline; adriamycin; a topoisomerase I inhibitor; a topoisomerase II inhibitor; 5-fluorouracil (5-FU); leucovorin; irinotecan; a receptor tyrosine kinase inhibitor; erlotinib; gefitinib; a COX-2 inhibitor; celecoxib; a kinase inhibitor; an angiogenesis inhibitor; an anti-VEGF antibody; aflibercept; a co-stimulation molecule blocker; an anti-B7.1 antibody; an anti-B7.2 antibody; a CTLA4-lg; an anti-CD20 antibody; an adhesion molecule blocker; an anti-LFA-1 antibody; an anti-E selectin antibody; and anti-L selectin antibody; a small molecule inhibitor; an anti-cytokine antibody or functional fragment thereof; an anti-IL-18 antibody; anti-TNF antibody; an anti-IL-6 antibody; an anti-cytokine receptorantibody; a detectable label or reporter; a TNF antagonist; an antirheumatic; a muscle relaxant; a narcotic; an analgesic; an anesthetic; a sedative; a local anesthetic; a neuromuscular blocker; an antimicrobial agent; an antipsoriatic drug; a corticosteroid; an anabolic steroid; an erythropoietin; an immunization; an immunoglobulin; an immunosuppressive agent; a growth hormone; a hormone replacement drug; a radiopharmaceutical drug; an antidepressant; an antipsychotic drug; a stimulant; an asthma medication; a beta agonist; an inhaled steroid; an epinephrine; an epinephrine analog; a cytokine; and a cytokine antagonist.

81. The binding protein according to claim 1, wherein the binding protein is an antibody.

82. The antibody according to claim 81, wherein the antibody is selected from the group consisting of a monoclonal antibody, a full-length tetrameric immunoglobulin, an IgG molecule, an IgG1 molecule, a chimeric antibody, a CDR-grafted antibody, a humanized antibody, and an affinity matured antibody.

83. The antibody according to claim 82, wherein the antibody is a monoclonal antibody.

84. The binding protein according to claim 8, wherein said two variable domains have the amino acid sequences selected from the group consisting of:
   SEQ ID NO:188 and SEQ ID NO:197,
   SEQ ID NO:190 and SEQ ID NO:197, and
   SEQ ID NO:191 and SEQ ID NO:197.

85. A binding protein comprising a heavy chain variable domain sequence and a light chain variable domain sequence that together form a functional binding site for DLL4, wherein the variable domains comprise CDRs 1-3 from SEQ ID NO:187 and CDRs 1-3 from SEQ ID NO:197.

86. The binding protein of claim 85, wherein the variable domains comprise SEQ ID NO:187 and SEQ ID NO:197.

87. The binding protein according to claim 1, wherein the binding protein is a dual variable domain immunoglobulin (DVD-Ig) binding protein.

88. A DVD-Ig binding protein comprising a heavy chain variable domain sequence and a light chain variable domain sequence that together form a functional binding site for DLL4, wherein the variable domains comprise CDRs 1-3 from SEQ ID NO:187 and CDRs 1-3 from SEQ ID NO:197.

89. The DVD-Ig binding protein of claim 88, wherein the variable domains comprise SEQ ID NO:187 and SEQ ID NO:197.

90. The binding protein of claim 85, wherein the binding protein is an antibody.

91. The binding protein of claim 86, wherein the binding protein is an antibody.

* * * * *